US012553042B2

(12) United States Patent
Hennig et al.

(10) Patent No.: US 12,553,042 B2
(45) Date of Patent: Feb. 17, 2026

(54) METHOD FOR QUANTIFYING AN AMOUNT OF CAPPED MESSENGER RNA

(71) Applicant: ReCode Therapeutics, Inc., Menlo Park, CA (US)

(72) Inventors: Mirko Hennig, Mountain View, CA (US); Sakya Sing Mohapatra, Sunnyvale, CA (US); Daniella Ishimaru, Mountain View, CA (US); Joseph S. Cefalu, Menlo Park, CA (US); Ali Ahmed Alfaifi, Redwood City, CA (US); Julia Jung-un Baek, San Jose, CA (US); Hu Meng, Menlo Park, CA (US); Jeremy Monroe, Menlo Park, CA (US)

(73) Assignee: ReCode Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 18/433,225

(22) Filed: Feb. 5, 2024

(65) Prior Publication Data

US 2025/0188440 A1 Jun. 12, 2025

Related U.S. Application Data

(60) Provisional application No. 63/605,181, filed on Dec. 1, 2023.

(51) Int. Cl.

| | |
|---|---|
| ***C12Q 1/6872*** | (2018.01) |
| ***C12N 15/10*** | (2006.01) |
| ***C12Q 1/6806*** | (2018.01) |

(52) U.S. Cl.

CPC ........... *C12N 15/10* (2013.01); *C12Q 1/6806* (2013.01)

(58) Field of Classification Search

CPC ........ C12N 15/10; C12Q 1/68; C12Q 1/6806; C12Q 2565/137; C12Q 2521/337; C12Q 2521/525

See application file for complete search history.

(56) References Cited

U.S. PATENT DOCUMENTS

| | | | |
|---|---|---|---|
| 5,820,873 | A | 10/1998 | Choi et al. |
| 7,404,969 | B2 | 7/2008 | Chen et al. |
| 7,893,302 | B2 | 2/2011 | Chen et al. |

(Continued)

FOREIGN PATENT DOCUMENTS

| | | | |
|---|---|---|---|
| CN | 112626177 | A | 4/2021 |
| WO | 2008103276 | A2 | 8/2008 |

(Continued)

OTHER PUBLICATIONS

Bauer et al. (Jan. 3, 2015) "Generation of Genomic Deletions in Mammalian Cell Lines via CRISPR/Cas9", Journal of Visualized Experiments, (95):e52118(21 pages).

(Continued)

*Primary Examiner* — Terra C Gibbs

(74) *Attorney, Agent, or Firm* — Mintz Levin Cohn Ferris Glovsky and Popeo, P.C.

(57) ABSTRACT

Provided are a method for quantifying an amount of capped messenger RNA (mRNA) in an mRNA sample comprising contacting the mRNA with two or more of a nuclease, an alkaline phosphatase, and a polynucleotide kinase and separating the capped mRNA and the uncapped mRNA occurs using chromatography.

19 Claims, 66 Drawing Sheets

Specification includes a Sequence Listing.

(56) References Cited

U.S. PATENT DOCUMENTS

| | | | | |
|---|---|---|---|---|
| 8,283,333 | B2 | 10/2012 | Yaworski et al. | |
| 8,309,335 | B2 * | 11/2012 | Jendrisak | C12N 15/1096 435/194 |
| 8,450,298 | B2 | 5/2013 | Mahon et al. | |
| 8,466,122 | B2 | 6/2013 | Heyes et al. | |
| 2010/0036115 | A1 | 2/2010 | Beigelman et al. | |
| 2012/0202871 | A1 | 8/2012 | Heyes et al. | |
| 2013/0064894 | A1 | 3/2013 | Martin et al. | |
| 2013/0129785 | A1 | 5/2013 | Manoharan et al. | |
| 2013/0150625 | A1 | 6/2013 | Budzik et al. | |
| 2013/0178541 | A1 | 7/2013 | Stanton et al. | |
| 2013/0225836 | A1 | 8/2013 | Stanton et al. | |
| 2014/0200257 | A1 | 7/2014 | Rajeev et al. | |
| 2018/0274009 | A1 | 9/2018 | Marquardt et al. | |
| 2021/0259980 | A1 | 8/2021 | Cheng et al. | |
| 2022/0071916 | A1 | 3/2022 | Cheng et al. | |
| 2022/0349006 | A1 | 11/2022 | Amato et al. | |

FOREIGN PATENT DOCUMENTS

| | | | | |
|---|---|---|---|---|
| WO | 2010021865 | A1 | 2/2010 | |
| WO | 2010080724 | A1 | 7/2010 | |
| WO | 2010141069 | A2 | 12/2010 | |
| WO | 2010144740 | A1 | 12/2010 | |
| WO | 2011022460 | A1 | 2/2011 | |
| WO | 2011043913 | A2 | 4/2011 | |
| WO | 2011090965 | A1 | 7/2011 | |
| WO | 2011149733 | A2 | 12/2011 | |
| WO | 2011153120 | A1 | 12/2011 | |
| WO | 2012040184 | A2 | 3/2012 | |
| WO | 2012044638 | A1 | 4/2012 | |
| WO | 2012054365 | A2 | 4/2012 | |
| WO | 2012061259 | A2 | 5/2012 | |
| WO | 2012099755 | A1 | 7/2012 | |
| WO | 2013063468 | A1 | 5/2013 | |
| WO | 2013086354 | A1 | 6/2013 | |
| WO | 2013086373 | A1 | 6/2013 | |
| WO | 2013149140 | A1 | 10/2013 | |
| WO | WO-2014152659 | A1 * | 9/2014 | C07K 14/505 |
| WO | 2015095340 | A1 | 6/2015 | |
| WO | 2015184256 | A2 | 12/2015 | |
| WO | 2015199952 | A1 | 12/2015 | |
| WO | 2016004202 | A1 | 1/2016 | |
| WO | 2016118724 | A1 | 7/2016 | |
| WO | 2016118725 | A1 | 7/2016 | |
| WO | 2016205691 | A1 | 12/2016 | |
| WO | 2017004143 | A1 | 1/2017 | |
| WO | 2017049245 | A2 | 3/2017 | |
| WO | 2017075531 | A1 | 5/2017 | |
| WO | 2017117528 | A1 | 7/2017 | |
| WO | 2017173054 | A1 | 10/2017 | |
| WO | 2022204215 | A1 | 9/2022 | |
| WO | 2022204219 | A1 | 9/2022 | |
| WO | 2022256597 | A1 | 12/2022 | |
| WO | 2024123633 | A1 | 6/2024 | |
| WO | 2024256674 | A1 | 12/2024 | |

OTHER PUBLICATIONS

Cheng et al. (Apr. 6, 2020) "Selective Organ Targeting (SORT) Nanoparticles for Tissue-specific mRNA Delivery and CRISPR-Cas Gene Editing", Nature Nanotechnology, 15(4):313-320.

Deltcheva et al. (Mar. 31, 2011) "CRISPR RNA Maturation by Trans-Encoded Small RNA and Host Factor RNase III", Nature, 471(7340):602-607.

Dilliard et al. (Dec. 28, 2021) "On the Mechanism of Tissue-specific mRNA Delivery by Selective Organ Targeting Nanoparticles", Proceedings of the National Academy of Sciences of the United States of America, 118(52):e2109256118(10 pages).

Jinek et al. (Aug. 17, 2012) "A Programmable Dual-RNA-Guided DNA Endonuclease in Adaptive Bacterial Immunity", Science, 337(6069):816-821.

Koonin et al. (Jun. 2017) "Diversity, Classification and Evolution of CRISPR-Cas Systems", Current Opinion in Microbiology, 37:67-78.

Makarova et al. (Sep. 28, 2015) "An Update Eevolutionary Classification of CRISPR-Cas Systems", Nature Reviews Microbiology, 13:722-736.

Needleman et al. (Mar. 1970) "A General Method Applicable to the Search for Similarities in the Amino Acid Sequence of Two Proteins", Journal of Molecular Biology, 48(3):443-453.

Shmakov et al. (Nov. 5, 2015) "Discovery and Functional Characterization of Diverse Class 2 CRISPR-Cas Systems", Molecular Cell, 60(3):385-397.

Vlatkovic et al. (2022) "Ribozyme Assays to Quantify the Capping Efficiency of In Vitro-Transcribed mRNA", Pharmaceutics, 14(2):328.

Wang et al. (Jan. 2023) "Preparation of Selective Organ-targeting (SORT) Lipid Nanoparticles (LNPs) Using Multiple Technical Methods for Tissue-specific mRNA Delivery", Nature Protocols, 18:265-291.

Beverly, M. et al. (Jul. 2016, e-published May 18, 2016). "Label-free analysis of mRNA capping efficiency using RNase H probes and LC-MS," *Anal Bioanal Chem* 408(18):5021-5030.

Zhang, N. (Feb. 8, 2022). "DNAzyme as a rising gene-silencing agent in theranostic settings," *Neural Regen Res* 17(9):1989-1990.

Muthmann et al. (May 28, 2021) "Quantification of mRNA cap-Modifications by Means of LC-QqQ-MS", Methods, 203:196-206.

* cited by examiner

| Formulations | Group(s) | Dendrimer/SORT/Helper/Chol/PEG | Size (nm) | PDI | EE% | Concentration (mg/mL) |
|---|---|---|---|---|---|---|
| 0% DOTAP | 1 | 4A3-SC7/DOTAP/DOPE/Chol/DMG-PEG | 69.8 | 0.13 | 94 | 0.62 |
| 10% DOTAP | 2 | 4A3-SC7/DOTAP/DOPE/Chol/DMG-PEG | 67.0 | 0.05 | 88 | 0.52 |
| 20% DOTAP | 3 | 4A3-SC7/DOTAP/DOPE/Chol/DMG-PEG | 52.5 | 0.07 | 99 | 0.49 |
| 30% DOTAP | 4 | 4A3-SC7/DOTAP/DOPE/Chol/DMG-PEG | 55.9 | 0.07 | 100 | 0.50 |
| 40% DOTAP | 5 | 4A3-SC7/DOTAP/DOPE/Chol/DMG-PEG | 57.9 | 0.04 | 100 | 0.55 |
| 50% DOTAP | 6 | 4A3-SC7/DOTAP/DOPE/Chol/DMG-PEG | 65.2 | 0.02 | 100 | 0.51 |

FIG. 1C

| Formulations | Groups(s) | Dendrimer/SORT/helper/Chol/PEG | Lipd:mRNA (wt/wt) | Size (nm) | PDI | EE% | Concentration (mg/mL) |
|---|---|---|---|---|---|---|---|
| Composition 2A | 6 | 4A3-SC7/16:0EPC/DOPE/Chol/DMG-PEG | high | 62.2 | 0.06 | 100 | 0.44 |
| Composition 2B | 4 | 4A3-SC7/16:0EPC/DOPE/Chol/DMG-PEG | low | 60.6 | 0.07 | 100 | 0.53 |

All formulations prepared fresh in PBS

| Formulations | Buffer | Dendrimer/SORT/helper/Chol/PEG | Size (nm) | PDI | EE% | Concentration (mg/mL) |
|---|---|---|---|---|---|---|
| Composition 2B | Fresh - PBS | 4A3-SC7/16:0EPC/DOPE/Chol/DMG-PEG | 60.6 | 0.07 | 100 | 0.53 |
| Composition 2B | Frozen - 15 mM Tris pH 7.5 + 10% sucrose | 4A3-SC7/16:0EPC/DOPE/Chol/DMG-PEG | 72.3 | 0.10 | 100 | 0.56 |

| Composition | Group(s) | Dendrimer/SORT/helper/Chol/PEG | Mol% | Lipid:mRNA (wt/wt) | Size (nm) | PDI | EE% | Concentration (mg/mL) |
|---|---|---|---|---|---|---|---|---|
| Composition 2B Tris 10% sucrose | 1 (MP) | 4A3-SC7/16:0EPC/DOPE/Chol/DMG-PEG | 16.67/30/16.67/33.33/3.33 | 30 | 78.0 | 0.08 | 101 | 0.60 |
| Composition 2B Tris 10% sucrose | 2 (DAL) | 4A3-SC7/18:0EPC/DOPE/Chol/DMG-PEG | 16.67/30/16.67/33.33/3.33 | 30 | 70.5 | 0.08 | 101 | 0.59 |
| Composition 2C Tris 10% sucrose | 3 (DAL) | 4A3-SC7/18:0EPC/DOPE/Chol/DMG-PEG | 14.29/40/14.29/28.57/2.86 | 30 | 70.2 | 0.10 | 101 | 0.65 |
| Composition 2D Tris 10% sucrose | 4 (DAL) | 4A3-SC7/16:0EPC/DOPE/Chol/DMG-PEG | 11.9/50/11.9/23.81/2.38 | 30 | 72.9 | 0.17 | 101 | 0.56 |
| Composition B Cit. 10% sucrose | 5 (MP) | 4A3-SC7/DODAP/DOPE/Chol/DMG-PEG | 19.05/20/19.05/38.09/3.81 | 40 | 62.2 | 0.12 | 68 | 0.56 |
| Composition B Tris 10% sucrose Mix pH4 | 6 (MP) | 4A3-SC7/DODAP/DOPE/Chol/DMG-PEG | 19.05/20/19.05/38.09/3.81 | 40 | 80.1 | 0.12 | 94 | 0.58 |
| Composition B Tris 10% sucrose Mix pH6 | 7 (MP) | 4A3-SC7/DODAP/DOPE/Chol/DMG-PEG | 19.05/20/19.05/38.09/3.81 | 40 | 73.0 | 0.11 | 98 | 0.65 |
| Composition B Tris NaCl 5% sucrose | 8 (MP) | 4A3-SC7/DODAP/DOPE/Chol/DMG-PEG | 19.05/20/19.05/38.09/3.81 | 40 | 75.4 | 0.12 | 98 | 0.61 |

FIG. 5B

| Composition | Group(s) | Dendrimer/SORT/helper/Chol/PEG | Mol% | N/P | Lipid:mRNA (wt/wt) | Size (nm) | PDI | EE% | Concentration (mg/mL) |
|---|---|---|---|---|---|---|---|---|---|
| 2F | 1 | 4A3-SC7/16:0EPC/DOPE/Chol/DMG-PEG | 23.81/0/23.81/47.62/4.76 | | 30 | 80.5 | 0.15 | 89.0 | 0.49 |
| 2G | 2 | 4A3-SC7/16:0EPC/DOPE/Chol/DMG-PEG | 21.43/10/21.43/42.85/4.29 | | 30 | 107.8 | 0.04 | 55.8 | 0.48 |
| 2E | 3 | 4A3-SC7/16:0EPC/DOPE/Chol/DMG-PEG | 19.05/20/19.05/38.09/3.81 | | 30 | 84.6 | 0.04 | 94.5 | 0.50 |
| 2B | 4 | 4A3-SC7/16:0EPC/DOPE/Chol/DMG-PEG | 16.67/30/16.67/33.3/3.33 | 10.1 | 30 | 64.9 | 0.07 | 100.4 | 0.55 |
| 2C | 5 | 4A3-SC7/16:0EPC/DOPE/Chol/DMG-PEG | 14.29/40/14.29/28.57/2.86 | 10.4 | 30 | 63.8 | 0.05 | 100.8 | 0.46 |
| 2D | 6 | 4A3-SC7/16:0EPC/DOPE/Chol/DMG-PEG | 11.9/50/11.9/23.81/2.38 | 10.8 | 30 | 66.4 | 0.10 | 102.0 | 0.47 |

FIG. 5D

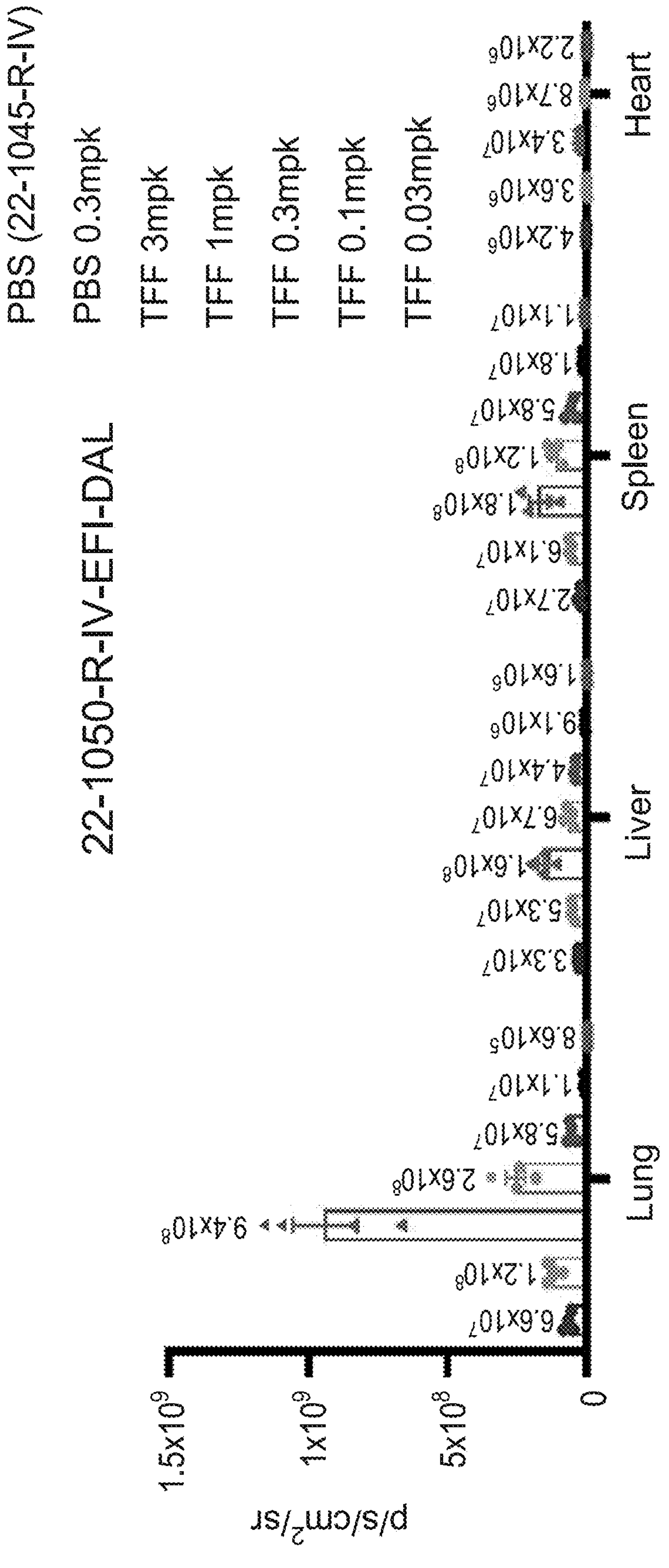
FIG. 7 continue

| Composition | Dendrimer/SORT/helper/Chol/PEG | Mol% | Lipid:mRNA (wt/wt) | Size (nm) | PDI | EE% | mRNA Concentration (mg/mL) HPLC | mRNA Batch |
|---|---|---|---|---|---|---|---|---|
| 2B EPC | 4A3-SC7/16:0EPC/DOPE/Chol/DMG-PEG | 16.67/30/16.67/33.33/3.33 | 30 | 57.5 | 0.12 | 95.5 | 0.581 | 13.6/7a |
| 2H | D-Lin-MC3-DMA/DSPC/Chol/DMG-PEG | 50/0/10/38.5/1.5 | 20 | 74.8 | 0.10 | 98.2 | 0.45 (ribogreen) | 13.6/7a |

Acquisition time: 10 sec color scale = 1.00e6 to 7.00e7

Average body weight and organ weight of young adult Cynomolgus Monkeys (Data from [1])

| | Average Body Weight (g) | Average Organ Weight (g) | | |
|---|---|---|---|---|
| | | Lung | Liver | Spleen |
| Male | 6600 | 40.87 | 137.82 | 7.97 |
| Female | 3340 | 18.03 | 83.06 | 6.94 |

$$\text{Delivered Lipid \%} = \frac{\text{Measured Organ Lipid Level } \left(\frac{mg}{g}\right) \text{ x Ave. Organ Weight}}{\text{Theoretical Dosing Level } \left(\frac{mg}{g}\right) \text{ x Ave. Body Weight}} \text{ x } 100\%$$

Estimated Percentage of Lipids Delivered in Each Organ (Only based on the last dose)

| Group | Formulation | mRNA Dose (mg/kg) | Estimated Percentage of Total Dose | | | | | | | | | | | |
|---|---|---|---|---|---|---|---|---|---|---|---|---|---|---|
| | | | Lung | | | Liver | | | Spleen | | | Total | | |
| | | | 4A3-SC7 | 16:0 EPC | DMG-PEG | 4A3-SC7 | 16:0 EPC | DMG-PEG | 4A3-SC7 | 16:0 EPC | DMG-PEG | 4A3-SC7 | 16:0 EPC | DMG-PEG |
| 2 | Composition 2B | 0.1 | 0.168% | 0.000% | 0.083% | 2.224% | 3.031% | 0.968% | 0.552% | 0.268% | 0.101% | 2.95% | 3.30% | 1.15% |
| 3 | Composition 2B | 0.03 | 0.213% | 0.000% | 0.103% | 1.995% | 0.896% | 1.174% | 0.851% | 0.217% | 0.126% | 3.06% | 1.11% | 1.40% |
| | | | 4A3-SC7 | DODAP | DMG-PEG | 4A3-SC7 | DODAP | DMG-PEG | 4A3-SC7 | DODAP | DMG-PEG | 4A3-SC7 | DODAP | DMG-PEG |
| 4 | Composition B | 0.3 | 0.571% | 0.988% | 0.362% | 5.772% | 4.093% | 3.732% | 1.381% | 1.251% | 0.909% | 7.72% | 6.33% | 5.00% |
| 5 | Composition B | 0.03 | 0.098% | 0.000% | 0.077% | 1.149% | 0.000% | 1.076% | 0.858% | 0.313% | 0.135% | 2.11% | 0.31% | 1.29% |
| | | | D-Lin-MC-DMA | | DMG-PEG | D-Lin-MC-DMA | | DMG-PEG | D-Lin-MC-DMA | | DMG-PEG | D-Lin-MC-DMA | | DMG-% |
| 6 | Composition B | 0.003 | 2.989% | | 1.773% | 13.897% | | 3.973% | 3.214% | | 0.390% | 20.10% | | 6.14 |

FIG. 17B

| | Peak area | Conc (µM) |
|---|---|---|
| Uncapped | 88,904 | 0.243 |
| Cap 1 | 134,057 | 0.362 |
| Cap 0 | 144,167 | 0.389 |
| Cap G | 107,958 | 0.292 |

METHOD FOR QUANTIFYING AN AMOUNT OF CAPPED MESSENGER RNA

CROSS-REFERENCE TO RELATED APPLICATION

This application claims priority to U.S. Provisional Patent Application No. 63/605,181 filed Dec. 1, 2023, incorporated by reference herein in its entirety.

INCORPORATION BY REFERENCE OF SEQUENCE LISTING

This application contains a Sequence Listing which has been submitted in .XML format via EFS-WEB and is hereby incorporated by reference in its entirety. The .XML file, created on Jul. 5, 2024, is named 061529-505001US_SeqList_ST26.xml and is 51.2 kilobytes in size.

BACKGROUND

There is an unmet need for lipid nanoparticle for systematical delivery to the lungs to the subject in need thereof. The present disclosure provides lipid nanoparticle compositions specifically deliver to the lungs for treatment of lung disease.

SUMMARY

The disclosure provides a method for quantifying an amount of capped messenger RNA (mRNA) in an mRNA sample, the method comprising steps of providing an mRNA sample comprising capped mRNA and uncapped mRNA, contacting mRNA in the sample with two or more of a nuclease, an alkaline phosphatase, and a polynucleotide kinase, separating the capped mRNA and the uncapped mRNA, identifying an amount of separated, capped mRNA and an amount of separated, uncapped mRNA, and comparing the amount of separated, capped mRNA to the amount of separated, uncapped mRNA; comparing the amount of separated, capped mRNA to the amount of total mRNA in the sample; and/or comparing the amount of separated, capped mRNA to a standard mRNA sample, thereby quantifying the amount of capped mRNA in the mRNA sample.

In some embodiments, the mRNA in the sample is contacted with each of the nuclease, the alkaline phosphatase, and the polynucleotide kinase. In some embodiments, the mRNA in the sample is contacted with the nuclease under conditions sufficient to create 5' end fragments of mRNA. In some embodiments, the mRNA in the sample is contacted with the alkaline phosphatase under conditions sufficient to remove a triphosphate group and/or a 3' linear phosphate group from an mRNA molecule. In some embodiments, the mRNA in the sample is contacted with the polynucleotide kinase under conditions sufficient to remove a cyclic phosphate group from the 3' end of an mRNA molecule. In some embodiments, the mRNA in the sample is contacted with the nuclease and the alkaline phosphatase sequentially or simultaneously. In some embodiments, the mRNA in the sample is contacted with the nuclease before the alkaline phosphatase. In some embodiments, the mRNA in the sample is contacted with polynucleotide kinase after contacting the mRNA with the nuclease and with the alkaline phosphatase.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, separating the capped mRNA and the uncapped mRNA occurs using chromatography. In some embodiments, the chromatography comprises liquid chromatography. In some embodiments, the liquid chromatography comprises liquid chromatography-mass spectrometry (LC-MS) or high-performance liquid chromatography (HPLC), e.g., HPLC-UV.

In some embodiments, the amount of total mRNA in the mRNA sample is known. In some embodiments, the accuracy of the quantifying in greater than the accuracy obtained from a method that does not comprise nuclease, the alkaline phosphatase, and/or the polynucleotide kinase.

In some embodiments, the mRNA is in vitro transcribed. In some embodiments, the mRNA was contacted with a vaccinia capping enzyme, a guanine-N7 methyltransferase, and/or a 2'-O-methyltransferase during in vitro transcription or after in vitro transcription. In some embodiments, the vaccinia capping enzyme comprises an RNA triphosphatase and/or an RNA guanyl transferase. In some embodiments, the standard mRNA sample comprises a known amount of capped mRNA and/or uncapped mRNA.

In another aspect, the disclosure provides a method for collecting capped messenger RNA (mRNA) from an mRNA sample comprising capped mRNA and uncapped mRNA, the method comprising steps of providing an mRNA sample comprising capped mRNA and uncapped mRNA, contacting mRNA in the sample with two or more of a nuclease, an alkaline phosphatase, and a polynucleotide kinase, separating the capped mRNA and the uncapped mRNA, and collecting the capped mRNA.

In some embodiments, the mRNA in the sample is contacted with each of the nuclease, the alkaline phosphatase, and the polynucleotide kinase.

In some embodiments, the mRNA in the sample is contacted with the nuclease under conditions sufficient to create 5' end fragments of mRNA. In some embodiments, the mRNA in the sample is contacted with the alkaline phosphatase under conditions sufficient to remove a triphosphate group and/or a 3' linear phosphate group from an mRNA molecule. In some embodiments, the mRNA in the sample is contacted with the polynucleotide kinase under conditions sufficient to remove a cyclic phosphate group from the 3' end of an mRNA molecule. In some embodiments, the mRNA in the sample is contacted with the nuclease and the alkaline phosphatase sequentially. In some embodiments, the mRNA in the sample is contacted with the nuclease before the alkaline phosphatase. In some embodiments, the mRNA in the sample is contacted with polynucleotide kinase after contacting the mRNA with the nuclease and with the alkaline phosphatase.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, separating the capped mRNA and the uncapped mRNA occurs using chromatography. In some embodiments, the chromatography comprises liquid chromatography. In some embodiments, the liquid chromatography comprises liquid chromatography-mass spectrometry (LC-MS) or high-performance liquid chromatography (HPLC), e.g., HPLC-UV.

In some embodiments, the amount of total mRNA in the mRNA sample is known. In some embodiments, the accuracy of the quantifying in greater than the accuracy obtained from a method that does not comprise nuclease, the alkaline phosphatase, and/or the polynucleotide kinase.

In some embodiments, the mRNA is in vitro transcribed. In some embodiments, the mRNA was contacted with a vaccinia capping enzyme, a guanine-N7 methyltransferase, and/or a 2'-O-methyltransferase during in vitro transcription or after in vitro transcription. In some embodiments, the vaccinia capping enzyme comprises an RNA triphosphatase and/or an RNA guanyl transferase. In some embodiments, the standard mRNA sample comprises a known amount of capped mRNA and/or uncapped mRNA.

In another aspect, the disclosure provides a method for collecting Cap G messenger RNA (mRNA), Gap 0 mRNA, and/or Cap 1 mRNA from an mRNA sample comprising uncapped mRNA and one or more of Cap G mRNA, Gap 0 mRNA, and Cap 1 mRNA, the method comprising steps of providing an mRNA sample comprising uncapped mRNA and one or more of Cap G mRNA, Gap 0 mRNA, and Cap 1 mRNA, contacting mRNA in the sample with two or more of a nuclease, an alkaline phosphatase, and a polynucleotide kinase, separating the uncapped mRNA from the Cap G mRNA, the Gap 0 mRNA, and/or the Cap 1 mRNA, and collecting one or more of the Cap G mRNA, Gap 0 mRNA, and Cap 1 mRNA.

In some embodiments, the mRNA in the sample is contacted with each of the nuclease, the alkaline phosphatase, and the polynucleotide kinase. In some embodiments, the mRNA in the sample is contacted with the nuclease under conditions sufficient to create 5' end fragments of mRNA. In some embodiments, the mRNA in the sample is contacted with the alkaline phosphatase under conditions sufficient to remove a triphosphate group and/or a 3' linear phosphate group from an mRNA molecule. In some embodiments, the mRNA in the sample is contacted with the polynucleotide kinase under conditions sufficient to remove a cyclic phosphate group from the 3' end of an mRNA molecule. In some embodiments, the mRNA in the sample is contacted with the nuclease and the alkaline phosphatase sequentially. In some embodiments, the mRNA in the sample is contacted with the nuclease before the alkaline phosphatase. In some embodiments, wherein the mRNA in the sample is contacted with polynucleotide kinase after contacting the mRNA with the nuclease and with the alkaline phosphatase.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, separating the uncapped mRNA from the Cap G mRNA, the Gap 0 mRNA, and/or the Cap 1 mRNA occurs using chromatography. In some embodiments, the chromatography comprises liquid chromatography. In some embodiments, the liquid chromatography comprises liquid chromatography-mass spectrometry (LC-MS) or high-performance liquid chromatography (HPLC), e.g., HPLC-UV.

In some embodiments, the amount of total mRNA in the mRNA sample is known. In some embodiments, the accuracy of the quantifying in greater than the accuracy obtained from a method that does not comprise nuclease, the alkaline phosphatase, and/or the polynucleotide kinase.

In some embodiments, the mRNA is in vitro transcribed. In some embodiments, the mRNA was contacted with a vaccinia capping enzyme, a guanine-N7 methyltransferase, and/or a 2'-O-methyltransferase during in vitro transcription or after in vitro transcription. In some embodiments, the vaccinia capping enzyme comprises an RNA triphosphatase and/or an RNA guanyl transferase. In some embodiments, the standard mRNA sample comprises a known amount of uncapped mRNA, a known amount of Cap G mRNA, a known amount of Gap 0 mRNA, and/or a known amount of Cap 1 mRNA.

In another aspect, the disclosure provides a kit for quantifying an amount of capped messenger RNA (mRNA) in an mRNA sample, the kit comprising two or more of a nuclease, an alkaline phosphatase, and a polynucleotide kinase. In some embodiments, the kit further comprising a standard mRNA sample comprising a known amount of capped mRNA and/or uncapped mRNA.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK). In some embodiments, the kit further comprising a vaccinia capping enzyme, a guanine-N7 methyltransferase, and/or a 2'-O-methyltransferase. In some embodiments, the vaccinia capping enzyme comprises an RNA triphosphatase and/or an RNA guanyl transferase. In some embodiments, the kit further comprising instructions for use.

In another aspect, the disclosure provides a kit for quantifying an amount of Cap G messenger RNA (mRNA), Gap 0 mRNA, and/or Cap 1 mRNA in an mRNA sample, the kit comprising two or more of a nuclease, an alkaline phosphatase, and a polynucleotide kinase. In some embodiments, the kit further comprising a standard mRNA sample comprising a known amount of uncapped mRNA, a known amount of Cap G mRNA, a known amount of Gap 0 mRNA, and/or a known amount of Cap 1 mRNA.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, the kit further comprising a vaccinia capping enzyme, a guanine-N7 methyltransferase, and/or a 2'-O-methyltransferase. In some embodiments, the vaccinia capping enzyme comprises an RNA triphosphatase and/or an RNA guanyl transferase. In some embodiments, the kit further comprising instructions for use.

BRIEF DESCRIPTION OF THE DRAWINGS

FIG. 5B shows characterization of lipid nanoparticles (size, PDI, EE %).

FIG. 5D shows characterization of lipid nanoparticles (size, PDI, EE %).

FIG. 8A shows tissue distribution. FIG. 8B shows lipid ratio.

FIG. 10A shows tissue distribution. FIG. 10B shows comparison results of tissue distribution between single dose and repeat dose. FIG. 10C shows comparison results of tissue distribution between single dose and repeat dose in rats and NHP.

FIG. 17B shows average body weight and organ weight of NHP and estimated percentage of lipids delivered in each organ.

DETAILED DESCRIPTION

Figure 1A:
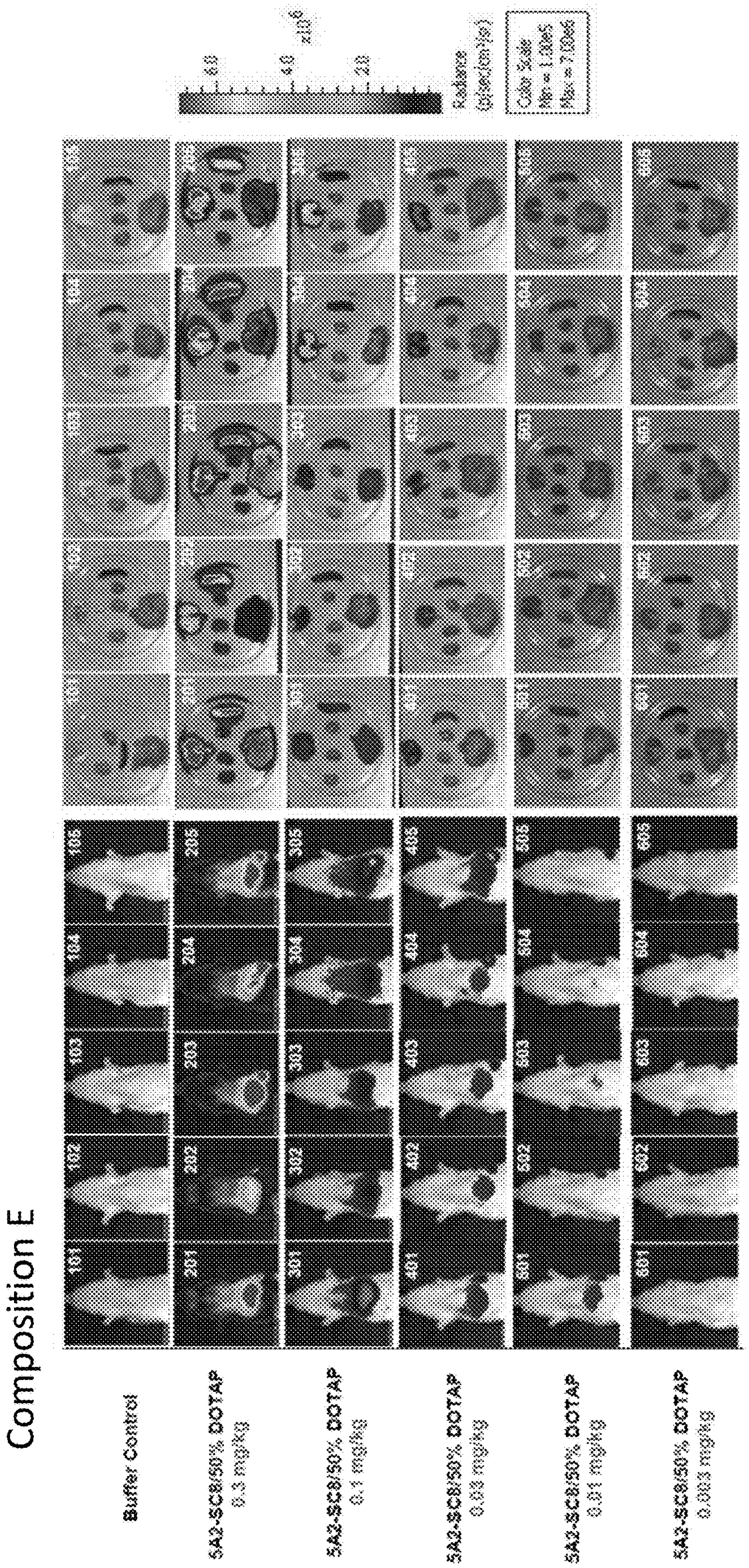
FIG. 1A shows whole body in vivo imaging (IVIS®) of rats dosed with Formulation J at indicated concentrations.

Provided herein are lipid nanoparticle (LNP) compositions comprising a payload, such as a therapeutic polypeptide, or a polynucleotide encoding a therapeutic polypeptide. In some embodiments, the LNP composition comprises a therapeutic polypeptide associated with a lung disease. The disclosure also provides for pharmaceutical compositions comprising the LNP compositions. Also provided herein are methods of use of LNP compositions, and pharmaceutical compositions.

Definitions

Before the embodiments of the disclosure are described, it is to be understood that such embodiments are provided by way of example only, and that various alternatives to the embodiments of the disclosure described herein may be employed in practicing the invention. Numerous variations, changes, and substitutions will now occur to those skilled in the art without departing from the invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole.

The singular forms “a,” “an,” and “the” are intended to include the plural forms as well, unless the context clearly indicates otherwise.

As used herein, the term “about” means a range of values including the specified value, which a person of ordinary skill in the art would consider reasonably similar to the specified value. For example, about means within a standard deviation using measurements generally acceptable in the art. For example, about means a range extending to +/−10%, +/−5%, +/−3%, or +/−1% of the specified value.

The term “at least” followed by a number is used herein to denote the start of a range beginning with that number (which may be a range having an upper limit or no upper limit, depending on the variable being defined). For example, "at least 1" means 1 or more than 1.

The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)" this means a range whose lower limit is the first number and whose upper limit is the second number. For example, 25 to 100 mm means a range whose lower limit is 25 mm, and whose upper limit is 100 mm.

As used herein, the term "lipid nanoparticle" refers to a carrier or vehicle, formed by one or more lipid components, for paylod (e.g., nucleic acid, protein, peptide, polypeptide, polynucleotide, or oligonucleotide) delivery in the context of pharmaceutical development. Lipid nanoparticle can have one or more lipids with at least one dimension on the order of nanometers (e.g., 1-1000 nm). Generally, lipid nanoparticle compositions for delivery are composed of one or more lipids, such as, but not limited to, a synthetic ionizable or cationic lipid, a phospholipid, a structural lipid, and a polyethylene glycol (PEG) lipid. These compositions may also include other lipids. In some embodiments, at least one therapeutic agent (e.g., mRNA) can be captured in the lipid portion of the lipid nanoparticle or an aqueous space enveloped by some or all of the lipid portion of the lipid nanoparticle, thereby protecting it from enzymatic degradation of other undesirable effect induced by the biological mechanism of a target subject, tissue, and/or cell, e.g., an adverse immune response. In some embodiments, lipid nanoparticles comprise at least one therapeutic agent (e.g., mRNA) that is either organized within inverse lipid micelles and encased within a lipid monolayer envelop or intercalated between adjacent lipid bilayers. In some embodiments, the morphology of lipid nanoparticles is not like a traditional liposome, which are characterized by a lipid bilayer surrounding an aqueous core. In some embodiments, lipid nanoparticles are substantially non-toxic. In some embodiments, the therapeutic agent (e.g., mRNA) is resistant in aqueous solution to degradation by intracellular or intercellular enzymes.

The term "SORT lipid" as used herein refers to a lipid that when included in an LNP composition enables the LNP to selectively and predictably target an organ, a cell type, or a tissue (for example as described in Cheng et al. *Nature* 15:313-320 (2020); Wang et al. *Nat. Protoc.* 18(1):265-291; and U.S. Pat. Pub. No. US 2022/0071916 A1 and US 2021/0259980 A1, the entire contents of which are incorporated herein). For example, addition of a specific SORT lipid to a LNP may re-target the LNP from the liver to the lung. SORT lipids include, but are not limited to, permanently cationic lipids, anionic lipids, zwitterionic lipids, and ionizable cationic lipids. Without being bound by theory, anionic SORT lipids generally favor delivery to the spleen, at least when administered intravenously; ionizable cationic SORT lipids generally favor delivery to the liver; permanently cationic SORT lipids generally favor delivery to the lungs; and zwitterionic SORT lipids favor delivery to the spleen.

As used herein, the term "ionizable cationic lipid" refers to lipid and lipid-like molecules having at least one pKa in the range of about 4.5-8, such that, without being bound by theory, they may facilitate release of LNP payloads upon uptake into the endosomal compartment of a cell. The ionizable cationic lipid may maintain a neutral charge in pH above the pKa of the lipid, while it becomes positively charged in the pH lower than pKa to facilitate membrane fusion and subsequent cytosolic release. Illustrative ionizable cationic lipids have one or more nitrogen atoms having pKa's in the range of about 4.5-8, such are tertiary amine groups.

As used herein, the term "permanently cationic lipid" refers to lipid or lipid-like molecules that are positively charged in physiologically relevant solutions, regardless of a pH (positively charged without pKa or with a pKa greater than 8). Illustrative permanently cationic lipids may include a quaternary ammonium group, and lack a negatively charged phosphate group. Without being bound by theory, a permanently cationic lipid may act as a SORT lipid by raising the apparent pKa of an LNP, as described, e.g., in Dilliard et al. PNAS USA. 118(52):e2109256118 (2021).

As used herein, the term "anionic lipid" refers to a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), ethylphosphocholines, and other anionic modifying groups joined to neutral lipids.

As used herein, the term "phospholipid" refers to lipids that comprise a phosphate group. The lipid component of a lipid nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties.

As used herein, the term "sterol" refers to a subgroup of steroids with a hydroxyl group at the 3-position of the A-ring of a gonane ringsystem. "Cholesterol" is a sterol that has a structure of four fused hydrocarbon rings (gonane ringsystem) with a polar hydroxyl group at one end and an eight-carbon branched aliphatic tail at the other end. Without begging bound by theory, the structure of the tetracyclic ring of cholesterol contributes to the fluidity of the cell membrane, as the molecule is in a trans conformation making all but the side chain of cholesterol rigid and planar. Cholesterol influences the fluidity, thickness, compressibility, water penetration and intrinsic curvature of lipid bilayers, for example in LNPs. For example, "sterol" can be cholesterol or sitosterol.

As used herein, the term "PEG-lipid" refers to a lipid modified with a polyethylene glycol unit. In some embodiments, the PEG-lipid comprises dimyristoyl glycerol (DMG). In some embodiments, the PEG-lipid comprises 1,2-distearoyl-sn-glycero-3-phosphorylethanolamine (DSPE).

As used herein, the phrase "N/P ratio" refers to a molar ratio of nitrogen in the lipid composition to phosphate in the polynucleotide payload.

As used herein, the term "apparent pKa" refers to the overall dissociation constant of all titratable groups in the lipid nanoparticles. Apparent pKa is an experimentally determined value of molecules or nanoparticles. Apparent pKa can be expressed as the pH at which the number of ionized (protonated) and deionized groups are equal in a system. The surface charge and ionic interaction of assembled nanomaterials in nanoparticles can be estimated according to apparent pKa. The apparent pKa of a nanoparticle can be the result of the average ratio of all the ionized to deionized groups in the nanoparticles. Thus, apparent pKa is not the intrinsic pKa value of any individual molecule. The apparent pKa of nanoparticles can be measured by various techniques. For example, acid-base titration of 2-(p-toluidino)-6-naphthalene sulfonic acid (TNS) fluorescent methods are widely used in determination of apparent pKa of blank nanoparticles.

As used herein, the phrase "lipid:RNA ratio" refers to milligram of lipid for each milligram of mRNA drug substance which influence the encapsulation efficiency of lipid nanoparticles.

The term "encapsulation," as used herein refers to the process of confining a payload within an LNP described herein. For example "encapsulation" refers to confining an mRNA molecule within an LNP described herein. The term "encapsulation efficiency" refers to the fraction of a payload that is encapsulated within or otherwise coupled with a lipid nanoparticle composition when LNPs are formed. Encapsulation efficiency may be determined by comparing the amount of input payload to the amount of payload in a sample of LNPs, or by comparing the amount of payload in the LNPs to the free excess payload in the sample. For example, a fluorescence detection assay (e.g., RiboGreen™) is used to determine encapsulation efficiency by measuring the free RNA in a sample with intact LNPs compared with the total RNA in a sample treated to disrupt the LNPs.

The terms "lung disease," "pulmonary disease," "pulmonary disorder," broadly refer to diseases or disorders of lungs. Lung diseases may be characterized by symptoms including, but not limited to, difficulty breathing, coughing, airway discomfort and inflammation, increased mucus, and/or pulmonary fibrosis. Non-limiting examples of lung diseases include Primary Ciliary Dyskinesia (PCD) (also referred to as Kartageners Syndrome, or Immotile Cilia Syndrome), cystic fibrosis, asthma, lung cancer, Chronic Obstructive Pulmonary Disease (COPD), bronchitis, emphysema, bronchiectasis, pulmonary edema, pulmonary fibrosis, sarcoidosis, pulmonary hypertension, pneumonia, tuberculosis, Interstitial Pulmonary Fibrosis (IPF), Interstitial Lung Disease (ILD), Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Idiopathic Interstitial Pneumonia (IIP), Bronchiolitis obliterans, with Organizing Pneumonia (BOOP), restrictive lung disease, and pleurisy.

The term "payload" refers to a bioactive molecule or molecules, such as a small molecule, biomolecule, nucleic acid (e.g., DNA, RNA, siRNA, shRNA), protein, or peptide, which is comprised in the LNP composition. For example, the payload can be bound covalently or non-covalently to the LNP, encapsulated in the LNP, coupled to the LNP, or complexed with the LNP within the LNP composition.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. When the polynucleotides are chemically and/or structurally modified the polynucleotides may be referred to as "modified polynucleotides."

The terms "identity," "identical," and "sequence identity" refer to the extend to which two optimally aligned polynucleotides or polypeptide sequences are invariant throughout a window of alignment of components, e.g., nucleotides or amino acids. "Identity" can readily be calculated by known methods, including, but not limited to, those described in Needleman and Wunsch, J. Mol. Biol. 48:443 (1970). as such one polynucleotide or polypeptide sequence has a certain percentage of sequence identity compared to another polynucleotide or polypeptide sequence. The term "percent sequence identity", "percent identity", or "identical to" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence. For sequence comparison, one sequence acts as a reference sequence, to which test sequences are compared. The term "reference sequence" refers to a molecule to which a test sequence is compared. Methods of sequence alignment for comparison and determination of percent sequence identity are well known in the art. Optimal alignment of sequences for comparison can be conducted, e.g., by the homology alignment algorithm of Needleman and Wunsch, (1970) J. Mol. Biol. 48:443.

As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

As used herein, the term "shRNA" or "short hairpin RNA" refers to a short sequence of RNA, which can make a tight hairpin turn and can be used to silence gene expression.

As used herein, the term "microRNA" refers to noncoding RNA consisting of about 22 ribonucleotides which regulates gene expression in the post transcriptional stage by silencing messenger RNA by base-pairing with a complementary sequence in its targeted mRNA.

The terms "polypeptide," "peptide" and "protein" are used interchangeably herein to refer to a polymer of amino acid residues and optionally one or more post-translational modifications (e.g., glycosylation) and/or other modifications.

As used herein, the term "gene-editing system" refers to a DNA or RNA editing system that comprises one or more guide RNA elements and one or more RNA-guided endonuclease elements. The guide RNA element comprises a target RNA comprising a nucleotide sequence substantially complementary to a nucleotide sequence at the one or more target genomic regions or a nucleic acid comprising a nucleotide sequence(s) encoding the target RNA. The RNA-guided endonuclease element comprises an endonuclease that is guided or brought to a target genomic region(s) by a guide RNA element or a nucleic acid comprising a nucleotide sequence(s) encoding such endonuclease.

The term "isolated" when applied to a polynucleotide or polypeptide, denotes that the polynucleotide or polypeptide is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high-performance liquid chromatography. A polynucleotide or polypeptide that is the predominant species present in a preparation is substantially purified.

The term "variant" refers to a polypeptide or polynucleotide having one or more insertions, deletions, or amino acid substitutions relative to a reference polypeptide or polynucleotide.

The terms "subject" refers to a living organism to which any of the compositions as described herein may be administered. The subject may be suffering from or be at risk for a disease or condition that can be treated by administration of an aerosolized pharmaceutical composition as provided herein. Non-limiting examples of subjects include humans, other mammals, bovines, rats, mice, dogs, monkeys, goat, sheep, cows, deer, and other non-mammalian animals. In some embodiments, the subject is human.

The term "therapeutically effective amount," as used herein, refers to an amount of the therapeutic agent sufficient to treat a disease, a disorder, or a condition. For example, with regard to the use of LNPs with mRNA payload to treat e.g., cystic fibrosis (CF) or primary ciliary dyskinesia (PCD), a therapeutically effective amount is the dosage or concentration of the mRNA (e.g., CFTR or PCD mRNA) capable of eradicating, inhibiting, preventing, slowing down the progression of all or part of e.g., CF or PCD respiratory symptoms or some combination thereof. For the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. The "therapeutically effective amount" can vary depending, for example, but not limited to, on the compound, the disease, or the condition and/or symptoms thereof, severity of the disease or the condition and/or symptoms thereof, the age, weight, and/or health of the subject to be treated, and the judgment of the prescribing physician. An appropriate amount in any given instance can be ascertained by those skilled in the art or capable of determination by routine experimentation.

As used herein, the term "delivering" means causing, through chemical or biophysical properties of a composition (e.g., an LNP composition), a payload (e.g., a polynucleotide) to pass from a site of administration to a subject to a target organ, target tissue, or target cell. As used herein, the term "selectively delivering" refers to the delivery to a target organ, tissue, or cell at a greater rate or in a great amount than to a reference, non-target organ, tissue, or cell, or that a greater fraction of total the amount administered to a subject is delivered to a target organ, tissue, or cell by the composition than by a reference composition. For example, selective delivery may mean that at least 25% (e.g., at least 30%, 35%, 40%, 45%, 50%, 55%, 60%, 65%, 70%, or 75%) of the total amount administered is delivered to the target organ, tissue, or cell. "Selective delivery" is determined by comparing the fraction of an LNP composition or payload that is delivered to a target organ (e.g., the lung) by an LNP composition comprises a selected lipid (e.g., SORT lipid) compared to a reference LNP composition in which the selected lipid is replaced by a control lipid.

"Prevention" or "preventing" refers to inhibiting the onset of a disease in a subject or patient which may be at risk and/or predisposed to the disease but does not yet experience or display any or all of the pathology or symptomatology of the disease, and/or slowing the onset of the pathology or symptomatology of a disease in a subject or patient which may be at risk and/or predisposed to the disease but does not yet experience or display any or all of the pathology or symptomatology of the disease. The prevention may be complete (no detectable symptoms) or partial, such that fewer symptoms are observed than would likely occur absent treatment.

The term "administering" refers to providing a composition to a subject in a manner that permits the composition to have its intended effect. Administration for may be performed by intramuscular injection, intravenous injection, intraperitoneal injection, or any other suitable route.

"Co-administer" means that a composition described herein is administered at the same time, just prior to, or just after the administration of one or more additional therapies. The compositions provided herein can be administered alone or can be co-administered to the subject. Co-administration is meant to include simultaneous or sequential administration of the compounds individually or in combination (more than one compound). Thus, the preparations can also be combined, when desired, with other active substances (e.g., to reduce metabolic degradation).

The term "pharmaceutically acceptable excipients" and "pharmaceutically acceptable carrier" refer to a substance that aids the administration of an active agent to and absorption by a subject and can be included in the compositions of the present disclosure without causing a significant adverse toxicological effect on the patient and can mean excipients approved by a regulatory agency of the Federal or a state government or listed in the U.S. Pharmacopeia or other generally recognized pharmacopeia for use in animals, and more particularly in humans. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

Lung Diseases

Cystic Fibrosis

Cystic fibrosis is a progressive, genetic disease that affects the lungs, pancreas, liver, kidneys, and other organs. Mutations in the cystic fibrosis transmembrane conductance regulator (CFTR) gene cause the CFTR protein to become dysfunctional, resulting in thick and sticky mucus that blocks airways and leads to lung damage and traps germs and makes infections more likely.

Primary Ciliary Dyskinesis (PCD)

Primary ciliary dyskinesia is a disorder characterized by chronic respiratory tract infections. Mutations in genes which provide instructions for making proteins that form the inner structure of cilia and produce the force needed for cilia to bend because the disease and it results in defective cilia that move abnormally or are unable to move. Mutations in the DNAI1 and DNAH5 gene account for up to 30 percent of all cases of PCD.

Chronic Obstructive Pulmonary Disease (COPD)

Chronic obstructive pulmonary disease is a chronic inflammatory lung disease that causes obstructed airflow from the lungs. In the vast majority of people with COPD, the lung damage that leads to COPD is caused by long-term cigarette smoking. In about 1% of people with COPD, the disease results from a genetic disorder that causes low levels of a protein called alpha-1-antitrypsin (AAT). AAT is made in the liver and secreted into the bloodstream to help protect the lungs. Alpha-1-antitrypsin deficiency can cause liver disease, lung disease, or both.

Lipid Nanoparticle Composition

Ionizable Cationic Lipids

In one aspect, the disclosure provides a lipid nanoparticle composition comprising a therapeutic polypeptide or a polynucleotide encoding an therapeutic polypeptide, a helper lipid, a sterol, and/or a polyethylene glycol-conjugated lipid (PEG-lipid) and an ionizable cationic lipid and a selective organ targeting (SORT) lipid.

In some embodiments, the lipid composition comprises an ionizable cationic lipid. In some embodiments, the ionizable cationic lipids contain one or more groups which is protonated at physiological pH but may deprotonate and has no charge at a pH above the pKa of the lipid. The ionizable group may contain one or more protonatable amines which are able to form a cationic group at physiological pH. The ionizable cationic lipid compound may also further comprise one or more lipid components such as two or more fatty acids with $C_6$-$C_{24}$ alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

A lipid nanoparticle composition may include one or more ionizable (e.g., ionizable amino) lipids (e.g., lipids that may have a positive or partial positive charge at physiological pH). Ionizable cationic lipids may be selected from the non-limiting group consisting of 3-(didodecylamino)-N1, N1,4-tridodecyl-1-piperazineethanamine (KL10), N1-[2-(didodecylamino)ethyl]N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl-4-(dimethylamino) butanoate (DLin-MC3-DMA), 2,2-dilinoleyl-4-(2 dimethylaminoethyl)-[1,3]-dioxolane (DLin-KC2-DMA), 1,2-dioleyloxy-N,Ndimethylaminopropane (DODMA), 2-({8[(3(3)-cholest-5-en-3-yloxy]octylloxy)N,Ndimethy 1-3-[(9Z, 12Z)-octadeca-9,12-dien-1-yloxy]propan-1-amine (Octyl-CLinDMA), (2R)-2-({8-[(3(3)-cholest-5-en-3-yloxy] octylloxy)-N,N-dimethyl-3-[(9Z,12Z)-octadeca-9,12-dien-1-yloxy]propan-1-amine(Octyl-CLinDMA (2R)), and (2S) 2-({8-[(3(3)-chol e st-5-en-3-yloxy]octyl}oxy)-N,N-dimethyl-3-[(9Z,12Z)-octadeca-9,12-di en-1-yloxy]propan-1-amine (Octyl-CLinDMA (2S)), 4-hydroxybutyl) azanediyl) bis(hexane-6,1-diyl)bis(2-hexyldecanoate (ALC-0315), or heptadecan-9-yl 8-((2-hydroxyethyl) (6-oxo-6-(undecyloxy) hexyl) amino) octanoate (SM-102). In addition to these, an ionizable cationic lipid may also be a lipid including a cyclic amine group.

Ionizable cationic lipids can also be the compounds disclosed in International Publication No. WO2017075531, hereby incorporated by reference in its entirety. Ionizable cationic lipids can also be the compounds disclosed in International Publication No. WO2015199952, hereby incorporated by reference in its entirety. In one embodiment, the ionizable cationic lipid may be selected from, but not limited to, an ionizable cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466, 122 and US Patent Publication No. US20100036115, US20120202871, US20130064894, US20130129785, US20130150625, US20130178541 and S20130225836; the contents of each of which are herein incorporated by reference in their entirety.

In some embodiments, an ionizable cationic lipid comprises between 2 and 6 hydrophobic chains, often alkyl or alkenyl such as $C_6$-$C_{24}$ alkyl or alkenyl groups, but may have at least 1 or more that 6 tails.

Dendrimers

In some embodiments, the ionizable cationic lipids are dendrimers, which are a polymer exhibiting regular dendritic branching, formed by the sequential or generational addition of branched layers to or from a core and are characterized by a core, at least one interior branched layer, and a surface branched layer. (See Petar R. Dvornic and Donald A. Tomalia in *Chem. in Britain,* 641-645, August 1994.) In other embodiments, the term "dendrimer" as used herein is intended to include, but is not limited to, a molecular architecture with an interior core, interior layers (or "generations") of repeating units regularly attached to this initiator core, and an exterior surface of terminal groups attached to the outermost generation. A "dendron" is a species of dendrimer having branches emanating from a focal point which is or can be joined to a core, either directly or through a linking moiety to form a larger dendrimer. In some embodiments, the dendrimer structures have radiating repeating groups from a central core which doubles with each repeating unit for each branch. In some embodiments, the dendrimers described herein may be described as a small molecule, medium-sized molecules, lipids, or lipid-like material. These terms may be used to describe compounds described herein which have a dendron like appearance (e.g., molecules which radiate from a single focal point).

While dendrimers are polymers, dendrimers may be preferable to traditional polymers because they have a controllable structure, a single molecular weight, numerous and controllable surface functionalities, and traditionally adopt a globular conformation after reaching a specific generation. Dendrimers can be prepared by sequentially reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bioattachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible resulting from only the first condensation reaction with the amine and not the second condensation reaction with the thiol.

Preparation of dendrimers requires a level of synthetic control achieved through series of stepwise reactions comprising building the dendrimer by each consecutive group. Dendrimer synthesis can be of the convergent or divergent type. During divergent dendrimer synthesis, the molecule is assembled from the core to the periphery in a stepwise process involving attaching one generation to the previous and then changing functional groups for the next stage of reaction. Functional group transformation is necessary to prevent uncontrolled polymerization. Such polymerization would lead to a highly branched molecule that is not monodisperse and is otherwise known as a hyperbranched polymer. Due to steric effects, continuing to react dendrimer repeat units leads to a sphere shaped or globular molecule, until steric overcrowding prevents complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some embodiments of the lipid composition of the present application, the dendrimers are assembled using the differential reactivity of the acrylate and methacrylate groups with amines and thiols. The dendrimers may include secondary or tertiary amines and thioethers formed by the reaction of an acrylate group with a primary or secondary amine and a methacrylate with a mercapto group. Additionally, the repeating units of the dendrimers may contain groups which are degradable under physiological conditions. In some embodiments, these repeating units may contain one or more germinal diethers, esters, amides, or disulfides groups. In some embodiments, the core molecule is a monoamine which allows dendritic polymerization in only one direction. In other embodiments, the core molecule is a polyamine with multiple different dendritic branches which each may comprise one or more repeating units. The dendrimer may be formed by removing one or more hydrogen atoms from this core. In some embodiments, these hydrogen atoms are on a heteroatom such as a nitrogen atom. In some embodiments, the terminating group is a lipophilic groups such as a long chain alkyl or alkenyl group. In other embodiments, the terminating group is a long chain haloalkyl or haloalkenyl group. In other embodiments, the terminating group is an aliphatic or aromatic group containing an ionizable group such as an amine ($—NH_2$) or a carboxylic acid ($—CO_2H$). In still other embodiments, the terminating group is an aliphatic or aromatic group containing one or more hydrogen bond donors such as a hydroxide group, an amide group, or an ester.

The ionizable cationic lipids of the present application may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Ionizable cationic lipids may occur as racemates and racemic mixtures, single enantiomers, diastereomeric mixtures and individual diastereomers. In some embodiments, a single diastereomer is obtained. The chiral centers of the ionizable cationic lipids of the present application can have the S or the R configuration. Furthermore, it is contemplated that one or more of the ionizable cationic lipids may be present as constitutional isomers. In some embodiments, the compounds have the same formula but different connectivity to the nitrogen atoms of the core. Without wishing to be bound by any theory, it is believed that such ionizable cationic lipids exist because the starting monomers react first with the primary amines and then statistically with any secondary amines present. Thus, the constitutional isomers may present the fully reacted primary amines and then a mixture of reacted secondary amines.

Chemical formulas used to represent ionizable cationic lipids of the present application will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given formula, and regardless of which one is most prevalent, all tautomers of a given chemical formula are intended.

The ionizable cationic lipids of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the ionizable cationic lipids of the present application are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of an ionizable cationic lipids provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

In some embodiments of the lipid composition of the present application, the ionizable lipid is a dendrimer or dendron. In some embodiments, the ionizable cationic lipid comprises an ammonium group which is positively charged at physiological pH and contains at least two hydrophobic groups. In some embodiments, the ammonium group is positively charged at a pH from about 6 to about 8. In some embodiments, the ionizable cationic lipid is a dendrimer or dendron. In some embodiments, the ionizable cationic lipid comprises at least two $C_6$-$C_{24}$ alkyl or alkenyl groups.

Dendrimers of Formula (I)

In some embodiments of the lipid composition, the ionizable cationic lipid comprises at least two $C_8$-$C_{24}$ alkyl groups. In some embodiments, the ionizable cationic lipid is a dendrimer further defined by the formula:

Core-(Repeating Unit)$_n$-Terminating Group (D-I)

wherein one or more hydrogen atoms of the core are replaced with a repeating unit and wherein:

the core has the formula:

(DII)

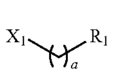

wherein:

$X_1$ is amino or $C_1$-$C_{12}$ alkylamino, $C_1$-$C_{12}$ dialkylamino, $C_3$-$C_{12}$ heterocycloalkyl, $C_8$-$C_{12}$ heteroaryl, or a substituted version thereof;

$R_1$ is amino, hydroxy, mercapto, $C_1$-$C_{12}$ alkylamino, or $C_1$-$C_{12}$ dialkylamino, or a substituted version of either of these groups; and a is 1, 2, 3, 4, 5, or 6; or the core has the formula:

(D-III)

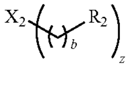

wherein:

$X_2$ is $N(R_5)_y$;

$R_5$ is hydrogen, $C_1$-$C_{18}$ alkyl, or substituted $C_1$-$C_{18}$ alkyl; and y is 0, 1, or 2, provided that the sum of y and z is 3;

$R_2$ is amino, hydroxy, mercapto, $C_1$-$C_{12}$ alkylamino, or $C_1$-$C_{12}$ dialkylamino, or a substituted version of either of these groups;

b is 1, 2, 3, 4, 5, or 6; and z is 1, 2, or 3; provided that the sum of z and y is 3; or the core has the formula:

(D-IV)

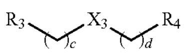

wherein:

$X_3$ is —$NR_6$—, wherein $R_6$ is hydrogen, $C_1$-$C_8$ alkyl, or $C_1$-$C_8$ substituted alkyl, —O—, or $C_1$-$C_8$ alkylaminodiyl, $C_1$-$C_8$ alkoxydiyl, $C_6$-$C_8$ arenediyl, $C_5$-$C_8$ heteroarenediyl, $C_3$-$C_8$ heterocycloalkanediyl, or a substituted version of any of these groups;

$R_3$ and $R_4$ are each independently amino, hydroxy, mercapto, $C_1$-$C_{12}$ alkylamino, or $C_1$-$C_{12}$ dialkylamino, or a substituted version of either of these groups; or a group of the formula: $—N(R_f)_f(CH_2CH_2N(R_c))_eR_d$,

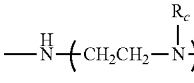

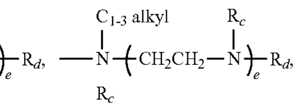 or

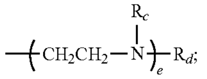

wherein:

e and f are each independently 1, 2, or 3; provided that the sum of e and f is 3;

$R_c$, $R_d$, and $R_f$ are each independently hydrogen, $C_1$-$C_6$ alkyl, or substituted $C_1$-$C_6$ alkyl;

c and d are each independently 1, 2, 3, 4, 5, or 6; or the core is $C_1$-$C_{18}$ alkylamine, $C_1$-$C_{36}$ dialkylamine, $C_3$-$C_{12}$ heterocycloalkane, or a substituted version of any of these groups;

wherein the repeating unit comprises a degradable diacyl or a degradable diacyl and a linker;

the degradable diacyl group has the formula:

(D-VII)

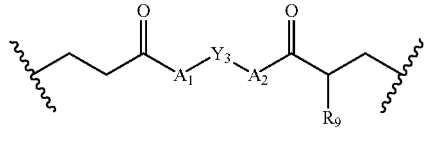

wherein:

$A_1$ and $A_2$ are each independently —O—, —S—, or —$NR_a$—, wherein:

$R_a$ is hydrogen, $C_1$-$C_6$ alkyl, or substituted $C_1$-$C_6$ alkyl;

$Y_3$ is $C_1$-$C_{12}$ alkanediyl, $C_1$-$C_{12}$ alkenediyl, $C_6$-$C_{12}$ arenediyl, or a substituted version of any of these groups; or a group of the formula:

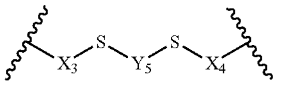
or
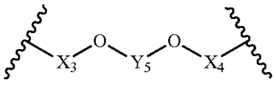

wherein:

$X_3$ and $X_4$ are $C_1$-$C_{12}$ alkanediyl, $C_2$-$C_{12}$ alkenediyl, $C_6$-$C_{12}$ arenediyl, or a substituted version of any of these groups;

$Y_5$ is a covalent bond, $C_1$-$C_{12}$ alkanediyl, $C_1$-$C_{12}$ alkenediyl, $C_6$-$C_{12}$ arenediyl, or a substituted version of any of these groups; and $R_9$ is $C_1$-$C_8$ alkyl or substituted $C_1$-$C_8$ alkyl;

the linker group has the formula:

(D-VI)

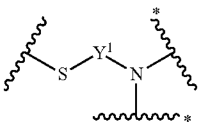

wherein:

$Y_1$ is $C_1$-$C_{12}$ alkanediyl, $C_1$-$C_{12}$ alkenediyl, $C_6$-$C_{12}$ arenediyl, or a substituted version of any of these groups; and wherein each

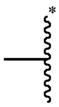

independently denotes a point of attachment to another repeating unit or a terminating group; and the terminating group has the formula:

(D-VIII)

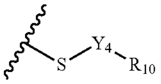

wherein:

$Y_4$ is alkanediyl or an $C_1$-$C_{18}$ alkanediyl wherein one or more of the hydrogen atoms on the $C_1$-$C_{18}$ alkanediyl has been replaced with —OH, —F, —Cl, —Br, —I, —SH, —$OCH_3$, —$OCH_2CH_3$, —$SCH_3$, or —$OC(O)CH_3$;

$R_{10}$ is hydrogen, carboxy, hydroxy, $C_6$-$C_{12}$ aryl, $C_1$-$C_{12}$ alkylamino, $C_1$-$C_{12}$ dialkylamino, $C_3$-$C_{12}$N-heterocycloalkyl, —C(O)N($R_{11}$)—$C_1$-$C_6$ alkanediyl-$C_3$-$C_{12}$ heterocycloalkyl, —C(O)—$C_1$-$C_{12}$ alkylamino, —C(O)—$C_1$-$C_{12}$ dialkylamino, or —C(O)—$C_3$-$C_{12}$N-heterocycloalkyl, wherein:

$R_{11}$ is hydrogen, $C_1$-$C_6$ alkyl, or substituted $C_1$-$C_6$ alkyl;

wherein the final degradable diacyl in the chain is attached to a terminating group;

n is 0, 1, 2, 3, 4, 5, or 6;

or a pharmaceutically acceptable salt thereof.

In some embodiments, the terminating group is further defined by the formula:

(D-VIII)

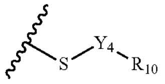

wherein:

$Y_4$ is $C_1$-$C_{18}$ alkanediyl; and $R_{10}$ is hydrogen. In some embodiments, $A_1$ and $A_2$ are each independently —O— or —$NR_a$—.

In some embodiments of the dendrimer of formula (D-I), the terminating group is a structure selected from the structures in Table 1.

In some embodiments of the dendrimer of formula (D-I), the core is further defined by the formula:

(D-III)

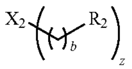

wherein:

$X_2$ is $N(R_5)_y$;

$R_5$ is hydrogen or $C_1$-$C_8$ alkyl, or substituted $C_1$-$C_{18}$ alkyl; and y is 0, 1, or 2, provided that the sum of y and z is 3;

$R_2$ is amino, hydroxy, or mercapto, or $C_1$-$C_{12}$ alkylamino, $C_1$-$C_{12}$ dialkylamino, or a substituted version of either of these groups;

b is 1, 2, 3, 4, 5, or 6; and z is 1, 2, 3; provided that the sum of z and y is 3.

In some embodiments of the dendrimer of formula (D-I), the core is further defined by the formula:

(D-IV)

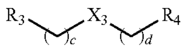

wherein:

$X_3$ is —$NR_6$—, wherein $R_6$ is hydrogen, $C_1$-$C_8$ alkyl, or substituted $C_1$-$C_8$ alkyl, —O—, or $C_1$-$C_8$ alkylaminodiyl, $C_1$-$C_8$ alkoxydiyl, $C_1$-$C_8$ arenediyl, $C_1$-$C_8$ heteroarenediyl, $C_1$-$C_8$ heterocycloalkanediyl, or a substituted version of any of these groups;

$R_3$ and $R_4$ are each independently amino, hydroxy, or mercapto, or $C_1$-$C_{12}$ alkylamino, dialkylamino, or a substituted version of either of these groups; or a group of the formula: —$N(R_f)_f(CH_2CH_2N(R_c))_eR_d$,

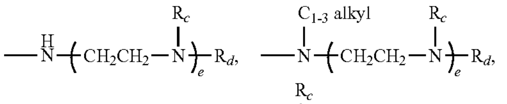
or
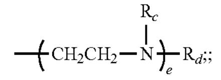

wherein:

e and f are each independently 1, 2, or 3; provided that the sum of e and f is 3;

$R_c$, $R_d$, and $R_f$ are each independently hydrogen, $C_1$-$C_6$ alkyl, or substituted $C_1$-$C_6$ alkyl;

c and d are each independently 1, 2, 3, 4, 5, or 6.

In some embodiments of the dendrimer of formula (I), the terminating group is represented by the formula:

(D-VIII)

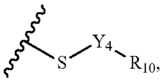

wherein:

$Y_4$ is alkanediyl$_{(C\leq 18)}$; and $R_{10}$ is hydrogen.

In some embodiments of the dendrimer of formula (D-I), a core of the structure of formula (D-IV) is:

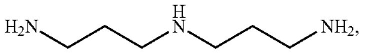

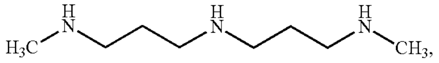

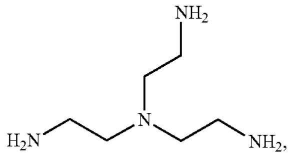

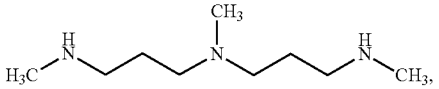

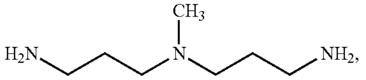

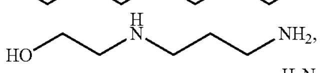

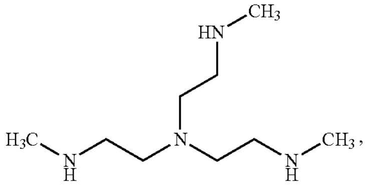

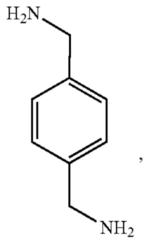

,

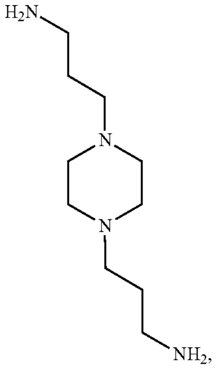

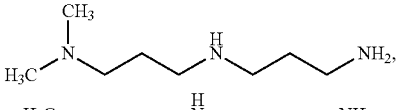

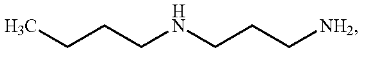

-continued

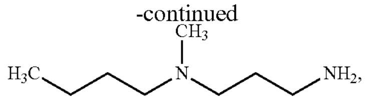

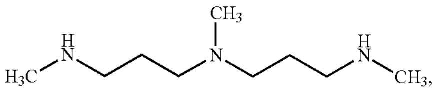

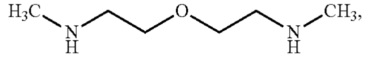

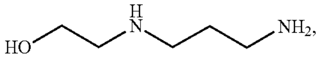

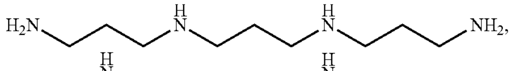

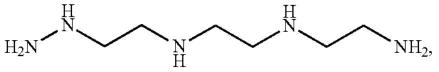

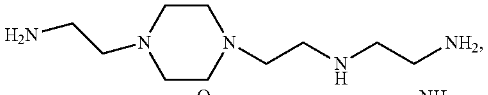

or

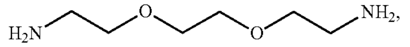

or a pharmaceutically acceptable salt thereof.

In some embodiments of the dendrimer of formula (D-I), the core comprises a structural formula set forth in Table 2 and pharmaceutically acceptable salts thereof, wherein * indicates a point of attachment of the core to a repeating unit (i.e., where a hydrogen of the core is replaced with a repeating unit).

In some embodiments of the dendrimer of formula (D-I), the degradable diacyl is further defined as:

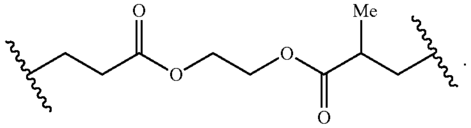 [SMILES: *CCC(=O)OCCOC(=O)C(C)C*]

In some embodiments of the dendrimer of formula (D-I), the linker is further defined as (D-VI)

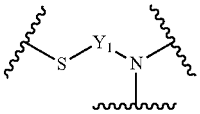

wherein $Y_1$ is $C_1$-$C_8$ alkanediyl or substituted $C_1$-$C_{12}$ alkanediyl.

In some embodiments, in the core of formula (D-IV), $R_6$ is H. In some embodiments, in the core of formula (D-IV), $R_6$ is $C_1$-$C_8$ alkyl. In some embodiments, in the core of formula (D-IV), $R_6$ is substituted alkyl (e.g., alkyl substituted with —$NH_2$, alkyl substituted with —$NHCH_3$, or alkyl substituted with —$NHCH_2CH_3$).

In some embodiments one or two hydrogen atoms of the core are replaced with a repeating unit. In some embodiments three or four hydrogen atoms of the core is replaced with a repeating unit. In some embodiments five hydrogen atoms of the core is replaced with a repeating unit. In some embodiments six hydrogen atoms of the core is replaced with a repeating unit.

In some embodiments of the dendrimer of formula (D-I), the dendrimer is selected from the group consisting of:

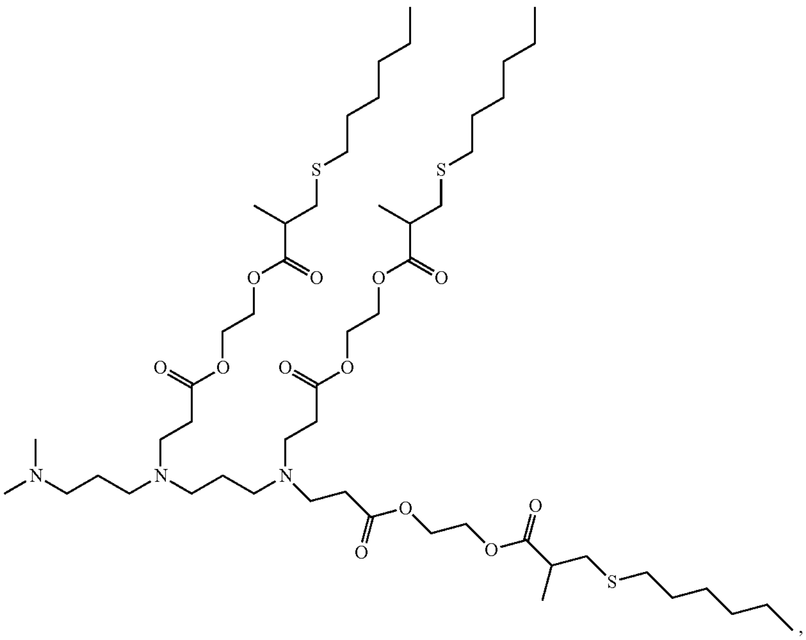
,
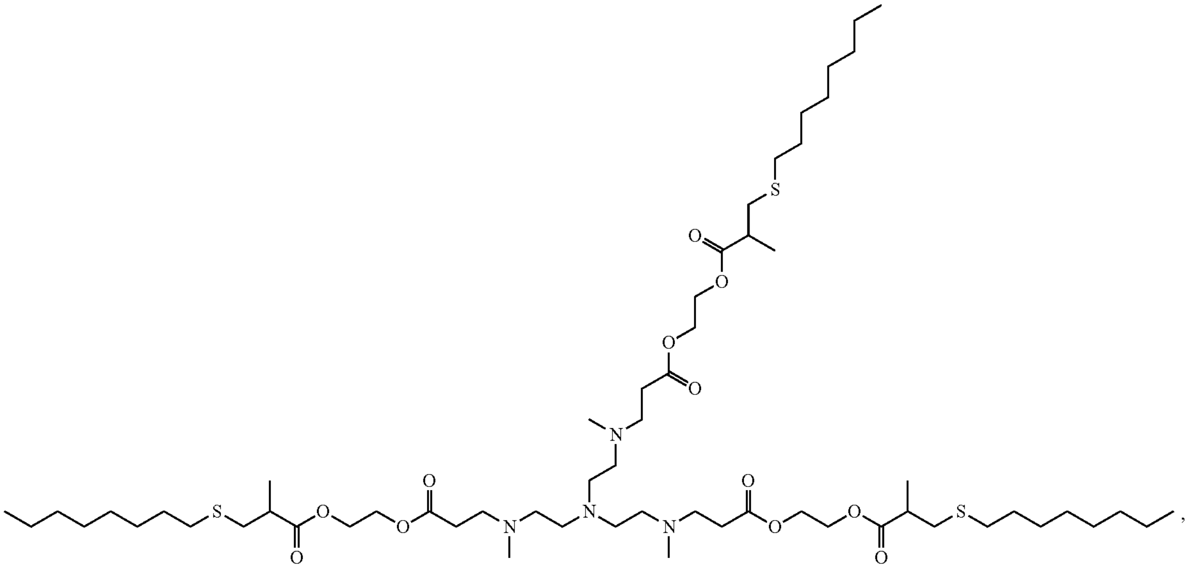
,
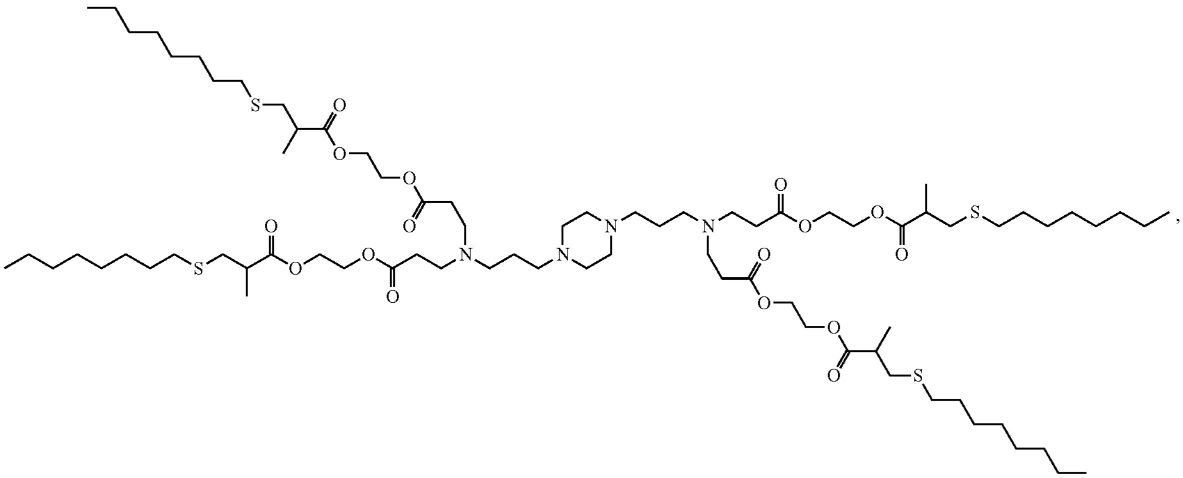
,

-continued
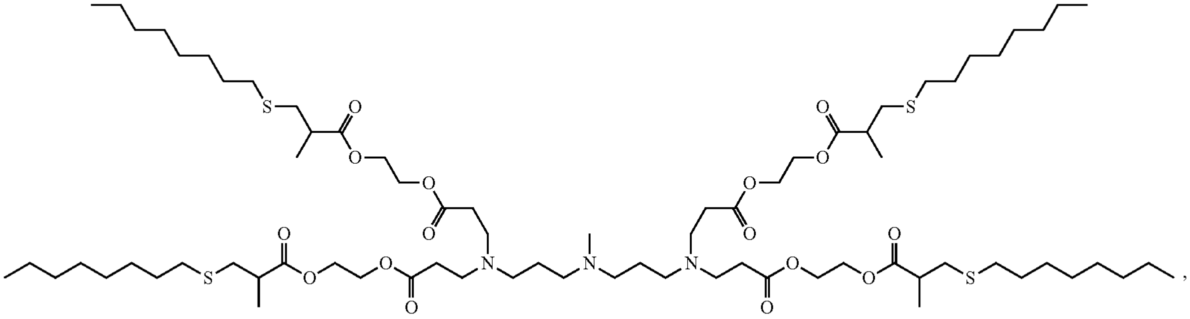
,
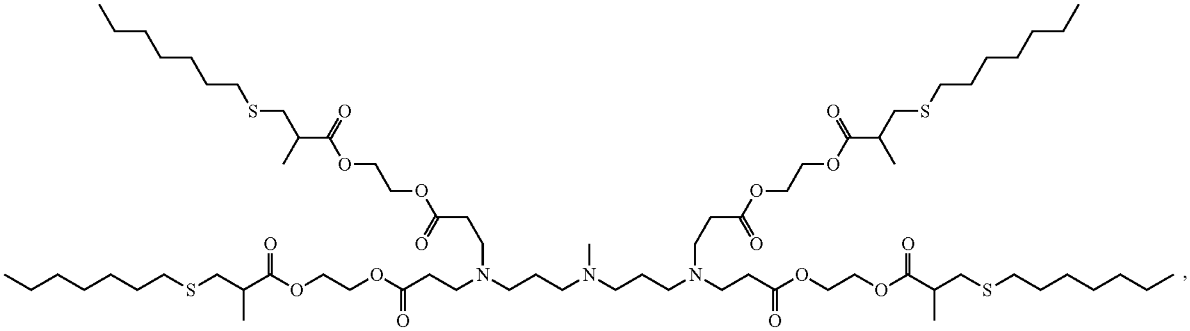
,
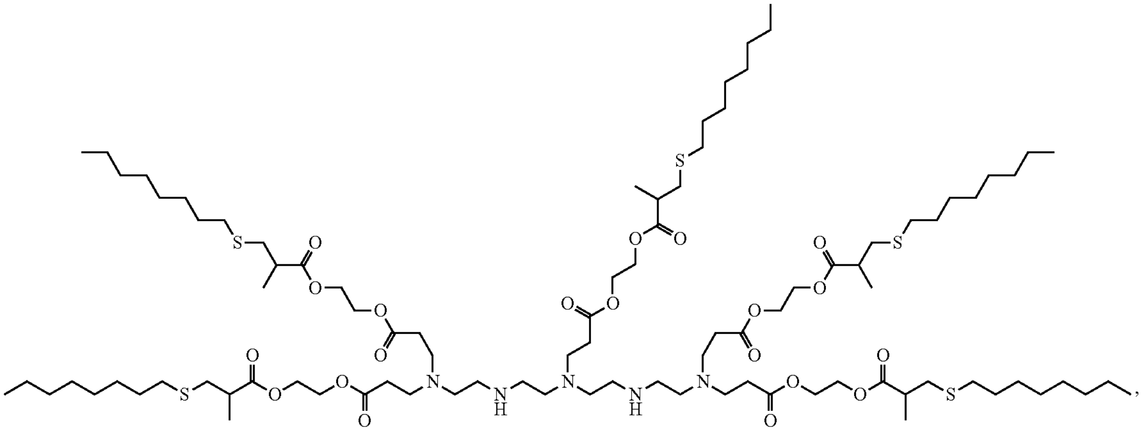
, and

-continued

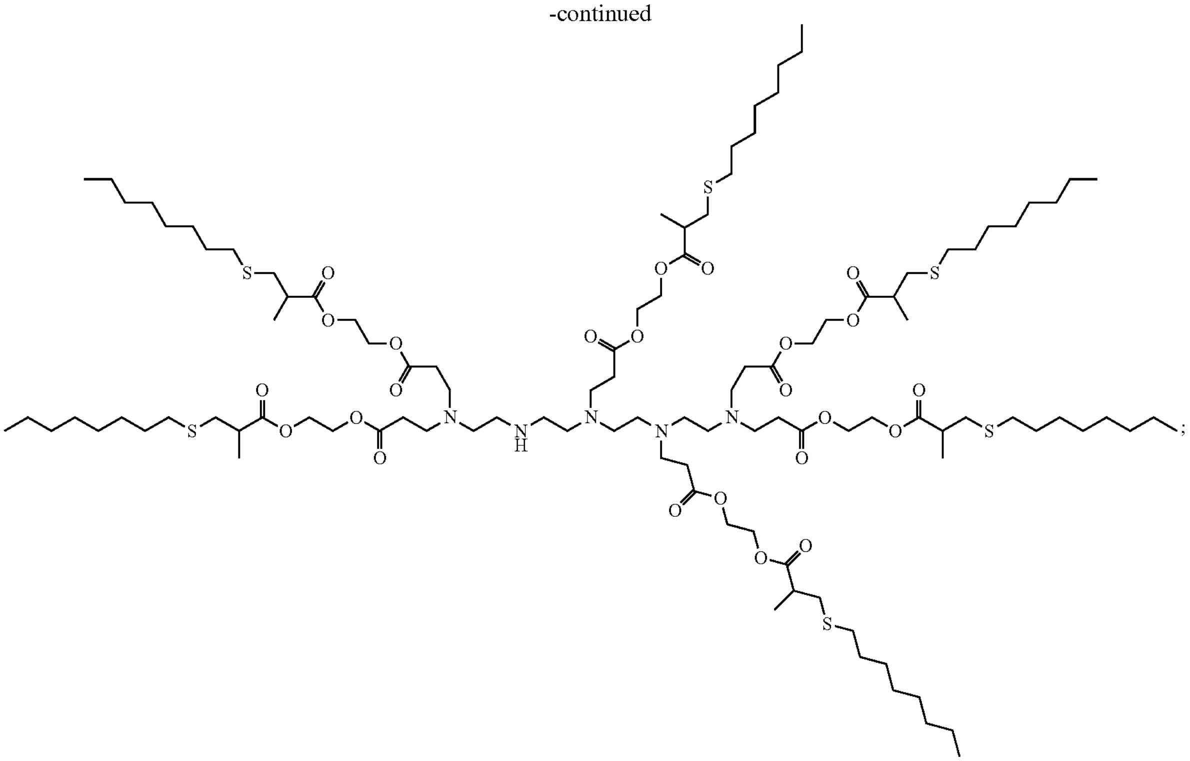

and pharmaceutically acceptable salts thereof.

Dendrimers of Formula (X)

In some embodiments of the lipid composition, the ionizable cationic lipid is a dendrimer of the formula $$\text{Core}\!-\!(\text{Branch})_N .$$

In some embodiments, the ionizable cationic lipid is a dendrimer of the formula (X)

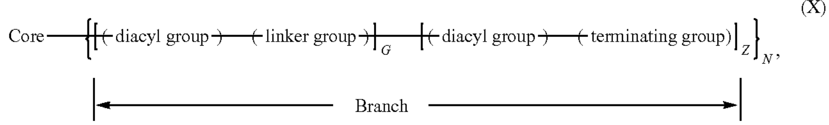

In some embodiments of the lipid composition, the ionizable cationic lipid is a dendrimer of a generation (g) having a structural formula:

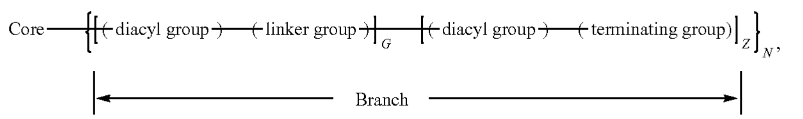

or a pharmaceutically acceptable salt thereof, wherein:

(a) the core comprises a structural formula ($X_{Core}$):

($X_{Core}$)

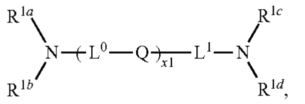

wherein:

Q is independently at each occurrence a covalent bond, —O—, —S—, —$NR_2$—, or —$CR^{3a}R^{3b}$—;

$R^2$ is independently at each occurrence $R^{19}$ or -$L^2$-$NR^{1e}R^{1f}$;

$R^{3a}$ and $R^{3b}$ are each independently at each occurrence hydrogen or an optionally substituted (e.g., $C_1$-$C_6$, such as $C_1$-$C_3$) alkyl;

$R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen, or an optionally substituted (e.g., $C_1$-$C_{12}$) alkyl;

$L^0$, $L^1$, and $L^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of $L^1$ form a (e.g., $C_4$-$C_6$) heterocycloalkyl (e.g., containing one or two nitrogen atoms and, optionally, an additional heteroatom selected from oxygen and sulfur) with one of $R^{1c}$ and $R^{1d}$; and $x^1$ is 0, 1, 2, 3, 4, 5, or 6; and (b) each branch of the plurality (N) of branches independently comprises a structural formula ($X_{Branch}$):

($X_{Branch}$)

$$*\text{—}\left[(\text{diacyl group})\text{—}(\text{linker group})\right]_G\left[(\text{diacyl group})\text{—}(\text{terminating group})\right]_Z,$$

wherein:

* indicates a point of attachment of the branch to the core;

g is 1, 2, 3, or 4;

$Z=2^{(g-1)}$;

G=0, when g=1; or $G=\Sigma_{i=0}^{i=g-2} 2^i$, when g≠1;

(c) each diacyl group independently comprises a structural formula

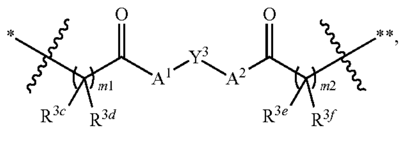

wherein:

* indicates a point of attachment of the diacyl group at the proximal end thereof,

** indicates a point of attachment of the diacyl group at the distal end thereof, $Y^3$ is independently at each occurrence an optionally substituted (e.g., $C_1$-$C_{12}$); alkylene, an optionally substituted (e.g., $C_1$-$C_{12}$) alkenylene, or an optionally substituted (e.g., $C_1$-$C_{12}$) arenylene;

$A^1$ and $A^2$ are each independently at each occurrence —O—, —S—, or —$NR^4$—, wherein:

$R^4$ is hydrogen or optionally substituted (e.g., $C_1$-$C_6$) alkyl;

$m^1$ and $m^2$ are each independently at each occurrence 1, 2, or 3; and $R^{3c}$, $R^{3d}$, $R^{3c}$, and $R^{3f}$ are each independently at each occurrence hydrogen or an optionally substituted (e.g., $C_1$-$C_8$) alkyl; and (d) each linker group independently comprises a structural formula

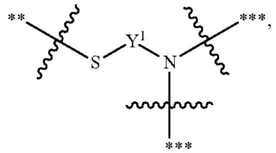

wherein:

** indicates a point of attachment of the linker to a proximal diacyl group;

*** indicates a point of attachment of the linker to a distal diacyl group; and $Y_1$ is independently at each occurrence an optionally substituted (e.g., $C_1$-$C_{12}$) alkylene, an optionally substituted (e.g., $C_1$-$C_{12}$) alkenylene, or an optionally substituted (e.g., $C_1$-$C_{12}$) arenylene; and (e) each terminating group is independently selected from optionally substituted (e.g., $C_1$-$C_{18}$, such as $C_4$-$C_{18}$) alkylthiol, and optionally substituted (e.g., $C_1$-$C_{18}$, such as $C_4$-$C_{18}$) alkenylthiol.

In some embodiments of $X_{Core}$, Q is independently at each occurrence a covalent bond, —O—, —S—, —$NR^2$—, or —$CR^{3a}R^{3b}$. In some embodiments of $X_{Core}$ Q is independently at each occurrence a covalent bond. In some embodiments of $X_{Core}$ Q is independently at each occurrence an —O—. In some embodiments of $X_{Core}$ Q is independently at each occurrence a —S—. In some embodiments of $X_{Core}$ Q is independently at each occurrence a —$NR^2$ and $R^2$ is independently at each occurrence $R^{19}$ or -$L^2$-$NR^{1e}R^{1f}$. In some embodiments of $X_{Core}$ Q is independently at each occurrence a —$CR^{3a}R^{3b}$ $R^{3a}$, and $R^{3a}$ and $R^{3b}$ are each independently at each occurrence hydrogen or an optionally substituted alkyl (e.g., $C_1$-$C_6$, such as $C_1$-$C_3$).

In some embodiments of $X_{Core}$, $R^{1a}$, $R^{1b}$, $R^{1c}$, $R^{1d}$, $R^{1e}$, $R^{1f}$, and $R^{19}$ (if present) are each independently at each occurrence a point of connection to a branch, hydrogen, or an optionally substituted alkyl. In some embodiments of $X_{Core}$, $R^{1a}$, $R^{1b}$, $R^{1c}$, $R^{1d}$, $R^{1e}$, $R^{1f}$, and $R^{19}$ (if present) are each independently at each occurrence a point of connection to a branch, hydrogen. In some embodiments of $X_{Core}$, $R^{1a}$, $R^{1b}$, $R^{1c}$, $R^{1d}$, $R^{1e}$, $R^{1f}$, and $R^{19}$ (if present) are each independently at each occurrence a point of connection to a branch an optionally substituted alkyl (e.g., $C_1$-$C_{12}$).

In some embodiments of $X_{Core}$, $L^0$, $L^1$, and $L^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of $L^1$ form a heterocycloalkyl (e.g., $C_4$-$C_6$ and containing one or two nitrogen atoms and, optionally, an additional heteroatom selected from oxygen and sulfur) with one of $R^{1c}$ and $R^{1d}$In some embodiments of $X_{Core}$, $L^0$, $L^1$, and $L^2$ are each independently at each occurrence can be a covalent bond. In some embodiments of $X_{Core}$, $L^0$, $L^1$, and $L^2$ are each independently at each occurrence can be a hydrogen. In some embodiments of $X_{Core}$, $L^0$, $L^1$, and $L^2$ are each independently at each occurrence can be an alkylene (e.g., $C_1$-$C_{12}$, such as $C_1$-$C_6$ or $C_1$-$C_3$). In some embodiments of $X_{Core}$, $L^0$, $L^1$, and $L^2$ are each independently at each occurrence can be a heteroalkylene (e.g., $C_1$-$C_{12}$, such as $C_1$-$C_8$ or $C_1$-$C_6$). In some embodiments of $X_{Core}$, $L^0$, $L^1$, and $L^2$ are each independently at each occurrence can be a heteroalkylene (e.g., $C_2$-$C_8$ alkyleneoxide, such as oligo(ethyleneoxide)). In some embodiments of $X_{Core}$, $L^0$, $L^1$, and $L^2$ are each independently at each occurrence can be a [alkylene]-[heterocycloalkyl]-[alkylene][(e.g., $C_1$-$C_6$) alkylene]-[(e.g., $C_4$-$C_6$) heterocycloalkyl]-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene][(e.g., $C_1$-$C_6$) alkylene]-(arylene)-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene](e.g., [(e.g., $C_1$-$C_6$) alkylene]-phenylene-[(e.g., $C_1$-$C_6$) alkylene]). In some embodiments of $X_{Core}$, $L^0$, $L^1$, and $L^2$ are each independently at each occurrence can be a heterocycloalkyl (e.g., $C_4$-$C_6$heterocycloalkyl). In some embodiments of $X_{Core}$, $L^0$, $L^1$, and $L^2$ are each independently at each occurrence can be an arylene (e.g., phenylene). In some embodiments of $X_{Core}$, part of $L^1$ form a heterocycloalkyl with one of $R^{1c}$ and $R^{1d}$. In some embodiments of $X_{Core}$, part of $L^1$ form a heterocycloalkyl (e.g., $C_4$-$C_6$ heterocycloalkyl) with one of $R^{1c}$ and $R^{1d}$ and the heterocycloalkyl can contain one or two nitrogen atoms and, optionally, an additional heteroatom selected from oxygen and sulfur.

In some embodiments of $X_{Core}$, $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$) alkyleneoxide (e.g., oligo(ethyleneoxide), such as $—(CH_2CH_2O)_{1-4}—(CH_2CH_2)—$), [($C_1$-$C_4$) alkylene]-[($C_4$-$C_6$) heterocycloalkyl]-[($C_1$-$C_4$) alkylene](e.g.,

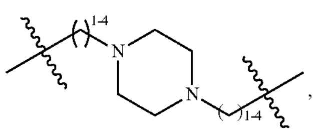

, and [($C_1$-$C_4$) alkylene]-phenylene-[($C_1$-$C_4$) alkylene](e.g.,

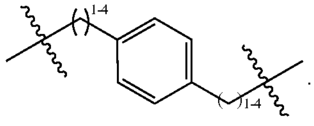

.

In some embodiments of $X_{Core}$, $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$-($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-. In some embodiments of $X_{Core}$, $L^0$, $L^1$, and $L^2$ are each independently at each occurrence $C_1$-$C_6$ alkylene (e.g., $C_1$-$C_3$ alkylene). In some embodiments, $L^0$, $L^1$, and $L^2$ are each independently at each occurrence $C_2$-$C_{12}$ (e.g., $C_2$-$C_8$) alkyleneoxide (e.g., —($C_1$-$C_3$ alkylene-O)$_{1-4}$-($C_1$-$C_3$ alkylene)). In some embodiments of $X_{Core}$, $L^0$, $L^1$, and $L^2$ are each independently at each occurrence selected from [($C_1$-$C_4$) alkylene]-[($C_4$-$C_6$) heterocycloalkyl]-[($C_1$-$C_4$) alkylene](e.g., —($C_1$-$C_3$ alkylene)-phenylene-($C_1$-$C_3$ alkylene)-) and [($C_1$-$C_4$) alkylene]-[($C_4$-$C_6$) heterocycloalkyl]-[($C_1$-$C_4$) alkylene](e.g., —($C_1$-$C_3$ alkylene)-piperazinyl-($C_1$-$C_3$ alkylene)-).

In some embodiments of $X_{Core}$, $x^1$ is 0, 1, 2, 3, 4, 5, or 6. In some embodiments of $X_{Core}$, $x^1$ is 0. In some embodiments of $X_{Core}$, $x^1$ is 1. In some embodiments of $X_{Core}$, $x^1$ is 2. In some embodiments of $X_{Core}$, $x^1$ is 0, 3. In some embodiments of $X_{Core}$ $x^1$ is 4. In some embodiments of $X_{Core}$ $x^1$ is 5. In some embodiments of $X_{Core}$, $x^1$ is 6.

In some embodiments of $X_{Core}$, the core comprises a structural formula:

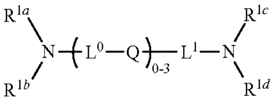

(e.g.,

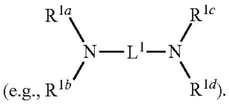

).

In some embodiments of $X_{Core}$, the core comprises a structural formula:

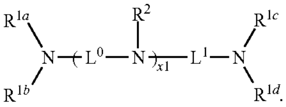

.

In some embodiments of $X_{Core}$, the core comprises a structural formula:

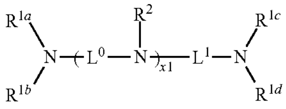

(e.g.,

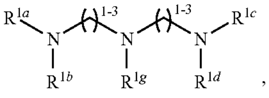

,

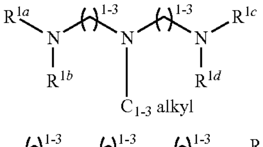

,

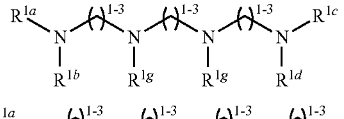

, or

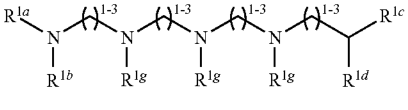

).

In some embodiments of $X_{Core}$, the core comprises a structural formula:

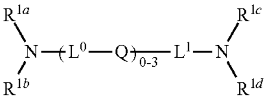
(e.g.,
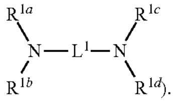
).

In some embodiments of $X_{Core}$, the core comprises a structural formula:

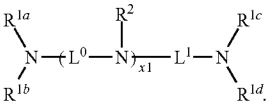

In some embodiments of $X_{Core}$, the core comprises a structural formula:

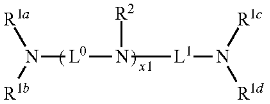

(e.g.,
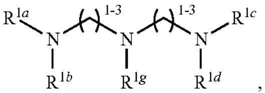
,
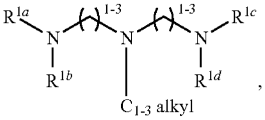
,
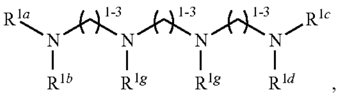
, or
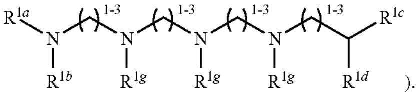
).

In some embodiments of $X_{Core}$, the core comprises a structural formula:

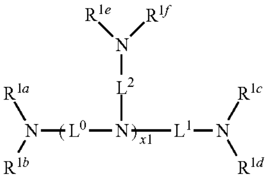

(e.g.,
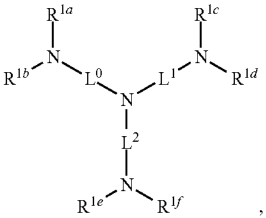
, such as

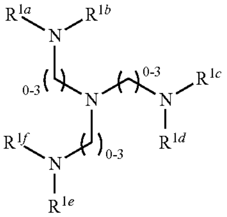
or
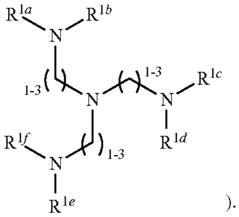
).

In some embodiments of $X_{Core}$, the core comprises a structural formula:

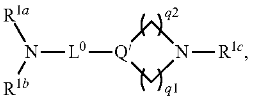

wherein Q' is —$NR^2$— or —$CR^{3a}R^{3b}$—; $q^1$ and $q^2$ are each independently 1 or 2. In some embodiments of $X_{Core}$, the core comprises a structural formula:

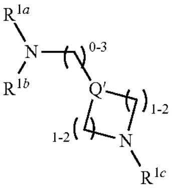
or
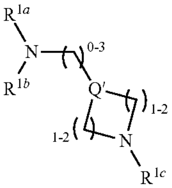

(e.g.,
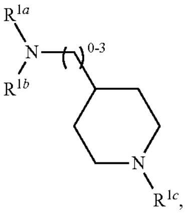
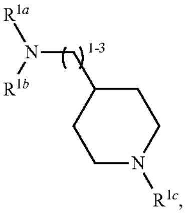
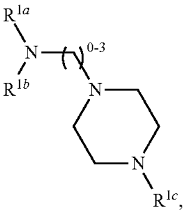
or
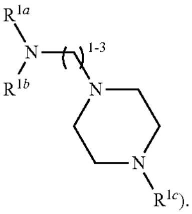
).

In some embodiments of $X_{Core}$, the core comprises a structural formula

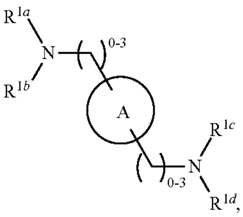
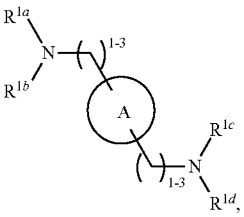

-continued

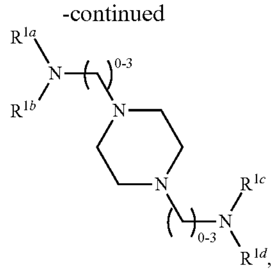

(e.g.,

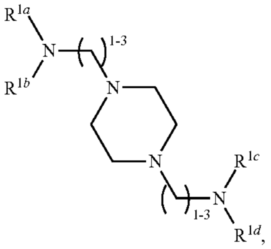

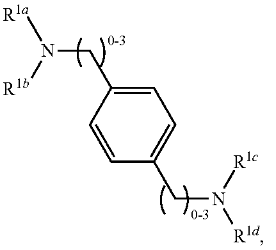

or

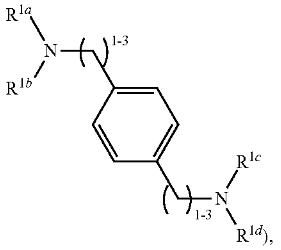

wherein ring A is an optionally substituted aryl or an optionally substituted (e.g., $C_3$-$C_{12}$, such as $C_3$-$C_5$) heteroaryl. In some embodiments of $X_{Core}$, the core comprises has a structural formula

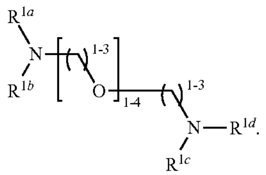

In some embodiments of $X_{Core}$, the core comprises a structural formula set forth in Table 7 and pharmaceutically acceptable salts thereof, wherein * indicates a point of attachment of the core to a branch of the plurality of branches.

In some embodiments, the plurality (N) of branches comprises at least 3 branches, at least 4 branches, at least 5 branches. In some embodiments, the plurality (N) of branches comprises at least 3 branches. In some embodiments, the plurality (N) of branches comprises at least 4 branches. In some embodiments, the plurality (N) of branches comprises at least 5 branches.

In some embodiments of $X_{Branch}$, g is 1, 2, 3, or 4. In some embodiments of $X_{Branch}$, g is 1. In some embodiments of $X_{Branch}$, g is 2. In some embodiments of $X_{Branch}$, g is 3. In some embodiments of $X_{Branch}$, g is 4.

In some embodiments of $X_{Branch}$, $Z=2^{(g-1)}$ and when g=1, G=0. In some embodiments of $X_{Branch}$, $Z=2^{(g-1)}$ and $G=\Sigma_{i=0}^{i=g-2} 2^i$, when g≠1.

In some embodiments of $X_{Branch}$, g=1, G=0, Z=1, and each branch of the plurality of branches comprises a structural formula each branch of the plurality of branches comprises a structural formula

*—(diacyl group)—(terminating group).

In some embodiments of $X_{Branch}$, g=2, G=1, Z=2, and each branch of the plurality of branches comprises a structural formula

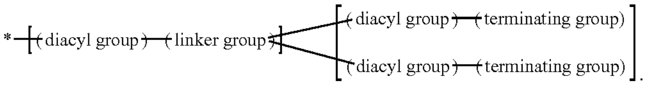

In some embodiments of $X_{Branch}$, g=3, G=3, Z=4, and each branch of the plurality of branches comprises a structural formula

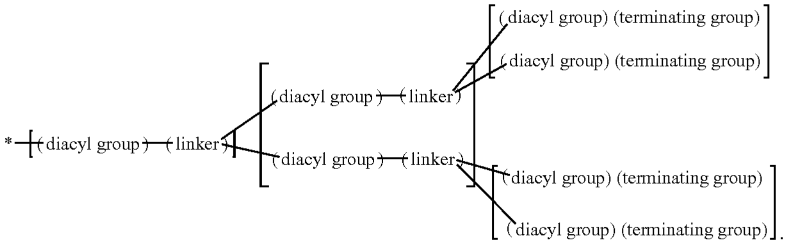

In some embodiments of $X_{Branch}$, g=4, G=7, Z=8, and each branch of the plurality of branches comprises a structural formula

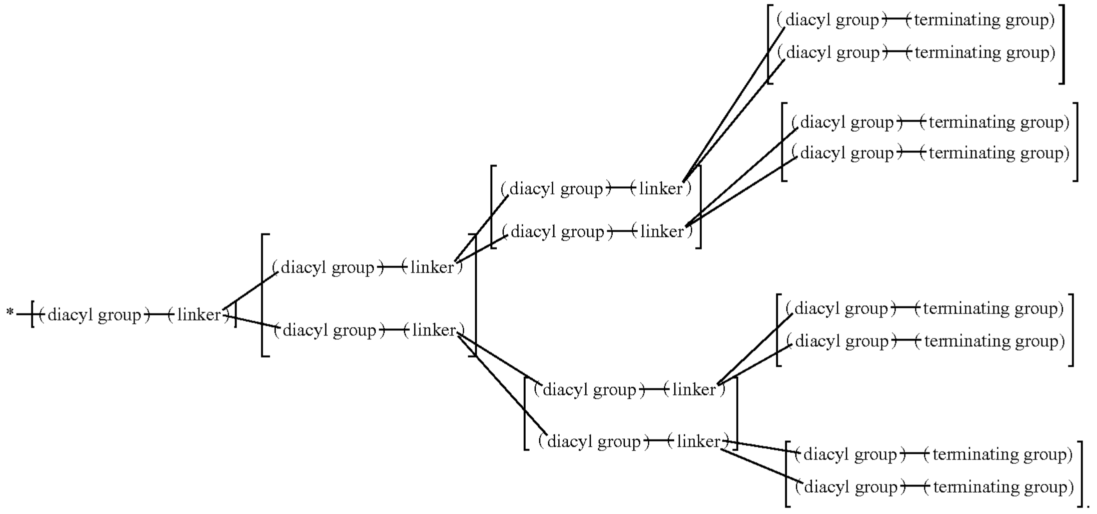

In some embodiments, the dendrimers described herein with a generation (g)=1 has the structure:

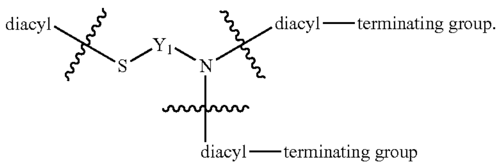

In some embodiments, the dendrimers described herein with a generation (g)=1 has, Gen "g-2" GEN "g-1" GEN "g" the structure:

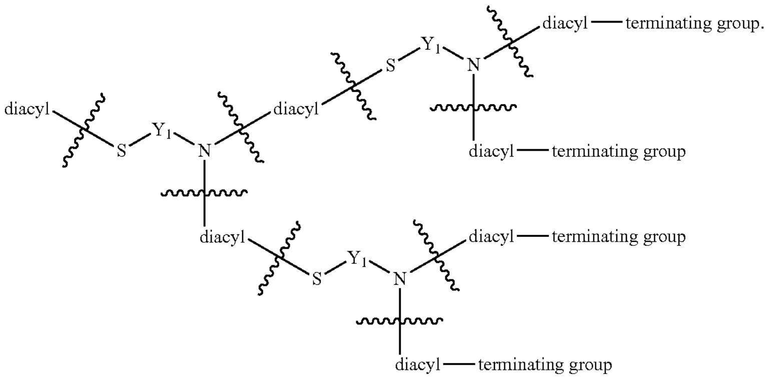

An example formulation of the dendrimers described herein for generations 1-4 is shown in Table 3. The number of diacyl groups, linker groups, and terminating groups can be calculated based on g.

TABLE 3

| Formulation of Dendrimer Groups Based on Generation (g) | | | | | |
|---|---|---|---|---|---|
| | g = 1 | g = 2 | g = 3 | g = 4 | |
| # of diacyl grp | 1 | 1 + 2 = 3 | $1 + 2 + 2^2 = 7$ | $1 + 2 + 2^2 + 2^3 = 15$ | $1 + 2 + \ldots + 2^{g-1}$ |
| # of linker grp | 0 | 1 | 1 + 2 | $1 + 2 + 2^2$ | $1 + 2 + \ldots + 2^{g-2}$ |
| # of terminating grp | 1 | 2 | $2^2$ | $2^3$ | $2^{(g-1)}$ |

In some embodiments, the diacyl group independently comprises a structural formula

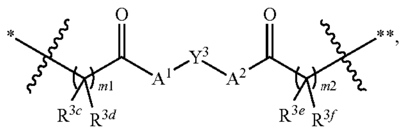

* indicates a point of attachment of the diacyl group at the proximal end thereof, and ** indicates a point of attachment of the diacyl group at the distal end thereof.

In some embodiments of the diacyl group of $X_{Branch}$, $Y^3$ is independently at each occurrence an optionally substituted; alkylene, an optionally substituted alkenylene, or an optionally substituted arenylene. In some embodiments of the diacyl group of $X_{Branch}$, $Y^3$ is independently at each occurrence an optionally substituted alkylene (e.g., $C_1$-$C_{12}$). In some embodiments of the diacyl group of $X_{Branch}$, $Y^3$ is independently at each occurrence an optionally substituted alkenylene (e.g., $C_1$-$C_{12}$). In some embodiments of the diacyl group of $X_{Branch}$, $Y^3$ is independently at each occurrence an optionally substituted arenylene (e.g., $C_1$-$C_{12}$).

In some embodiments of the diacyl group of $X_{Branch}$, $A^1$ and $A^2$ are each independently at each occurrence —O—, —S—, or —$NR_4$—. In some embodiments of the diacyl group of $X_{Branch}$, $A^1$ and $A^2$ are each independently at each occurrence —O—. In some embodiments of the diacyl group of $X_{Branch}$, $A^1$ and $A^2$ are each independently at each occurrence —S—. In some embodiments of the diacyl group of $X_{Branch}$, $A^1$ and $A^2$ are each independently at each occurrence —$NR^4$— and $R^4$ is hydrogen or optionally substituted alkyl (e.g., $C_1$-$C_6$). In some embodiments of the diacyl group of $X_{Branch}$, $m^1$ and $m^2$ are each independently at each occurrence 1, 2, or 3. In some embodiments of the diacyl group of $X_{Branch}$, $m^1$ and $m^2$ are each independently at each occurrence 1. In some embodiments of the diacyl group of $X_{Branch}$, $m^1$ and $m^2$ are each independently at each occurrence 2. In some embodiments of the diacyl group of $X_{Branch}$, $m^1$ and $m^2$ are each independently at each occurrence 3. In some embodiments of the diacyl group of $X_{Branch}$, $R^{3c}$, $R^{3d}$, $R^{3c}$, and $R^{3f}$ are each independently at each occurrence hydrogen or an optionally substituted alkyl. In some embodiments of the diacyl group of $X_{Branch}$, $R^{3c}$, $R^{3d}$, $R^{3c}$, and $R^{3f}$ are each independently at each occurrence hydrogen. In some embodiments of the diacyl group of $X_{Branch}$, $R^{3c}$, $R^{3d}$, $R^{3c}$, and $R^{3f}$ are each independently at each occurrence an optionally substituted (e.g., $C_1$-$C_8$) alkyl.

In some embodiments of the diacyl group, $A^1$ is —O— or —NH—. In some embodiments of the diacyl group, $A^1$ is —O—. In some embodiments of the diacyl group, $A^2$ is —O— or —NH—. In some embodiments of the diacyl group, $A^2$ is —O—. In some embodiments of the diacyl group, $Y^3$ is $C_1$-$C_{12}$ (e.g., $C_1$-$C_6$, such as $C_1$-$C_3$) alkylene.

In some embodiments of the diacyl group, the diacyl group independently at each occurrence comprises a structural formula

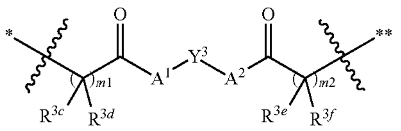

(e.g.

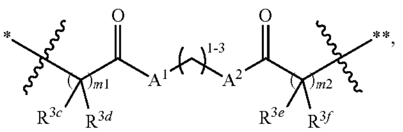

such as

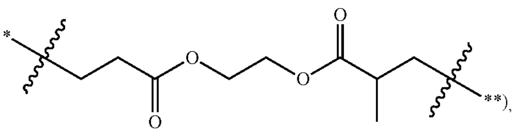

and optionally $R^{3c}$, $R^{3d}$, $R^{3c}$, and $R^{3f}$ are each independently at each occurrence hydrogen or $C_1$-$C_3$ alkyl.

In some embodiments, linker group independently comprises a structural formula

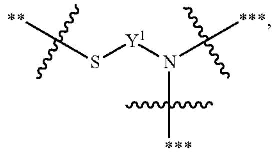

indicates a point of attachment of the linker to a proximal diacyl group, and * indicates a point of attachment of the linker to a distal diacyl group.

In some embodiments of the linker group of $X_{Branch}$ if present, $Y_1$ is independently at each occurrence an optionally substituted alkylene, an optionally substituted alkenylene, or an optionally substituted arenylene. In some embodiments of the linker group of $X_{Branch}$ if present, $Y_1$ is independently at each occurrence an optionally substituted alkylene (e.g., $C_1$-$C_{12}$). In some embodiments of the linker group of $X_{Branch}$ if present, $Y_1$ is independently at each occurrence an optionally substituted alkenylene (e.g., $C_1$-$C_{12}$). In some embodiments of the linker group of $X_{Branch}$ if present, $Y_1$ is independently at each occurrence an optionally substituted arenylene (e.g., $C_1$-$C_{12}$).

In some embodiments of the terminating group of $X_{Branch}$, each terminating group is independently selected from optionally substituted alkylthiol and optionally substituted alkenylthiol. In some embodiments of the terminating group of $X_{Branch}$, each terminating group is an optionally substituted alkylthiol (e.g., $C_1$-$C_{18}$, such as $C_4$-$C_{18}$). In some embodiments of the terminating group of $X_{Branch}$, each terminating group is optionally substituted alkenylthiol (e.g., $C_1$-$C_{18}$, such as $C_4$-$C_{18}$).

In some embodiments of the terminating group of $X_{Branch}$, each terminating group is independently $C_1$-$C_{15}$ alkenylthiol or $C_1$-$C_{15}$ alkylthiol, and the alkyl or alkenyl moiety is optionally substituted with one or more substituents each independently selected from halogen, $C_6$-$C_{12}$ aryl, $C_1$-$C_{12}$ alkylamino, $C_4$-$C_6$ N-heterocycloalkyl, —OH, —C(O)OH, —C(O)N($C_1$-$C_3$ alkyl)-($C_1$-$C_6$ alkylene)-($C_1$-$C_{12}$ alkylamino), —C(O)N($C_1$-$C_3$ alkyl)-($C_1$-$C_6$ alkylene)-($C_4$-$C_6$ N-heterocycloalkyl), —C(O)—($C_1$-$C_{12}$ alkylamino), and —C(O)—($C_4$-$C_6$ N-heterocycloalkyl), and the $C_4$-$C_6$ N-heterocycloalkyl moiety of any of the preceding substituents is optionally substituted with $C_1$-$C_3$ alkyl or $C_1$-$C_3$ hydroxyalkyl.

In some embodiments of the terminating group of $X_{Branch}$, each terminating group is independently $C_1$-$C_{15}$ (e.g., $C_4$-$C_{18}$) alkenylthiol or $C_1$-$C_{15}$ (e.g., $C_4$-$C_{18}$) alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as

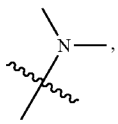, 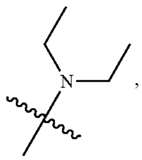, 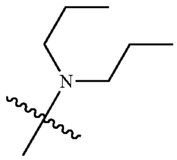,

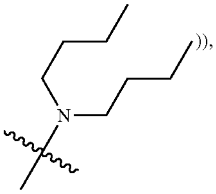)), $C_4$-$C_6$ N-heterocycloalkyl (e.g., N-pyrrolidinyl (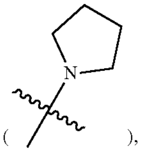), N-piperidinyl (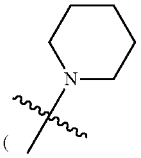), N-azepanyl (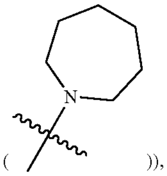)), —OH, —C(O)OH, —C(O)N($C_1$-$C_3$ alkyl)-($C_1$-$C_6$ alkylene)-($C_1$-$C_{12}$ alkylamino (e.g., mono- or di-alkylamino)) (e.g.,

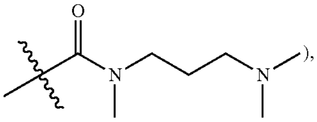 [SMILES: *C(=O)N(C)CCCN(C)C]),

—C(O)N($C_1$-$C_3$ alkyl)-($C_1$-$C_6$ alkylene)-($C_4$-$C_6$ N-heterocycloalkyl) (e.g.,

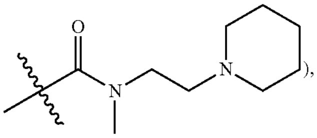 [SMILES: *C(=O)N(C)CCN1CCCCC1]),

—C(O)—($C_1$-$C_{12}$ alkylamino (e.g., mono- or di-alkylamino)), and —C(O)—($C_4$-$C_6$ N-heterocycloalkyl) (e.g.

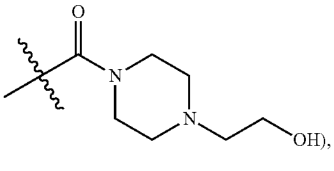), wherein the $C_4$-$C_6$ N-heterocycloalkyl moiety of any of the preceding substituents is optionally substituted with $C_1$-$C_3$ alkyl or $C_1$-$C_3$ hydroxyalkyl. In some embodiments of the terminating group of $X_{Branch}$, each terminating group is independently $C_1$-$C_{18}$ (e.g., $C_4$-$C_{18}$) alkylthiol, wherein the alkyl moiety is optionally substituted with one substituent —OH. In some embodiments of the terminating group of $X_{Branch}$, each terminating group is independently $C_1$-$C_{18}$ (e.g., $C_4$-$C_{18}$) alkylthiol, wherein the alkyl moiety is optionally substituted with one substituent selected from $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as

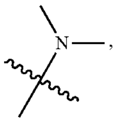, 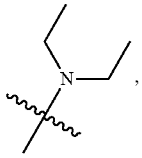, 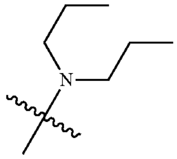,

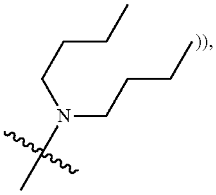)), and $C_4$-$C_6$ N-heterocycloalkyl (e.g., N-pyrrolidinyl ( 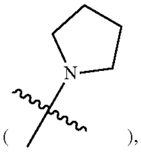 ), N-piperidinyl ( 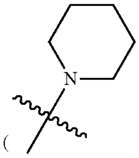 ), N-azepanyl ( 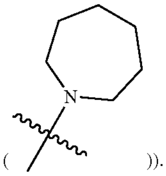 )).

In some embodiments of the terminating group of $X_{Branch}$, each terminating group is independently $C_1$-$C_{18}$ (e.g., $C_4$-$C_{18}$) alkenylthiol or $C_1$-$C_{18}$ (e.g., $C_4$-$C_{18}$) alkylthiol. In some embodiments of the terminating group of $X_{Branch}$, each terminating group is independently $C_1$-$C_{18}$ (e.g., $C_4$-$C_{18}$) alkylthiol.

TABLE 2

Example core structures

| ID # | Structure |
|---|---|
| 1A1 | 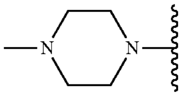 [SMILES: *N1CCN(C)CC1] |
| 1A2 | 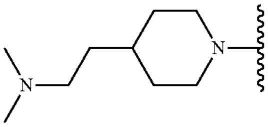 [SMILES: *N1CCC(CCN(C)C)CC1] |
| 1A3 | 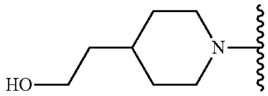 [SMILES: *N1CCC(CCO)CC1] |
| 1A4 | 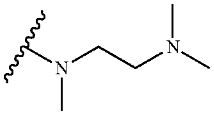 [SMILES: *N(C)CCN(C)C] |
| 1A5 | 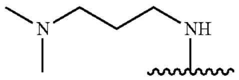 [SMILES: *NCCCN(C)C] |
| 2A1 | 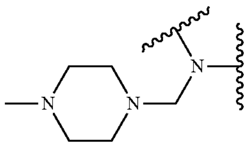 [SMILES: *N(*)CN1CCN(C)CC1] |

TABLE 2-continued
| Example core structures | |
|---|---|
| ID # | Structure |
| 2A2 | 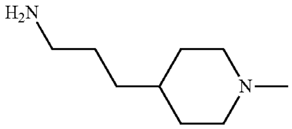 |
| 2A3 | 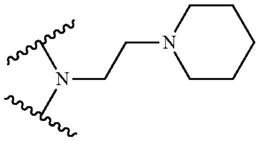 [SMILES: *N(*)CCN1CCCCC1] |
| 2A4 | 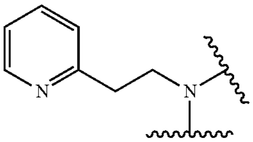 [SMILES: *N(*)CCc1ccccn1] |
| 2A5 | 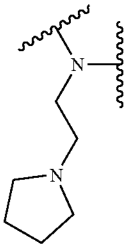 [SMILES: *N(*)CCN1CCCC1] |
| 2A6 | 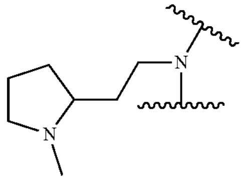 [SMILES: *N(*)CCC1CCCN1C] |
| 2A7 | 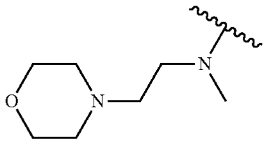 [SMILES: *N(C)CCN1CCOCC1] |
| 2A8 | 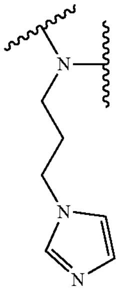 [SMILES: *N(*)CCCn1ccnc1] |
| 2A9 | 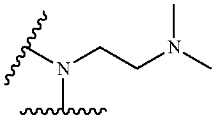 [SMILES: *N(*)CCN(C)C] |

TABLE 2-continued
| Example core structures | |
|---|---|
| ID # | Structure |
| 2A10 | 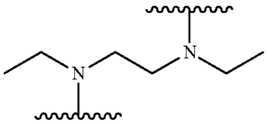 [SMILES: *N(CC)CCN(*)CC] |
| 2A11 | 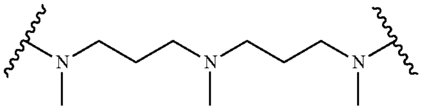 [SMILES: *N(C)CCCN(C)CCCN(*)C] |
| 2A12 | 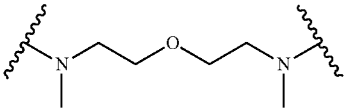 [SMILES: *N(C)CCOCCN(*)C] |
| 3A1 | 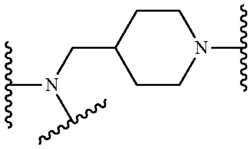 [SMILES: *N(*)CC1CCN(*)CC1] |
| 3A2 | 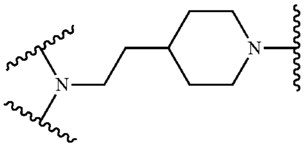 [SMILES: *N(*)CCC1CCN(*)CC1] |
| 3A3 | 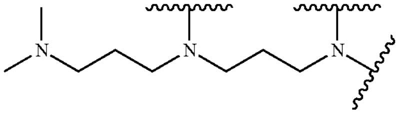 [SMILES: *N(*)CCCN(*)CCCN(C)C] |
| 3A4 | 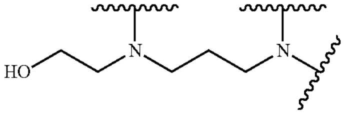 [SMILES: *N(*)CCCN(*)CCO] |
| 3A5 | 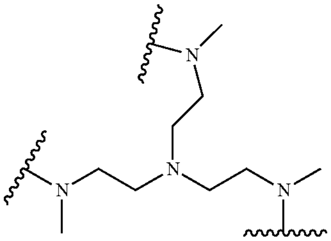 [SMILES: *N(C)CCN(CCN(*)C)CCN(*)C] |
| 4A1 | 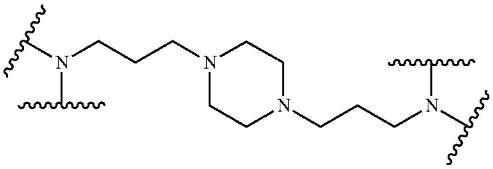 [SMILES: *N(*)CCCN1CCN(CCCN(*)*)CC1] |
| 4A2 | 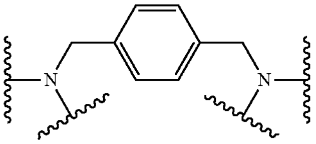 [SMILES: *N(*)Cc1ccc(CN(*)*)cc1] |

TABLE 2-continued
| Example core structures | |
|---|---|
| ID # | Structure |
| 4A3 | 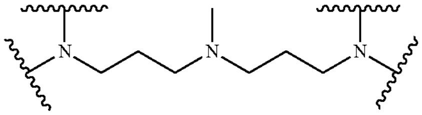 [SMILES: *N(*)CCCN(C)CCCN(*)*] |
| 4A4 | 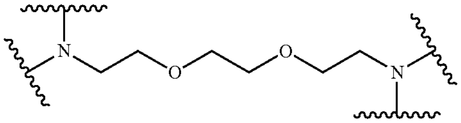 [SMILES: *N(*)CCOCCOCCN(*)*] |
| 5A1 | 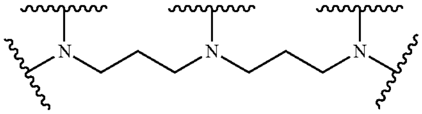 [SMILES: *N(*)CCCN(*)CCCN(*)*] |
| 5A2 | 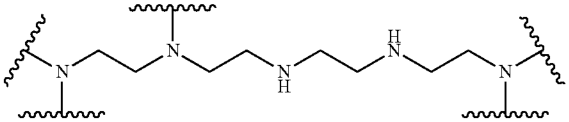 [SMILES: *N(*)CCNCCNCCN(*)CCN(*)*] |
| 5A3 | 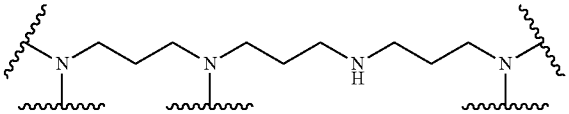 [SMILES: *N(*)CCCNCCCN(*)CCCN(*)*] |
| 5A4 | 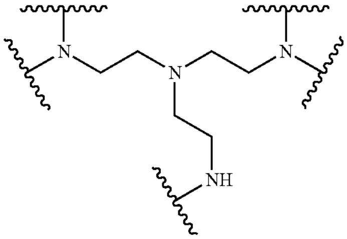 [SMILES: *NCCN(CCN(*)*)CCN(*)*] |
| 5A5 | 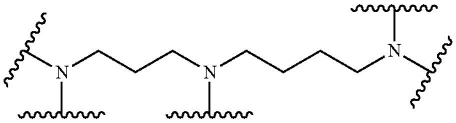 [SMILES: *N(*)CCCCN(*)CCCN(*)*] |
| 6A1 | 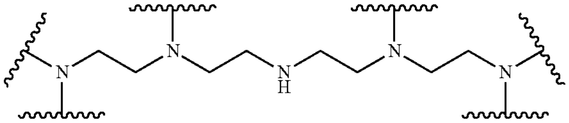 [SMILES: *N(*)CCN(*)CCNCCN(*)CCN(*)*] |
| 6A2 | 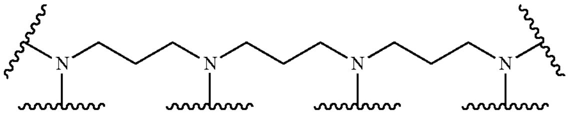 [SMILES: *N(*)CCCN(*)CCCN(*)CCCN(*)*] |

TABLE 2-continued
| Example core structures | |
|---|---|
| ID # | Structure |
| 6A3 | 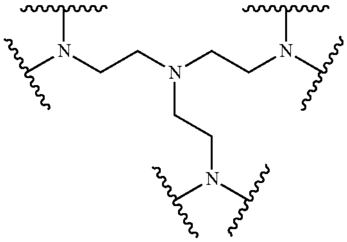 [SMILES: *N(*)CCN(CCN(*)*)CCN(*)*] |
| 6A4 | 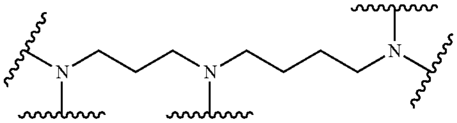 [SMILES: *N(*)CCCCN(*)CCCN(*)*] |
| 1H1 | 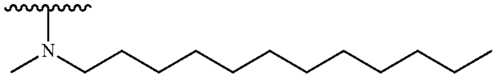 [SMILES: *N(C)CCCCCCCCCCCC] |
| 1H2 | 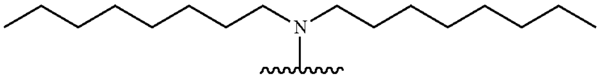 [SMILES: *N(CCCCCCCC)CCCCCCCC] |
| 1H3 | 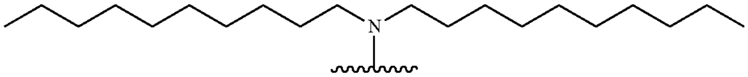 [SMILES: *N(CCCCCCCCCC)CCCCCCCCCC] |
| 2H1 | 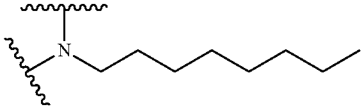 [SMILES: *N(*)CCCCCCCC] |
| 2H2 | 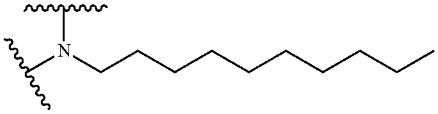 [SMILES: *N(*)CCCCCCCCCC] |
| 2H3 | 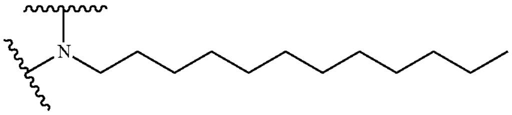 [SMILES: *N(*)CCCCCCCCCCCC] |
| 2H4 | 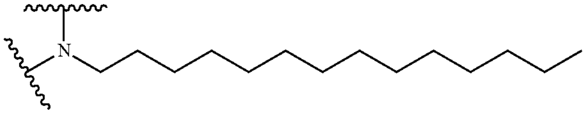 [SMILES: *N(*)CCCCCCCCCCCCCC] |
| 2H5 | 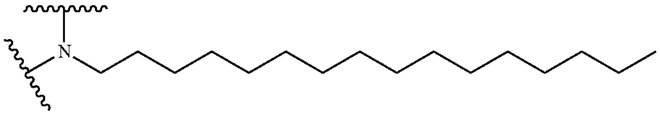 [SMILES: *N(*)CCCCCCCCCCCCCCCC] |
| 2H6 | 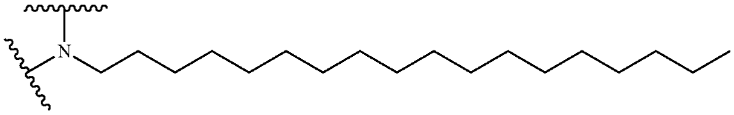 [SMILES: *N(*)CCCCCCCCCCCCCCCCCC] |

In some embodiments of $X_{Core}$, the core comprises a structural formula selected from the group consisting of:
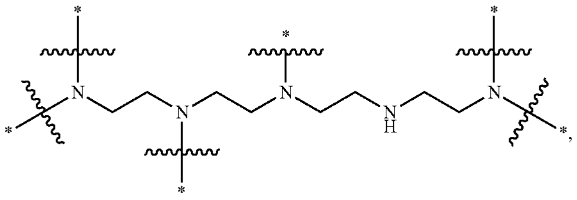
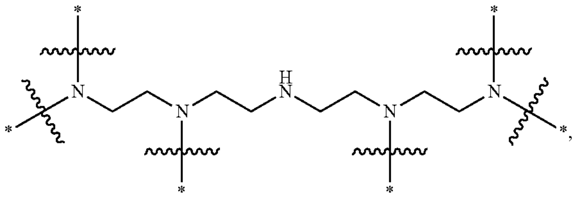
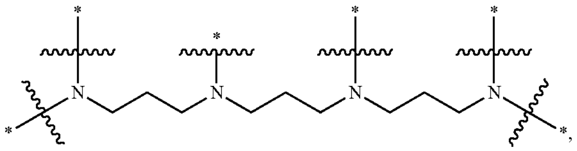
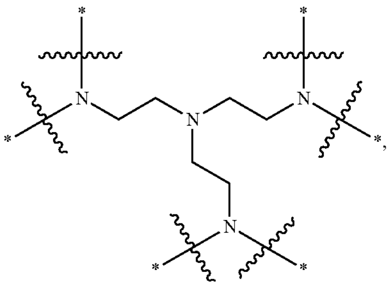
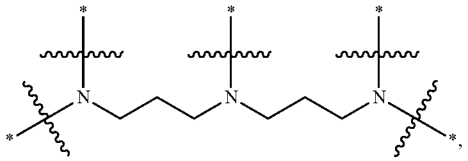
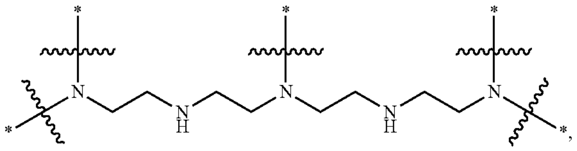
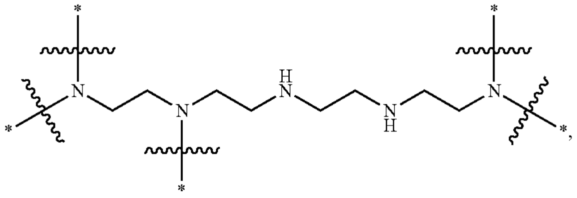
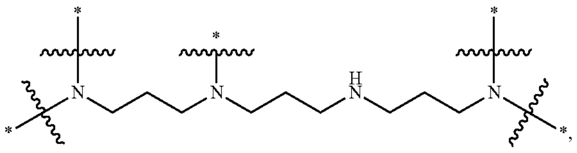
-continued
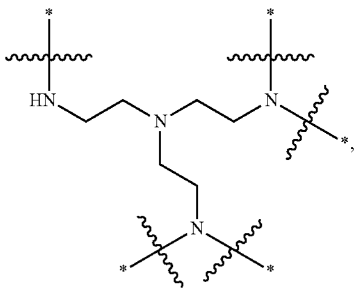
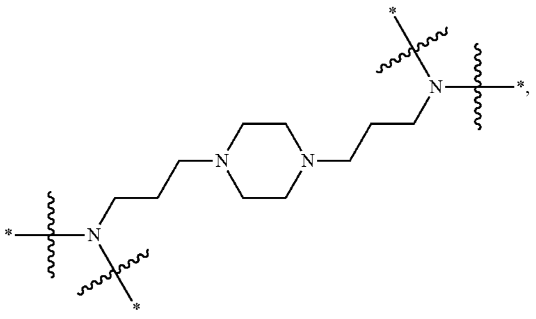
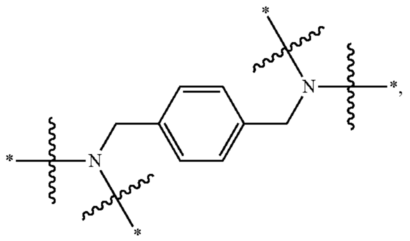
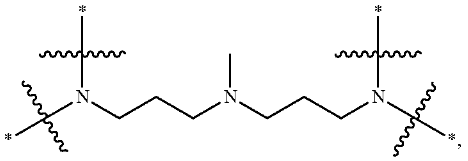
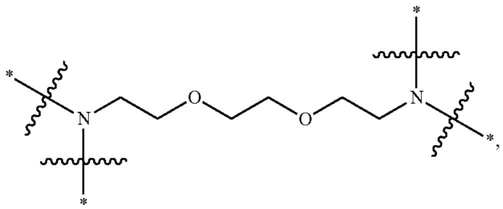
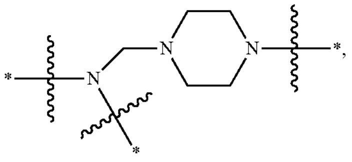
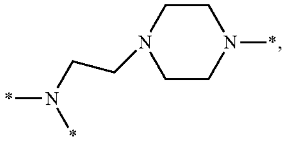
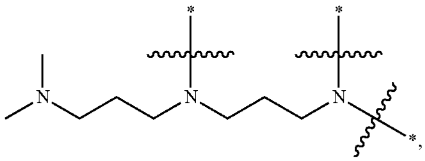

-continued

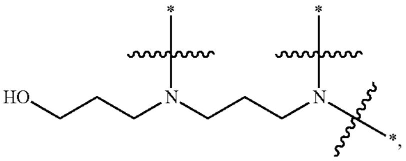

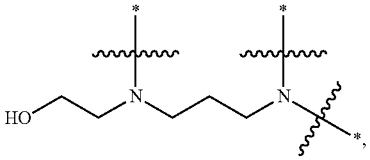

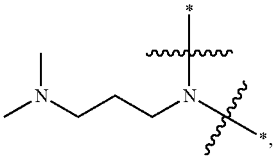

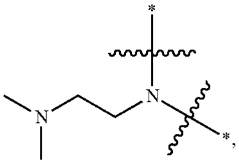

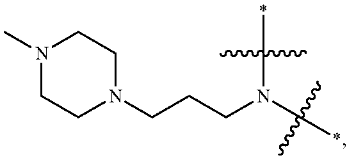

-continued

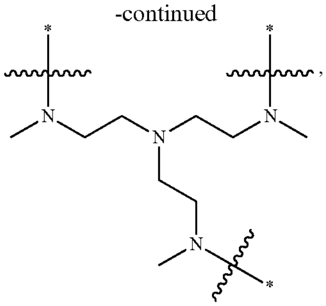

and pharmaceutically acceptable salts thereof, wherein * indicates a point of attachment of the core to a branch of the plurality of branches.

In some embodiments of the terminating group of $X_{Branch}$, each terminating group is independently a structure selected from the structure in Table 1. In some embodiments, the dendrimers described herein can comprise a terminating group or pharmaceutically acceptable salt, or thereof selected in Table 1.

TABLE 1

Example terminating group/peripheries structures

| ID # | Structure |
|---|---|
| SC1 | 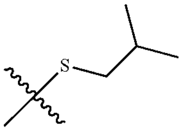 [SMILES: *SCC(C)C] |
| SC2 | 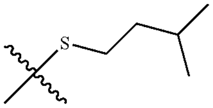 [SMILES: *SCCC(C)C] |
| SC3 | 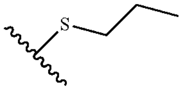 [SMILES: *SCCC] |
| SC4 | 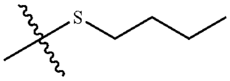 [SMILES: *SCCCC] |
| SC5 | 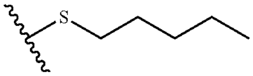 [SMILES: *SCCCCC] |
| SC6 | 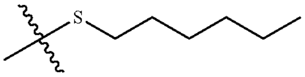 [SMILES: *SCCCCCC] |
| SC7 | 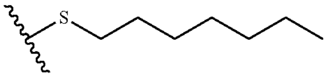 [SMILES: *SCCCCCCC] |
| SC8 | 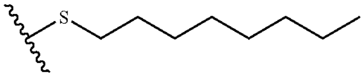 [SMILES: *SCCCCCCCC] |

TABLE 1-continued
| Example terminating group/peripheries structures | |
|---|---|
| ID # | Structure |
| SC9 | 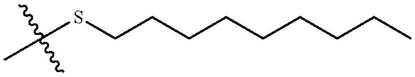 [SMILES: *SCCCCCCCCC] |
| SC10 | 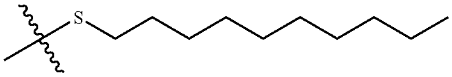 [SMILES: *SCCCCCCCCCC] |
| SC11 | 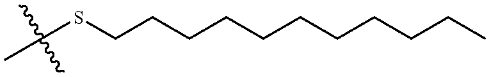 [SMILES: *SCCCCCCCCCCC] |
| SC12 | 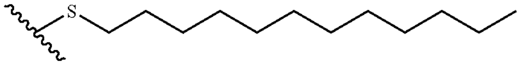 [SMILES: *SCCCCCCCCCCCC] |
| SC14 | 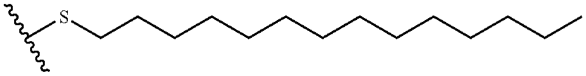 [SMILES: *SCCCCCCCCCCCCCC] |
| SC16 | 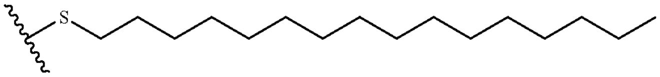 [SMILES: *SCCCCCCCCCCCCCCCC] |
| SC18 | 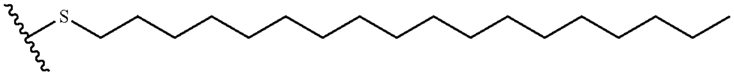 [SMILES: *SCCCCCCCCCCCCCCCCCC] |
| SC19 | 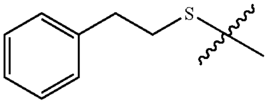 [SMILES: *SCCc1ccccc1] |
| SO1 | 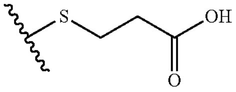 [SMILES: *SCCC(=O)O] |
| SO2 | 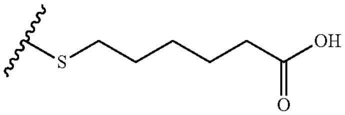 [SMILES: *SCCCCCC(=O)O] |
| SO3 | 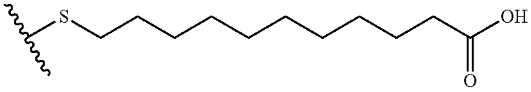 [SMILES: *SCCCCCCCCCCC(=O)O] |
| SO4 | 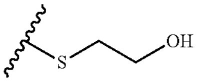 [SMILES: *SCCO] |
| SO5 | 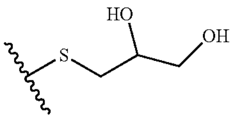 [SMILES: *SCC(O)CO] |
| SO6 | 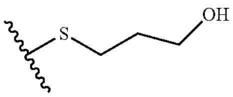 [SMILES: *SCCCO] |

TABLE 1-continued
| Example terminating group/peripheries structures | |
|---|---|
| ID # | Structure |
| SO7 | 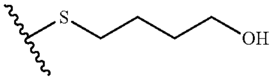 [SMILES: *SCCCCO] |
| SO8 | 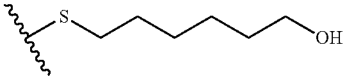 [SMILES: *SCCCCCCO] |
| SO9 | 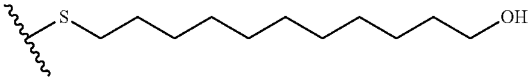 [SMILES: *SCCCCCCCCCCCO] |
| SN1 | 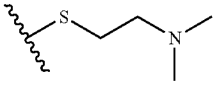 [SMILES: *SCCN(C)C] |
| SN2 | 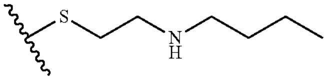 [SMILES: *SCCNCCCC] |
| SN3 | 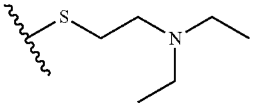 [SMILES: *SCCN(CC)CC] |
| SN4 | 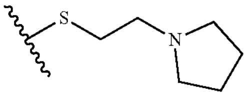 [SMILES: *SCCN1CCCC1] |
| SN5 | 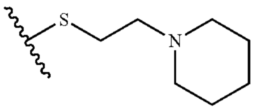 [SMILES: *SCCN1CCCCC1] |
| SN6 | 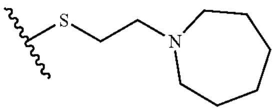 [SMILES: *SCCN1CCCCCC1] |
| SN7 | 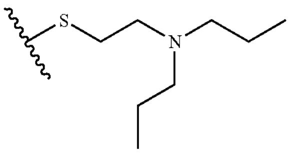 [SMILES: *SCCN(CCC)CCC] |
| SN8 | 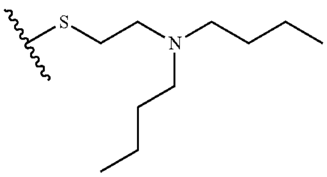 [SMILES: *SCCN(CCCC)CCCC] |
| SN9 | 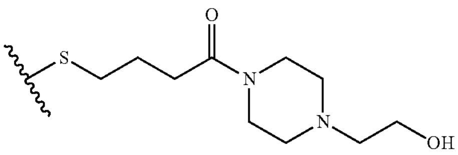 [SMILES: *SCCCC(=O)N1CCN(CCO)CC1] |

TABLE 1-continued
| Example terminating group/peripheries structures | |
|---|---|
| ID # | Structure |
| SN10 | 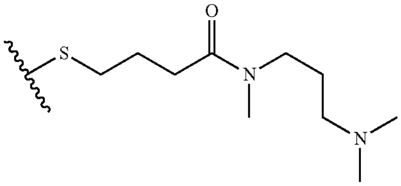 [SMILES: *SCCCC(=O)N(C)CCCN(C)C] |
| SN11 | 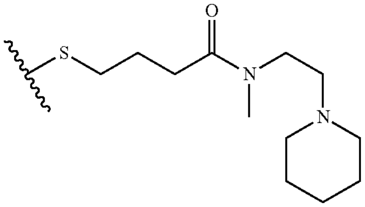 [SMILES: *SCCCC(=O)N(C)CCN1CCCCC1] |
In some embodiments, the dendrimer of Formula (X) is selected from those set forth in Table 4 and pharmaceutically acceptable salts thereof.
TABLE 4
| Example ionizable cationic lipid dendrimers | |
|---|---|
| ID # | Structure |
| 2A2-SC14 | 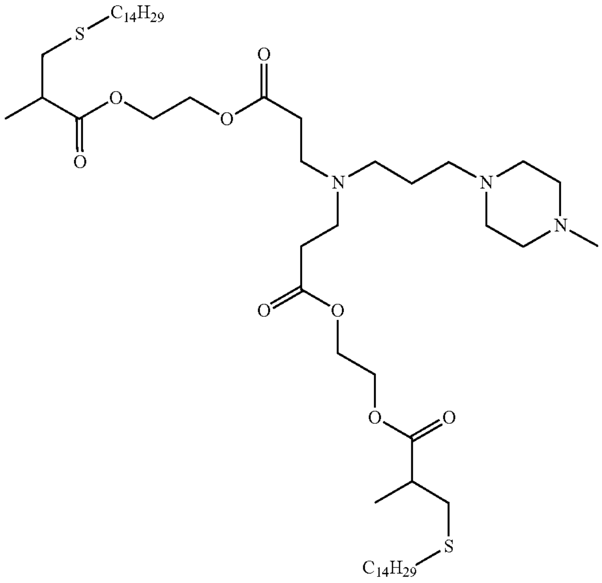 |
| 2A6-SC14 | 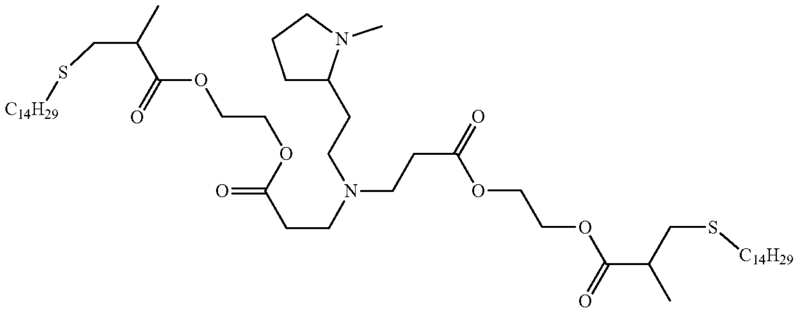 |

TABLE 4-continued
| Example ionizable cationic lipid dendrimers | |
|---|---|
| ID # | Structure |
| 2A9-SC14 | 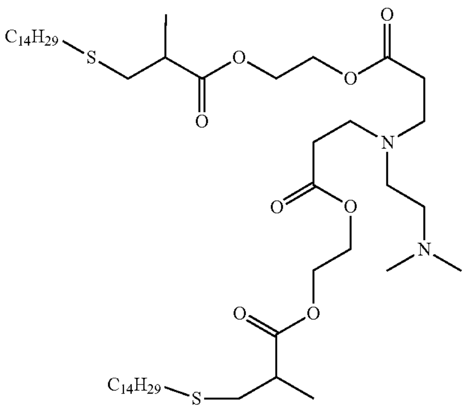 |
| 3A3-SC10 | 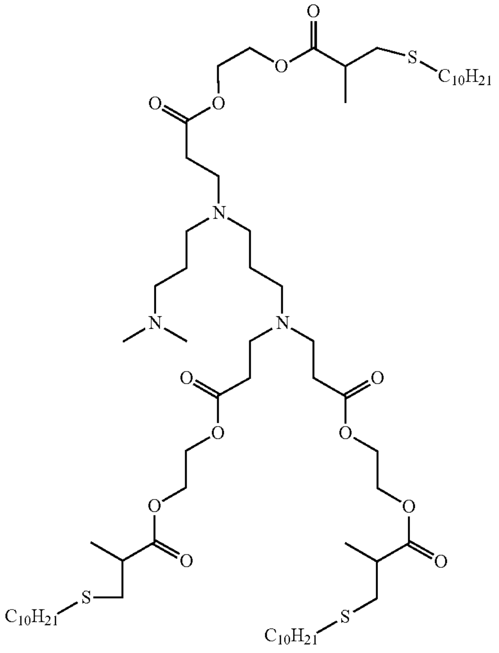 |

TABLE 4-continued
| Example ionizable cationic lipid dendrimers | |
|---|---|
| ID # | Structure |
| 3A3-SC14 | 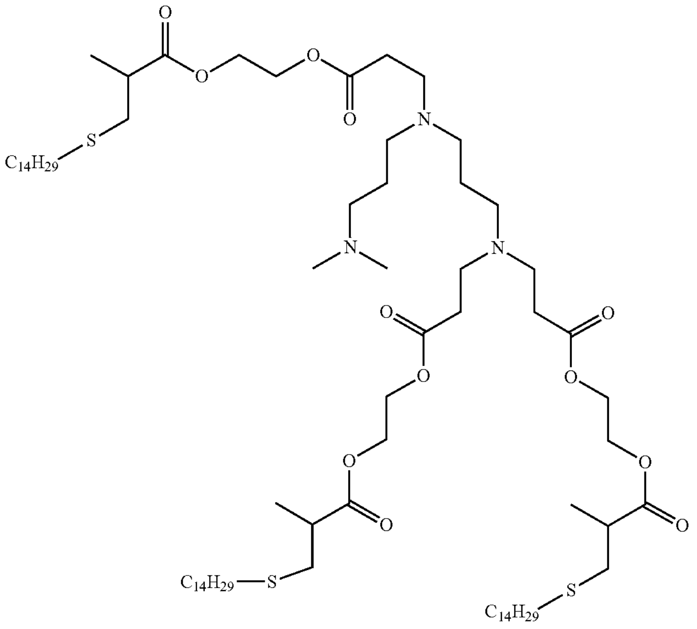 |
| 3A5-SC10 | 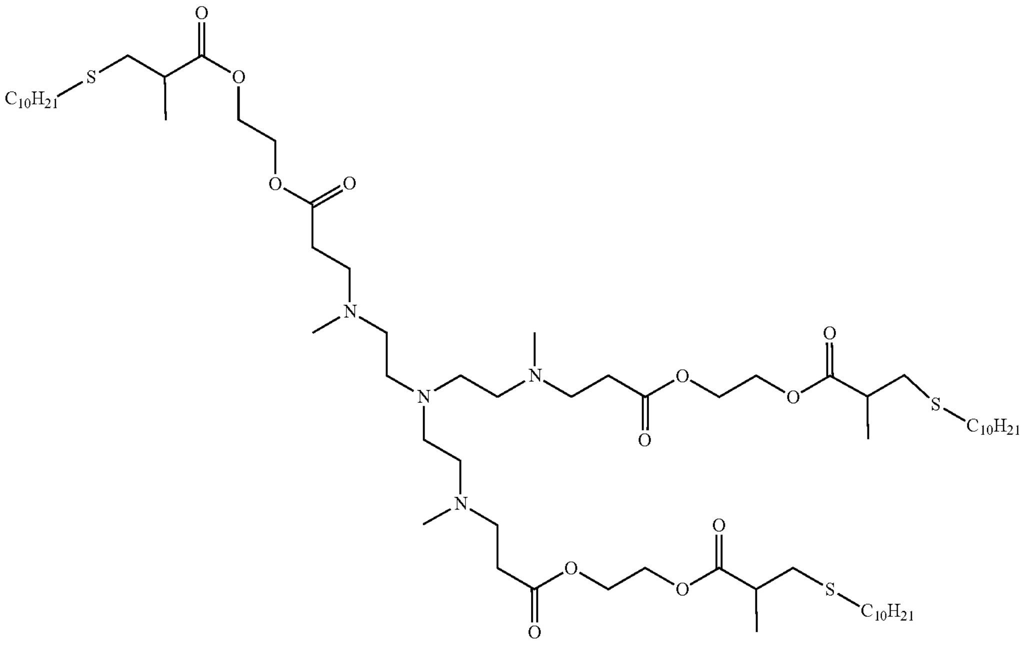 |

TABLE 4-continued
| Example ionizable cationic lipid dendrimers | |
|---|---|
| ID # | Structure |
| 3A5-SC14 | 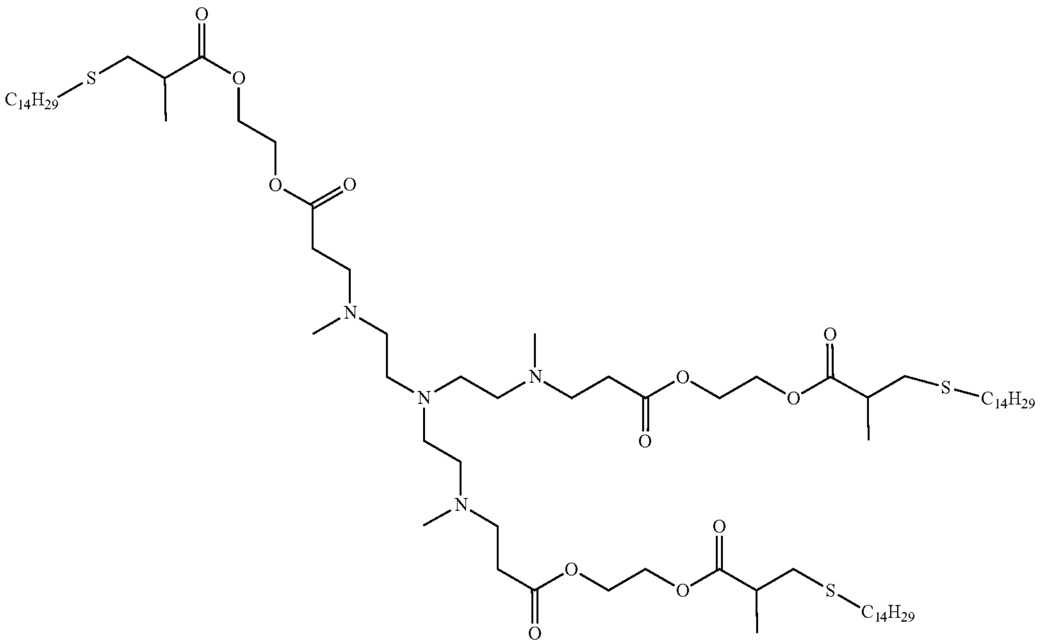 |
| 4A1-SC12 | 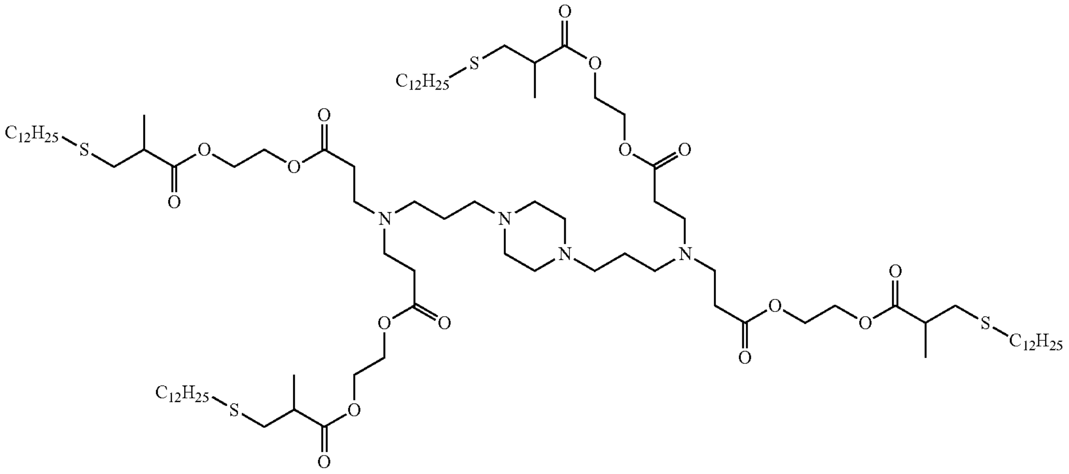 |

TABLE 4-continued
| Example ionizable cationic lipid dendrimers | |
|---|---|
| ID # | Structure |
| 4A3-SC12 | 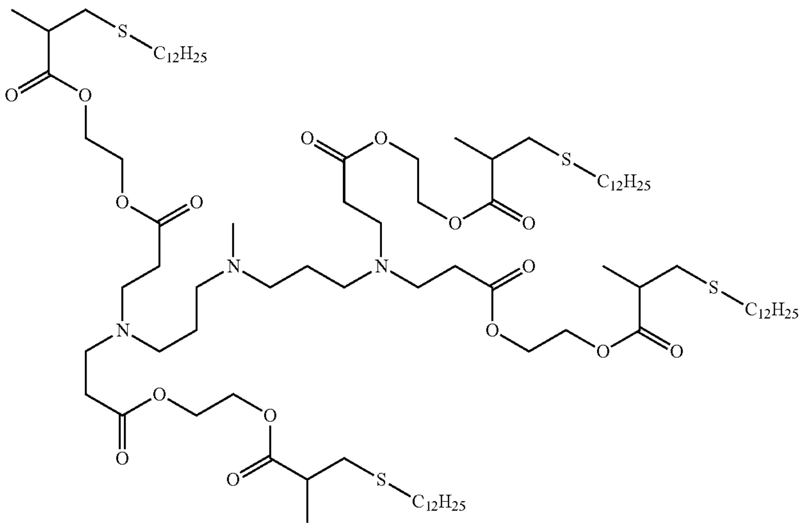 |
| 5A1-SC12 | 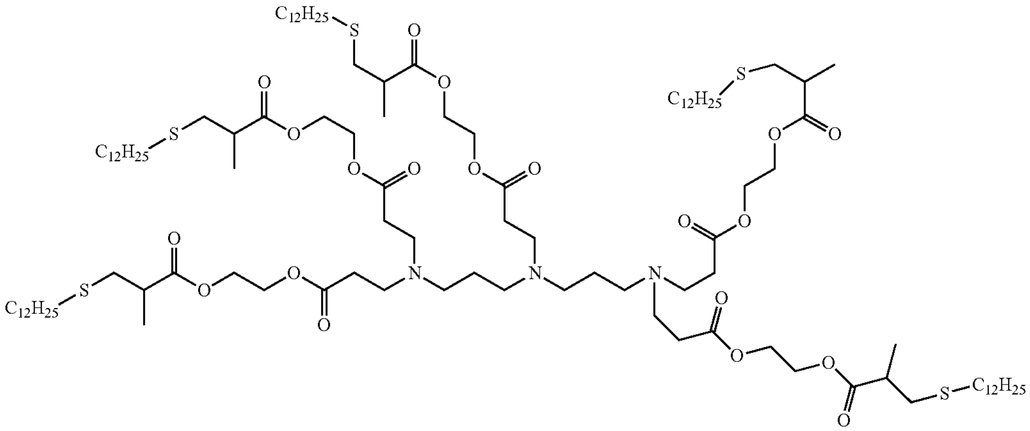 |
| 5A1-SC8 | 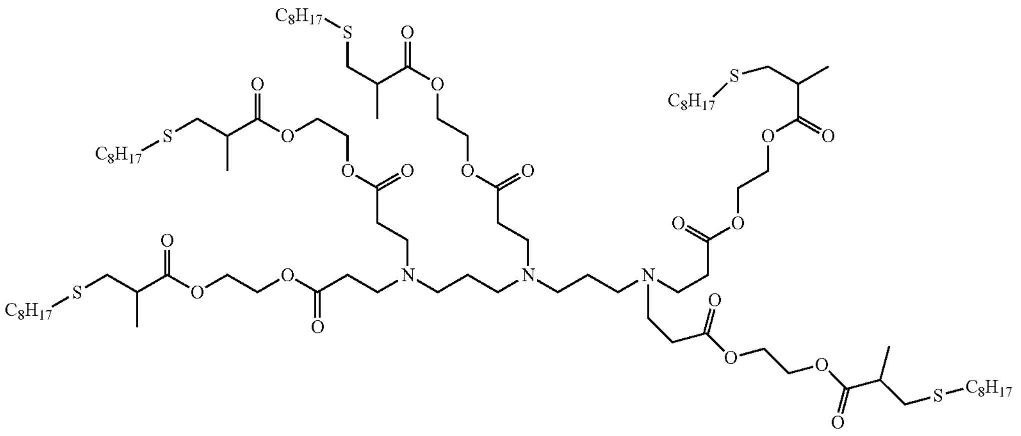 |

TABLE 4-continued
| Example ionizable cationic lipid dendrimers | |
|---|---|
| ID # | Structure |
| 5A2-2-SC12 (5-arm) | 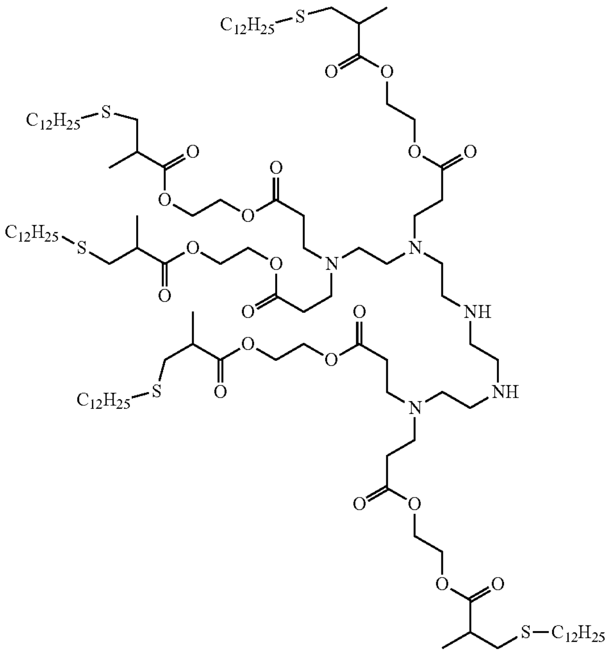 |
| 5A3-1-SC12 (5 arm) | 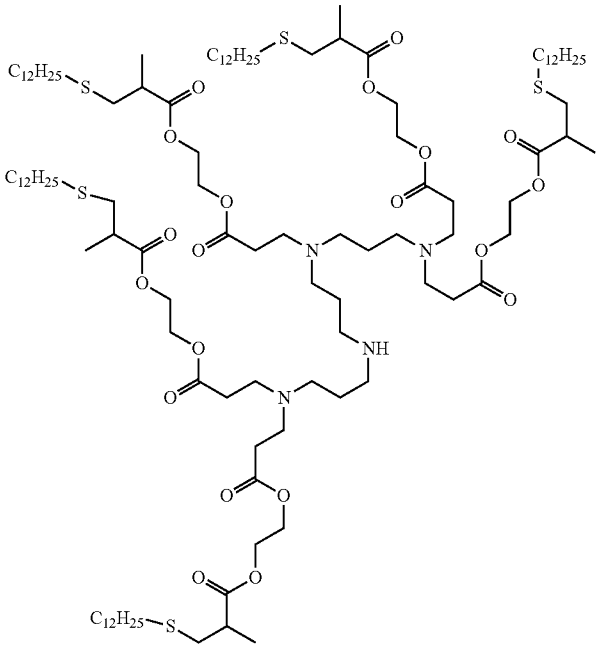 |

TABLE 4-continued
| Example ionizable cationic lipid dendrimers | |
|---|---|
| ID # | Structure |
| 5A3-1-SC8 (5-arm) | 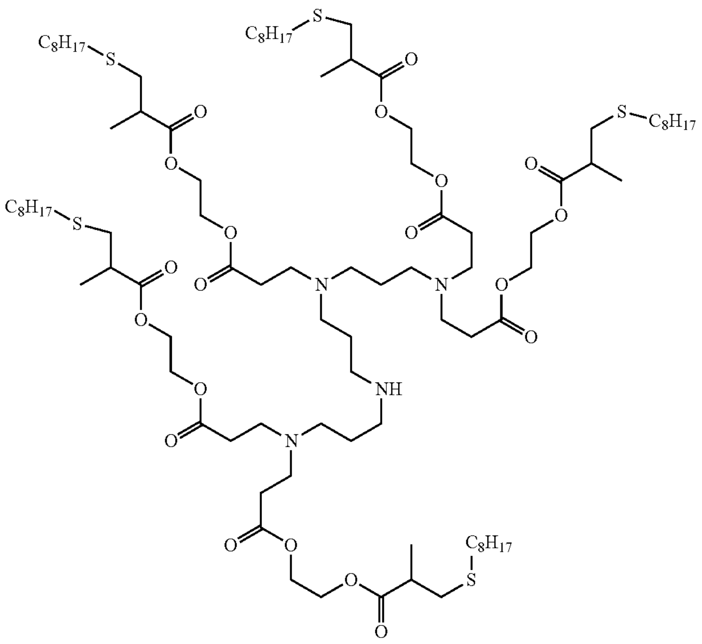 |
| 5A4-1-SC12 (5-arm) | 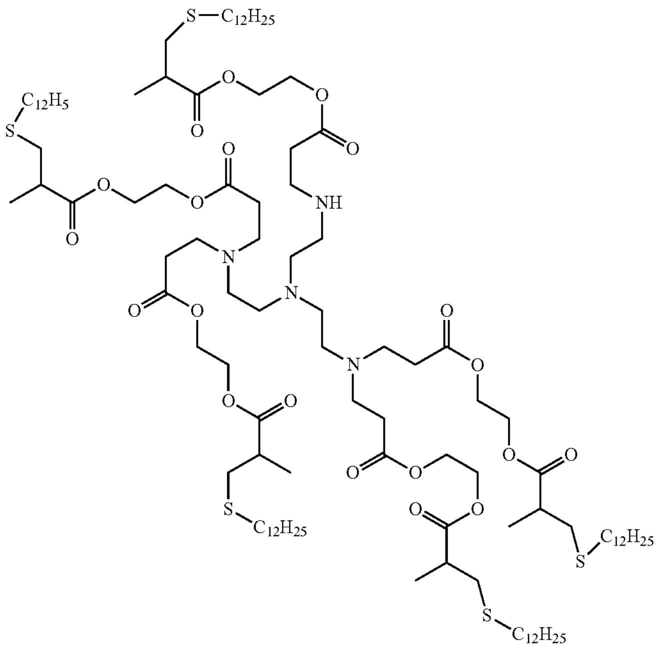 |

TABLE 4-continued
| Example ionizable cationic lipid dendrimers | |
|---|---|
| ID # | Structure |
| 5A4-1-SC8 (5-arm) | 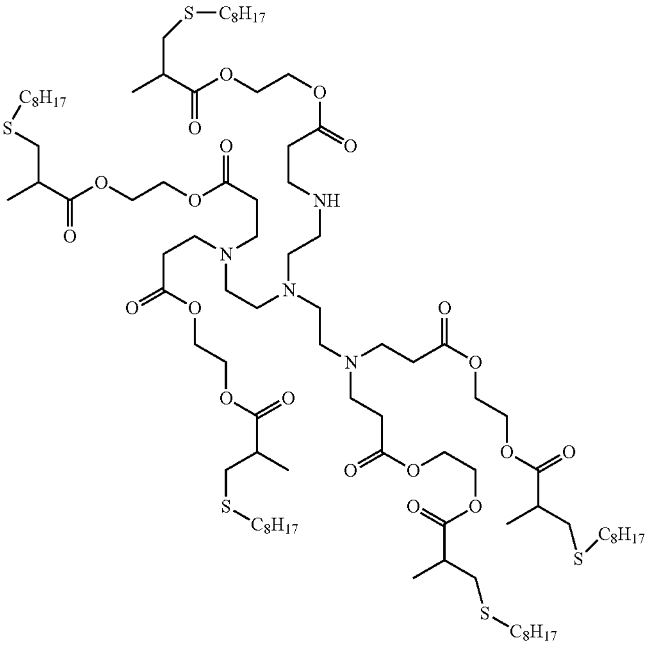 |
| 5A5-SC8 | 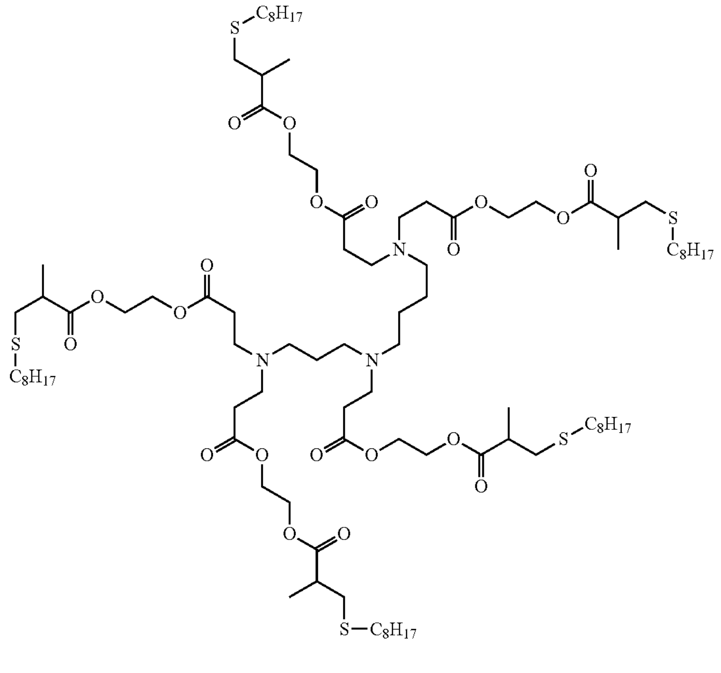 |

TABLE 4-continued
| Example ionizable cationic lipid dendrimers | |
|---|---|
| ID # | Structure |
| 5A5-SC12 | 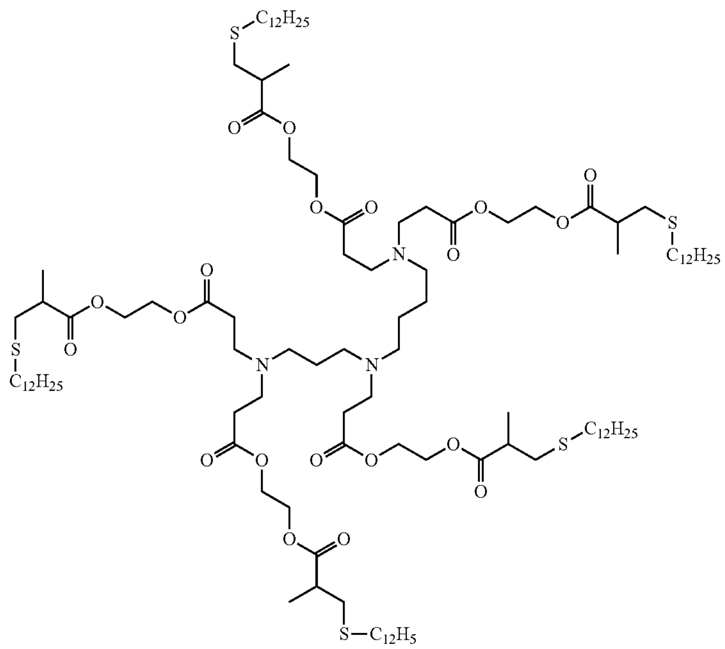 |
| 5A2-4-SC12 (6-arm) | 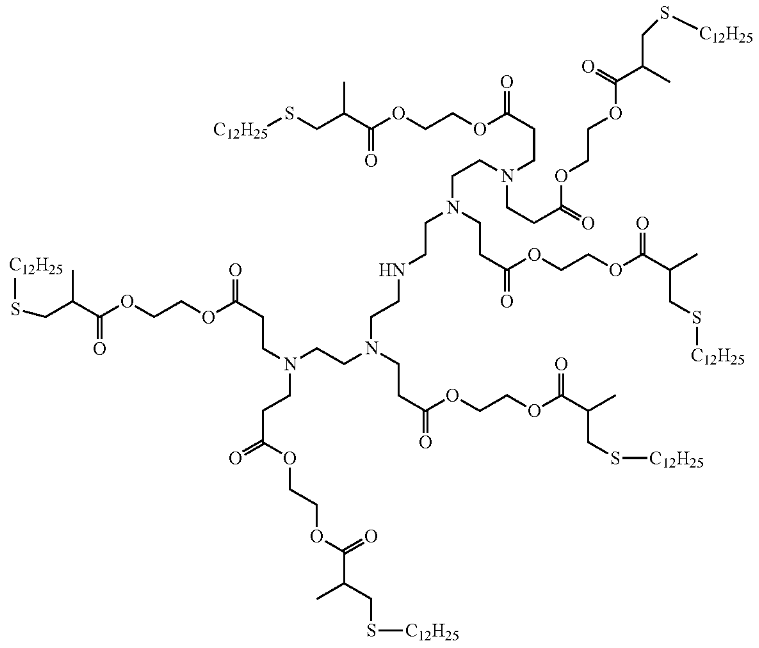 |

TABLE 4-continued
| Example ionizable cationic lipid dendrimers | |
|---|---|
| ID # | Structure |
| 5A2-4-SC10 (6-arm) | 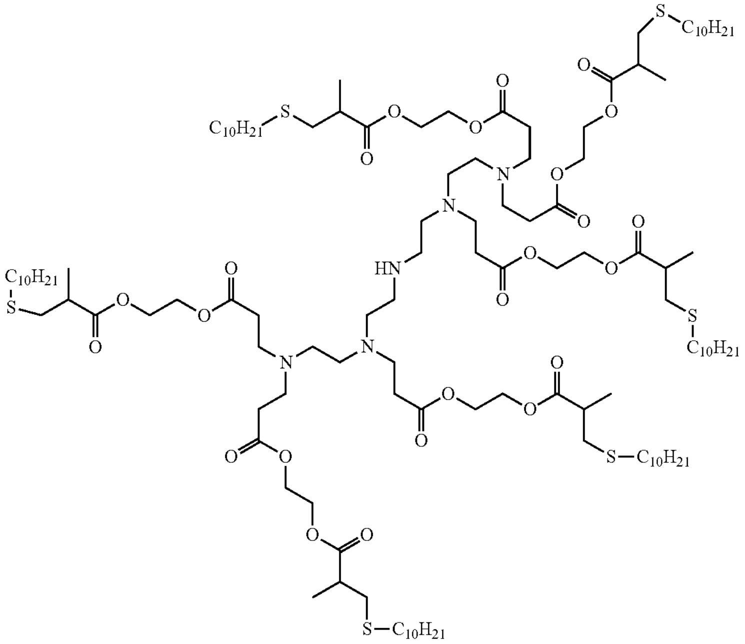 |
| 5A3-2--SC8 (6-arm) | 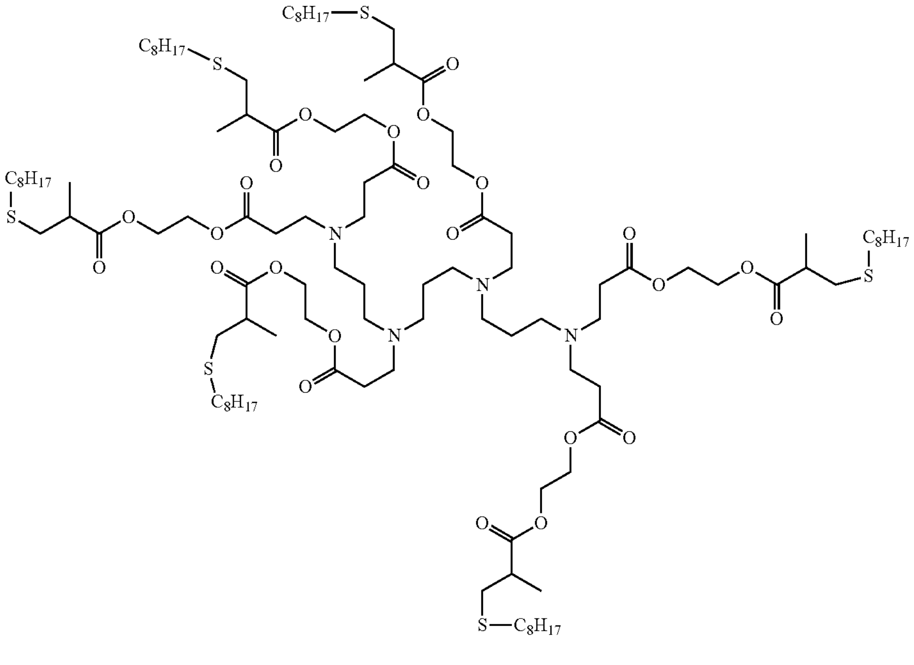 |

TABLE 4-continued
Example ionizable cationic lipid dendrimers
| ID # | Structure |
| --- | --- |
| 5A3-2-SC12 (6-arm) | 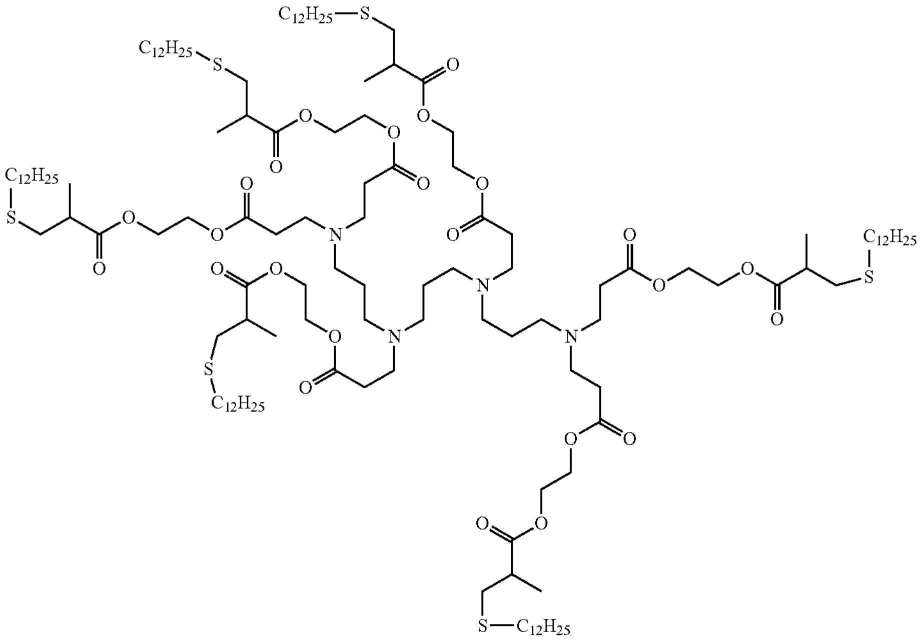 |
| 5A4-2-SC8 (6-arm) | 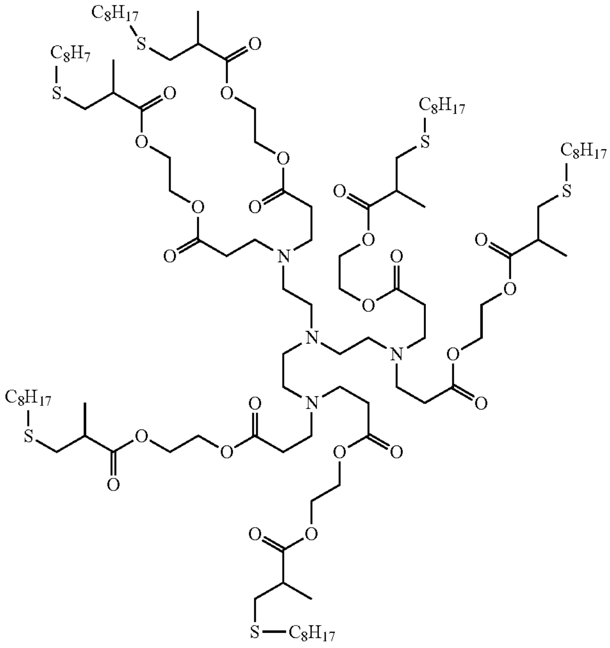 |

TABLE 4-continued
| Example ionizable cationic lipid dendrimers | |
|---|---|
| ID # | Structure |
| 5A4-2-SC12 (6-arm) | 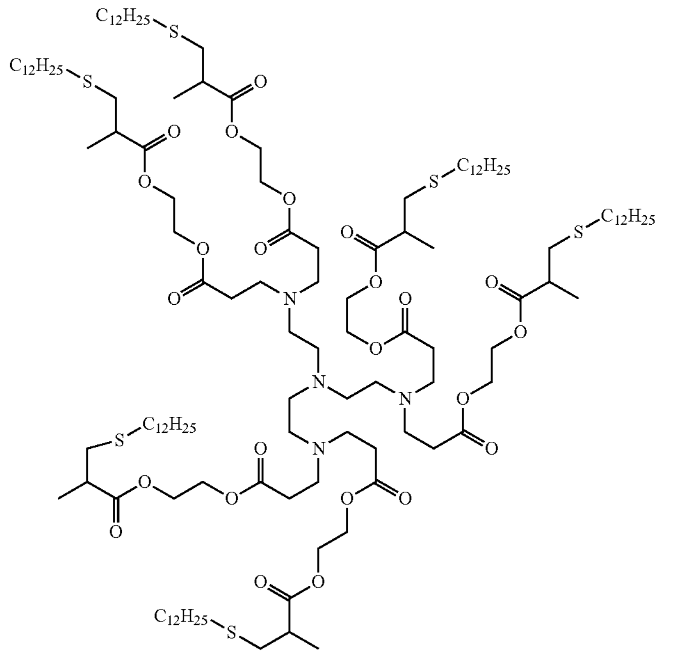 |
| 6A4-SC8 | 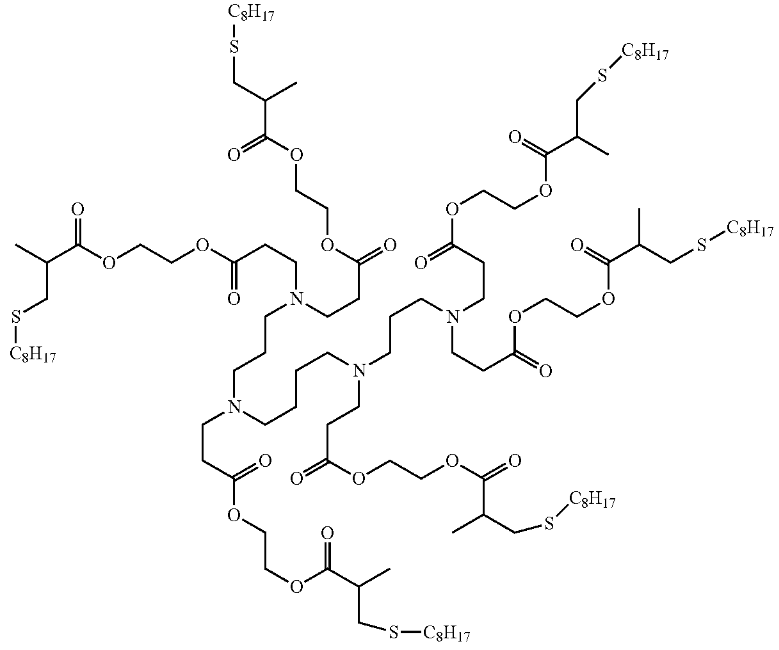 |

TABLE 4-continued
| Example ionizable cationic lipid dendrimers | |
|---|---|
| ID # | Structure |
| 6A4-SC12 | 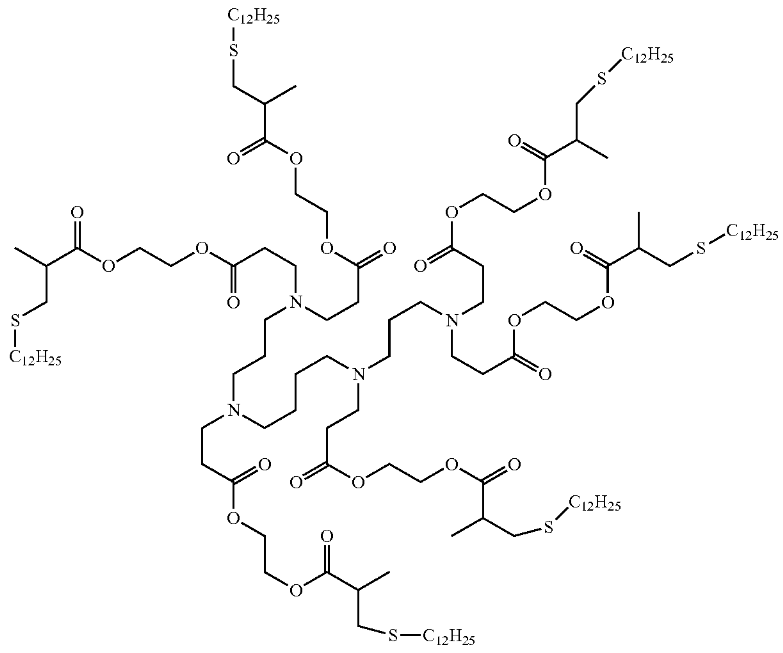 |
| 2A2-g2-SC12 | 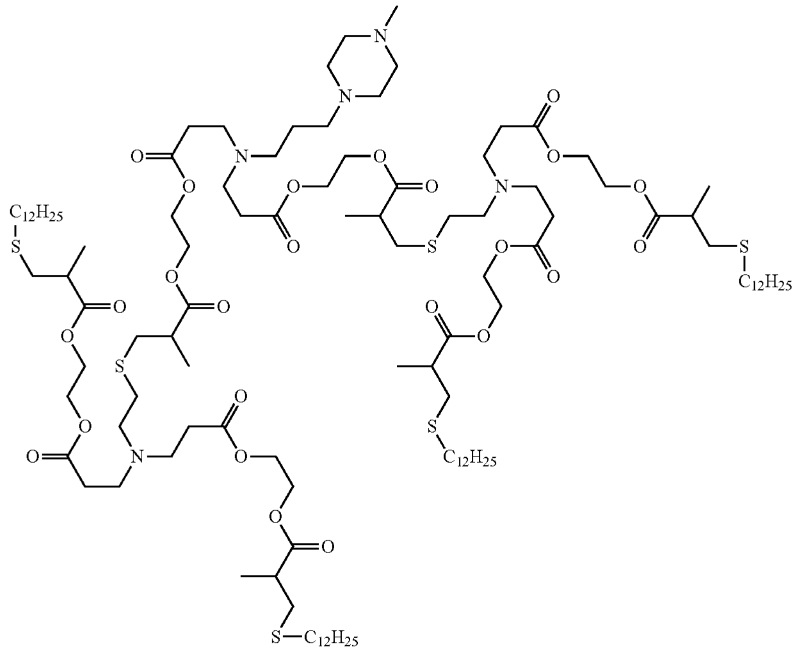 |

TABLE 4-continued
| Example ionizable cationic lipid dendrimers | |
|---|---|
| ID # | Structure |
| 2A2-g2-SC8 | 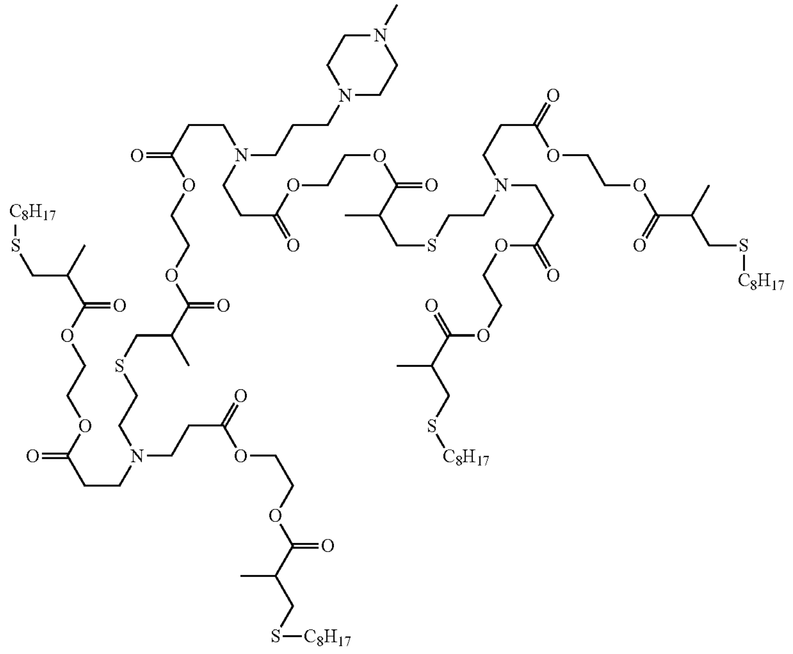 |
| 2A11-g2-SC12 | 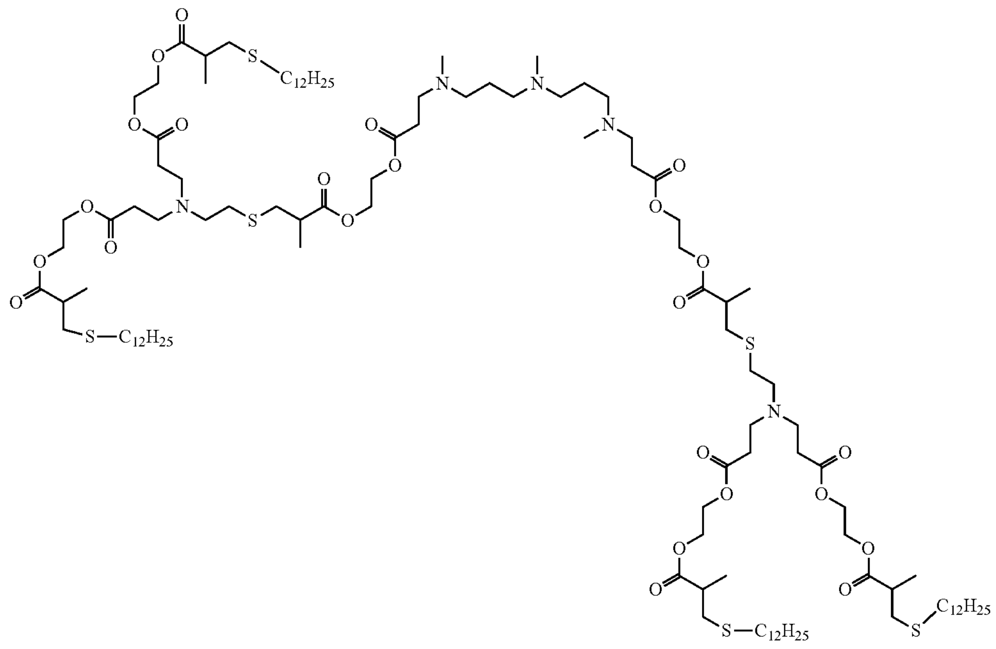 |

TABLE 4-continued
| Example ionizable cationic lipid dendrimers | |
|---|---|
| ID # | Structure |
| 2A11-g2-SC8 | 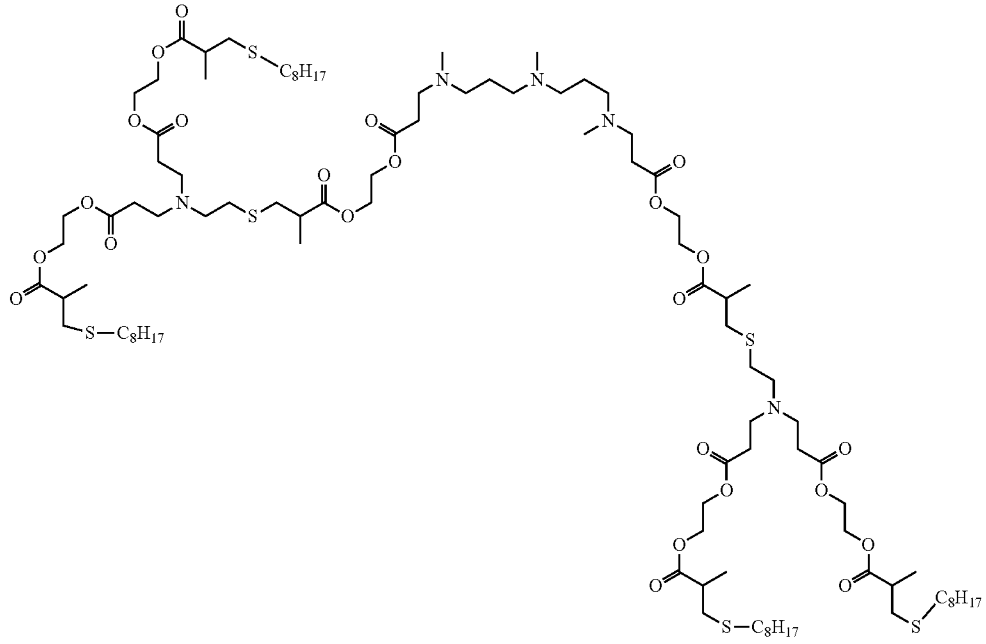 |
| 3A3-g2-SC12 | 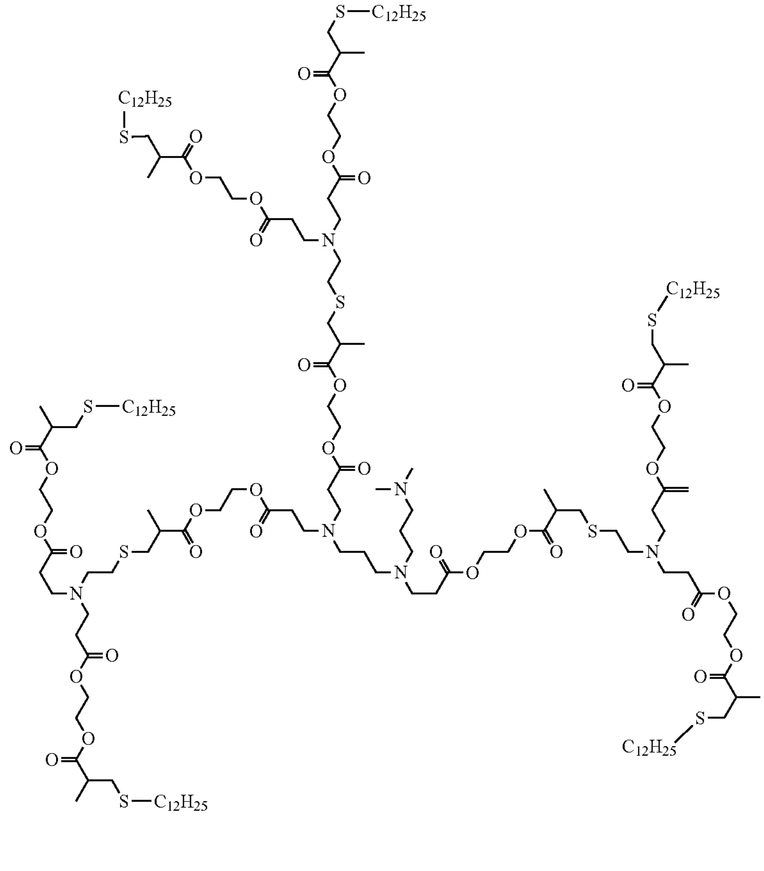 |

TABLE 4-continued
| Example ionizable cationic lipid dendrimers | |
|---|---|
| ID # | Structure |
| 3A3-g2-SC8 | 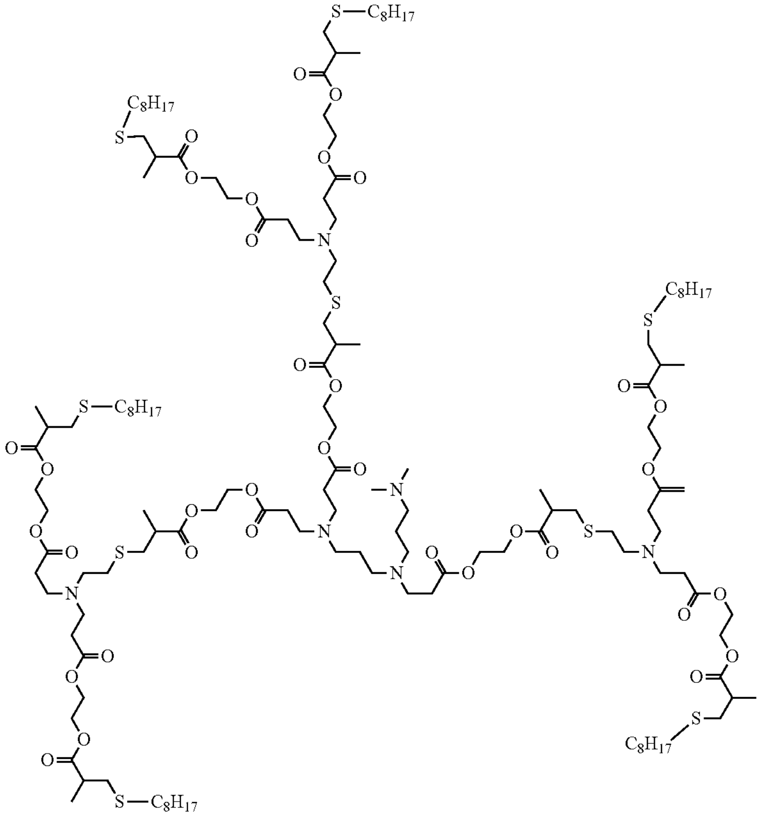 |
| 3A5-g2-SC12 | 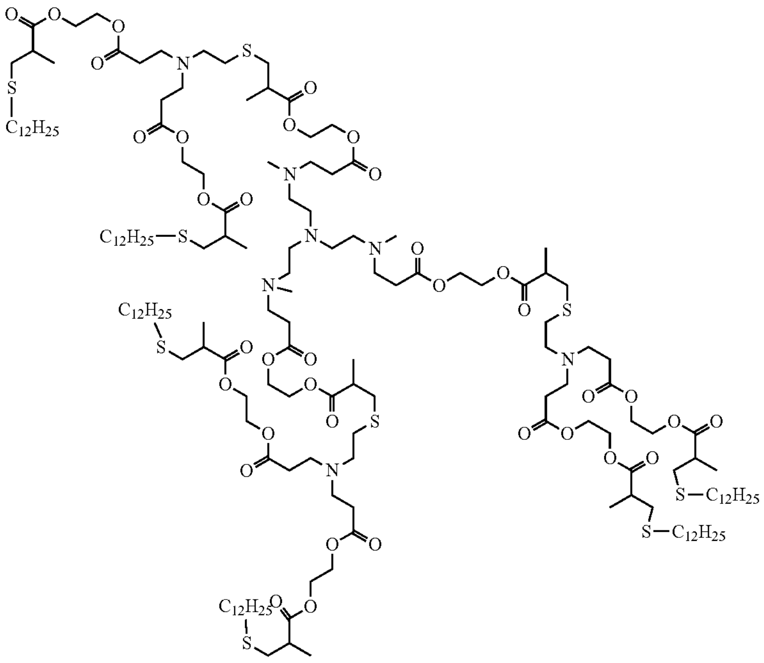 |

TABLE 4-continued
| Example ionizable cationic lipid dendrimers | |
|---|---|
| ID # | Structure |
| 2A11-g3-SC12 | 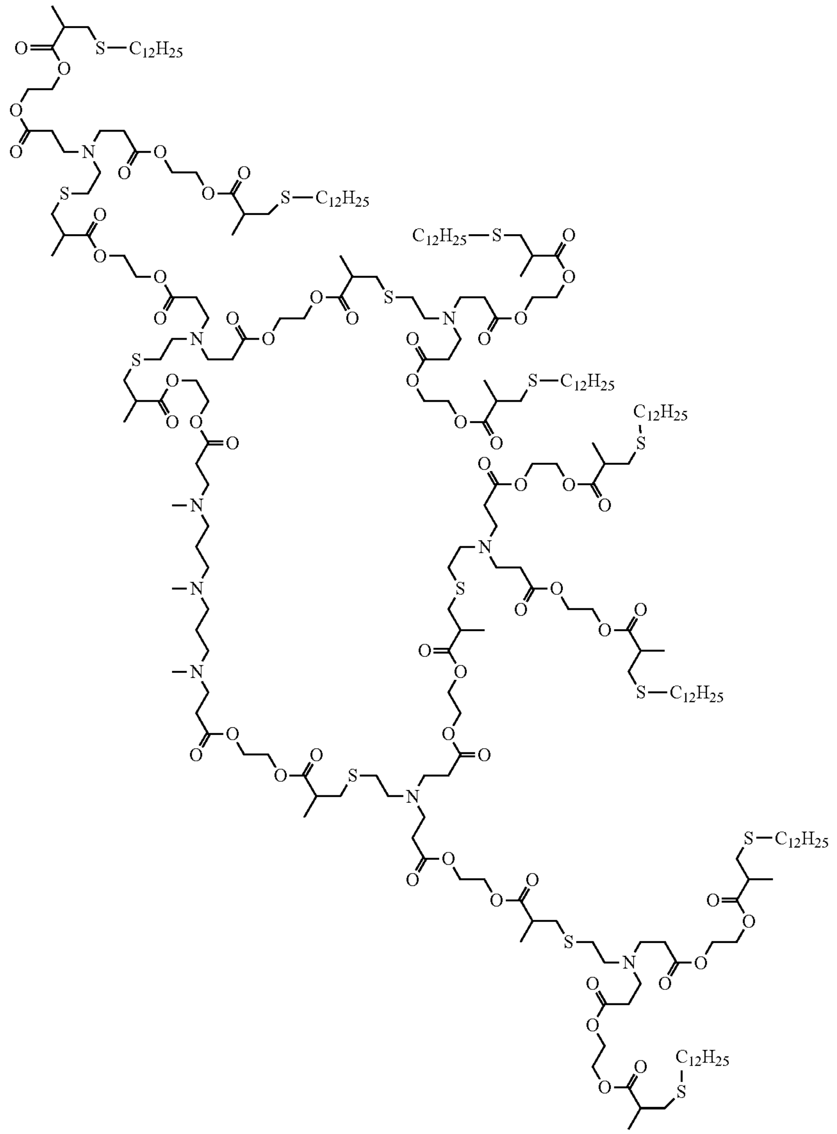 |

TABLE 4-continued
| Example ionizable cationic lipid dendrimers | |
|---|---|
| ID # | Structure |
| 2A11-g3-SC8 | 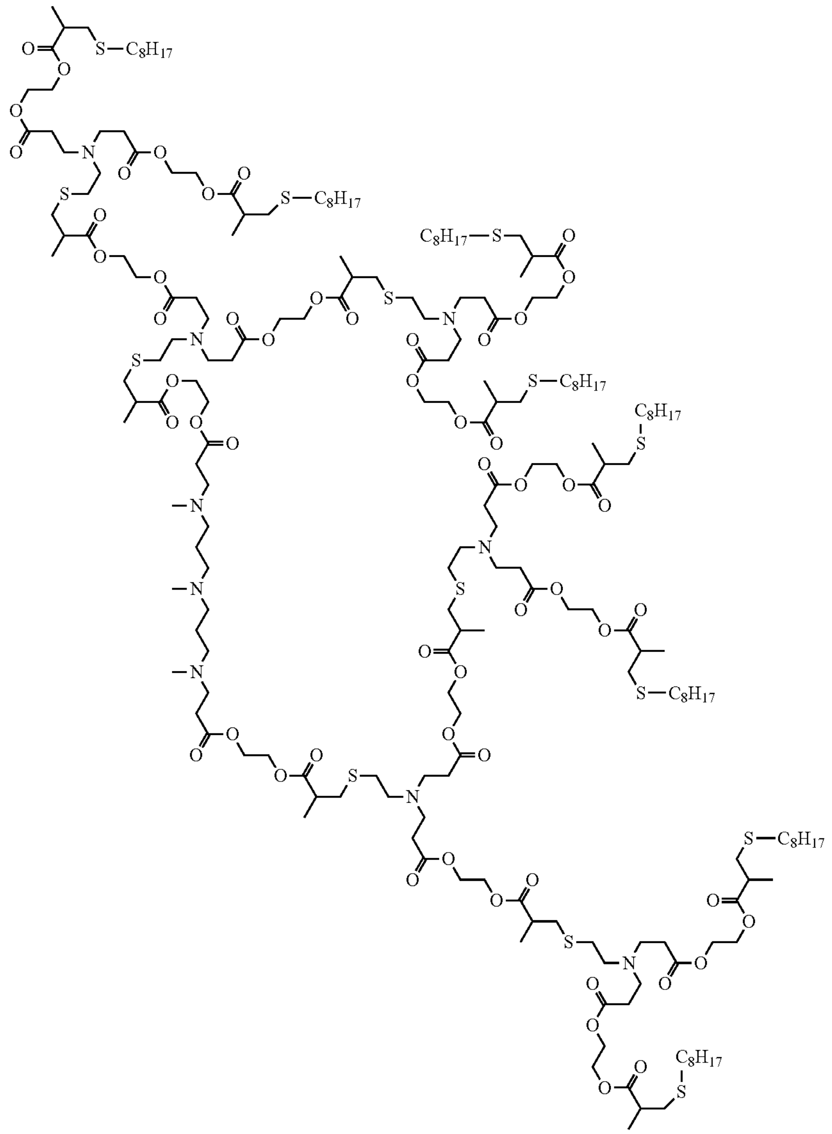 |

TABLE 4-continued
| Example ionizable cationic lipid dendrimers | |
|---|---|
| ID # | Structure |
| 1A2-g4-SC12 | 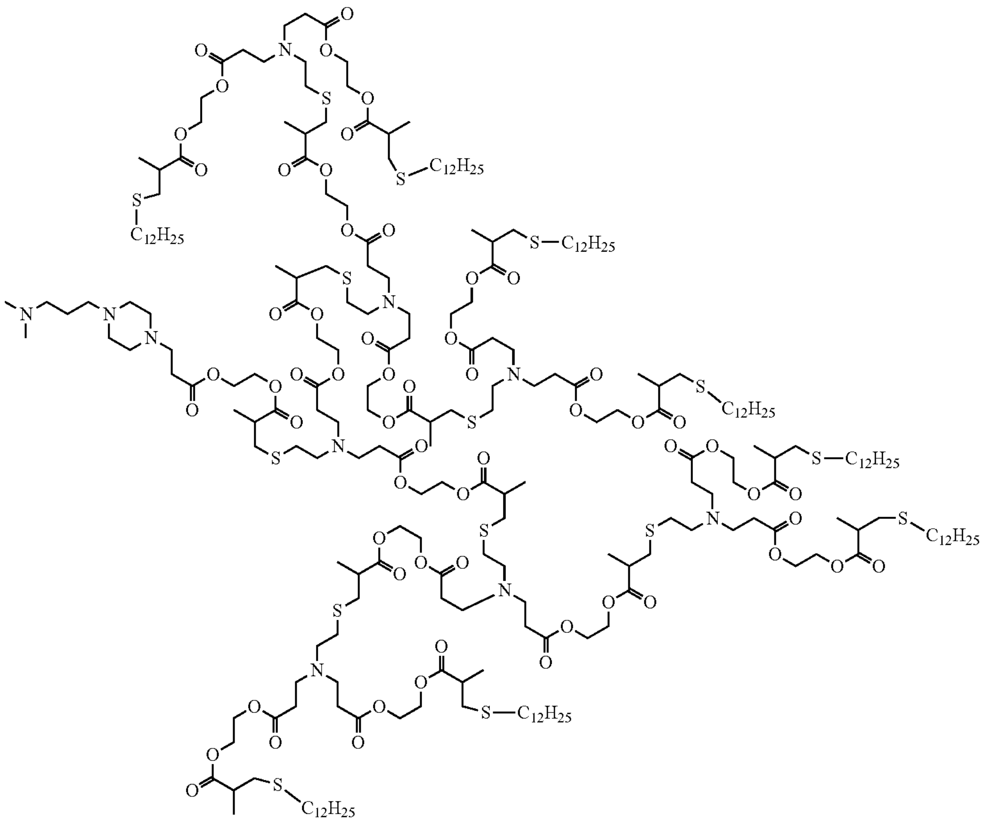 |
| 4A1-g2-SC12 | 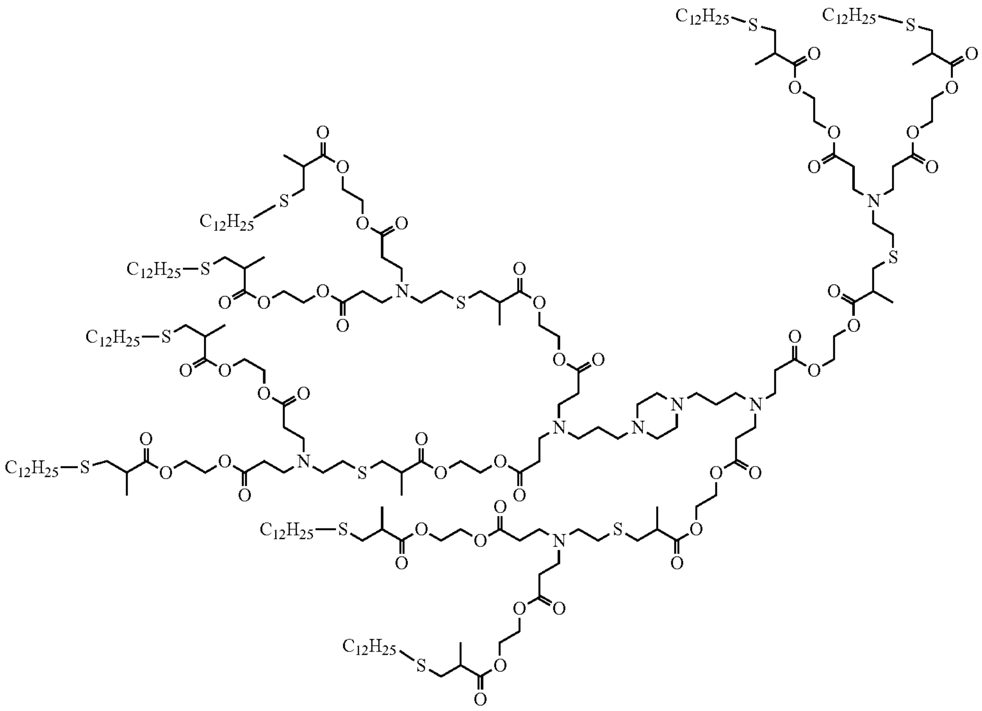 |

TABLE 4-continued
Example ionizable cationic lipid dendrimers
| ID # | Structure |
| --- | --- |
| 1A2-g4-SC8 | 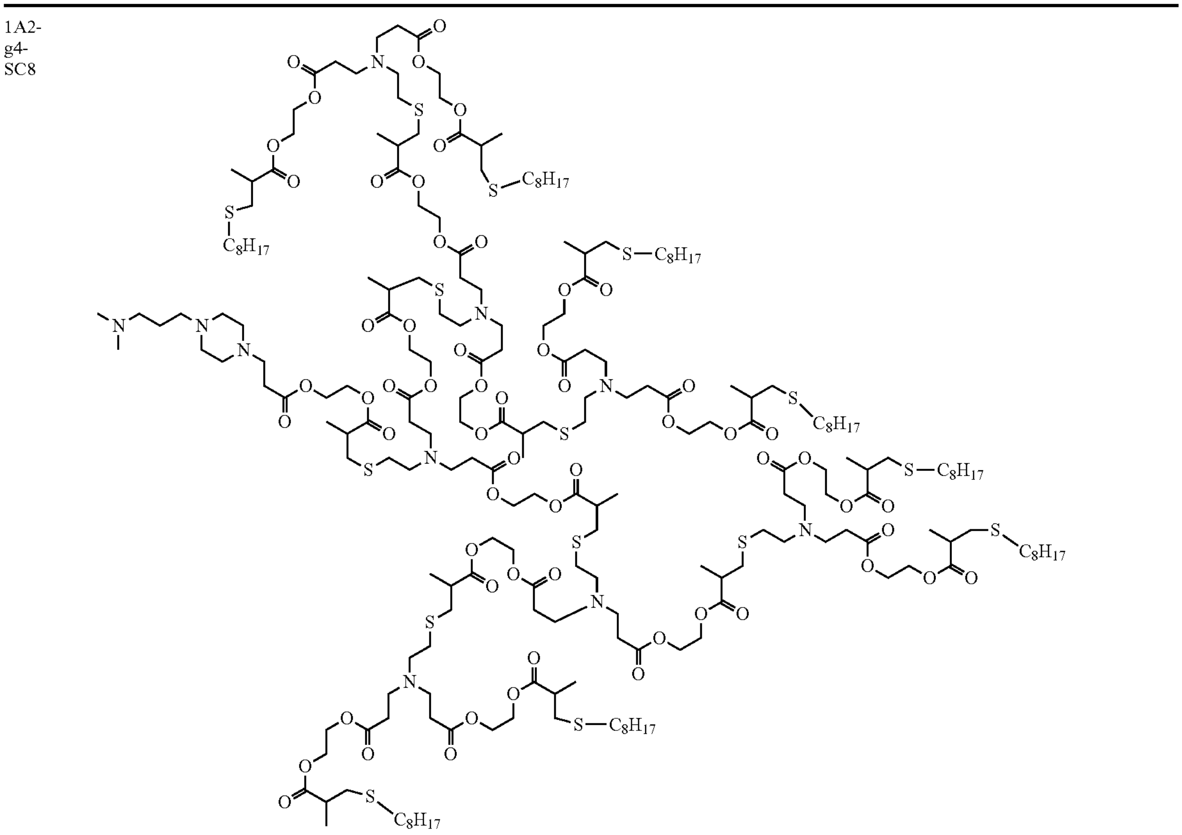 |
| 4A1-g2-SC8 | 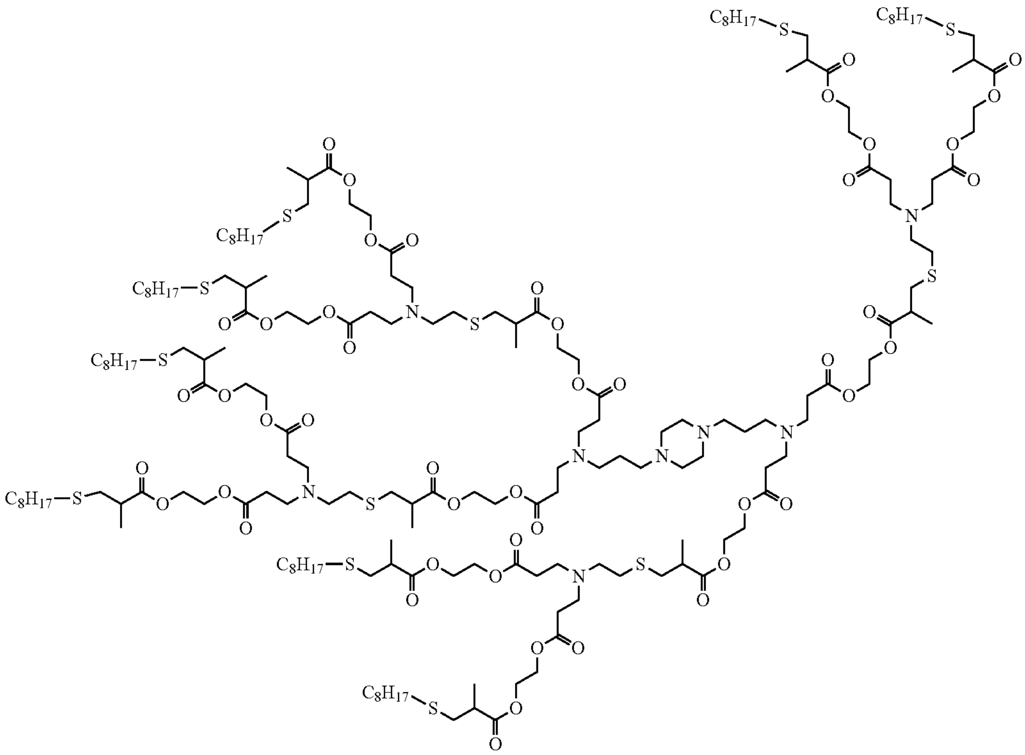 |

TABLE 4-continued
| Example ionizable cationic lipid dendrimers | |
|---|---|
| ID # | Structure |
| 4A3-g2-SC12 | 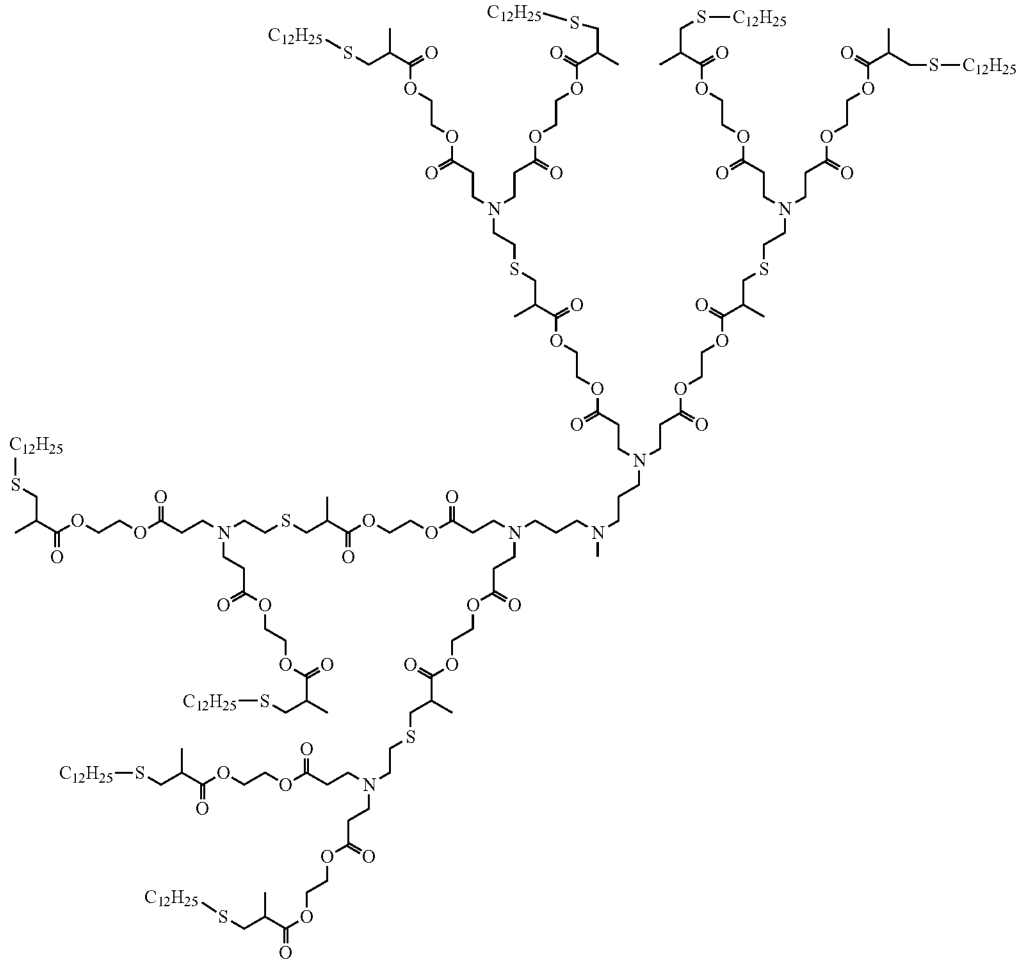 |

TABLE 4-continued
| Example ionizable cationic lipid dendrimers | |
|---|---|
| ID # | Structure |
| 4A3-g2-SC8 | 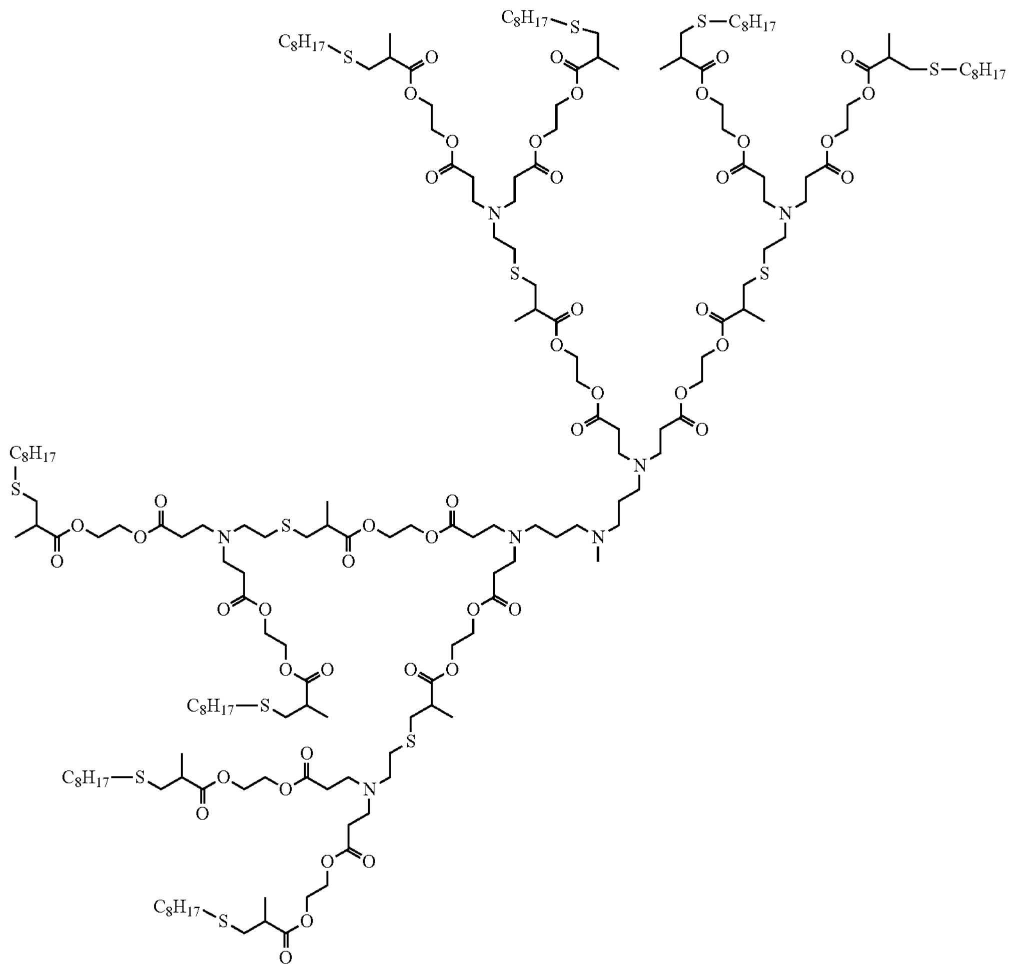 |

TABLE 4-continued
| Example ionizable cationic lipid dendrimers | |
|---|---|
| ID # | Structure |
| 1A2-g3-SC12 | 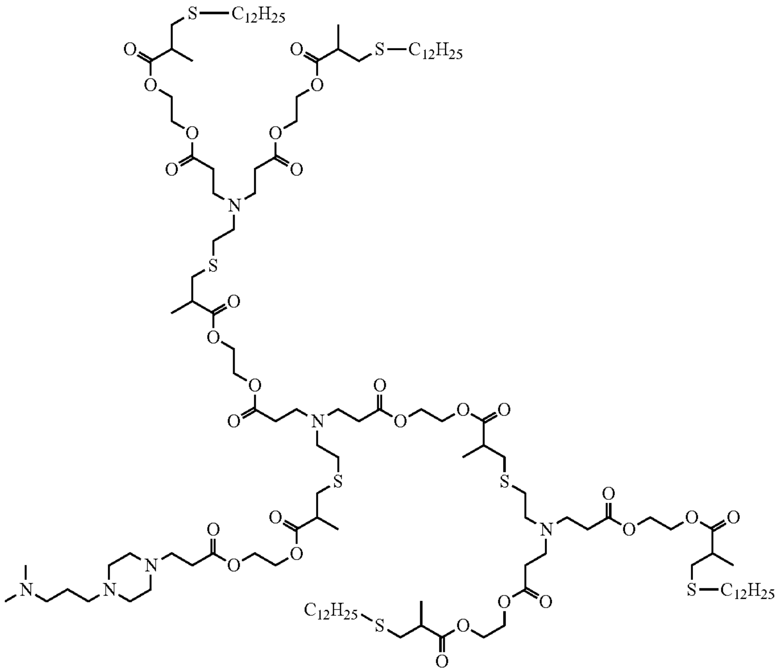 |
| 1A2-g3-SC8 | 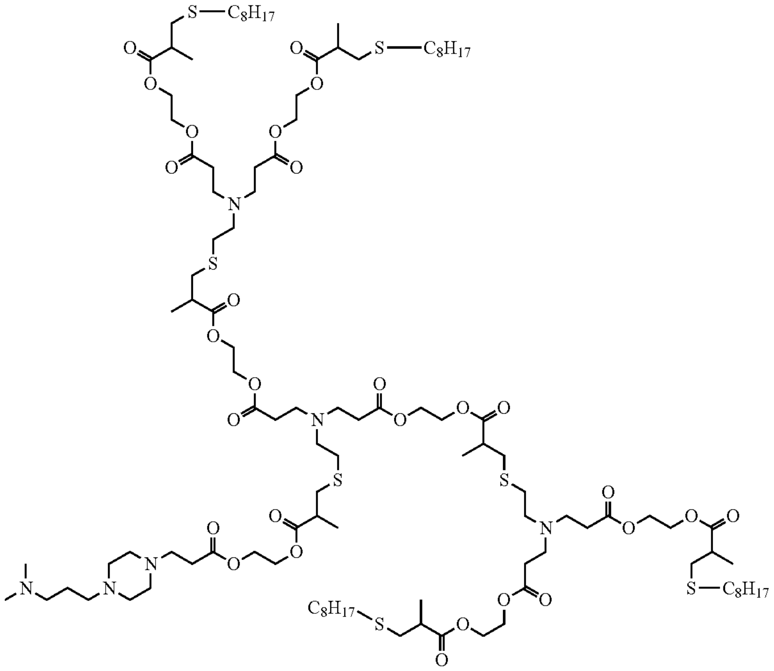 |

TABLE 4-continued
| Example ionizable cationic lipid dendrimers | |
|---|---|
| ID # | Structure |
| 2A2-g3-SC12 | 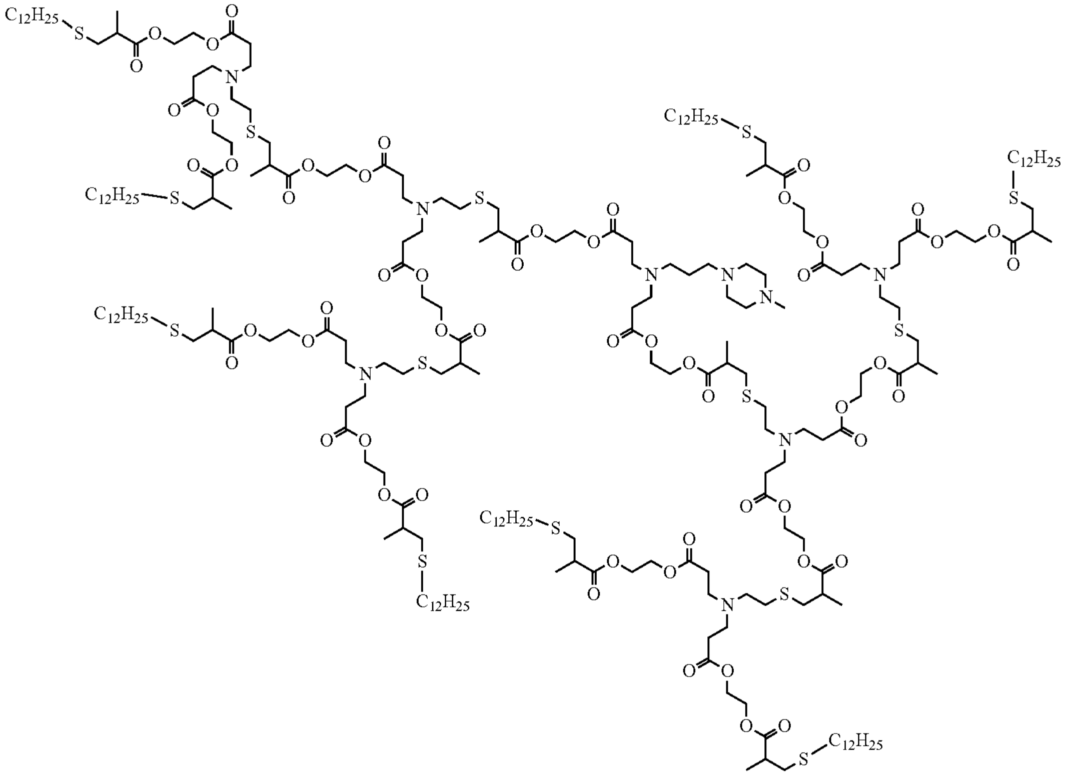 |
| 2A2-g3-SC8 | 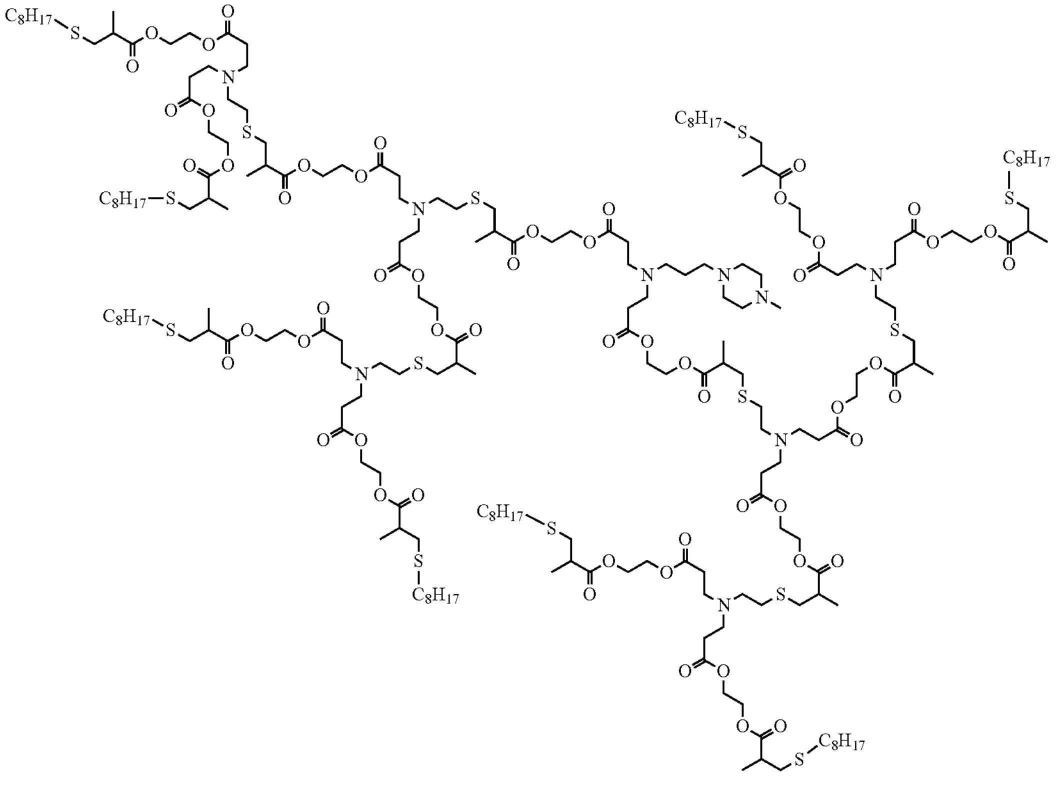 |

TABLE 4-continued
| Example ionizable cationic lipid dendrimers | |
|---|---|
| ID # | Structure |
| 5A2-4-SC8 (6-arm) | 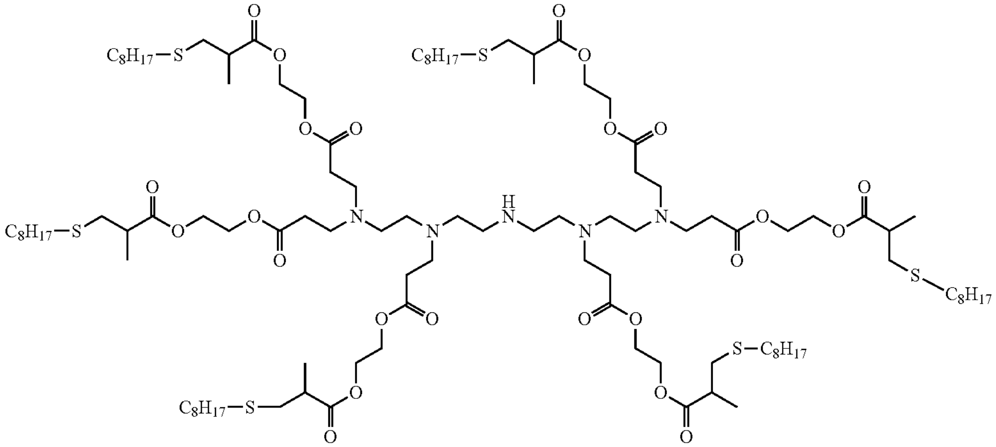 |
| 5A-5-SC8 (6 arm) | 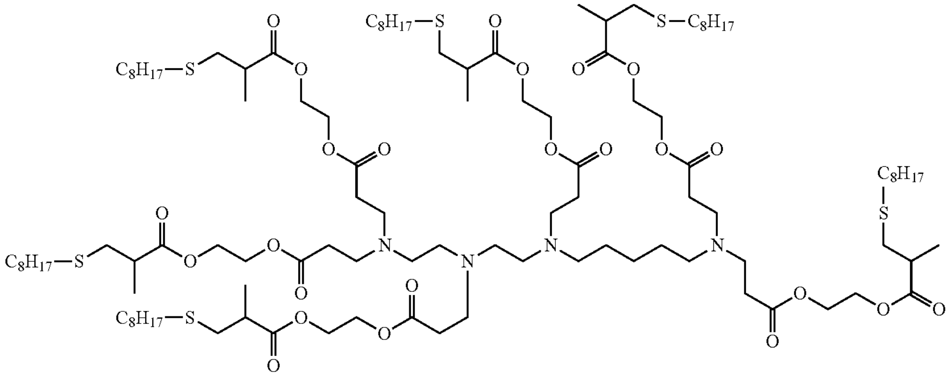 |
| 5A2-6-SC8 (6 arm) | 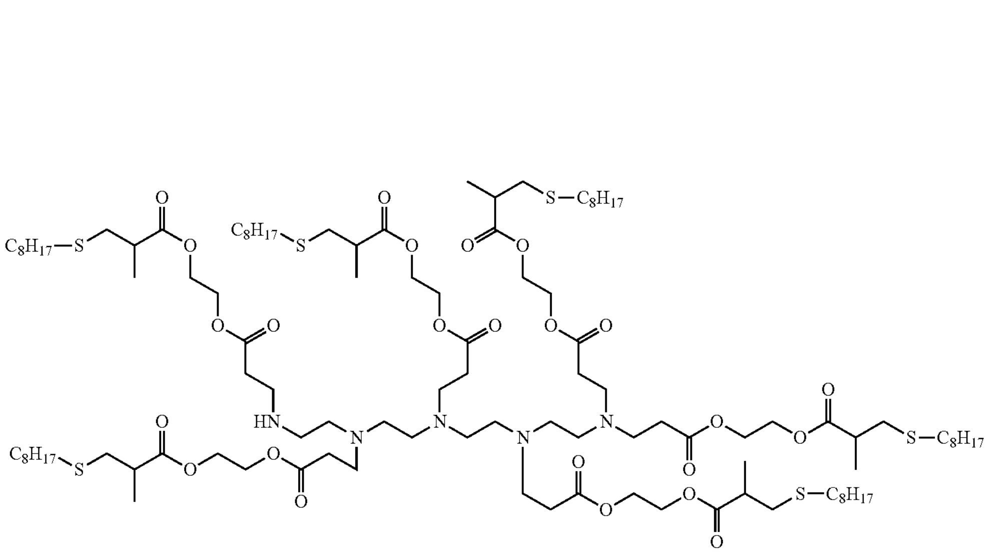 |

TABLE 4-continued
| Example ionizable cationic lipid dendrimers | |
|---|---|
| ID # | Structure |
| 5A2-1-SC8 (5-arm) | 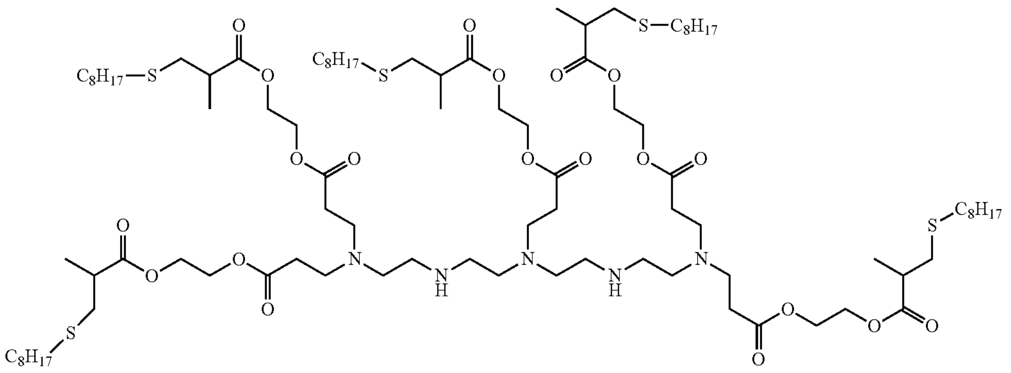 |
| 5A2-2-SC8 | 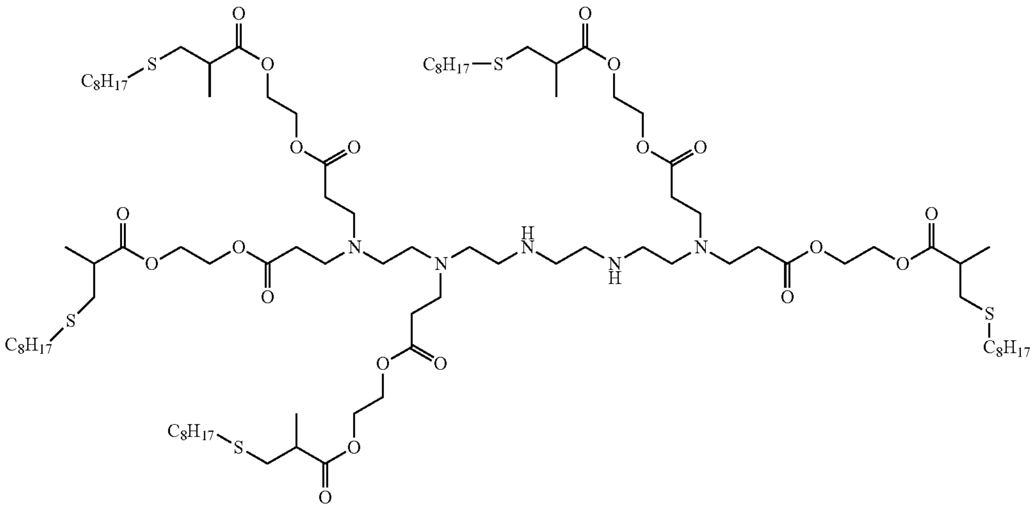 |
| 4A1-SC5 | 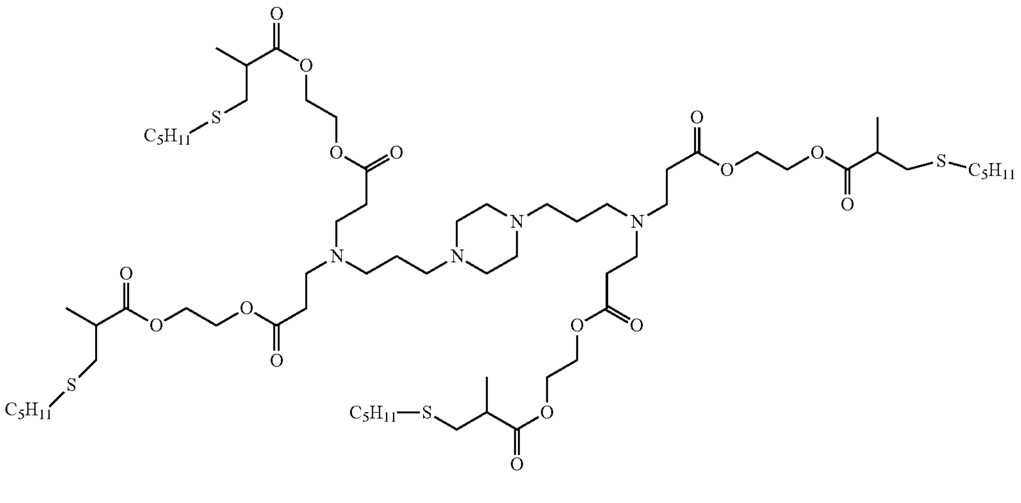 |

TABLE 4-continued
| Example ionizable cationic lipid dendrimers | |
| --- | --- |
| ID # | Structure |
| 4A1-SC8 | 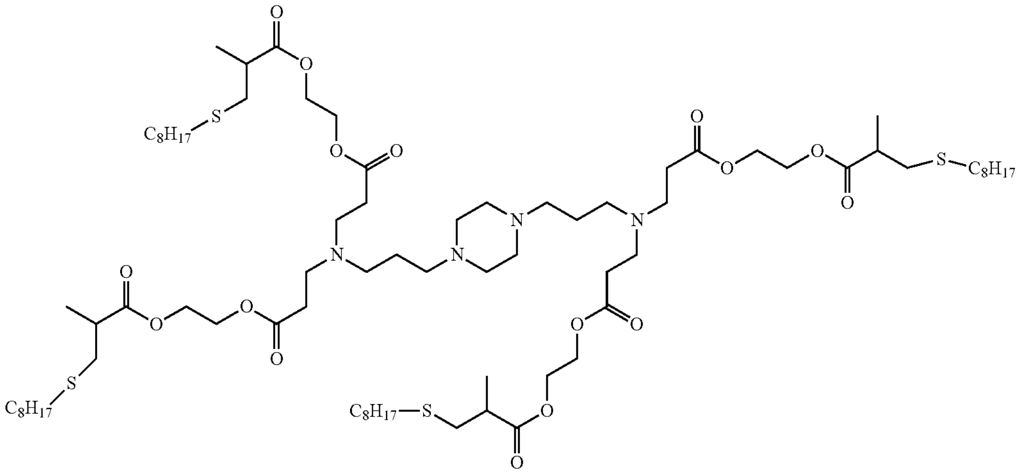 |
| 4A3-SC6 | 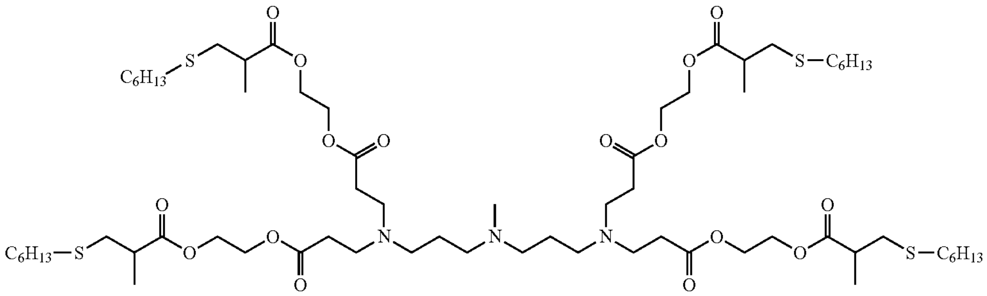 |
| 4A3-SC7 | 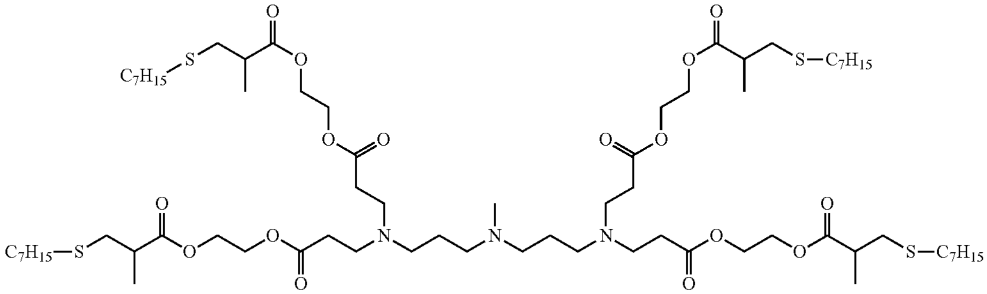 |
| 4A3-SC8 | 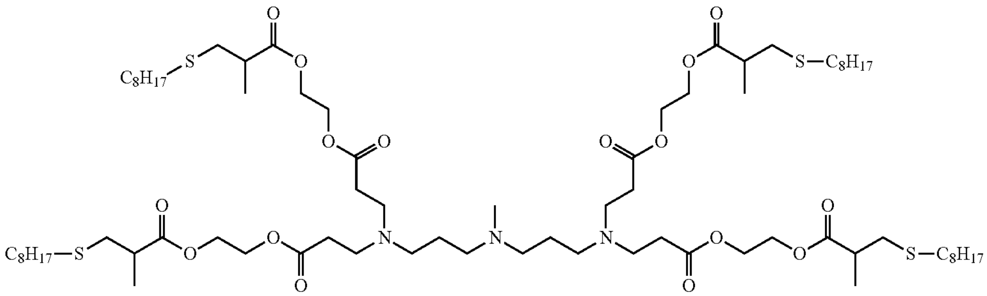 |

TABLE 4-continued
| Example ionizable cationic lipid dendrimers | |
| --- | --- |
| ID # | Structure |
| 5A4-2-SC5 (6 arm) | 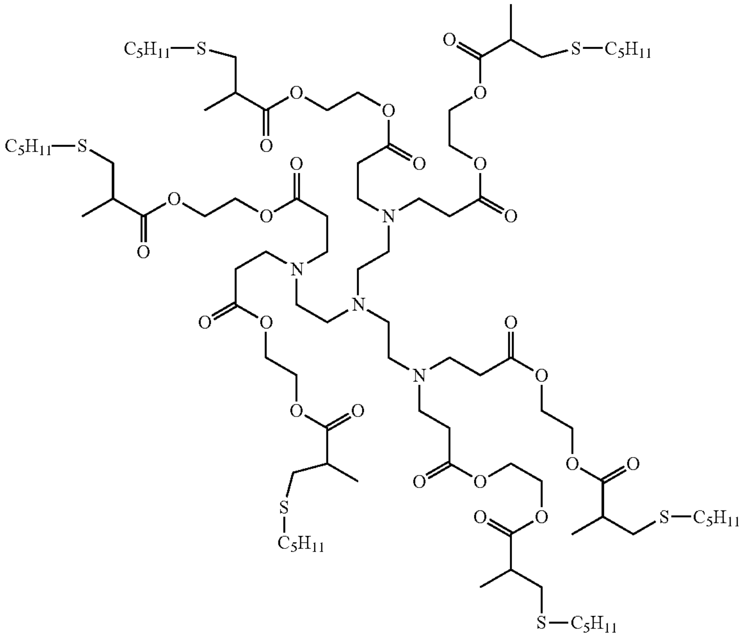 |
| 5A4-2-SC6 (6 arm) | 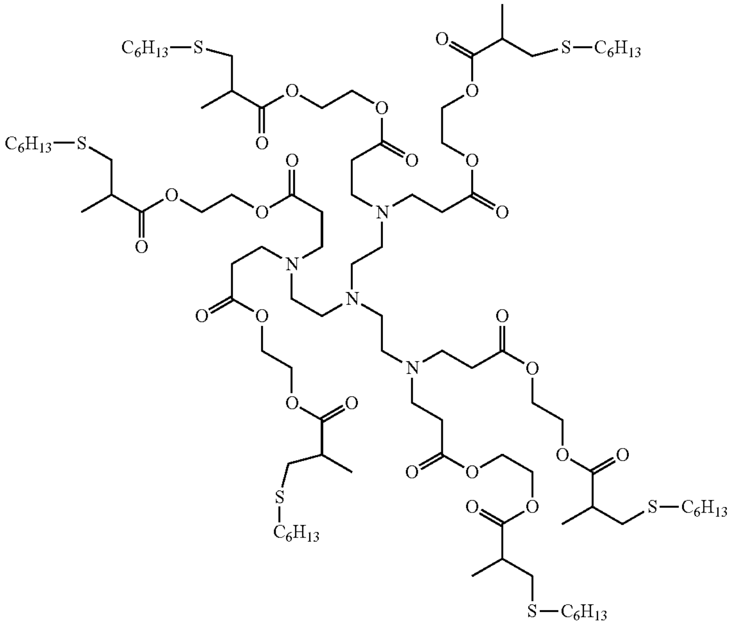 |

TABLE 4-continued
| Example ionizable cationic lipid dendrimers | |
|---|---|
| ID # | Structure |
| 5A2-4-SC8 (5-arm) | 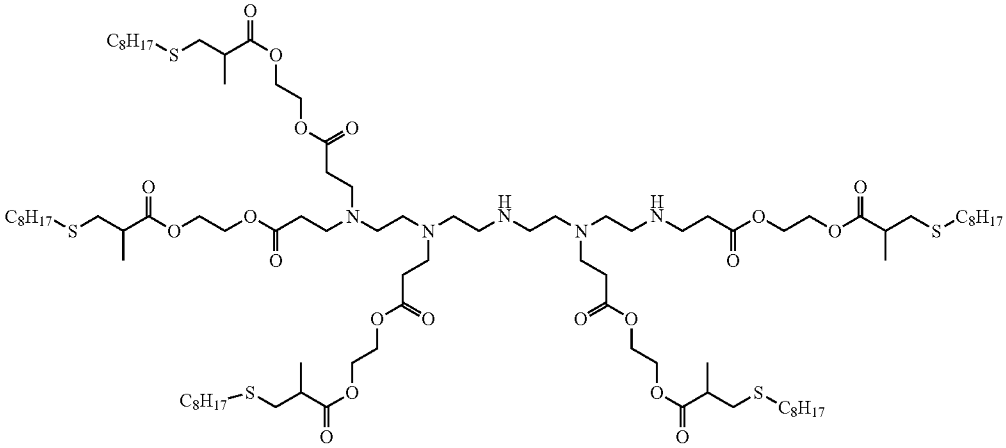 |
| 3A5-g2-SC8 | 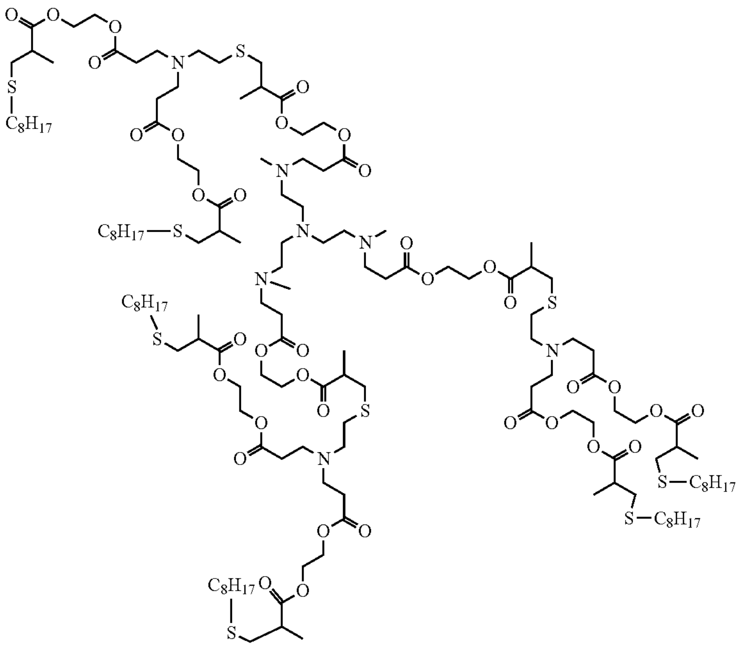 |
| 5A2-SC8 | 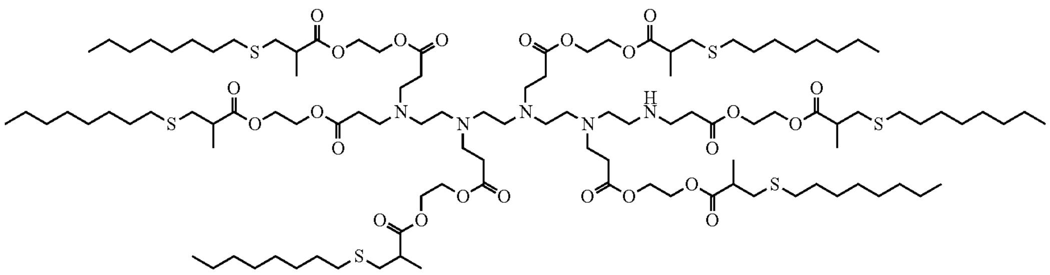 [SMILES: CCCCCCCCSCC(C)C(=O)OCCOC(=O)CCNCCN(CCC(=O)OCCOC(=O)C(C)CSCCCCCCCC)CCN(CCC(=O)OCCOC(=O)C(C)CSCCCCCCCC)CCN(CCC(=O)OCCOC(=O)C(C)CSCCCCCCCC)CCN(CCC(=O)OCCOC(=O)C(C)CSCCCCCCCC)CCC(=O)OCCOC(=O)C(C)CSCCCCCCCC] |

Other Ionizable cationic lipids

In some embodiments of the lipid composition, the ionizable cationic lipid comprises a structural formula (D-I'):

(D-I')

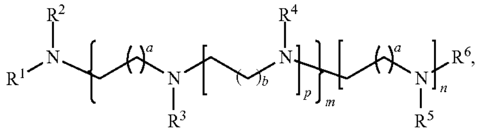

wherein:

a is 1 and b is 2, 3, or 4; or, alternatively, b is 1 and a is 2, 3, or 4;

m is 1 and n is 1; or, alternatively, m is 2 and n is 0; or, alternatively, m is 2 and n is 1; and $R^1$, $R^2$, $R^3$, $R^4$, $R^5$, and $R^6$ are each independently selected from the group consisting of H, —$CH_2CH(OH)R^7$, —$CH(R^7)CH_2OH$, —$CH_2CH_2C(=O)OR^7$, —$CH_2CH_2C(=O)NHR^7$, and —$CH_2R^7$, wherein $R^7$ is independently selected from $C_3$-$C_{18}$ alkyl, $C_3$-$C_{18}$ alkenyl having one C=C double bond, a protecting group for an amino group, —$C(=NH)NH_2$, a poly(ethylene glycol) chain, and a receptor ligand;

provided that at least two moieties among $R^1$ to $R^6$ are independently selected from —$CH_2CH(OH)R^7$, —$CH(R^7)CH_2OH$, —$CH_2CH_2C(=O)OR^7$, —$CH_2CH_2C(=O)NR^7$, or —$CH_2R^7$, wherein $R^7$ is independently selected from $C_3$-$C_{18}$ alkyl or $C_3$-$C_{18}$ alkenyl having one C=C double bond; and wherein one or more of the nitrogen atoms indicated in formula (D-I') may be protonated to provide an ionizable cationic lipid.

In some embodiments of the ionizable cationic lipid of formula (D-I'), a is 1. In some embodiments of the ionizable cationic lipid of formula (D-I'), b is 2. In some embodiments of the ionizable cationic lipid of formula (D-I'), m is 1. In some embodiments of the ionizable cationic lipid of formula (D-I'), n is 1. In some embodiments of the ionizable cationic lipid of formula (D-I'), $R^1$, $R^2$, $R^3$, $R^4$, $R^5$, and $R^6$ are each independently H or —$CH_2CH(OH)R^7$. In some embodiments of the ionizable cationic lipid of formula (D-I'), $R^1$, $R^2$, $R^3$, $R^4$, $R^5$, and $R^6$ are each independently H or

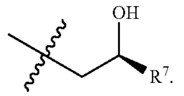

In some embodiments of the ionizable cationic lipid of formula (D-I'), $R^1$, $R^2$, $R^3$, $R^4$, $R^5$, and $R^6$ are each independently H or

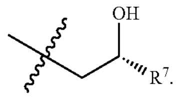

In some embodiments of the ionizable cationic lipid of formula (D-I'), $R^7$ is $C_3$-$C_{18}$ alkyl (e.g., $C_6$-$C_{12}$ alkyl).

In some embodiments, the ionizable cationic lipid of formula (D-I') is 13,16,20-tris(2-hydroxydodecyl)-13,16,20,23-tetraazapentatricontane-11,25-diol:

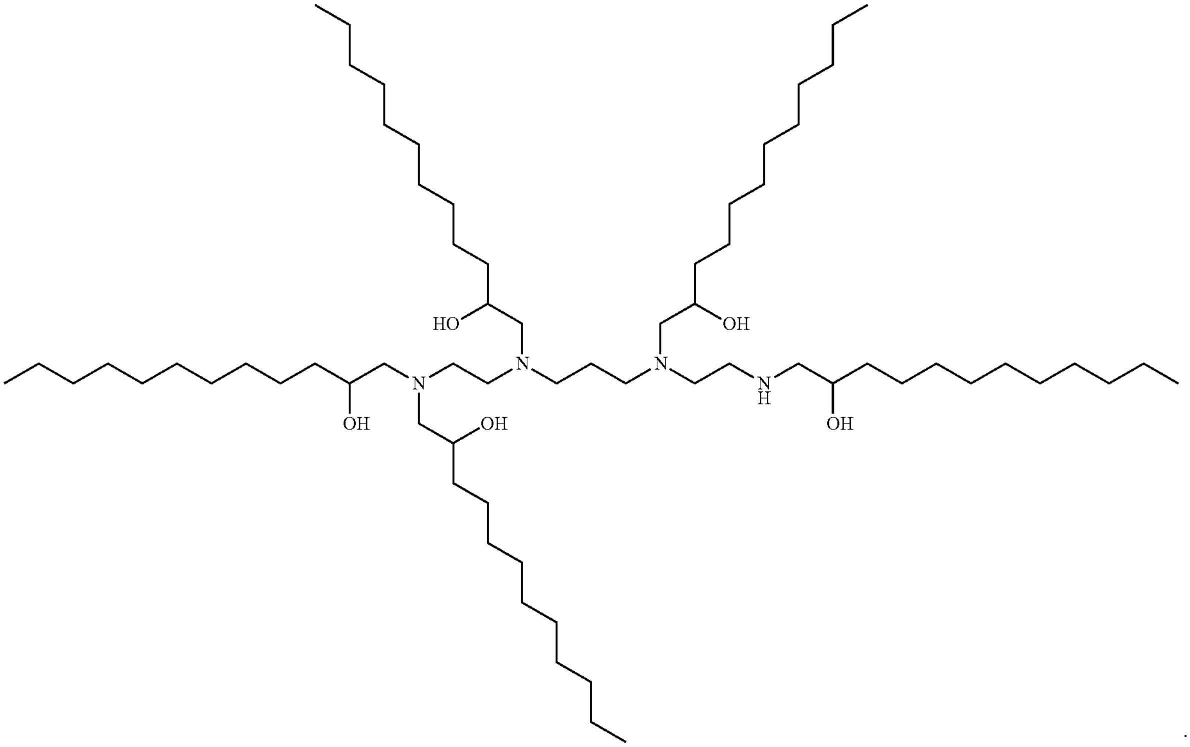 [SMILES: CCCCCCCCCCC(O)CNCCN(CCCN(CCN(CC(O)CCCCCCCCCC)CC(O)CCCCCCCCCC)CC(O)CCCCCCCCCC)CC(O)CCCCCCCCCC]

In some embodiments, the ionizable cationic lipid of formula (D-I') is (11R,25R)-13,16,20-tris((R)-2-hydroxydodecyl)-13,16,20,23-tetraazapentatricontane-11,25-diol:

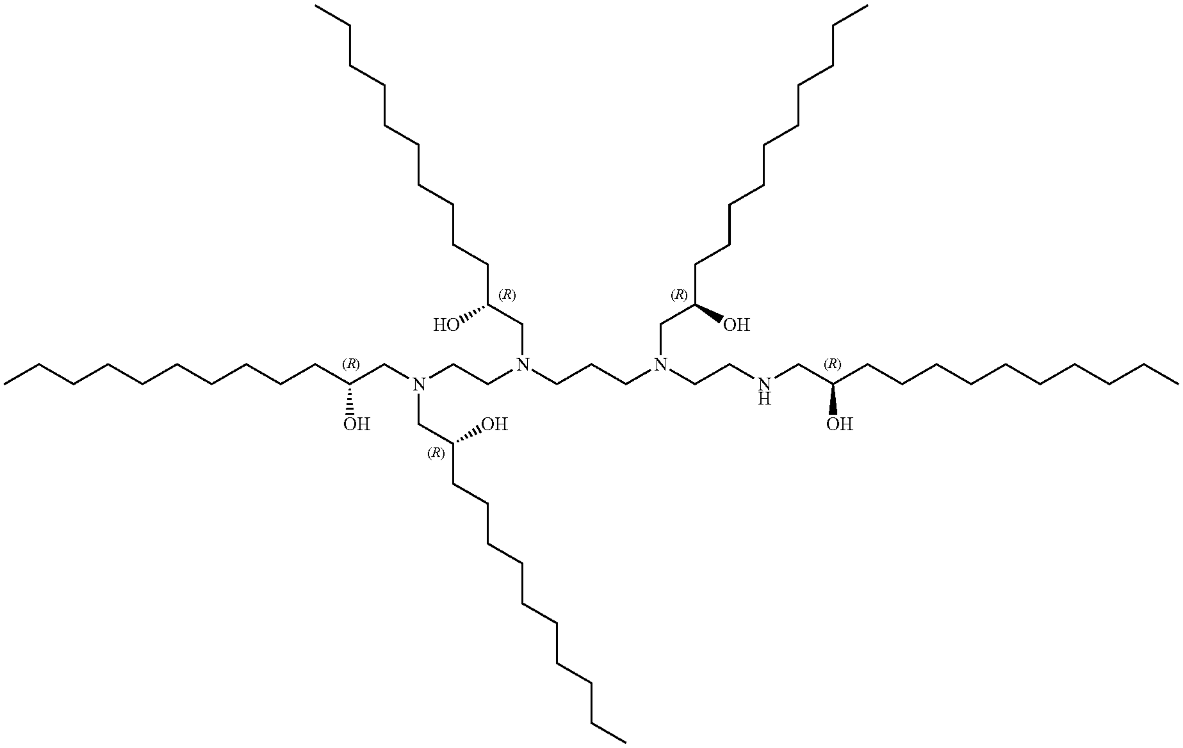

Additional ionizable cationic lipids that can be used in the compositions and methods of the present application include those ionizable cationic lipids as described in International Patent Publication WO2010144740, WO2013149140, WO2016118725, WO2016118724, WO2013063468, WO2016205691, WO2015184256, WO2016004202, WO2015199952, WO2017004143, WO2017075531, WO2017117528, WO2017049245, WO2017173054 and WO2015095340, which are incorporated herein by reference for all purposes. Examples of those ionizable cationic lipids include but are not limited to those as shown in Table 5.

TABLE 5

| # | Example Ionizable cationic lipids<br>Structure of example ionizable cationic lipid |
|---|---|
| 1 | 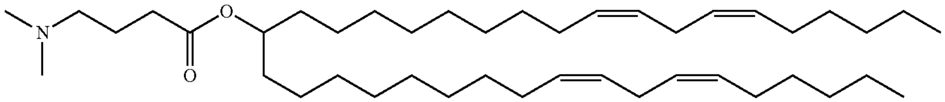 [SMILES: CCCCC/C=C\C/C=C\CCCCCCCCC(CCCCCCCC/C=C\C/C=C\CCCCC)OC(=O)CCCN(C)C] |
| 2 | 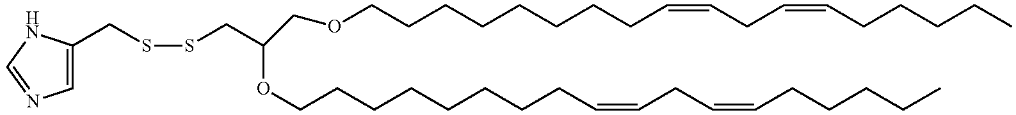 [SMILES: CCCCC/C=C\C/C=C\CCCCCCCCOCC(CSSCc1cnc[nH]1)OCCCCCCCC/C=C\C/C=C\CCCCC]<br>(HGT4004) |
| 3 | 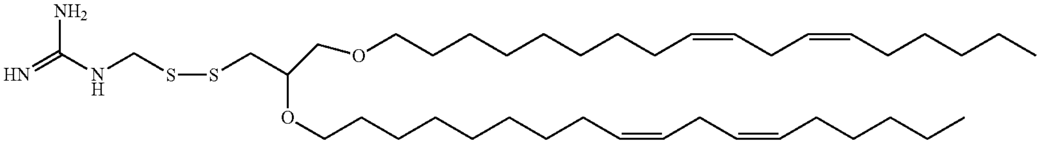 [SMILES: CCCCC/C=C\C/C=C\CCCCCCCCOCC(CSSCNC(=N)N)OCCCCCCCC/C=C\C/C=C\CCCCC]<br>(HGT4000) |

TABLE 5-continued
| # | Example Ionizable cationic lipids<br>Structure of example ionizable cationic lipid |
|---|---|
| 4 | 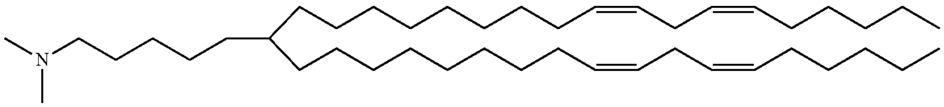 [SMILES: CCCCC/C=C\C/C=C\CCCCCCCCC(CCCCCCCC/C=C\C/C=C\CCCCC)CCCCCN(C)C]<br>(HGT5000) |
| 5 | 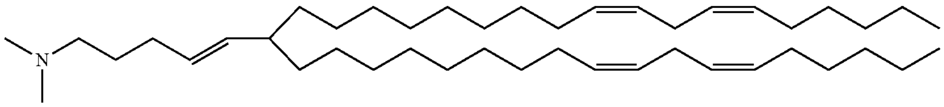 [SMILES: CCCCC/C=C\C/C=C\CCCCCCCCC(/C=C/CCCN(C)C)CCCCCCCC/C=C\C/C=C\CCCCC]<br>(HGT5001) |
| 6 | 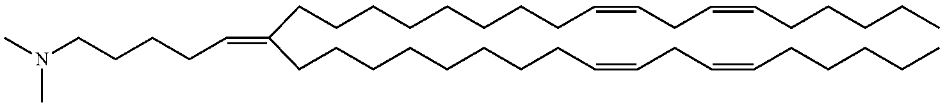 [SMILES: CCCCC/C=C\C/C=C\CCCCCCCCC(=CCCCCN(C)C)CCCCCCCC/C=C\C/C=C\CCCCC]<br>(HGT5002) |
| 7 | 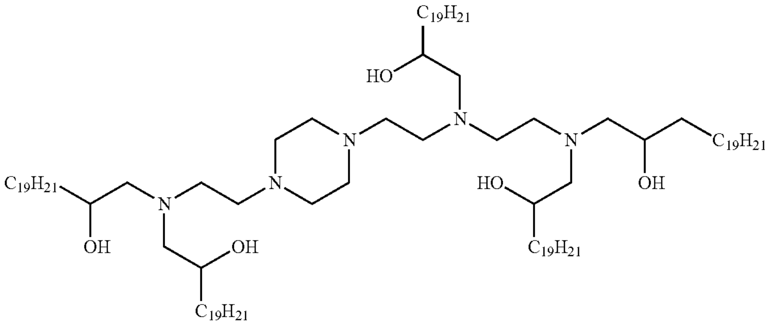 |
| 8 | 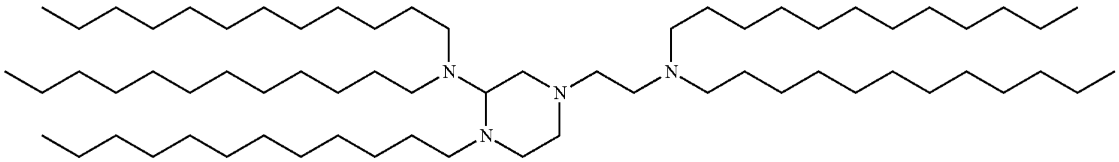 [SMILES: CCCCCCCCCCCCN(CCCCCCCCCCCC)CCN1CCN(CCCCCCCCCCCC)C(N(CCCCCCCCCCCC)CCCCCCCCCCCC)C1] |
| 9 | 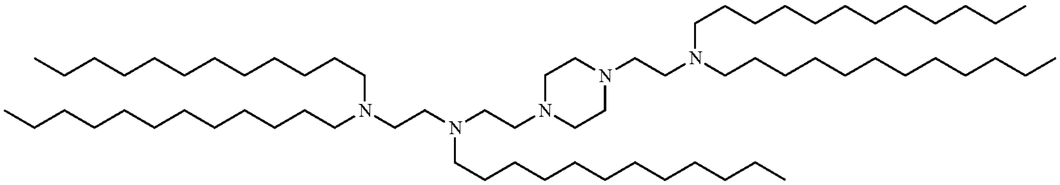 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1] |

TABLE 5-continued
| # | Example Ionizable cationic lipids<br>Structure of example ionizable cationic lipid |
|---|---|
| 10 | 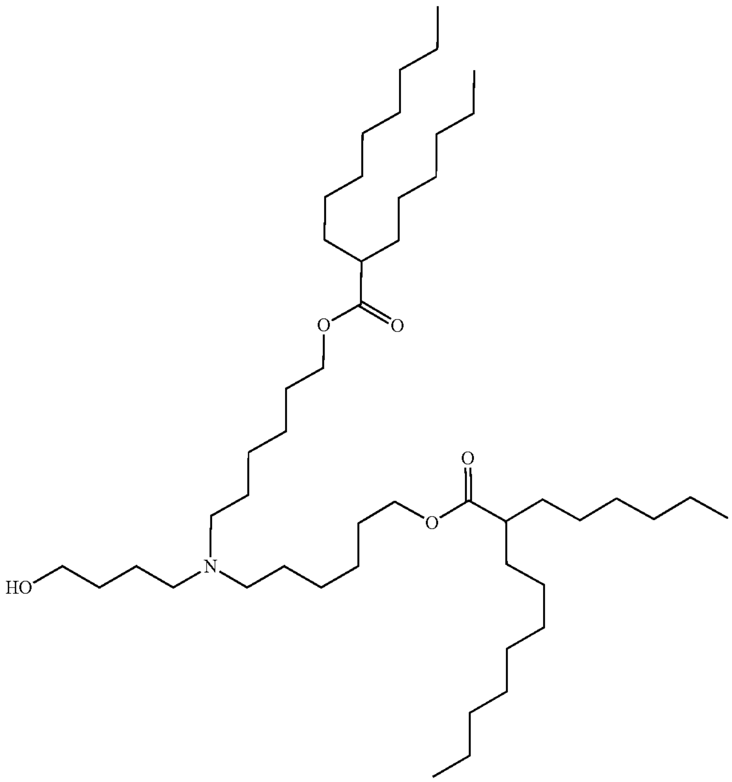 [SMILES: CCCCCCCCC(CCCCCC)C(=O)OCCCCCCN(CCCCO)CCCCCCOC(=O)C(CCCCCC)CCCCCCCC] |
| 11 | 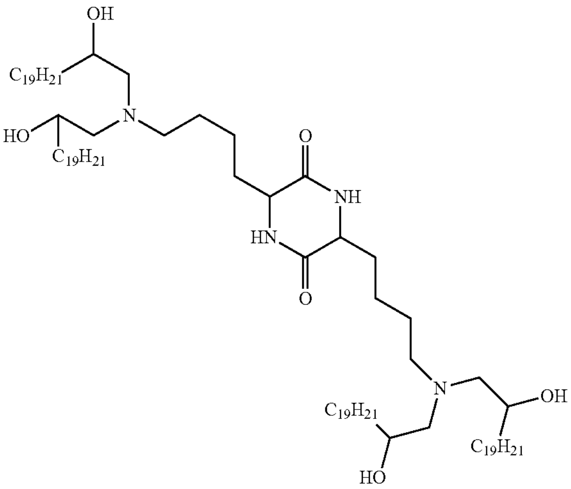 |

TABLE 5-continued
| # | Example Ionizable cationic lipids<br>Structure of example ionizable cationic lipid |
|---|---|
| 12 | 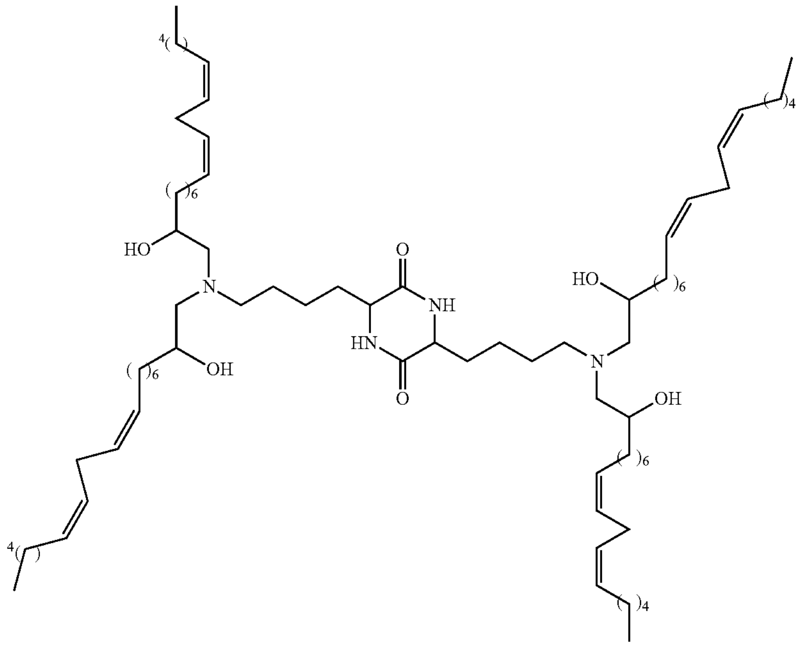 |
| 13 | 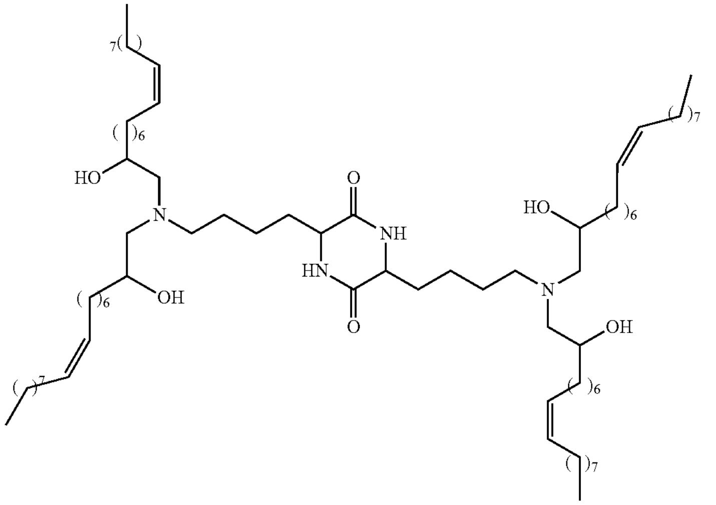 |

TABLE 5-continued
| # | Example Ionizable cationic lipids<br>Structure of example ionizable cationic lipid |
|---|---|
| 14 | 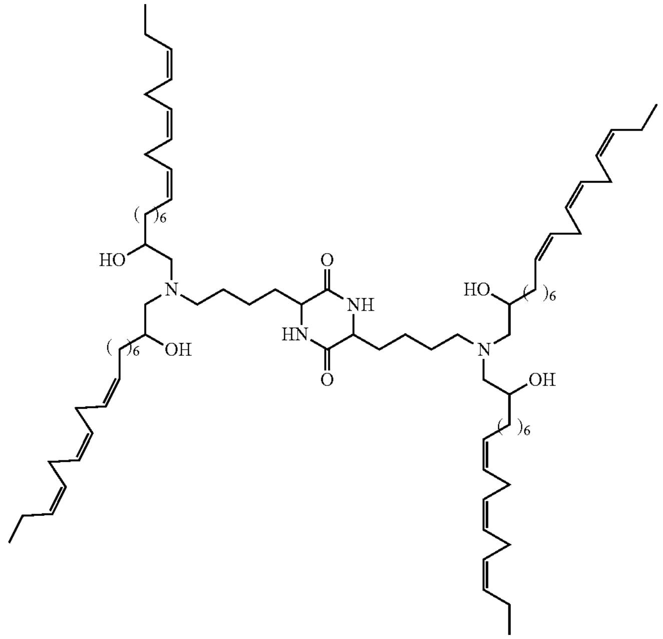 |
| 15 | 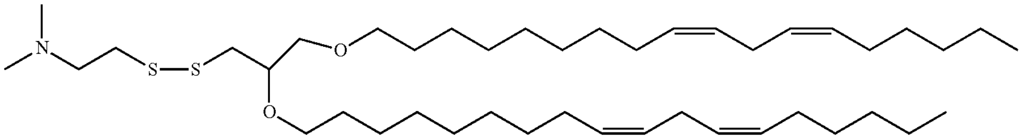 [SMILES: CCCCC/C=C\C/C=C\CCCCCCCCOCC(CSSCCN(C)C)OCCCCCCCC/C=C\C/C=C\CCCCC]<br>(HGT4003) |
| 16 | 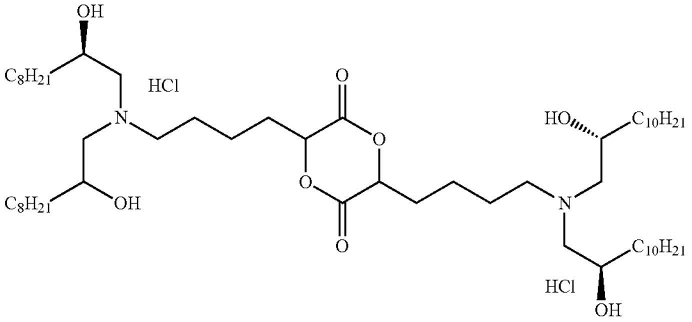<br>(Target 23); |
| 17 | 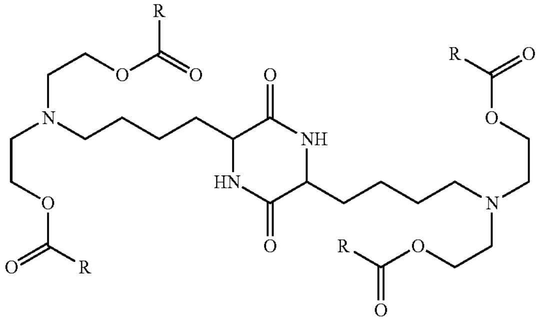 |

TABLE 5-continued
| # | Example Ionizable cationic lipids<br>Structure of example ionizable cationic lipid |
|---|---|
| | 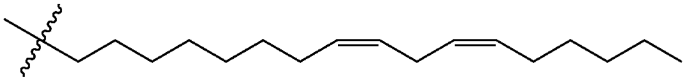 [SMILES: *CCCCCCC/C=C\C/C=C\CCCCC] |
| 18 | 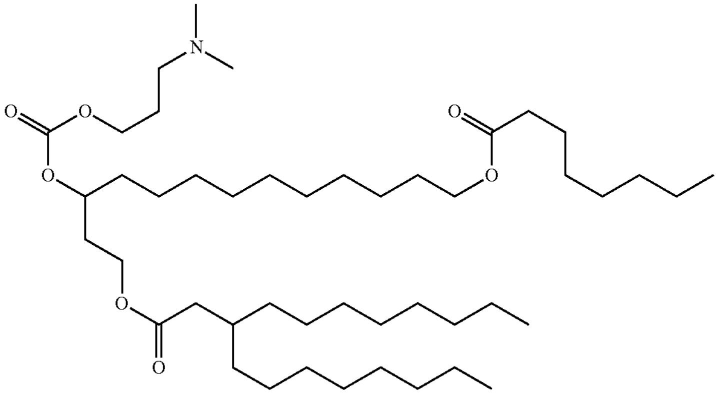 [SMILES: CCCCCCCCC(CCCCCCCC)CC(=O)OCCC(CCCCCCCCCCOC(=O)CCCCCCC)OC(=O)OCCCN(C)C] |
| 19 | 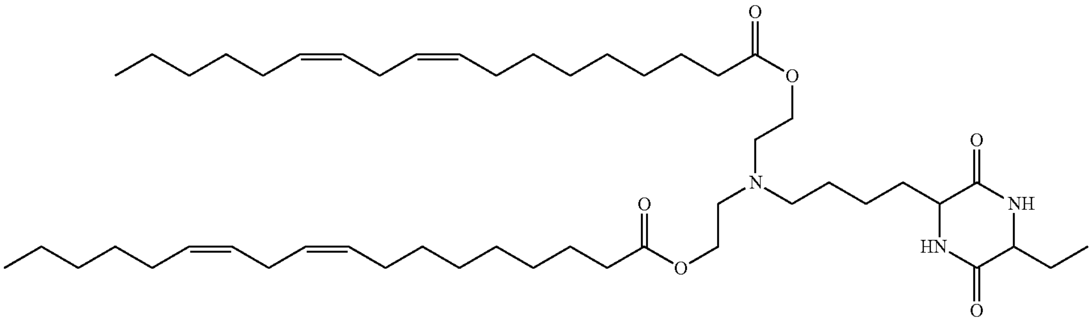 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC] |
| 20 | 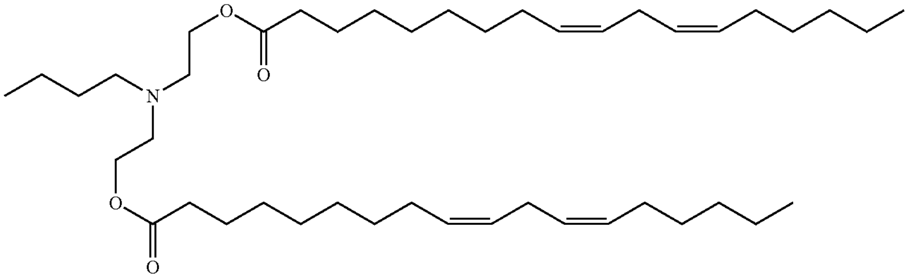 [SMILES: CCCCC/C=C\C/C=C\CCCCCCCC(=O)OCCN(CCCC)CCOC(=O)CCCCCCC/C=C\C/C=C\CCCCC] |
| 21 | 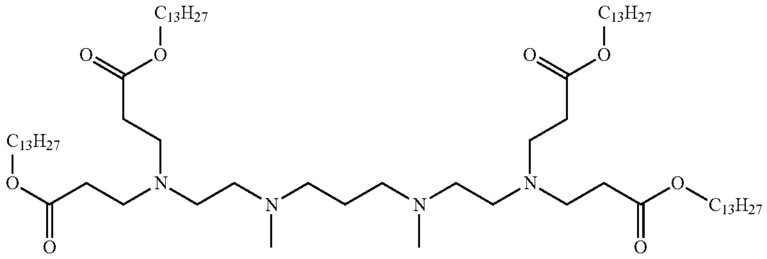 |

TABLE 5-continued
| # | Example Ionizable cationic lipids<br>Structure of example ionizable cationic lipid |
| --- | --- |
| 22 | 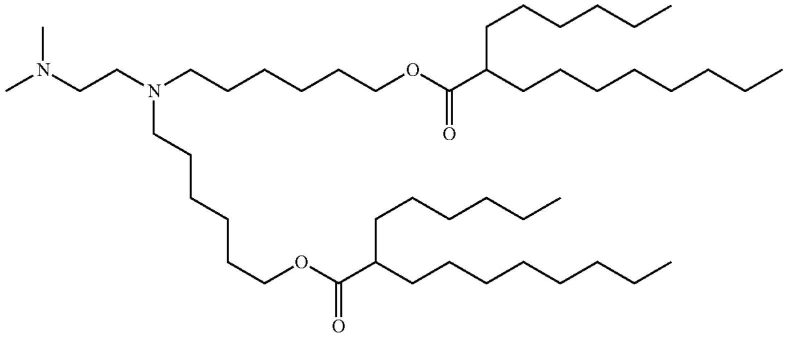 [SMILES: CCCCCCCCC(CCCCCC)C(=O)OCCCCCCN(CCCCCCOC(=O)C(CCCCCC)CCCCCCCC)CCN(C)C] |
| 23 | 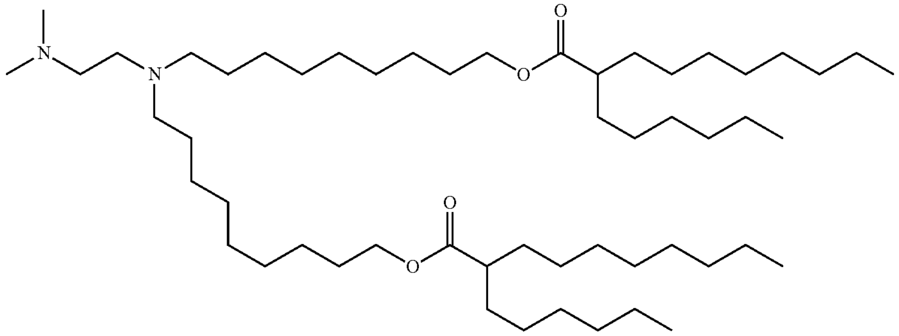 [SMILES: CCCCCCCCC(CCCCCC)C(=O)OCCCCCCCCCN(CCCCCCCCCOC(=O)C(CCCCCC)CCCCCCCC)CCN(C)C] |
| 24 | 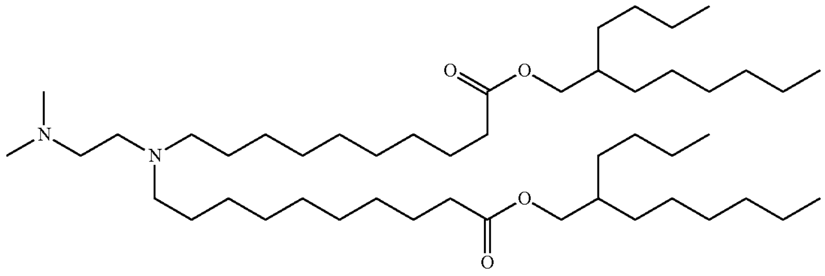 [SMILES: CCCCCCC(CCCC)COC(=O)CCCCCCCCCN(CCCCCCCCCC(=O)OCC(CCCC)CCCCCC)CCN(C)C] |
| 25 | 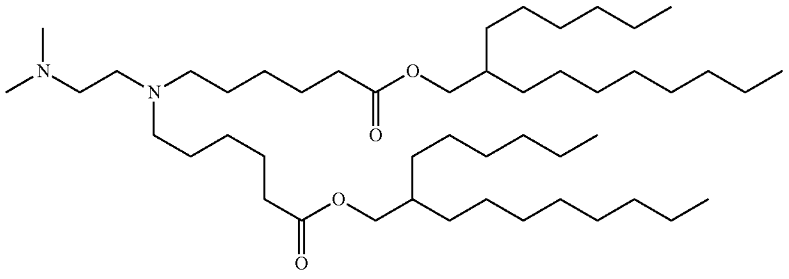 [SMILES: CCCCCCCCC(CCCCCC)COC(=O)CCCCCN(CCCCCC(=O)OCC(CCCCCC)CCCCCCCC)CCN(C)C] |
| 26 | 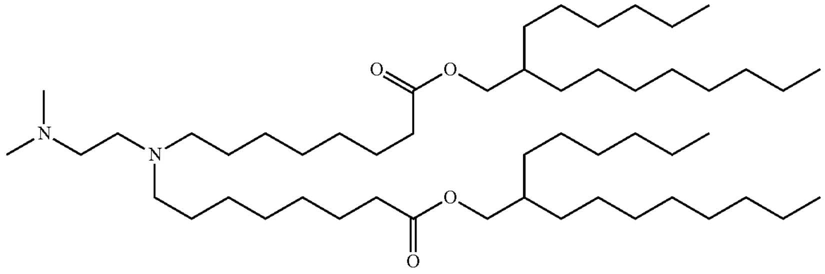 [SMILES: CCCCCCCCC(CCCCCC)COC(=O)CCCCCCCN(CCCCCCCC(=O)OCC(CCCCCC)CCCCCCCC)CCN(C)C] |

TABLE 5-continued
| # | Example Ionizable cationic lipids<br>Structure of example ionizable cationic lipid |
|---|---|
| 27 | 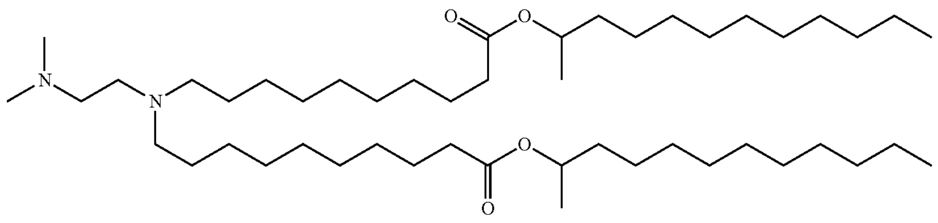 [SMILES: CCCCCCCCCCC(C)OC(=O)CCCCCCCCCN(CCCCCCCCCC(=O)OC(C)CCCCCCCCCC)CCN(C)C] |
| 28 | 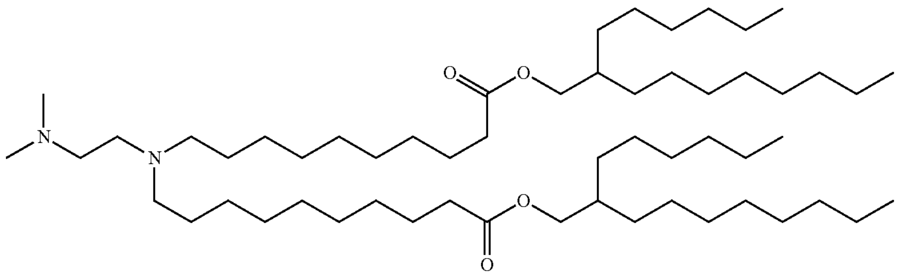 [SMILES: CCCCCCCCC(CCCCCC)COC(=O)CCCCCCCCCN(CCCCCCCCCC(=O)OCC(CCCCCC)CCCCCCCC)CCN(C)C] |
| 29 | 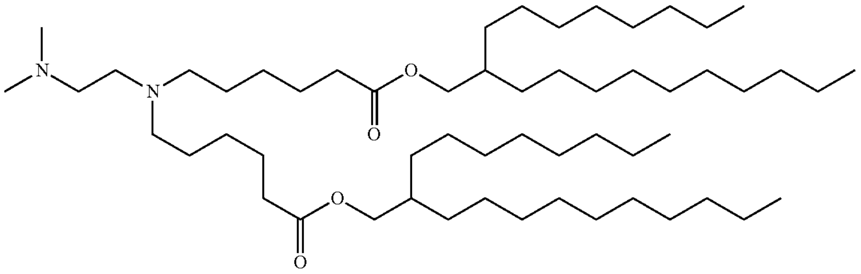 [SMILES: CCCCCCCCCCC(CCCCCCCC)COC(=O)CCCCCN(CCCCCC(=O)OCC(CCCCCCCC)CCCCCCCCCC)CCN(C)C] |
| 30 | 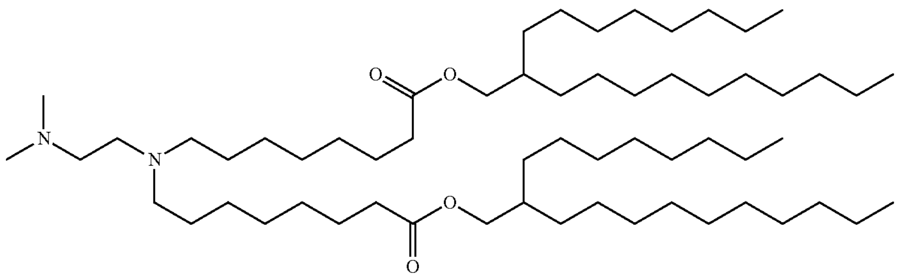 [SMILES: CCCCCCCCCCC(CCCCCCCC)COC(=O)CCCCCCCN(CCCCCCCC(=O)OCC(CCCCCCCC)CCCCCCCCCC)CCN(C)C] |
| 31 | 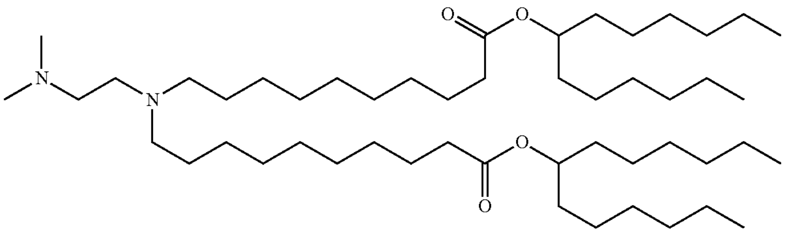 [SMILES: CCCCCCC(CCCCCC)OC(=O)CCCCCCCCCN(CCCCCCCCCC(=O)OC(CCCCCC)CCCCCC)CCN(C)C] |
| 32 | 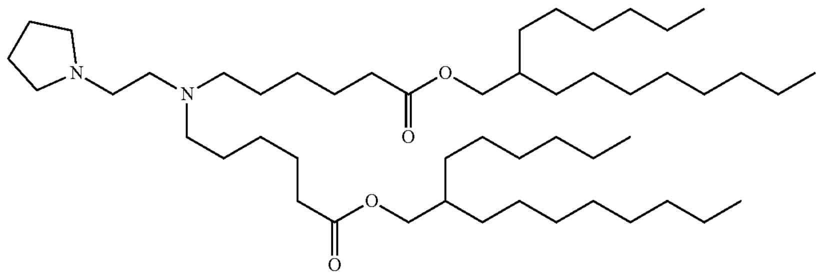 [SMILES: CCCCCCCCC(CCCCCC)COC(=O)CCCCCN(CCCCCC(=O)OCC(CCCCCC)CCCCCCCC)CCN1CCCC1] |

TABLE 5-continued
| # | Example Ionizable cationic lipids<br>Structure of example ionizable cationic lipid |
|---|---|
| 33 | 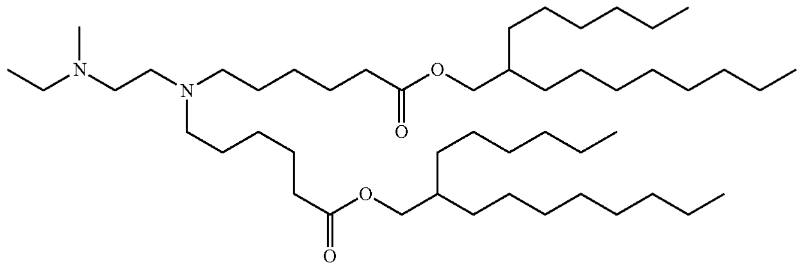 [SMILES: CCCCCCCCC(CCCCCC)COC(=O)CCCCCN(CCCCCC(=O)OCC(CCCCCC)CCCCCCCC)CCN(C)CC] |
| 34 | 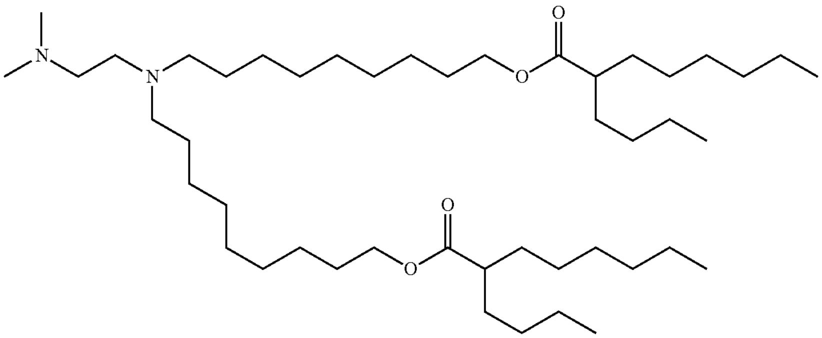 [SMILES: CCCCCCC(CCCC)C(=O)OCCCCCCCCCN(CCCCCCCCCOC(=O)C(CCCC)CCCCCC)CCN(C)C] |
| 35 | 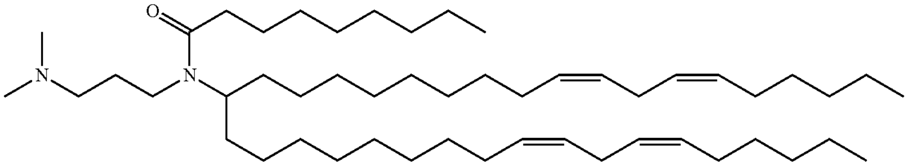 [SMILES: CCCCC/C=C\C/C=C\CCCCCCCCC(CCCCCCCC/C=C\C/C=C\CCCCC)N(CCCN(C)C)C(=O)CCCCCCCC] |
| 36 | 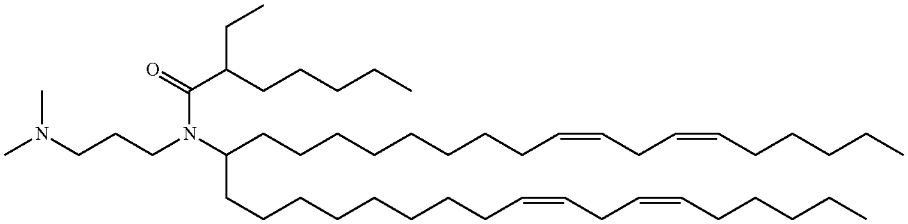 [SMILES: CCCCC/C=C\C/C=C\CCCCCCCCC(CCCCCCCC/C=C\C/C=C\CCCCC)N(CCCN(C)C)C(=O)C(CC)CCCCC] |
| 37 | 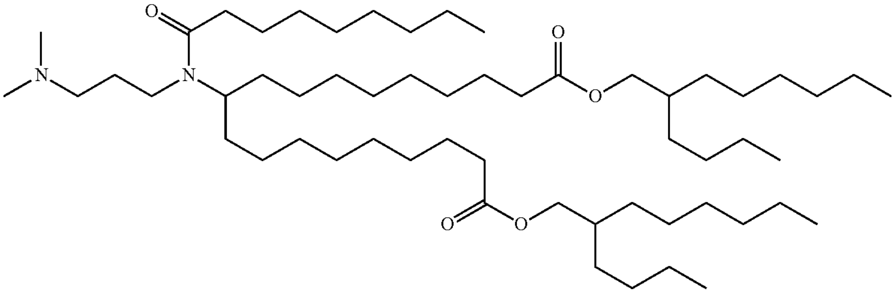 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] |
| 38 | 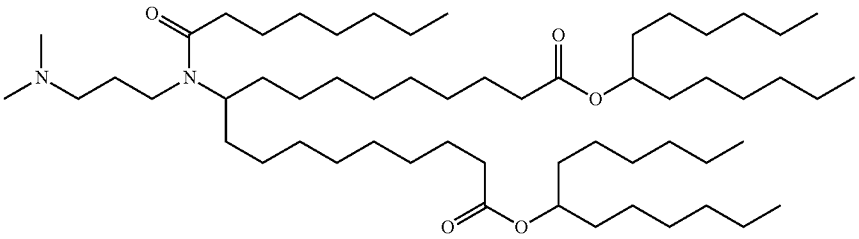 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

TABLE 5-continued
| # | Example Ionizable cationic lipids<br>Structure of example ionizable cationic lipid |
|---|---|
| 39 | 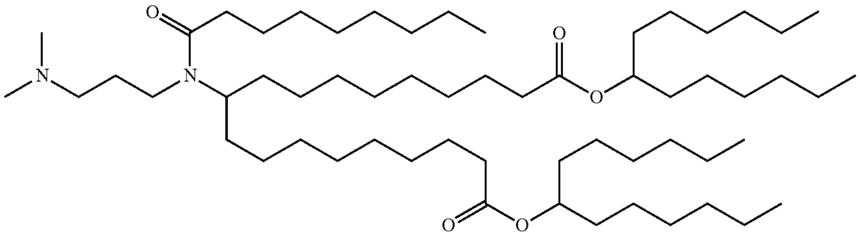 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] |
| 40 | 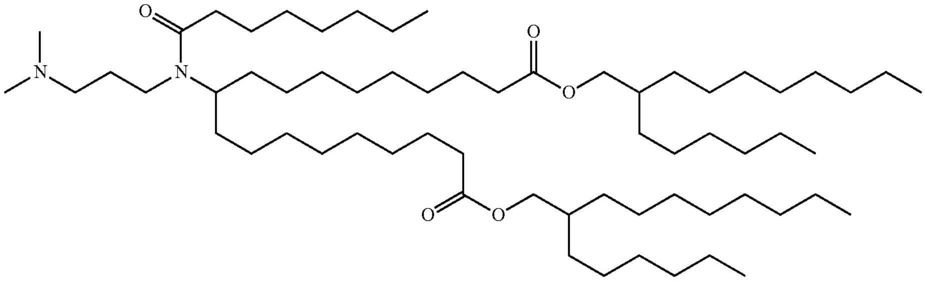 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] |
| 41 | 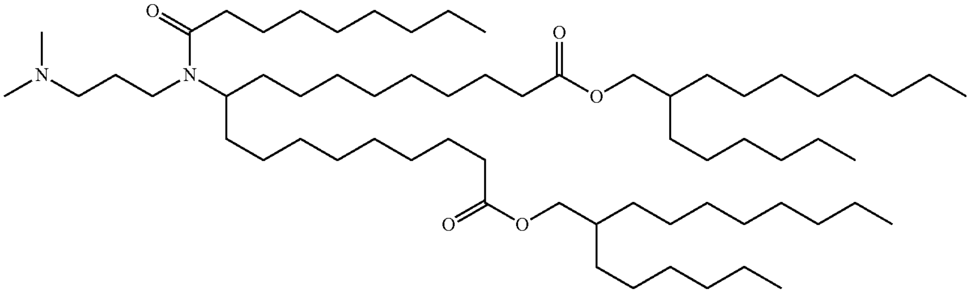 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] |
| 42 | 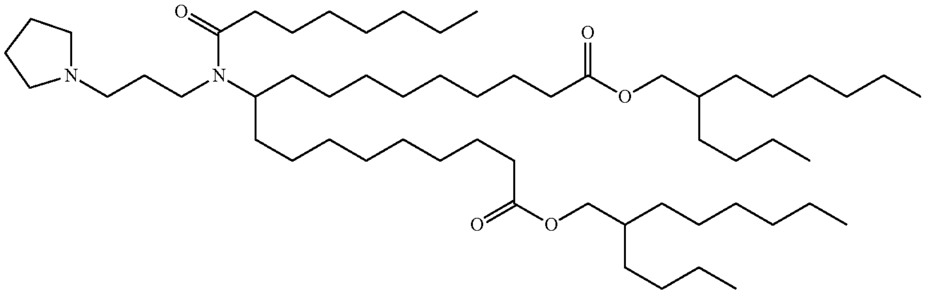 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] |
| 43 | 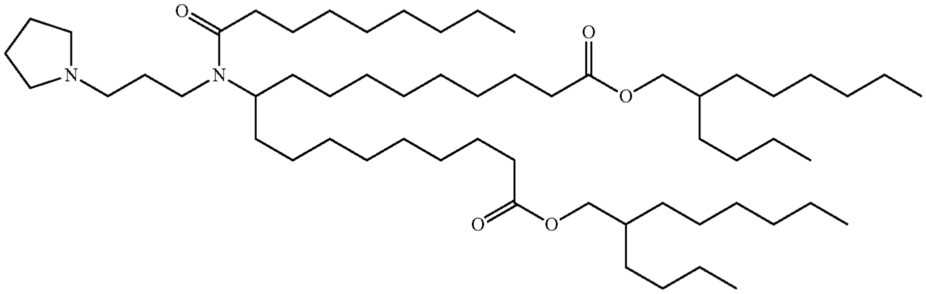 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] |

TABLE 5-continued
| # | Example Ionizable cationic lipids<br>Structure of example ionizable cationic lipid |
|---|---|
| 44 | 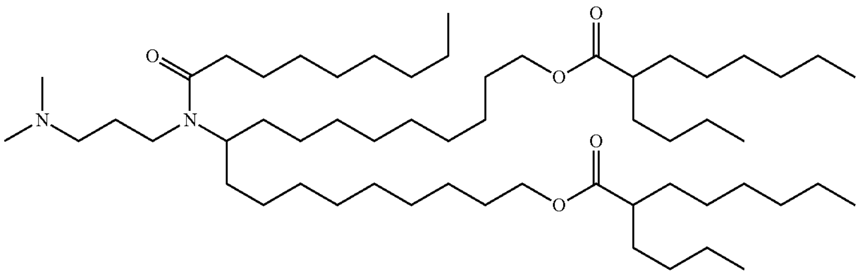 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] |
| 45 | 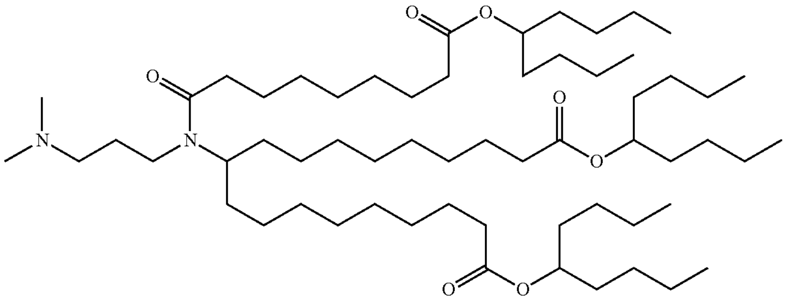 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] |
| 46 | 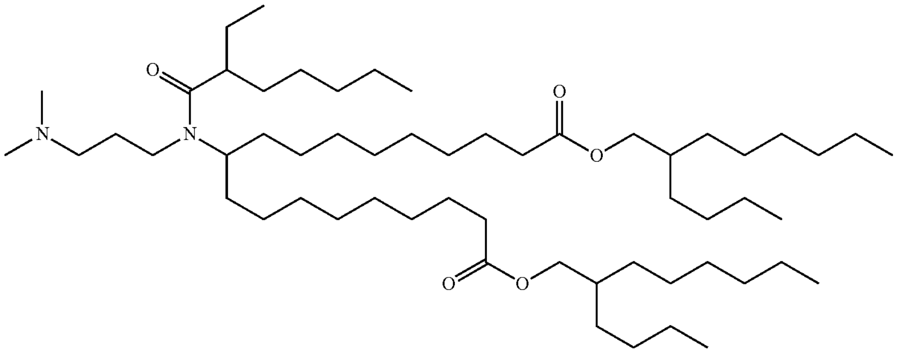 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC] |
| 47 | 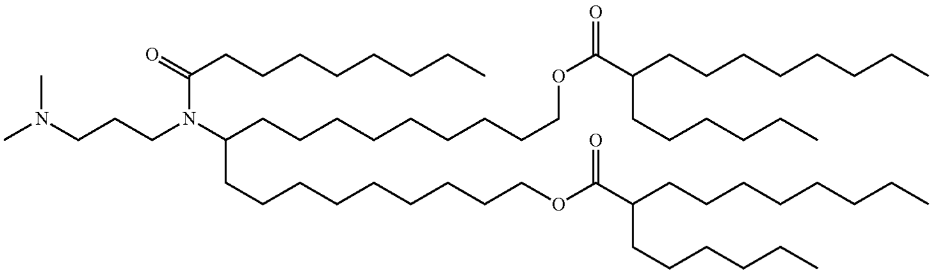 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC] |
| 48 | 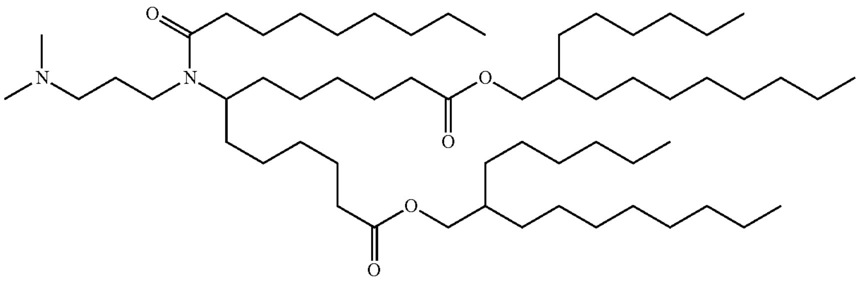 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC] |

TABLE 5-continued
| # | Example Ionizable cationic lipids<br>Structure of example ionizable cationic lipid |
|---|---|
| 49 | 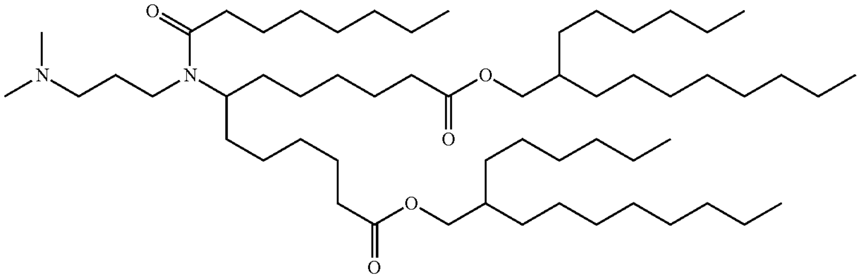 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC] |
| 50 | 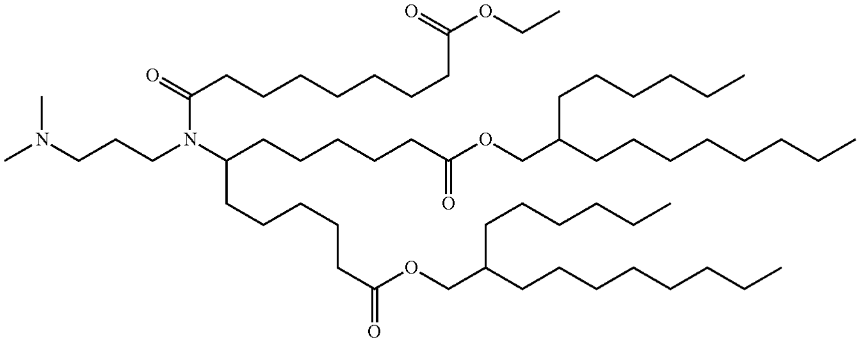 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] |
| 51 | 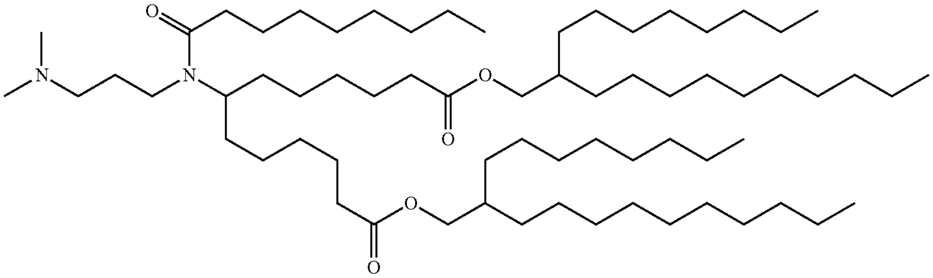 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] |
| 52 | 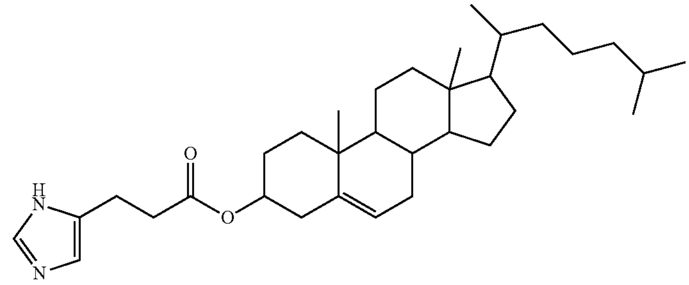 [SMILES: CC(C)CCCC(C)C1CCC2C3CC=C4CC(OC(=O)CCc5cnc[nH]5)CCC4(C)C3CCC12C] |
| 53 | 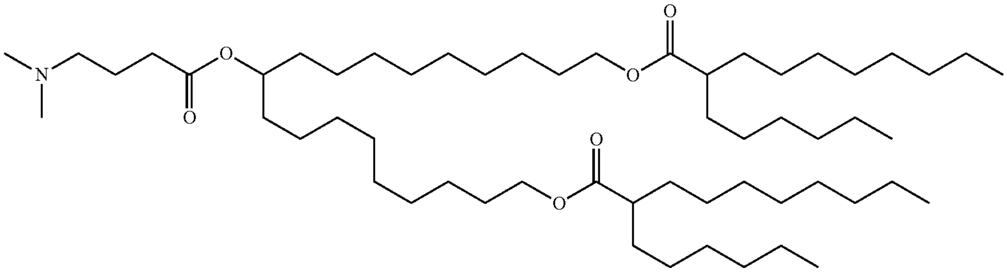 [SMILES: CCCCCCCCC(CCCCCC)C(=O)OCCCCCCCCCC(CCCCCCCCCOC(=O)C(CCCCCC)CCCCCCCC)OC(=O)CCCN(C)C] |

TABLE 5-continued
| # | Example Ionizable cationic lipids<br>Structure of example ionizable cationic lipid |
|---|---|
| 54 | 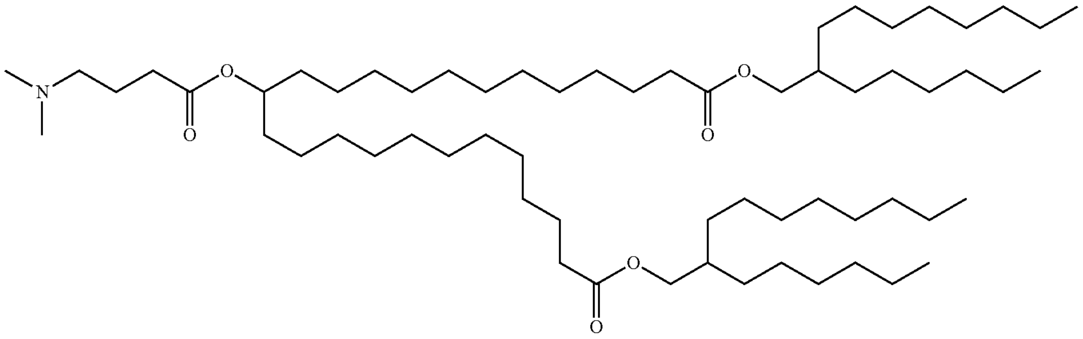 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C] |
| 55 | 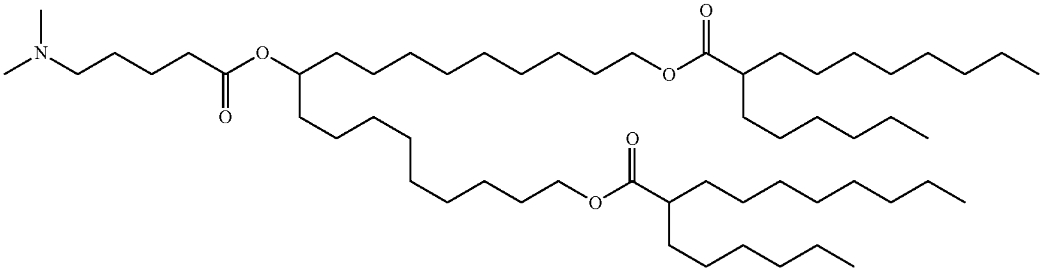 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] |
| 56 | 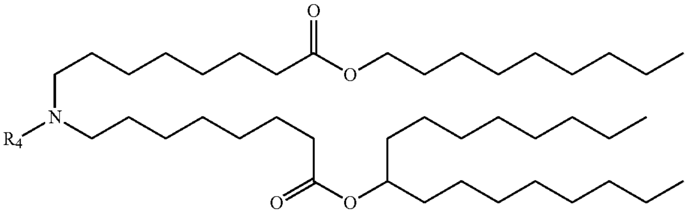<br>$R_4$ = —$(CH_2)_2OH$, —$(CH_2)_3OH$, —$(CH_2)_4OH$; |
| 57 | 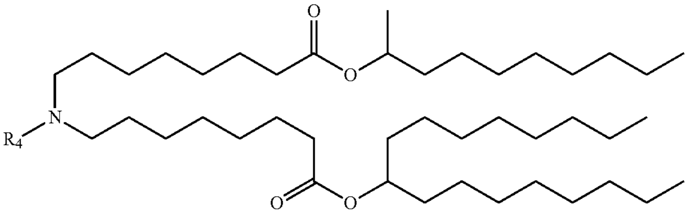<br>$R_4$ = —$(CH_2)_2OH$, —$(CH_2)_3OH$, —$(CH_2)_4OH$; |
| 58 | 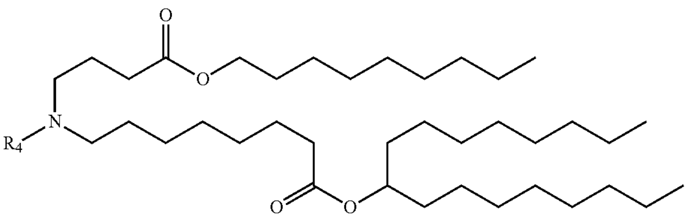<br>$R_4$ = —$(CH_2)_2OH$, —$(CH_2)_3OH$, —$(CH_2)_4OH$; |

TABLE 5-continued
| # | Example Ionizable cationic lipids<br>Structure of example ionizable cationic lipid |
|---|---|
| 59 | 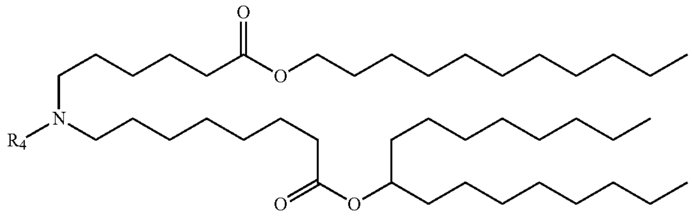<br>$R_4$ = —$(CH_2)_2OH$, —$(CH_2)_3OH$, —$(CH_2)_4OH$; |
| 60 | 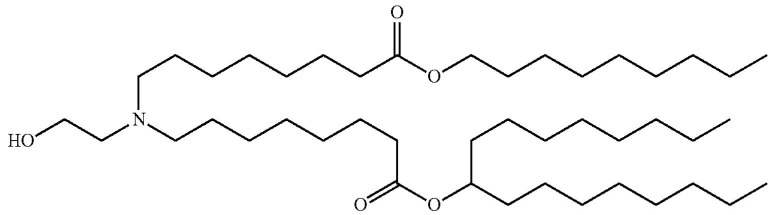 [SMILES: CCCCCCCCCOC(=O)CCCCCCCN(CCO)CCCCCCCC(=O)OC(CCCCCCCC)CCCCCCCC] |
| 61 | 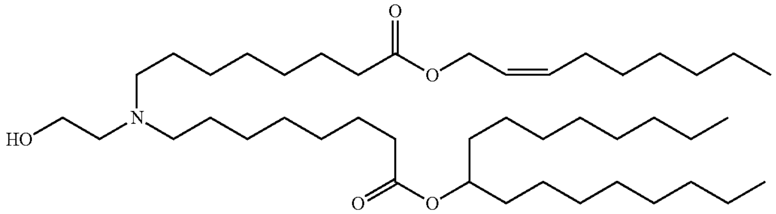 [SMILES: CCCCCC/C=C\COC(=O)CCCCCCCN(CCO)CCCCCCCC(=O)OC(CCCCCCCC)CCCCCCCC] |
| 62 | 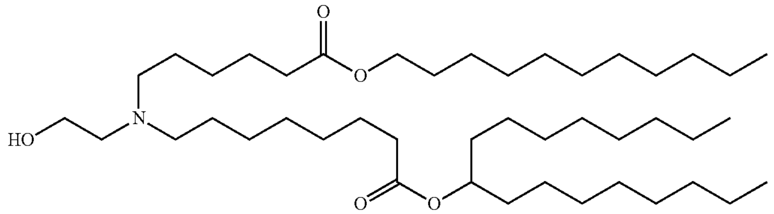 [SMILES: CCCCCCCCCCCOC(=O)CCCCCN(CCO)CCCCCCCC(=O)OC(CCCCCCCC)CCCCCCCC] |
| 63 | 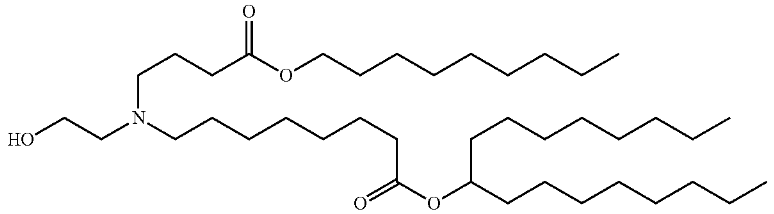 [SMILES: CCCCCCCCCOC(=O)CCCN(CCO)CCCCCCCC(=O)OC(CCCCCCCC)CCCCCCCC] |
| 64 | 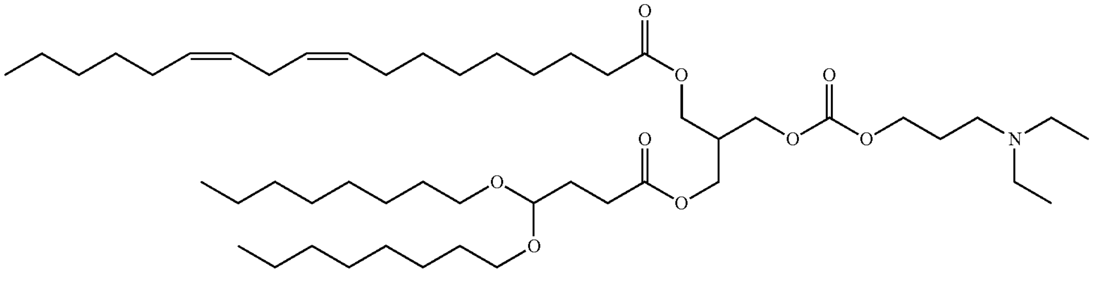 [SMILES: CCCCC/C=C\C/C=C\CCCCCCCC(=O)OCC(COC(=O)CCC(OCCCCCCCC)OCCCCCCCC)COC(=O)OCCCN(CC)CC] |

TABLE 5-continued

| # | Example Ionizable cationic lipids<br>Structure of example ionizable cationic lipid |
|---|---|
| 65 | 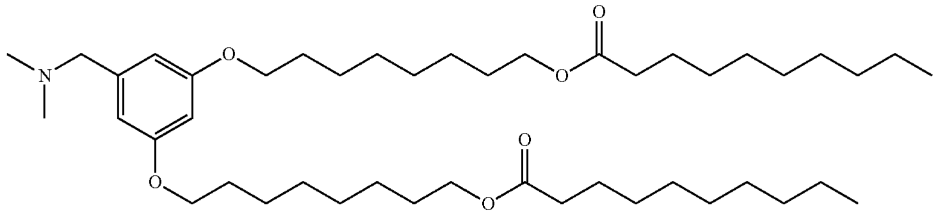 [SMILES: CCCCCCCCCC(=O)OCCCCCCCCOc1cc(CN(C)C)cc(OCCCCCCCCOC(=O)CCCCCCCCC)c1] |
| 66 | 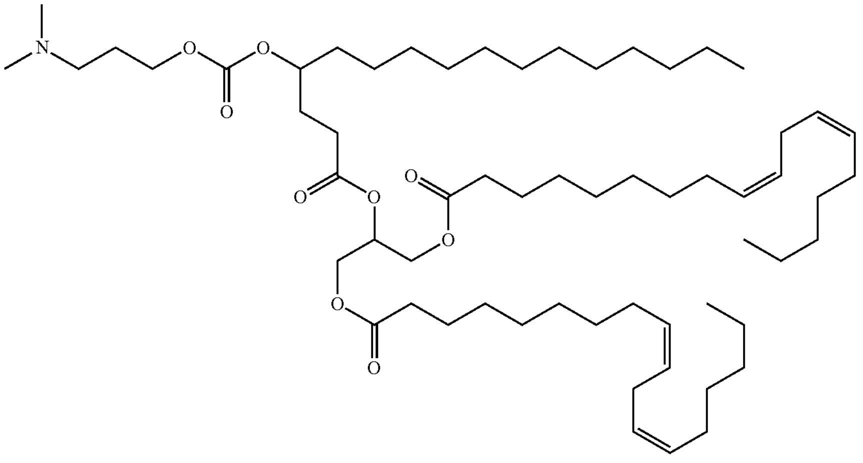 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C] |
| 67 | 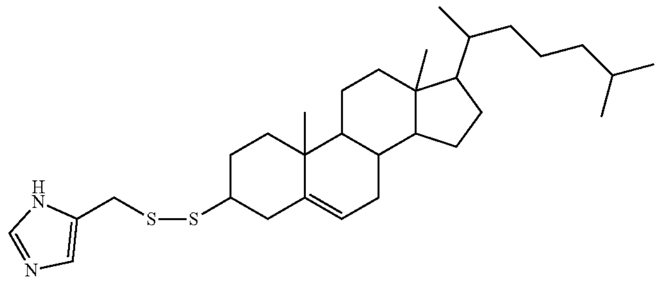 [SMILES: CC(C)CCCC(C)C1CCC2C3CC=C4CC(SSCc5cnc[nH]5)CCC4(C)C3CCC12C] |
| 68 | 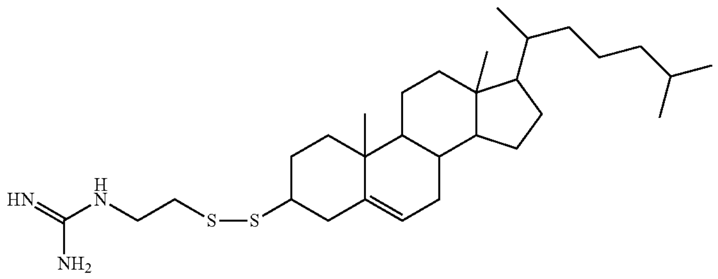 [SMILES: CC(C)CCCC(C)C1CCC2C3CC=C4CC(SSCCNC(=N)N)CCC4(C)C3CCC12C]<br>(HGT4002) |

In some embodiments of the lipid composition of the present application, the ionizable cationic lipid is present in the composition at a molar percentage from about 10% to about 25%.

In some embodiments of the lipid composition of the present application, the ionizable cationic lipid is present in the composition at a molar percentage about 5%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, or about 60%.

In some embodiments of the lipid composition of the present application, the ionizable cationic lipid is present in the composition at a molar percentage from about 5% to about 60%, from about 10% to about 50%, from about 10% to about 40%, from about 10% to about 30%, from about 10% to about 25%, from about 10% to about 20%, from about 15% to about 60%, from about 15% to about 50%, from about 15% to about 40%, from about 15% to about 30%, from about 15% to about 20%, from about 20% to about 60%, from about 20% to about 50%, from about 20% to about 40%, from about 20% to about 30%, or from about 10% to about 25%.

In some embodiments of the lipid composition of the present application, the ionizable lipid is present at a molar percentage of at least (about) 5%, at least (about) 10%, at least (about) 15%, at least (about) 20%, at least (about) 25%, or at least (about) 30%. In some embodiments of the lipid composition of the present application, the ionizable lipid is present at a molar percentage of at most (about) 5%, at most (about) 10%, at most (about) 15%, at most (about) 20%, at most (about) 25%, or at most (about) 30%.

Selective Organ Targeting (SORT) Lipid

The lipid composition may include an additional anionic lipid, ionizable cationic lipid, or permanently cationic lipid. In some embodiments of the lipid composition of the present application, the lipid (e.g., nanoparticle) composition is preferentially delivered to a target organ.

In some embodiments of the lipid compositions, the additional lipid comprises a permanently positively charged moiety (i.e., is a permanently cationic lipid). The permanently positively charged moiety may be positively charged at a physiological pH such that the additional lipid (e.g., SORT lipid) comprises a positive charge upon delivery of a polynucleotide to a cell. In some embodiments the positively charged moiety is quaternary amine or quaternary ammonium ion. In some embodiments, the additional lipid (e.g., additional lipid (e.g., SORT lipid)) comprises, or is otherwise complexed to or interacting with, a counterion.

In some embodiments of the lipid compositions, the additional lipid is a permanently cationic lipid (i.e., comprising one or more hydrophobic components and a permanently cationic group). The permanently cationic lipid may contain a group which has a positive charge regardless of the pH. One permanently cationic group that may be used in the permanently cationic lipid is a quaternary ammonium group. The permanently cationic lipid may comprise a structural formula:

(S-I)

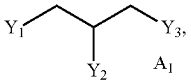

wherein:

- $Y_1$, $Y_2$, or $Y_3$ are each independently $X_1C(O)R_1$ or $X_2N^*R_3R_4R_5$;
- provided at least one of $Y_1$, $Y_2$, and $Y_3$ is $X_2N^*R_3R_4R_5$;
- $R_1$ is $C_1$-$C_{24}$ alkyl, $C_1$-$C_{24}$ substituted alkyl, $C_1$-$C_{24}$ alkenyl, $C_1$-$C_{24}$ substituted alkenyl;
- $X_1$ is O or $NR_a$, wherein $R_a$ is hydrogen, $C_1$-$C_4$ alkyl, or $C_1$-$C_4$ substituted alkyl;
- $X_2$ is $C_1$-$C_6$ alkanediyl or $C_1$-$C_6$ substituted alkanediyl;
- $R_3$, $R_4$, and $R_5$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; and
- $A_1$ is an anion with a charge equal to the number of $X_2N^*R_3R_4R_5$ groups in the compound.

In some embodiments, the permanently cationic additional lipid (e.g., SORT lipid) has a structural formula:

(S-II)

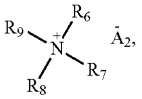

wherein:

- $R_6$-$R_9$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; provided at least one of $R_6$-$R_9$ is a group of $C_8$-$C_{24}$; and
- $A_2$ is a monovalent anion.

In some embodiments, the permanently cationic lipids is 1,2-dilauroyl-sn-glycero-3-ethylphosphocholine (12:0 EPC), 1,2-dimyristoyl-sn-glycero-3-ethylphosphocholine (14:0 EPC), 1,2-dipalmitoyl-sn-glycero-3-ethylphosphocholine (16:0 EPC), 1,2-distearoyl-sn-glycero-3-ethylphosphocholine (18:0 EPC), 1,2-dioleoyl-sn-glycero-3-ethylphosphocholine (18:1 EPC), 1-palmitoyl-2-oleoyl-sn-glycero-3-ethylphosphocholine (16:0-18:0 EPC), 1,2-dimyristoleoyl-sn-glycero-3-ethylphosphocholine (14:1 EPC), Dimethyldioctadecylammonium (18:0 DDAB), 1,2-dimyristoyl-3-trimethylammonium-propane (14:0 TAP), 1,2-dipalmitoyl-3-trimethylammonium-propane (16:0 TAP), 1,2-stearoyl-3-trimethylammonium-propane (18:0 TAP), 1,2-dioleoyl-3-trimethylammonium-propane (18:1 TAP, DOTAP), or 1,2-di-O-octadecenyl-3-trimethylammonium propane (DOTMA).

In some embodiments of the lipid compositions, the SORT (additional) lipid is an ionizable cationic lipid (e.g., comprising one or more hydrophobic components and an ionizable group, e.g., a tertiary amino group). The ionizable positively charged moiety may be positively charged at a physiological pH. One ionizable group that may be used in the ionizable cationic lipid is a tertiary ammine group. In some embodiments of the lipid compositions disclosed herein, the additional lipid (e.g., additional lipid (e.g., SORT lipid)) has a structural formula:

(S-I'a)

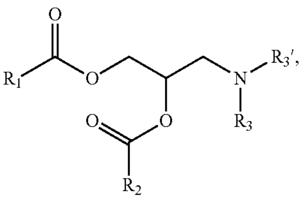

wherein:

- $R_1$ and $R_2$ are each independently $C_8$-$C_{24}$ alkyl, $C_8$-$C_{24}$ alkenyl, or a substituted version of either group; and
- $R_3$ and $R_3'$ are each independently $C_1$-$C_6$ alkyl or substituted $C_1$-$C_6$ alkyl.

In some embodiments of formula (S—I'a) $R_1$ and $R_2$ are each independently $C_8$-$C_{24}$ alkenyl (e.g., hexadecane, heptadecene, or octadecene). In some embodiments of formula (S—I'a), $R_3$ and $R_3'$ are each independently $C_1$-$C_6$ alkyl (e.g., methyl or ethyl). In some embodiments of formula (S—I'a) $R_1$ and $R_2$ are each independently $C_8$-$C_{24}$ alkenyl, (e.g., hexadecane, heptadecene, or octadecene) and $R_3$ and $R_3'$ are each independently $C_1$-$C_6$ alkyl (e.g., methyl or ethyl).

In some embodiments, the ionizable cationic lipids is 1,2-distearoyl-3-dimethylammonium-propane (18:0 DAP), 1,2-dipalmitoyl-3-dimethylammonium-propane (16:0 DAP), 1,2-dimyristoyl-3-dimethylammonium-propane (14:0 DAP), 1,2-dioleoyl-3-dimethylammonium-propane (18:1 DAP, DODAP), or 1,2-dioleyloxy-3-dimethylamino-propane (DODMA).

In some embodiments of the lipid compositions, the additional ionizable cationic lipid or permanently cationic lipid comprises a head group of a particular structure. In some embodiments, the additional lipid (e.g., additional lipid (e.g., SORT lipid)) comprises a headgroup having a structural formula:

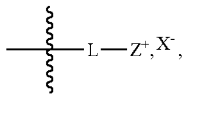

wherein L is a linker; $Z^+$ is positively charged moiety and $X^-$ is a counterion. In some embodiment, the linker is a biodegradable linker. The biodegradable linker may be degradable under physiological pH and temperature. The biodegradable linker may be degraded by proteins or enzymes from a subject. In some embodiments, the positively charged moiety is a quaternary ammonium ion or quaternary amine.

In some embodiments of the lipid compositions, the SORT (additional ionizable cationic lipid or permanently cationic) lipid has a structural formula:

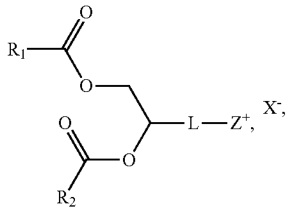

wherein $R^1$ and $R^2$ are each independently an optionally substituted $C_6$-$C_{24}$ alkyl, or an optionally substituted $C_6$-$C_{24}$ alkenyl.

In some embodiments of the lipid compositions, the additional lipid (e.g., additional lipid (e.g., SORT lipid)) has a structural formula:

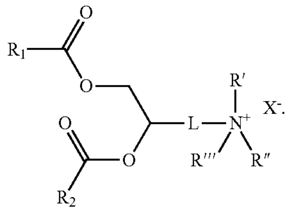

In some embodiments of the lipid compositions, the additional lipid (e.g., additional lipid (e.g., SORT lipid)) comprises a Linker (L). In some embodiments, L is

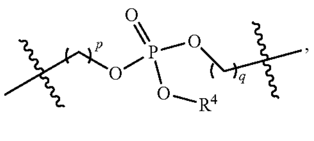

wherein:

and q are each independently 1, 2, or 3; and $R^4$ is an optionally substituted $C_1$-$C_6$ alkyl In some embodiments of the lipid compositions, the additional lipid (e.g., additional lipid (e.g., SORT lipid)) has a structural formula:

(IA)

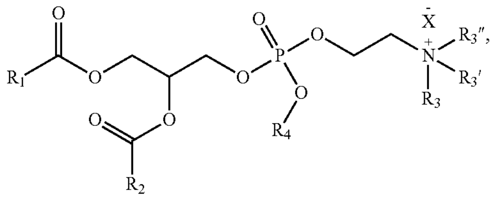

wherein:

$R_1$ and $R_2$ are each independently $C_8$-$C_{24}$ alkyl, $C_8$-$C_{24}$ alkenyl, or a substituted version of either group;

$R_3$, $R_3'$, and $R_3''$ are each independently $C_1$-$C_6$ alkyl or substituted $C_1$-$C_6$ alkyl;

$R_4$ is $C_1$-$C_6$ alkyl or substituted $C_1$-$C_6$ alkyl; and $X^-$ is a monovalent anion.

In some embodiments of the lipid compositions, the additional lipid (e.g., additional lipid (e.g., SORT lipid)) is a phosphatidylcholine (e.g., 14:0 EPC). In some embodiments, the phosphatidylcholine compound is further defined as:

(IA)

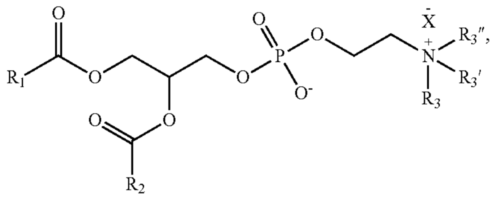

wherein:

$R_1$ and $R_2$ are each independently $C_8$-$C_{24}$ alkyl, $C_8$-$C_{24}$ alkenyl, or a substituted version of either group;

$R_3$, $R_3'$, and $R_3''$ are each independently $C_1$-$C_6$ alkyl or substituted $C_1$-$C_6$ alkyl; and $X^-$ is a monovalent anion.

In some embodiments of the lipid compositions, the additional lipid (e.g., additional lipid (e.g., SORT lipid)) is a phosphocholine lipid. In some embodiments, the additional lipid (e.g., additional lipid (e.g., SORT lipid)) is an ethylphosphocholine. The ethylphosphocholine may be, by way of example, without being limited to, 1,2-dimyristoleoyl-sn-glycero-3-ethylphosphocholine (14:1 EPC), 1,2-dioleoyl-sn-glycero-3-ethylphosphocholine (18:1 EPC), 1,2-distearoyl-sn-glycero-3-ethylphosphocholine (18:0 EPC), 1,2-dipalmitoyl-sn-glycero-3-ethylphosphocholine (16:0 EPC), 1,2-dimyristoyl-sn-glycero-3-ethylphosphocholine (14:0 EPC), 1,2-dilauroyl-sn-glycero-3-ethylphosphocholine (12:0 EPC), 1-palmitoyl-2-oleoyl-sn-glycero-3-ethylphosphocholine (16:0-18:0 EPC).

In some embodiments of the lipid compositions, the lipid has a structural formula:

(S-I')

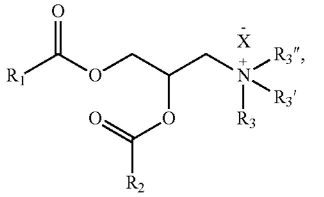

wherein:

$R_1$ and $R_2$ are each independently $C_8$-$C_{24}$ alkyl, $C_8$-$C_{24}$ alkenyl, or a substituted version of either group;

$R_3$, $R_3'$, and $R_3''$ are each independently $C_1$-$C_6$ alkyl or substituted $C_1$-$C_6$ alkyl;

$X^-$ is a monovalent anion.

By way of example, and without being limited thereto, a additional lipid (e.g., additional lipid (e.g., SORT lipid)) of the structural formula of the immediately preceding paragraph is 1,2-dioleoyl-3-trimethylammonium-propane (18:1 DOTAP) (e.g., chloride salt).

In some embodiments of the lipid compositions, the additional lipid (e.g., additional lipid (e.g., SORT lipid)) has a structural formula:

(S-II')

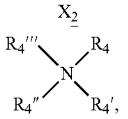

wherein:

$R_4$ and $R_4'$ are each independently alkyl$_{(C6\text{-}C24)}$, alkenyl $_{(C6\text{-}C24)}$, or a substituted version of either group;

$R_4''$ is alkyl$_{(C\leq 24)}$, alkenyl$_{(C\leq 24)}$, or a substituted version of either group;

$R_4'''$ is alkyl$_{(C1\text{-}C8)}$, alkenyl$_{(C2\text{-}C8)}$, or a substituted version of either group; and $X_2$ is a monovalent anion.

By way of example, and without being limited thereto, an additional lipid (e.g., additional lipid (e.g., SORT lipid)) of the structural formula of the immediately preceding paragraph is dimethyldioctadecylammonium (DDAB).

In some embodiments of the lipid compositions, the additional lipid (e.g., additional lipid (e.g., SORT lipid)) is

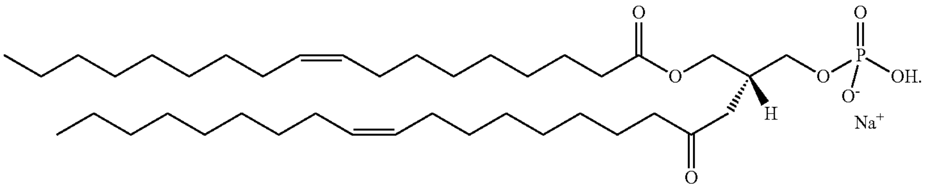

1,3-dioleoyl-sn-glycero-3-phosphate (18:1 PA)

In some embodiments of the lipid compositions, the additional lipid is selected from the lipids set forth in Table 6.

TABLE 6

Example additional lipid (e.g., SORT lipids)

| Lipid Name | Structure |
|---|---|
| 1,2-Dioleoyl-3-dimethyl-ammonium-propane (18:1 DODAP) | 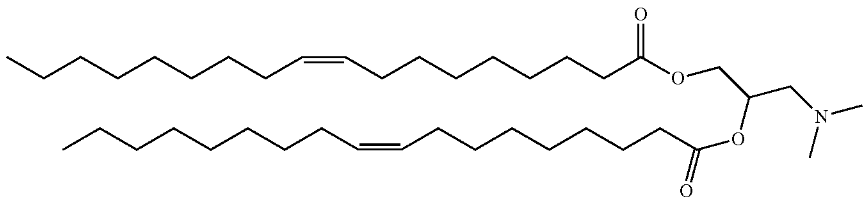 [SMILES: CCCCCCCC/C=C\CCCCCCCC(=O)OCC(CN(C)C)OC(=O)CCCCCCC/C=C\CCCCCCCC] |
| 1,2-dimyristoyl-3-trimethyl-ammonium-propane (14:0 TAP) (e.g., chloride salt) | 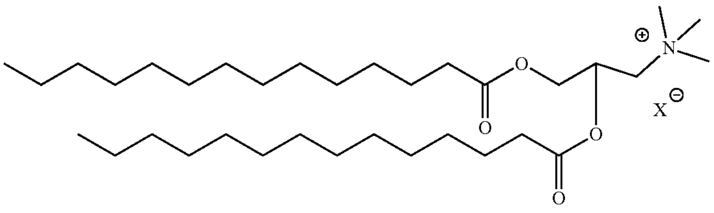 |

TABLE 6-continued

Example additional lipid (e.g., SORT lipids)

| Lipid Name | Structure |
| --- | --- |
| 1,2-dipalmitoyl-3-trimethyl-ammonium-propane (16:0 TAP) (e.g., chloride salt) | 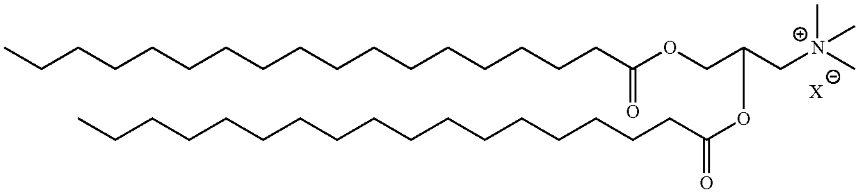 |
| 1,2-stearoyl-3-trimethyl-ammonium-propane (18:0 TAP) (e.g., chloride salt) | 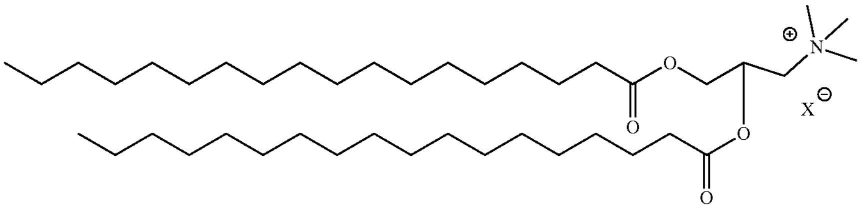 |
| 1,2-Dioleoyl-3-trimethyl-ammonium-propane (18:1 DOTAP) (e.g., chloride salt) | 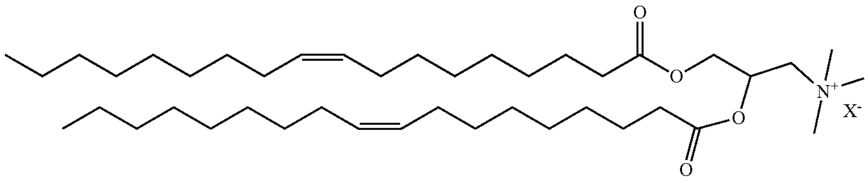 |
| 1,2-Di-O-octadecenyl-3-trimethyl-ammonium propane (DOTMA) (e.g., chloride salt) | 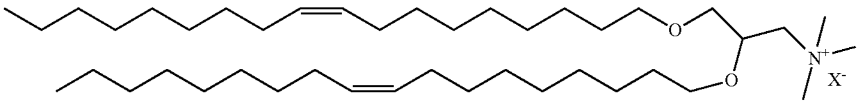 |
| Dimethyl-diocta-decyl-ammonium (DDAB) (e.g., bromide salt) | 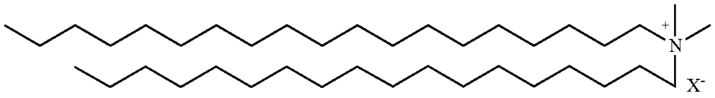 |
| 1,2-dilauroyl-sn-glycero-3-ethyl-phospho-choline (12:0 EPC) (e.g., chloride salt) | 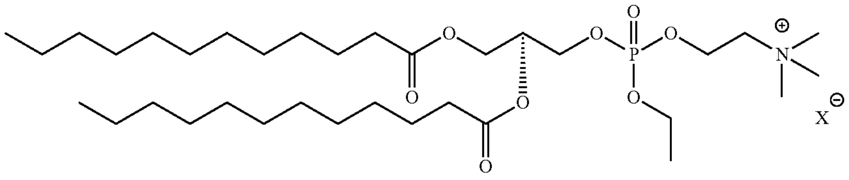 |
| 1,2-Dioleoyl-sn-glycero-3-ethyl-phospho-choline (14:0 EPC) (e.g., chloride salt) | 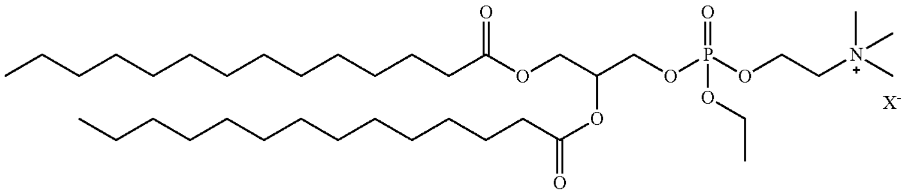 |

TABLE 6-continued

| Example additional lipid (e.g., SORT lipids) | |
|---|---|
| Lipid Name | Structure |
| 1,2-dimyristoleoyl-sn-glycero-3-ethylphosphocholine (14:1 EPC) (e.g., triflate salt) | 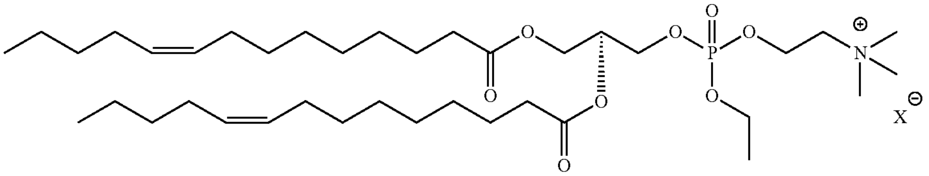 |
| 1,2-dipalmitoyl-sn-glycero-3-ethylphosphocholine (16:0 EPC) (e.g., chloride salt) | 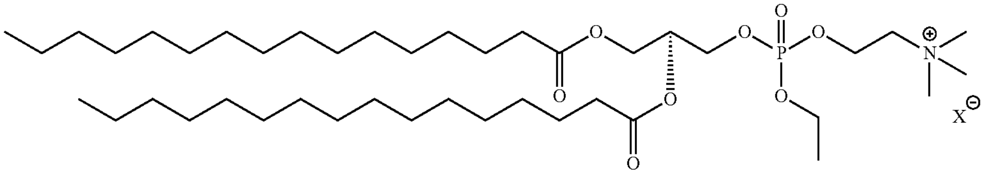 |
| 1,2-distearoyl-sn-glycero-3-ethylphosphocholine (18:0 EPC) (e.g., chloride salt) | 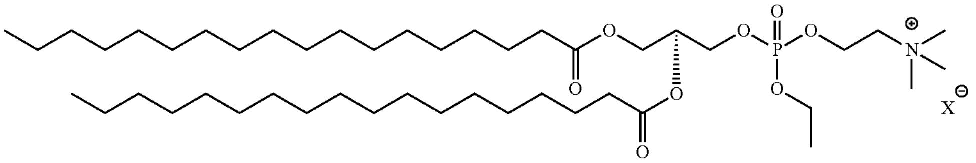 |
| 1,2-dioleoyl-sn-glycero-3-ethylphosphocholine (18:1 EPC) (e.g., chloride salt) | 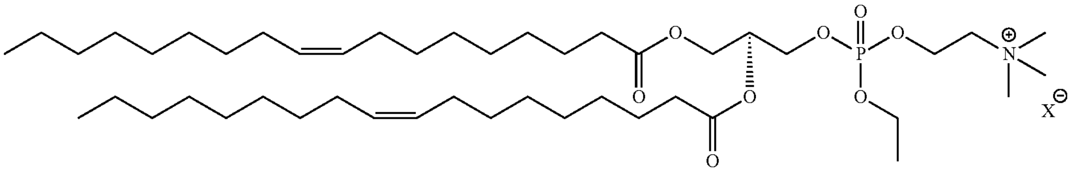 |
| 1-palmitoyl-2-oleoyl-sn-glycero-3-ethylphosphocholine (16:0-18:1 EPC) (e.g., chloride salt) | 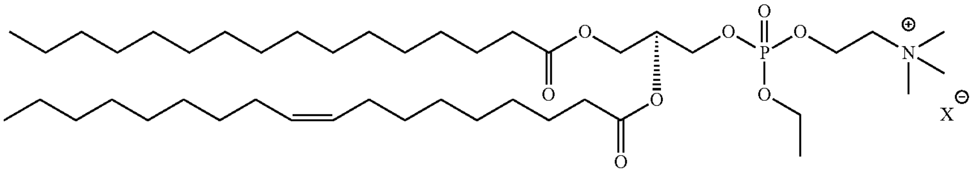 |
| 1,2-di-O-octadecenyl-3-trimethylammonium propane (18:1 DOTMA) (e.g., chloride salt) | 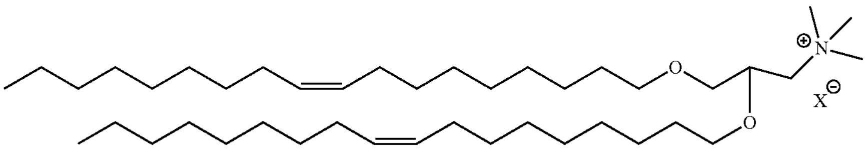 |

$X^-$ is a counterion (e.g., $Cl^-$, $Br^-$, etc.)

TABLE 7

| Example additional lipid (e.g., SORT lipids) | |
|---|---|
| Lipid Name | Structure |
| 1,2-dioleoyl-sn-glycero-3-phosphate (18:1 PA) | 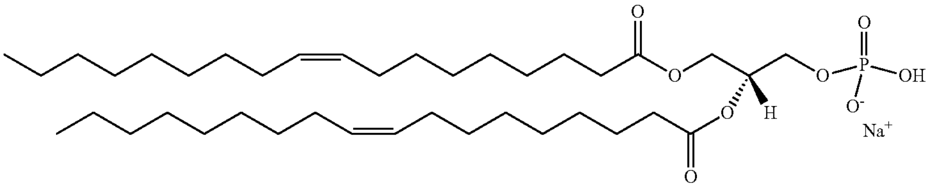 [SMILES: CCCCCCCC/C=C\CCCCCCCC(=O)OC[C@H](COP(=O)([O-])O)OC(=O)CCCCCCC/C=C\CCCCCCCC ; [Na+]] |
| 1,2-distearoyl-sn-glycero-3-phosphate (18:0 PA) | 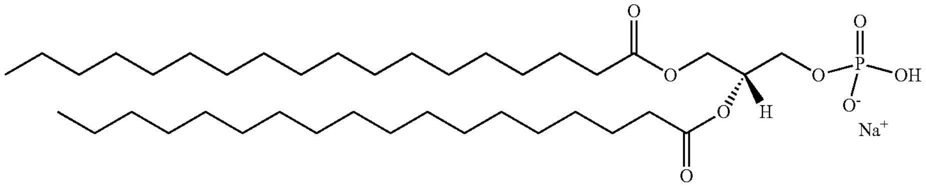 [SMILES: CCCCCCCCCCCCCCCCCC(=O)OC[C@H](COP(=O)([O-])O)OC(=O)CCCCCCCCCCCCCCCCC ; [Na+]] |
| 1,2-dipalmitoyl-sn-glycero-3-phosphate (16:0 PA) | 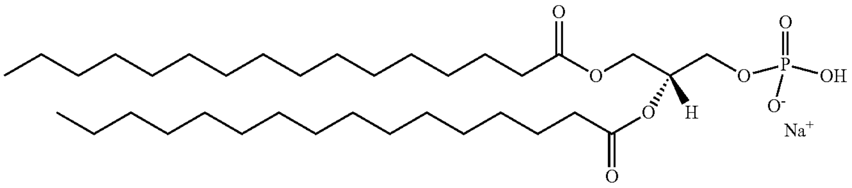 [SMILES: CCCCCCCCCCCCCCCC(=O)OC[C@H](COP(=O)([O-])O)OC(=O)CCCCCCCCCCCCCCC ; [Na+]] |
| 1,2-dimyristoyl-sn-glycero-3-phosphate (14:0 PA) | 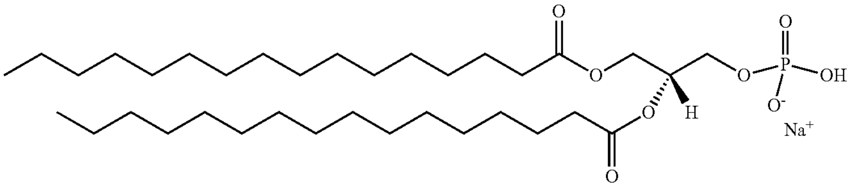 [SMILES: CCCCCCCCCCCCCCCC(=O)OC[C@H](COP(=O)([O-])O)OC(=O)CCCCCCCCCCCCCCC ; [Na+]] |
| 1,2-dilauroyl-sn-glycero-3-phosphate (12:0 PA) | 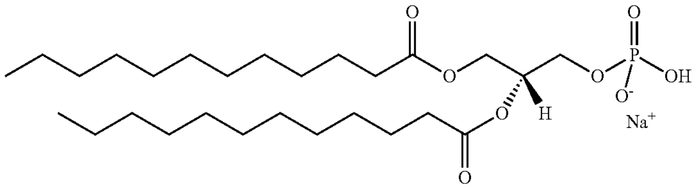 [SMILES: CCCCCCCCCCCC(=O)OC[C@H](COP(=O)([O-])O)OC(=O)CCCCCCCCCCC ; [Na+]] |

In some embodiments of the lipid composition of the present application, the SORT lipid is present in the composition at a molar percentage from about 5% to about 50%.

In some embodiments of the lipid composition of the present application, the SORT lipid is present in the composition at a molar percentage about 5%, about 10%, about 15%, about 20%, about 25%, about 30%, about 35%, about 40%, about 45%, about 50%, about 55%, or about 60%.

In some embodiments of the lipid composition of the present application, the SORT lipid is present in the composition at a molar percentage from about 5% to about 60%, from about 5% to about 50%, from about 5% to about 40%, from about 5% to about 30%, from about 5% to about 20%, from about 5% to about 10%, from about 10% to about 50%, from about 10% to about 40%, from about 10% to about 30%, from about 10% to about 25%, from about 10% to about 20%, from about 15% to about 60%, from about 15% to about 50%, from about 15% to about 40%, from about 15% to about 30%, from about 15% to about 20%, from about 20% to about 60%, from about 20% to about 50%, from about 20% to about 40%, from about 20% to about 30%, or from about 20% to about 25%.

In some embodiments of the lipid composition of the present application, the SORT lipid is present at a molar percentage of at least (about) 5%, at least (about) 10%, at least (about) 15%, at least (about) 20%, at least (about) 25%, at least (about) 30%, at least (about) 35%, at least (about) 40%, at least (about) 45%, at least (about) 50%, or at least (about) 55%. In some embodiments of the lipid composition of the present application, the ionizable lipid is present at a molar percentage of at most (about) 60%, at most (about) 55%, at most (about) 50%, at most (about) 45%, at most (about) 40%, at most (about) 35%, at most (about) 30%, or at most (about) 25%.

Helper Lipids

In some embodiments, helper lipids are phospholipids. Phospholipids, as defined herein, are any lipids that comprise a phosphate group. The lipid component of a lipid nanoparticle composition may include one or more phospholipids, such as one or more (poly) unsaturated lipids. Phospholipids may assemble into one or more lipid bilayers. In general, phospholipids may include a phospholipid moiety and one or more fatty acid moieties. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids useful or potentially useful in the compositions and methods may be selected from: 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-diphytanoyl-sn-glycero-3-phosphocholine (4ME 16:0 PC), 1,2-diphytanoyl-sn-glycero-3-phospho-(1'-rac-glycerol) (sodium salt) (4ME 16:0 PG), 1,2-diphytanoyl-sn-glycero-3-phospho-L-serine (sodium salt) (4ME 16:0 PS), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, and 1,2-dioleoyl-sn-glycero-3-phospho-rac-(1-glycerol) sodium salt (DOPG), and sphingomyelin.

In some embodiments, the phospholipid may contain one or two long chain (e.g., $C_6$-$C_{24}$) alkyl or alkenyl groups, a glycerol or a sphingosine, one or two phosphate groups, and, optionally, a small organic molecule. The small organic molecule may be an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some embodiments of the lipid composition of the present application, the helper lipid is present in the composition at a molar percentage from about 7.5% to about 30%.

In some embodiments of the lipid composition of the present application, the helper lipid is present in the composition at a molar percentage about 5%, about 7.5%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, or about 60%.

In some embodiments of the lipid composition of the present application, the helper lipid is present in the composition at a molar percentage from about 5% to about 50%, from about 10% to about 50%, from about 10% to about 40%, from about 10% to about 30%, from about 10% to about 25%, from about 10% to about 20%, from about 15% to about 60%, from about 15% to about 50%, from about 15% to about 40%, from about 15% to about 30%, from about 15% to about 20%, from about 20% to about 60%, from about 20% to about 50%, from about 20% to about 40%, from about 20% to about 30%, or from about 10% to about 25%.

In some embodiments of the lipid composition of the present application, the helper lipid is present at a molar percentage of at least (about) 5%, at least (about) 10%, at least (about) 15%, at least (about) 20%, at least (about) 25%, or at least (about) 30%. In some embodiments of the lipid composition of the present application, the ionizable lipid is present at a molar percentage of at most (about) 5%, at most (about) 10%, at most (about) 15%, at most (about) 20%, at most (about) 25%, or at most (about) 30%.

Structural Lipids

The lipid nanoparticle may include one or more structural lipids. Structural lipids can be steroids or steroid derivatives. In some embodiments of the lipid composition of the present application, the lipid composition further comprises a steroid or steroid derivative. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula:

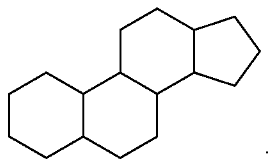 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

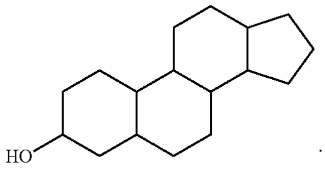 [SMILES: OC1CCC2C(CCC3C4CCCC4CCC23)C1]

In some embodiments of the present application, the steroid or steroid derivative is a cholestane or cholestane derivative. In a cholestane, the ring structure is further defined by the formula:

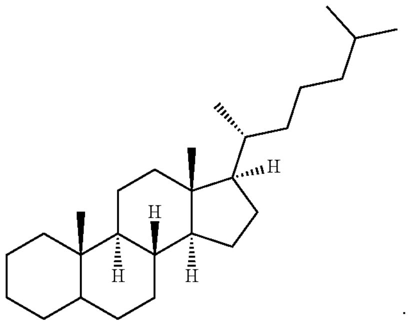

As described above, a cholestane derivative comprises one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholesterol and a sterol or a derivative thereof.

Sterol useful or potentially useful in the compositions and methods may be selected from: cholesterol, fecosterol, sitosterol, ergosterol, campesterol, stigmasterol, brassicasterol, tomatidine, ursolic acid, and alpha-tocopherol.

In some embodiments of the lipid composition of the present application, the sterol is present in the composition at a molar percentage from about 20% to about 50%.

In some embodiments of the lipid composition of the present application, the sterol is present in the composition at a molar percentage about 10%, about 15%, about 20%, about 21%, about 22%, about 23%, about 24%, about 25%, about 30%, about 35%, about 40%, about 41%, about 42%, about 43%, about 44%, about 45%, about 50%, about 55%, or about 60%.

In some embodiments of the lipid composition of the present application, the sterol is present in the composition at a molar percentage from about 10% to about 60%, from about 20% to about 50%, from about 20% to about 40%, from about 20% to about 30%, from about 20% to about 25%, from about 25% to about 50%, from about 25% to about 40%, from about 25% to about 30%, from about 30% to about 50%, from about 30% to about 40%, from about 30% to about 35%, from about 35% to about 50%, from about 35% to about 45%, from about 35% to about 40%, from about 40% to about 50%, from about 40% to about 45%, or from about 45% to about 50%.

In some embodiments of the lipid composition of the present application, the sterol is present at a molar percentage of at least (about) 20%, at least (about) 25%, at least (about) 30%, at least (about) 35%, at least (about) 40%, or at least (about) 50%. In some embodiments of the lipid composition of the present application, the ionizable lipid is present at a molar percentage of at most (about) 60%, at most (about) 15%, at most (about) 45%, at most (about) 40%, at most (about) 35%, at most (about) 30%, at most (about) 25%, or at most (about) 20%.

Polyethylene Glycol-Conjugated Lipid (PEG-Lipid)

The lipid compositions of the disclosure may include lipids conjugated to polymers, such as lipids conjugated to polyethylene glycol ("PEG-lipid"). Illustrative methods for making and using PEG-lipids are described for example in Int'l Pat. Pub. No. WO2012099755 and U.S. Pat. Pub No. 2014/0200257.

A PEG-lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG-lipid may be PEG-c-DOMG, PEG-DMG, PEG-DLPE, PEG-DMPE, PEG-DPPC, or a PEG-DSPE lipid.

In one embodiment, PEG-lipids useful in the present invention can be PEG-lipids described in Int'l Pat. Pub. No. WO 2012/099755, the contents of which is herein incorporated by reference in its entirety. Any of these exemplary PEG-lipids described herein may be modified to comprise a hydroxyl group on the PEG chain. In certain embodiments, the PEG-lipid is a PEG-OH lipid. As generally defined herein, a "PEG-OH lipid" is a PEG-lipid having one or more hydroxyl (—OH) groups on the lipid. In certain embodiments, the PEG-OH lipid comprises one or more hydroxyl groups on the PEG chain. In certain embodiments, a PEG-OH or hydroxy-PEG-lipid comprises an OH group at the terminus of the PEG chain. Each possibility represents a separate embodiment of the present invention.

In some embodiments of the lipid composition of the present application, the lipid composition further comprises a polymer conjugated lipid. In some embodiments, the polymer conjugated lipid is a PEG-lipid. In some embodiments, the PEG-lipid is a diglyceride which also comprises a PEG chain attached to the glycerol group. In other embodiments, the PEG-lipid is a compound which contains one or more $C_6$-$C_{24}$ long chain alkyl or alkenyl group or a $C_6$-$C_{24}$ fatty acid group attached to a linker group with a PEG chain. Some non-limiting examples of a PEG-lipid comprises a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present application are taught by U.S. Pat. No. 5,820,873, WO 2010/141069, or U.S. Pat. No. 8,450,298, which is incorporated herein by reference.

In some embodiments of the lipid composition of the present application, the PEG-lipid has a structural formula:

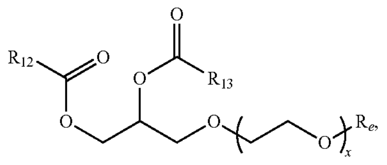

wherein: $R_{12}$ and $R_{13}$ are each independently alkyl$_{(C\leq24)}$, alkenyl$_{(C\leq24)}$, or a substituted version of either of these groups; $R_e$ is hydrogen, alkyl$_{(C\leq8)}$, or substituted alkyl$_{(C\leq8)}$; and x is 1-250. In some embodiments, $R_e$ is alkyl$_{(C\leq8)}$ such as methyl. $R_{12}$ and $R_{13}$ are each independently alkyl$_{(C\leq4-20)}$. In some embodiments, x is 5-250. In one embodiment, x is 5-125 or x is 100-250. In some embodiments, the PEG-lipid is 1,2-dimyristoyl-sn-glycerol, methoxypolyethylene glycol.

In some embodiments of the lipid composition of the present application, the PEG-lipid has a structural formula:

In some embodiments of the lipid composition of the present application, the PEG-lipid is present at a molar percentage of at least (about) 0.5%, at least (about) 1%, at least (about) 2%, at least (about) 2.5%, at least (about) 3%, or at least (about) 3.5%. In some embodiments of the lipid composition of the present application, the ionizable lipid is present at a molar percentage of at most (about) 10%, at most (about) 9%, at most (about) 8%, at most (about) 7%, at most (about) 6%, or at most (about) 5%.

In one aspect, the disclosure provides a lipid nanoparticle composition for delivering a payload to a cell in the lung of a subject, including a payload, a helper lipid, a sterol, a polyethylene glycol-conjugated lipid (PEG-lipid), an ionizable cationic lipid, and/or a permanently cationic lipid, optionally an ethylphosphocholine.

In some embodiments, the payload comprises a polynucleotide, optionally an mRNA, shRNA, or microRNA. In some embodiments, the mRNA encodes a polynucleotides

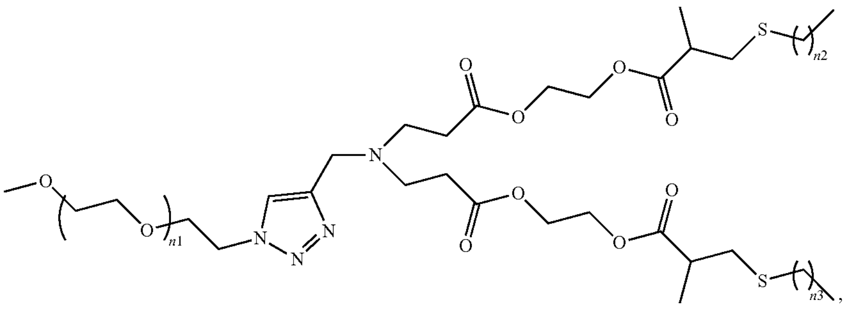

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments of the lipid composition of the present application, the PEG-lipid is present in the composition at a molar percentage from about 0.5% to about 10%.

In some embodiments of the lipid composition of the present application, the PEG-lipid is present in the composition at a molar percentage about 0.5%, about 1%, about 2%, about 3%, about 4%, about 5%, about 6%, about 7%, about 8%, about 9%, or about 10%.

In some embodiments of the lipid composition of the present application, the PEG-lipid is present in the composition at a molar percentage from about 0.5% to about 10%, from about 0.5% to about 5%, from about 0.5% to about 4%, from about 0.5% to about 3%, from about 0.5% to about 2%, from about 0.5% to about 1%, from about 1% to about 5%, from about 1% to about 4.5%, from about 1% to about 4%, from about 1% to about 3.5%, from about 1% to about 3%, from about 1% to about 2%, from about 2% to about 5%, from about 2% to about 4.5%, from about 2% to about 4%, from about 2% to about 3.5%, from about 2% to about 3%, from about 3% to about 5%, from about 3% to about 4.5%, from about 3% to about 4%, from about 3% to about 3.5%, from about 4% to about 5%, or from about 4% to about 4.5%.

selected from the group shown in Table 8 and/or SEQ ID NOs: 1-11. In some embodiments, the mRNA encodes a gene-editing system or component thereof. In some embodiments, the payload comprises a polypeptide or a protein.

In some embodiments, the ethylphosphocholine is 1,2-dipalmitoyl-sn-glycero-3-ethylphosphocholine (16:0 EPC). In some embodiments, the ionizable cationic lipid is 4A3—SC7. In some embodiments, the helper lipid is 1,2-dioleoyl-sn-glycero-3-phosphoethanolamine (DOPE).

In some embodiments, the composition comprises 4A3-SC7 at a molar percentage of about 5 to about 30%, 16:0 EPC at a molar percentage of about 20 to about 50%, DOPE at a molar percentage of about 8 to about 23%, cholesterol at a molar percentage of about 15 to about 46%, and/or DMG-PEG at a molar percentage of about 0.5 to about 10%. In some embodiments, the composition comprises 4A3-SC7 at a molar percentage of about 13 to about 20%, 16:0 EPC at a molar percentage of about 20 to about 40%, DOPE at a molar percentage of about 13 to about 20%, cholesterol at a molar percentage of about 30 to about 40%, and/or DMG-PEG at a molar percentage of about 3 to about 5%. In some embodiments, the composition comprises 4A3-SC7 at a molar percentage of about 16%, 16:0 EPC at a molar percentage of about 30%, DOPE at a molar percentage of about 16%, cholesterol at a molar percentage of about 33%, and/or DMG-PEG at a molar percentage of about 3%. In some embodiments, the composition comprises 4A3-SC7 at a molar percentage of about 14%, 16:0 EPC at a molar percentage of about 40%, DOPE at a molar percentage of about 14%, cholesterol at a molar percentage of about 39%, and/or DMG-PEG at a molar percentage of about 4%.

In some embodiments, the composition comprises 4A3-SC7 at a molar percentage of 19%, 16:0 EPC at a molar percentage of 20%, DOPE at a molar percentage of 19%, cholesterol at a molar percentage of 38%, and/or DMG-PEG at a molar percentage of 4%. In some embodiments, the composition comprises 4A3-SC7 at a molar percentage of 17%, 16:0 EPC at a molar percentage of 30%, DOPE at a molar percentage of 17%, cholesterol at a molar percentage of 33% and/or DMG-PEG at a molar percentage of 3%. In some embodiments, the composition comprises 4A3-SC7 at a molar percentage of 14%, 16:0 EPC at a molar percentage of 40%, DOPE at a molar percentage of 14%, cholesterol at a molar percentage of 39%, and/or DMG-PEG at a molar percentage of 4%. In some embodiments, the composition comprises 4A3-SC7 at a molar percentage of 12%, 16:0 EPC at a molar percentage of 50%, DOPE at a molar percentage of 12%, cholesterol at a molar percentage of 24%, and/or DMG-PEG at a molar percentage of 2%.

Payloads

The present disclosure contemplates delivery of various payloads useful in the treatment of a lung disease. Payloads comprise therapeutic polypeptides or polynucleotides encoding polypeptides. For example, the payload may be a polynucleotide encoding a gene related to lung disease, or a polynucleotide encoding a gene editor for editing a gene related to lung disease.

Polypeptides

In some embodiments, the disclosure provides polypeptides comprising one or more therapeutic proteins. Therapeutic proteins comprise, but are not limited to cytokines, chemokines, interleukins, interferons, growth factors, coagulation factors, anti-coagulants, blood factors, bone morphogenic proteins, immunoglobulins, or enzymes. Some non-limiting examples of particular therapeutic proteins include Erythropoietin (EPO), Granulocyte colony-stimulating factor (G-CSF), Alpha-galactosidase A, Alpha-L-iduronidase, Thyrotropin a, N-acetylgalactosamine-4-sulfatase (rhASB), Dornase alfa, Tissue plasminogen activator (TP A) Activase, Glucocerebrosidase, Interferon (IF) b-la, Interferon b-lb, Interferon gamma, Interferon alpha, TNF-alpha, IL-1 through TL-36, Human growth hormone (rHGH), Human insulin (BHI), Human chorionic gonadotropin a, Darbepoetin a, Follicle-stimulating hormone (FSH), and Factor VIII.

In some embodiments, the polypeptide comprises a peptide or protein that restores the function of a defective protein in a subject. For example, the polynucleotide encodes a cystic fibrosis transmembrane conductance regulator (CFTR) protein, Dynein axonemal heavy chain 5, Dynein axonemal heavy chain 11, Bone morphogenetic protein receptor type 2, Fumarylacetoacetate hydrolase, Phenylalanine hydroxylase, Alpha-L-iduronidase, Collagen type IV alpha 3 chain, Collagen type IV alpha 4 chain, Collagen type IV alpha 5 chain, Poly cystin 1, Polycystin 2, Fibrocystin (or polyductin), Solute carrier family 3 member 1, Solute carrier family 7 member 9, Paired box gene 9, Myosin VIIA, Cadherin related 23, Usherin, Clarin 1, Gap junction beta-2 protein, Gap junction beta-6 protein, Rhodopsin, dystrophia myotonica protein kinase, Dystrophin, Sodium voltage-gated channel alpha subunit 1, Sodium voltage-gated channel beta subunit 1, Coagulation factor VIII, Coagulation factor IX, N-glycanase 1, Palmitoyl-protein thioesterase 1, Tripeptidyl peptidase 1, Kvl 1.1 (alpha subunit of potassium ion channel), Palmitoyl-protein thioesterase 1, ATM serine/threonine kinase, or Fibrillin 1.

Polynucleotides

In some embodiments, the lipid composition described herein comprises one or more polynucleotides. In some embodiments, the polynucleotides encode for one or more polypeptides described herein.

Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a R-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

In addition, it should be clear that the present disclosure is not limited to the specific polynucleotides disclosed herein. The present disclosure is not limited in scope to any particular source, sequence, or type of polynucleotides, however, as one of ordinary skill in the art could readily identify related homologs in various other sources of the polynucleotides including polynucleotides from non-human species (e.g., mouse, rat, rabbit, dog, monkey, gibbon, chimp, ape, baboon, cow, pig, horse, sheep, cat and other species). It is contemplated that the polynucleotides used in the present disclosure can comprise a sequence based upon a naturally-occurring sequence. Allowing for the degeneracy of the genetic code, sequences that have at least about 50%, usually at least about 60%, more usually about 70%, most usually about 80%, preferably at least about 90% and most preferably about 95% of nucleotides that are identical to the nucleotide sequence of the naturally-occurring sequence. In some embodiments, the polynucleotide is a complementary sequence to a naturally occurring sequence, or complementary to at least 75%, at least 80%, at least 85%, at least 90%, at least 95% and 100%. Longer polynucleotides encoding 250, 500, 1000, 1212, 1500, 2000, 2500, 3000 or longer are contemplated herein.

In some embodiments, the polynucleotide used herein may be derived from genomic DNA, i.e., cloned directly from the genome of a particular organism. In some embodiments, the polynucleotide comprises complementary DNA (cDNA). Also contemplated is a cDNA plus a natural intron or an intron derived from another gene; such engineered molecules are sometime referred to as “mini-genes”. The term “cDNA” is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the polynucleotide comprises one or more segments comprising a small interfering ribonucleic acid (siRNA), a short hairpin RNA (shRNA), a micro-ribonucleic acid (miRNA), a primary micro-ribonucleic acid (pri-miRNA), a long non-coding RNA (lncRNA), a messenger ribonucleic acid (mRNA), a plasmid deoxyribonucleic acid (pDNA), a transfer ribonucleic acid (tRNA), an antisense oligonucleotide (ASO), an antisense ribonucleic acid (RNA), a guide ribonucleic acid, deoxyribonucleic acid (DNA), a double stranded deoxyribonucleic acid (dsDNA), a single stranded deoxyribonucleic acid (ssDNA), a single stranded ribonucleic acid (ssRNA), a or double stranded ribonucleic acid (dsRNA). In some embodiments, the polynucleotide encodes at least one of the therapeutic agent (or prophylactic agent) described herein.

In some embodiments, the polynucleotide is greater than 30 nucleotides, greater than 50 nucleotides, greater than 100 nucleotides, greater than 200 nucleotides, greater than 300 nucleotides, greater than 400 nucleotides, greater than 500 nucleotides, greater than 600 nucleotides, greater than 700 nucleotides, greater than 800 nucleotides, greater than 900 nucleotides, greater than 1000 nucleotides, greater than 1500 nucleotides, greater than 2000 nucleotides, greater than 2500 nucleotides, greater than 3000 nucleotides, greater than 3500 nucleotides, greater than 4000 nucleotides, greater than 4500 nucleotides, or greater than 5000 nucleotides in length.

In some embodiments, the mRNA is about 50 nucleotides in length. In some embodiments, the mRNA molecule is about 100 nucleotides in length. In some embodiments, the mRNA molecule is about 200 nucleotides in length. In some embodiments, the mRNA molecule is about 300 nucleotides in length. In some embodiments, the mRNA molecule is about 400 nucleotides in length. In some embodiments, the mRNA molecule is about 500 nucleotides in length. In some embodiments, the mRNA molecule is about 600 nucleotides in length. In some embodiments, the mRNA molecule is about 700 nucleotides in length. In some embodiments, the mRNA molecule is about 800 nucleotides in length. In some embodiments, the mRNA molecule is about 900 nucleotides in length. In some embodiments, the mRNA molecule is about 1000 nucleotides in length. In some embodiments, the mRNA molecule is about 2000 nucleotides in length. In some embodiments, the mRNA molecule is about 3000 nucleotides in length. In some embodiments, the mRNA molecule is about 4000 nucleotides in length. In some embodiments, the mRNA molecule is about 5000 nucleotides in length.

In some embodiments, the polynucleotide comprises about 50 to about 100000 nucleotides. In some embodiments, the polynucleotide comprises about 50 to about 5000 nucleotides. In some embodiments, the polynucleotide comprises about 50 to about 2500 nucleotides. In some embodiments, the polynucleotide comprises about 50 to about 1000 nucleotides. In some embodiments, the polynucleotide comprises about 50 to about 500 nucleotides. In some embodiments, the polynucleotide comprises about 50 to about 300 nucleotides. In some embodiments, the polynucleotide comprises about 50 to about 200 nucleotides. In some embodiments, the polynucleotide comprises about 50 to about 100 nucleotides. In some embodiments, the polynucleotide comprises about 100 to about 100000 nucleotides. In some embodiments, the polynucleotide comprises about 100 to about 5000 nucleotides. In some embodiments, the polynucleotide comprises about 100 to about 2500 nucleotides. In some embodiments, the polynucleotide comprises about 100 to about 1000 nucleotides. In some embodiments, the polynucleotide comprises about 100 to about 500 nucleotides. In some embodiments, the polynucleotide comprises about 100 to about 300 nucleotides. In some embodiments, the polynucleotide comprises about 100 to about 200 nucleotides. In some embodiments, the polynucleotide comprises about 500 to about 100000 nucleotides. In some embodiments, the polynucleotide comprises about 500 to about 5000 nucleotides. In some embodiments, the polynucleotide comprises about 500 to about 2500 nucleotides. In some embodiments, the polynucleotide comprises about 500 to about 1000 nucleotides. In some embodiments, the polynucleotide comprises about 1000 to about 100000 nucleotides. In some embodiments, the polynucleotide comprises about 1000 to about 5000 nucleotides. In some embodiments, the polynucleotide comprises about 1000 to about 2500 nucleotides. In some embodiments, the polynucleotide comprises about 1000 to about 2000 nucleotides.

In some embodiments, the LNP composition comprises mRNA at a lipid:mRNA (weight/weight) ratio is between 5:1 and 40:1. In some embodiments, the LNP comprises mRNA at a lipid:mRNA ratio between 10:1 and 40:1, between 15:1 and 40:1, between 20:1 and 40:1, between 25:1 and 40:1, between 30:1 and 40:1, between 35:1 and 40:1, between 20:1 and 35:1, between 25:1 and 35:1, between 30:1 and 35:1, between 20:1 and 30:1, between 25:1 and 30:1, between 20:1 and 25:1, between 25:1 and 30:1, between 25:1 and 35:1, between 20:1 and 36:1, between 25:1 and 36:1, between 5:1 and 45:1, between 20:1 and 40:1, between 25:1 and 40:1, between 35:1 and 40:1, or between 30:1 and 40:1. In some embodiments, the LNP comprises mRNA at a lipid:mRNA ratio of 30:1. In some embodiments, the LNP comprises mRNA a lipid:mRNA ratio of 40:1.

In some embodiments, the mRNA encodes a gene or a portion of a gene related to lung disease shown in Table 8 or Table 9.

It is understood that T is T in DNA and T is U in RNA polynucleotide sequences.

TABLE 8

Exemplary genes related to lung diseases

| Lung disease | Related Genes |
|---|---|
| Cystic fibrosis | CFTR |
| Primary Ciliary Dyskinesia (PCD) | ARMC4, CCDC114, CCDC39, CCDC40, DNAAF1, DNAAF2, DNAAF3, DNAAF4, DNAH11, DNAH5, DNAI1, DNAI2, LRRC6, LRRC50, RSPH1, RSPH4A, SPAG1, ZMYND10 |
| alpha-1 antitrypsin deficiency | AAT |
| pulmonary arterial hypertension | BMPR2(Bone morphogenetic protein receptor type 2) |
| Lung disease disorders | MUC5b |
| Chronic Obstructive Pulmonary Disease (COPD) | Upregulated genes strongly associated with COPD: ADAMTS4 (aggrecanase-1), ANDPT2, BMPR1 B, BTG2, CEBPA, DKK3, Fas, FGFR2, FZD6, GLI1, HK2, HMGA1, HMGA2, IGFIR, IGF2, IL6-R, MMP2, MMP13, MMP26, MUC1, SFRP5, SGPL1, SMAD4, STAT3, TACSTD2, TNF, TNFAIP33 |

TABLE 9

Exemplary sequences of genes related to lung diseases

| Gene | Sequence | SEQ ID NO |
|---|---|---|
| CFTR | GGGAGACCCAAGCTGGCTAGCGTTTAAACTTCAGCTTGGCAAT | 1 |
| | CCGGTACTGTTGGTAAAGCCACCATGCAGAGAAGCCCCCTGGA | |
| | AAAGGCCAGCGTGGTGAGCAAGCTGTTCTTCAGCTGGACCCGG | |
| | CCCATCCTGCGGAAGGGCTACAGACAGAGACTGGAACTGAGCG | |
| | ACATCTACCAGATCCCCAGCGTGGACAGCGCCGACAACCTGAG | |
| | CGAGAAGCTGGAAAGAGAGTGGGACAGAGAGCTGGCCAGCAAG | |
| | AAGAACCCCAAGCTGATCAACGCCCTGCGGCGGTGCTTCTTCT | |
| | GGCGGTTCATGTTCTACGGCATCTTCCTGTACCTGGGCGAAGT | |
| | GACCAAAGCCGTGCAGCCCCTGCTGCTGGGCAGAATCATCGCC | |
| | AGCTACGACCCCGACAACAAAGAGGAACGGAGCATCGCCATCT | |
| | ACCTCGGCATCGGCCTGTGCCTGCTGTTCATCGTCAGAACCCT | |
| | GCTGCTGCACCCCGCCATCTTCGGACTGCACCACATCGGCATG | |
| | CAGATGCGGATCGCCATGTTCAGCCTGATCTACAAGAAAACCC | |
| | TGAAGCTGAGCAGCAGAGTGCTGGACAAGATCAGCATCGGACA | |
| | GCTGGTGAGCCTGCTGAGCAACAACCTGAACAAGTTCGACGAA | |
| | GGCCTGGCCCTGGCCCACTTCGTGTGGATCGCCCCCCTGCAAG | |
| | TGGCCCTGCTGATGGGCCTGATCTGGGAACTGCTGCAGGCCAG | |
| | CGCCTTCTGCGGACTGGGATTCCTGATCGTGCTGGCCCTGTTC | |
| | CAGGCCGGACTGGGGAGAATGATGATGAAGTACCGGGACCAGA | |
| | GAGCCGGCAAGATCAGCGAGAGACTGGTCATCACCAGCGAGAT | |
| | GATCGAGAACATCCAGAGCGTGAAGGCCTACTGCTGGGAAGAG | |
| | GCCATGGAAAAGATGATCGAGAACCTGCGGCAGACCGAGCTGA | |
| | AGCTGACAAGAAAGGCCGCCTACGTGCGCTACTTCAACAGCAG | |
| | CGCCTTCTTCTTCAGCGGCTTCTTCGTGGTGTTCCTGAGCGTG | |
| | CTGCCCTACGCCCTGATCAAGGGCATCATCCTGAGAAAGATCT | |
| | TCACCACCATCAGCTTCTGCATCGTGCTGCGGATGGCCGTGAC | |
| | CAGACAGTTCCCCTGGGCCGTGCAGACCTGGTACGACAGCCTG | |
| | GGCGCCATCAACAAGATCCAGGACTTCCTGCAGAAGCAAGAGT | |
| | ACAAGACCCTCGAGTACAACCTGACCACCACCGAGGTGGTCAT | |
| | GGAAAACGTGACCGCCTTCTGGGAGGAAGGCTTCGGCGAGCTG | |
| | TTCGAGAAGGCCAAGCAGAACAACAACAACCGCAAGACCAGCA | |
| | ACGGCGACGACAGCCTGTTCTTCAGCAACTTCAGCCTGCTGGG | |
| | GACCCCCGTGCTGAAGGACATCAACTTCAAGATCGAGCGGGGA | |
| | CAGCTGCTGGCCGTGGCCGGAAGCACAGGCGCCGGAAAAACCA | |
| | GCCTGCTCATGGTCATCATGGGCGAGCTGGAACCCAGCGAGGG | |
| | CAAGATCAAGCACAGCGGCAGGATCAGCTTCTGCAGCCAGTTC | |
| | AGCTGGATCATGCCCGGCACCATCAAAGAGAACATCATCTTCG | |
| | GCGTGAGCTACGACGAGTACAGATACCGCAGCGTGATCAAGGC | |
| | CTGCCAGCTGGAAGAGGACATCAGCAAGTTCGCCGAGAAGGAC | |
| | AACATCGTGCTCGGCGAAGGCGGCATCACACTGAGCGGCGGAC | |
| | AGAGGGCCAGAATCAGCCTGGCCAGAGCCGTGTACAAGGACGC | |
| | CGACCTGTACCTGCTGGACAGCCCCTTCGGCTACCTGGACGTG | |
| | CTGACCGAGAAAGAGATCTTCGAGAGCTGCGTGTGCAAGCTGA | |
| | TGGCCAACAAGACCCGGATCCTGGTCACCAGCAAGATGGAACA | |
| | CCTGAAGAAGGCCGACAAGATCCTGATCCTGCACGAGGGCAGC | |
| | AGCTACTTCTACGGCACCTTCAGCGAGCTGCAGAACCTGCAGC | |
| | CCGACTTCAGCAGCAAACTGATGGGCTGCGACAGCTTCGACCA | |
| | GTTCAGCGCCGAGCGGAGAAACAGCATCCTGACAGAGACACTG | |
| | CACCGGTTCAGCCTGGAAGGCGACGCCCCCGTGAGCTGGACCG | |
| | AGACAAAGAAGCAGAGCTTCAAGCAGACCGGCGAGTTCGGCGA | |
| | GAAGCGGAAGAACAGCATCCTGAACCCCATCAACAGCATCCGG | |
| | AAGTTCAGCATCGTCCAGAAAACCCCCCTGCAGATGAACGGCA | |
| | TCGAAGAGGACAGCGACGAGCCCCTGGAAAGACGGCTGAGCCT | |
| | GGTGCCCGACAGCGAACAGGGCGAAGCCATCCTGCCCCGGATC | |
| | AGCGTGATCAGCACAGGCCCCACACTGCAGGCCCGGAGAAGGC | |
| | AGAGCGTGCTGAACCTGATGACCCACAGCGTGAACCAGGGACA | |
| | GAACATCCACAGAAAGACCACCGCCAGCACACGGAAAGTGAGC | |
| | CTGGCCCCCCAGGCCAACCTGACTGAGCTGGACATCTACAGCA | |
| | GACGGCTGAGCCAAGAGACAGGCCTGGAAATCAGCGAGGAAAT | |
| | CAACGAAGAGGACCTGAAAGAGTGCTTCTTCGACGACATGGAA | |
| | AGCATCCCCGCCGTGACAACCTGGAACACCTACCTGCGGTACA | |
| | TCACCGTGCACAAGAGCCTGATCTTCGTGCTGATCTGGTGCCT | |
| | CGTGATCTTCCTGGCCGAAGTGGCCGCCAGCCTGGTGGTGCTG | |
| | TGGCTGCTCGGAAACACCCCACTGCAGGACAAGGGCAACAGCA | |
| | CCCACAGCCGGAACAACAGCTACGCCGTGATCATCACCAGCAC | |
| | CAGCAGCTACTACGTGTTCTACATCTACGTGGGCGTCGCCGAC | |
| | ACTCTGCTCGCCATGGGCTTCTTCAGAGGACTGCCCCTGGTGC | |
| | ACACCCTGATCACCGTGAGCAAGATCCTGCACCACAAGATGCT | |
| | GCACAGCGTCCTGCAGGCCCCCATGAGCACACTGAACACCCTG | |
| | AAAGCCGGCGGAATCCTGAACAGATTCAGCAAGGACATCGCCA | |
| | TCCTGGACGACCTGCTGCCCCTGACCATCTTCGACTTCATCCA | |
| | GCTGCTGCTGATCGTGATCGGCGCCATCGCCGTGGTGGCCGTG | |
| | CTGCAGCCCTACATCTTCGTGGCCACCGTGCCCGTGATCGTGG | |
| | CCTTCATCATGCTGCGGGCCTACTTCCTGCAGACCAGCCAGCA | |
| | GCTGAAGCAGCTCGAGAGCGAGGGCAGAAGCCCCATCTTCACC | |

TABLE 9-continued

Exemplary sequences of genes related to lung diseases

| Gene | Sequence | SEQ ID NO |
|---|---|---|
| | CACCTCGTGACCAGCCTGAAAGGCCTGTGGACCCTGAGAGCCT<br>TCGGCAGACAGCCCTACTTCGAGACACTGTTCCACAAGGCCCT<br>GAACCTGCACACCGCCAACTGGTTCCTGTACCTGAGCACCCTG<br>CGGTGGTTCCAGATGAGGATCGAGATGATCTTCGTCATCTTCT<br>TCATCGCCGTGACCTTCATCAGCATCCTCACCACTGGCGAAGG<br>CGAGGGCAGAGTGGGAATCATCCTGACCCTGGCCATGAACATC<br>ATGAGCACACTCCAGTGGGCCGTGAACAGCAGCATCGACGTGG<br>ACAGCCTGATGCGGAGCGTGAGCCGGGTGTTCAAGTTCATCGA<br>CATGCCCACAGAGGGCAAGCCCACCAAGAGCACCAAGCCCTAC<br>AAGAACGGCCAGCTGAGCAAAGTCATGATCATCGAGAACAGCC<br>ACGTCAAGAAGGACGACATCTGGCCCAGCGGAGGCCAGATGAC<br>CGTGAAGGACCTGACCGCCAAGTACACCGAAGGCGGAAACGCC<br>ATCCTGGAAAACATCAGCTTCAGCATCAGCCCCGGCCAGCGCG<br>TGGGACTCCTGGGAAGAACCGGAAGCGGCAAGAGCACTCTGCT<br>GAGCGCCTTCCTGAGACTGCTGAACACCGAGGGCGAGATCCAG<br>ATCGACGGGGTGAGCTGGGACAGCATCACCCTGCAACAATGGC<br>GGAAGGCCTTCGGCGTGATCCCCCAGAAGGTGTTCATCTTCAG<br>CGGCACGTTCCGGAAGAACCTGGACCCCTACGAGCAGTGGAGC<br>GACCAAGAGATCTGGAAGGTGGCCGACGAAGTGGGACTGAGAA<br>GCGTGATCGAGCAGTTCCCCGGCAAGCTGGACTTCGTGCTGGT<br>GGACGGCGGCTGCGTGCTGAGCCACGGACACAAGCAGCTGATG<br>TGCCTGGCCAGAAGCGTGCTGAGCAAGGCCAAGATCCTGCTGC<br>TCGACGAGCCCAGCGCCCACCTGGACCCCGTGACCTACCAGAT<br>CATCCGGCGGACACTGAAGCAGGCCTTCGCCGACTGCACCGTG<br>ATCCTGTGCGAGCACAGAATCGAGGCCATGCTGGAATGCCAGC<br>AGTTCCTGGTGATCGAAGAGAACAAAGTGCGGCAGTACGACAG<br>CATCCAGAAGCTGCTGAACGAGCGGAGCCTGTTCAGACAGGCC<br>ATCAGCCCCAGCGACAGAGTGAAGCTGTTCCCCCACCGGAACA<br>GCAGCAAGTGCAAGAGCAAGCCCCAGATCGCCGCCCTGAAAGA<br>AGAAACCGAGGAAGAGGTGCAGGACACACGGCTGTGAGAATTC<br>tgcag | |
| DNAI1 | GGGAGACCCAAGCTGGCTAGCGTTTAAACTTCAGCTTGGCAAT<br>CCGGTACTGTTGGTAAAGCCACCATGATCCCAGCAAGCGCCAA<br>GGCACCACACAAGCAGCCCCACAAGCAGAGCATCAGCATCGGC<br>AGGGGCACAAGGAAGAGGGACGAGGACAGCGGAACCGAAGTGG<br>GAGAGGGAACAGACGAGTGGGCACAGAGCAAGGCAACCGTGCG<br>CCCACCCGACCAGCTGGAGCTGACAGACGCCGAGCTGAAGGAG<br>GAGTTCACCAGGATCCTGACAGCCAACAACCCACACGCCCCCC<br>AGAACATCGTGCGCTACAGCTTCAAGGAGGGCACATACAAGCC<br>AATCGGCTTCGTGAACCAGCTGGCCGTGCACTACACCCAAGTG<br>GGCAACCTGATCCCCAAGGACAGCGACGAGGGCCGGAGACAGC<br>ACTACAGGGACGAGCTGGTGGCAGGAAGCCAGGAGAGCGTGAA<br>AGTGATCAGCGAGACCGGCAACCTGGAGGAGGACGAGGAGCCA<br>AAGGAGCTGGAGACCGAGCCAGGAAGCCAGACAGACGTGCCCG<br>CAGCAGGAGCAGCAGAGAAGGTGACCGAGGAGGAGCTGATGAC<br>ACCCAAGCAGCCAAAGGAGCGGAAGCTGACCAACCAGTTCAAC<br>TTCAGCGAGAGAGCCAGCCAGACATACAACAACCCAGTGCGGG<br>ACAGAGAGTGCCAGACCGAGCCACCCCCCAGAACCAACTTCAG<br>CGCCACAGCCAACCAGTGGGAGATCTACGACGCCTACGTGGAG<br>GAGCTGGAGAAGCAGGAGAAGACCAAGGAGAAGGAGAAGGCCA<br>AGACACCCGTGGCCAAGAAGAGCGGCAAGATGGCCATGCGGAA<br>GCTGACCAGCATGGAGAGCCAGACAGACGACCTGATCAAGCTG<br>AGCCAGGCCGCCAAGATCATGGAGAGAATGGTGAACCAGAACA<br>CCTACGACGACATCGCCCAGGACTTCAAGTACTACGACGACGC<br>AGCAGACGAGTACAGGGACCAAGTGGGCACACTGCTGCCCCTG<br>TGGAAGTTCCAGAACGACAAGGCCAAGAGGCTGAGCGTGACCG<br>CCCTGTGCTGGAACCCCAAAGTACAGGGACCTGTTCGCAGTGGG<br>ATACGGAAGCTACGACTTCATGAAGCAGAGCAGAGGCATGCTG<br>CTGCTGTACAGCCTGAAGAACCCCAGCTTCCCCGAGTACATGT<br>TCAGCAGCAACAGCGGCGTGATGTGCCTGGACATCCACGTGGA<br>CCACCCCTACCTGGTGGCCGTGGGCCACTACGACGGCAACGTG<br>GCCATCTACAACCTGAAGAAGCCCCACAGCCAGCCCAGCTTCT<br>GCAGCAGCGCCAAGAGCGGCAAGCACAGCGACCCCGTGTGGCA<br>GGTGAAGTGGCAGAAGGACGACATGGACCAGAACCTGAACTTC<br>TTCAGCGTGAGCAGCGACGGCAGGATCGTGAGCTGGACCCTGG<br>TGAAGCGCAAGCTGGTGCACATCGACGTGATCAAGCTGAAGGT<br>GGAGGGCAGCACCACAGAGGTGCCAGAGGGACTGCAGCTGCAC<br>CCAGTGGGATGCGGCACAGCCTTCGACTTCCACAAGGAGATCG<br>ACTACATGTTCCTGGTGGGCACCGAGGAGGGCAAGATCTACAA<br>GTGCAGCAAGAGCTACAGCAGCCAGTTCCTGGACACATACGAC<br>GCCCACAACATGAGCGTGGACACCGTGAGCTGGAACCCCTACC<br>ACACAAAGGTGTTCATGAGCTGCAGCAGCGACTGGACCGTGAA<br>GATCTGGGACCACACCATCAAGACACCCATGTTCATCTACGAC<br>CTGAACAGCGCCGTGGGCGACGTGGCATGGGCACCATACAGCA | 2 |

TABLE 9-continued

| Exemplary sequences of genes related to lung diseases | | |
|---|---|---|
| Gene | Sequence | SEQ ID NO |
| | GCACAGTGTTCGCAGCAGTGACCACAGACGGCAAGGCACACAT<br>CTTCGACCTGGCCATCAACAAGTACGAGGCCATCTGCAACCAG<br>CCCGTGGCCGCCAAGAAGAACAGGCTGACCCACGTGCAGTTCA<br>ACCTGATCCACCCCATCATCATCGTGGGCGACGACCGGGGCCA<br>CATCATCAGCCTGAAGCTGAGCCCCAACCTGAGAAAGATGCCC<br>AAGGAGAAGAAGGGACAGGAGGTGCAGAAGGGACCAGCAGTGG<br>AGATCGCAAAGCTGGACAAGCTGCTGAACCTGGTGCGCGAGGT<br>GAAGATCAAGACCTGAGAATTCtgcag | |
| DNAH5 | ATGTTTAGGATTGGGAGGAGACAGCTCTGGAAGCATAGCGTCA<br>CTCGAGTTTTAACGCAAAGACTGAAGGGAGAGAAGGAAGCCAA<br>GCGGGCTCTTTTGGATGCGAGGCATAACTACTTATTTGCAATT<br>GTGGCTTCCTGTTTGGACCTGAACAAAACCGAAGTGGAGGATG<br>CCATTCTTGAAGGGAATCAGATTGAAAGAATTGATCAACTTTT<br>TGCTGTTGGAGGTCTCCGACACCTCATGTTTTACTATCAAGAT<br>GTGGAGGAAGCAGAAACAGGACAACTTGGCTCTCTAGGAGGGG<br>TAAATCTTGTTTCTGGAAAGATTAAAAAACCTAAGGTGTTCGT<br>GACCGAGGGAAACGATGTGGCTCTTACTGGGGTATGTGTGTTC<br>TTCATCAGGACTGACCCTTCCAAAGCCATCACCCCTGACAACA<br>TCCACCAGGAGGTGAGTTTTAACATGTTAGATGCGGCAGATGG<br>AGGCCTGCTCAACAGTGTGAGACGTTTGCTGTCGGACATCTTC<br>ATTCCTGCTCTCAGAGCCACGAGCCATGGCTGGGGCGAGCTCG<br>AGGGCCTTCAGGACGCAGCTAACATTCGCCAGGAGTTCTTGAG<br>CTCCCTGGAAGGCTTTGTGAACGTCCTGTCGGGTGCACAGGAG<br>AGTCTGAAGGAGAAGGTGAACCTTCGAAAGTGTGACATACTTG<br>AACTGAAAACCCTAAAGGAACCTACGGACTACTTGACTCTAGC<br>AAATAACCCTGAGACTTTGGGAAAAATAGAGGATTGCATGAAA<br>GTATGGATCAAACAGACAGAACAGGTTCTTGCTGAAAACAATC<br>AGCTGCTGAAGGAAGCGGATGACGTTGGGCCACGAGCGGAGCT<br>GGAGCACTGGAAAAAAAGACTCTCCAAGTTTAACTACCTTTTG<br>GAACAATTGAAAAGCCCGGATGTGAAGGCTGTGCTGGCAGTGC<br>TTGCGGCGGCCAAGTCGAAACTGCTGAAGACTTGGCGGGAGAT<br>GGATATTCGAATCACTGATGCAACTAATGAAGCAAAGGACAAT<br>GTGAAATACTTGTATACACTTGAAAAATGTTGTGACCCTTTGT<br>ACAGCAGTGATCCCCTATCCATGATGGATGCTATTCCTACACT<br>TATAAATGCAATTAAAATGATCTATAGTATCTCTCATTACTAT<br>AATACCTCTGAGAAGATCACATCTCTGTTTGTAAAGGTGACAA<br>ATCAGATTATATCTGCATGTAAAGCCTATATTACCAATAATGG<br>AACCGCTTCCATCTGGAACCAGCCACAGGATGTTGTTGAAGAA<br>AAAATACTATCTGCGATTAAACTGAAACAGGAATACCAGCTCT<br>GCTTTCACAAGACAAAACAAAAGCTTAAACAAAATCCAAATGC<br>AAAACAATTTGATTTTAGCGAGATGTATATTTTTGGAAAATTC<br>GAAACTTTTCACCGACGCCTTGCCAAGATAATAGACATCTTTA<br>CAACCCTCAAGACGTATTCAGTCCTGCAAGATTCCACAATTGA<br>AGGGCTGGAAGACATGGCCACTAAATACCAGGGCATTGTGGCA<br>ACCATAAAGAAAAAGGAATACAATTTCCTAGACCAGCGGAAAA<br>TGGATTTTGACCAAGATTACGAAGAGTTTTGCAAGCAGACTAA<br>TGACCTTCATAACGAGTTGCGGAAGTTCATGGATGTTACATTT<br>GCAAAGATTCAAAACACAAATCAAGCTCTAAGAATGTTGAAGA<br>AATTTGAAAGATTGAATATACCTAATCTTGGTATTGATGACAA<br>ATATCAACTTATCCTTGAGAACTATGGGGCTGACATTGATATG<br>ATTTCAAAGCTGTATACAAAGCAGAAATACGATCCTCCTCTGG<br>CTCGAAACCAGCCTCCCATCGCTGGAAAGATTTTGTGGGCCCG<br>CCAGCTCTTCCATAGGATTCAGCAGCCCATGCAGCTTTTCCAG<br>CAGCACCCAGCTGTGCTAAGCACGGCAGAAGCCAAACCTATAA<br>TTCGCAGTTACAACAGGATGGCCAAGGTCCTCCTGGAGTTTGA<br>GGTCCTCTTCCACAGGGCGTGGCTTCGGCAAATTGAAGAAATT<br>CATGTAGGTCTTGAGGCTTCATTATTGGTGAAGGCTCCAGGCA<br>CAGGGGAATTGTTTGTAAACTTTGACCCTCAGATATTAATCTT<br>ATTTAGAGAAACAGAGTGCATGGCCCAGATGGGTCTGGAAGTC<br>TCTCCACTGGCAACTTCCCTCTTCCAGAAACGAGATAGATACA<br>AAAGGAACTTCAGTAACATGAAGATGATGCTAGCTGAATATCA<br>GAGAGTGAAGTCAAAAATACCTGCTGCCATTGAGCAATTGATT<br>GTCCCTCACTTGGCCAAAGTGGATGAAGCTCTCCAACCTGGCT<br>TGGCTGCACTGACCTGGACATCACTGAATATTGAGGCTTATTT<br>AGAAAACACTTTTGCAAAGATCAAGGACCTGGAGTTGCTGCTT<br>GACAGGGTCAATGATTTGATTGAGTTCCGCATTGATGCCATTC<br>TAGAAGAAATGAGCAGCACGCCTCTTTGTCAGCTTCCCCAGGA<br>GGAGCCACTAACCTGTGAAGAGTTTCTCCAAATGACAAAGGAT<br>CTTTGTGTAAATGGTGCACAAATACTACATTTTAAAAGCTCAT<br>TAGTGGAGGAGGCAGTCAATGAGCTTGTAAATATGTTGCTGGA<br>TGTGGAAGTTTTATCTGAAGAAGAAAGTGAAAAAATATCCAAT<br>GAGAATAGTGTTAATTACAAAAATGAAAGTTCAGCAAAAAGAG<br>AAGAAGGAAATTTTGACACCTTGACATCATCTATTAATGCCAG<br>GGCCAATGCCCTGCTTTTGACGACAGTCACGAGGAAAAAGAAA | 3 |

TABLE 9-continued

Exemplary sequences of genes related to lung diseases

| Gene | Sequence | SEQ ID NO |
|---|---|---|
| | GAAACTGAGATGTTAGGGGAAGAAGCCCGCGAGTTACTCTCTC | |
| | ATTTCAACCATCAGAACATGGATGCTCTTCTGAAAGTTACAAG | |
| | GAATACACTAGAGGCCATTCGCAAACGTATTCATTCCTCTCAC | |
| | ACAATTAACTTCCGGGACAGTAACAGTGCCTCTAACATGAAGC | |
| | AGAACAGTTTGCCCATTTTCCGGGCAAGCGTCACTCTGGCCAT | |
| | TCCCAACATCGTCATGGCCCCTGCCCTGGAAGATGTACAGCAG | |
| | ACCCTGAACAAAGCCGTGGAGTGCATCATCAGTGTCCCTAAGG | |
| | GGGTCAGACAGTGGAGCAGTGAACTGTTGTCCAAGAAAAAGAT | |
| | ACAAGAAAGAAAAATGGCTGCTTTGCAGAGTAATGAAGACAGT | |
| | GATTCTGATGTTGAAATGGGAGAAAATGAACTTCAAGATACCT | |
| | TGGAGATAGCATCTGTAAATTTACCCATTCCCGTGCAAACCAA | |
| | GAACTATTATAAGAATGTTTCTGAAAACAAAGAGATTGTAAAA | |
| | TTAGTTTCTGTGCTTAGCACAATTATCAACTCCACCAAAAAGG | |
| | AAGTTATTACATCCATGGATTGCTTCAAACGCTACAATCACAT | |
| | TTGGCAAAAGGGAAAAGAAGAAGCCATTAAGACATTTATTACA | |
| | CAGAGCCCCTTGCTTTCTGAATTTGAGTCCCAGATTCTCTATT | |
| | TCCAAAACCTAGAGCAGGAAATTAATGCTGAGCCTGAATATGT | |
| | CTGTGTGGGTTCCATTGCTCTGTACACAGCTGACTTGAAGTTC | |
| | GCCCTGACTGCTGAGACAAAGGCCTGGATGGTTGTCATTGGAC | |
| | GCCACTGTAACAAAAAATACCGGAGTGAGATGGAAAACATTTT | |
| | TATGCTTATTGAAGAATTCAATAAGAAACTAAATCGTCCAATT | |
| | AAGGACCTAGATGATATTCGGATTGCAATGGCAGCGCTGAAAG | |
| | AAATAAGGGAGGAGCAAATCTCCATTGACTTTCAAGTAGGACC | |
| | TATTGAGGAATCTTATGCCCTGCTTAACAGATATGGACTTCTG | |
| | ATAGCAAGGGAAGAGATAGACAAAGTTGATACACTGCACTATG | |
| | CTTGGGAGAAGCTGCTGGCACGTGCTGGCGAAGTCCAGAATAA | |
| | ATTAGTCTCACTGCAGCCCAGTTTCAAGAAAGAGCTTATTAGT | |
| | GCTGTGGAGGTATTCCTCCAAGATTGTCACCAGTTTTATCTGG | |
| | ACTATGATTTGAATGGTCCAATGGCTAGCGGCTTGAAGCCCCA | |
| | GGAAGCCAGTGACAGGCTTATCATGTTTCAGAATCAATTTGAT | |
| | AATATCTATCGGAAATACATCACATATACTGGAGGAGAGGAGC | |
| | TTTTTGGCCTGCCAGCTACACAGTATCCTCAGCTTCTTGAAAT | |
| | AAAGAAGCAACTAAATCTTCTACAGAAAATATATACTCTGTAC | |
| | AACAGTGTCATAGAAACTGTAAATAGCTATTATGATATTCTTT | |
| | GGTCAGAGGTGAATATTGAAAAAATTAACAATGAACTCTTAGA | |
| | ATTCCAGAACAGATGTCGAAAGCTTCCCCGGGCCTTGAAGGAC | |
| | TGGCAGGCTTTTTTGGACCTGAAGAAGATCATTGATGATTTCA | |
| | GCGAGTGTTGCCCGCTGCTGGAATACATGGCCAGTAAAGCCAT | |
| | GATGGAGCGGCACTGGGAAAGGATAACCACCCTCACCGGGCAC | |
| | AGTCTGGATGTGGGGAATGAAAGCTTTAAGTTAAGAAATATCA | |
| | TGGAGGCACCTCTTCTGAAATATAAAGAGGAAATAGAGGACAT | |
| | CTGTATCAGTGCGGTGAAAGAGAGAGACATTGAGCAAAAGCTG | |
| | AAGCAAGTGATTAATGAATGGGACAATAAAACATTCACCTTCG | |
| | GCAGCTTTAAAACCCGTGGAGAGCTCCTCTTGAGAGGAGACAG | |
| | TACCTCGGAAATCATCGCCAACATGGAGGACAGCTTGATGTTG | |
| | CTGGGATCCCTACTGAGCAACAGGTACAATATGCCATTCAAAG | |
| | CCCAGATTCAAAAATGGGTGCAGTACCTTTCCAACTCAACAGA | |
| | CATCATCGAGAGCTGGATGACGGTGCAAAACCTGTGGATTTAT | |
| | TTAGAAGCTGTCTTTGTGGGAGGAGACATTGCCAAGCAGCTGC | |
| | CCAAGGAAGCCAAGCGGTTTTCTAACATAGATAAATCTTGGGT | |
| | GAAGATCATGACTCGGGCACATGAAGTGCCCAGTGTAGTCCAG | |
| | TGCTGTGTTGGAGATGAGACCCTGGGGCAGCTGTTACCACACT | |
| | TGCTGGACCAGTTGGAAATATGCCAGAAATCCCTTACTGGGTA | |
| | CTTGGAGAAAAAACGACTGTGCTTTCCTCGGTTTTTCTTCGTC | |
| | TCAGATCCTGCCCTTCTAGAGATTCTGGGGCAGGCGTCGGACT | |
| | CCCACACTATACAGGCCCATTTGCTGAATGTGTTTGACAACAT | |
| | TAAATCTGTCAAGTTCCACGAAAAGATCTATGATCGAATTCTG | |
| | TCAATTTCCTCTCAAGAGGGTGAGACGATTGAATTGGATAAAC | |
| | CTGTCATGGCAGAGGGCAATGTGGAAGTTTGGCTTAATTCTCT | |
| | TTTGGAAGAATCTCAGTCCTCATTGCATCTTGTGATTCGCCAG | |
| | GCAGCCGCAAATATTCAAGAAACAGGTTTCCAACTAACTGAAT | |
| | TTCTTTCATCCTTCCCTGCTCAGGTTGGATTATTAGGAATTCA | |
| | GATGATATGGACACGGGATTCAGAAGAAGCCCTTAGAAATGCC | |
| | AAGTTTGATAAAAAAATCATGCAGAAAACTAATCAGGCTTTCC | |
| | TGGAGCTACTCAATACATTGATAGACGTCACCACGAGGGATCT | |
| | GAGTTCCACGGAACGAGTGAAATACGAGACTCTGATTACTATT | |
| | CATGTGCACCAAAGGGATATCTTTGATGACCTGTGTCATATGC | |
| | ATATCAAGAGTCCCATGGACTTTGAGTGGCTGAAACAGTGCAG | |
| | ATTTTACTTTAACGAAGATTCTGACAAGATGATGATTCACATC | |
| | ACAGATGTGGCGTTCATATACCAGAATGAATTTTTAGGCTGCA | |
| | CTGACAGGCTTGTAATAACTCCACTTACAGACAGATGTTACAT | |
| | CACGCTGGCTCAAGCTCTGGGAATGAGCATGGGGGGAGCCCCT | |
| | GCTGGACCTGCAGGCACAGGCAAAACAGAAACCACTAAAGACA | |
| | TGGGACGATGCCTCGGGAAATACGTCGTGGTTTTCAATTGTTC | |
| | AGACCAGATGGATTTCCGAGGACTTGGACGGATTTTTAAGGGA | |

TABLE 9-continued

Exemplary sequences of genes related to lung diseases

| Gene | Sequence | SEQ ID NO |
|---|---|---|
| | CTGGCACAGTCTGGATCCTGGGGTTGTTTTGATGAATTTAACC | |
| | GTATTGATCTACCAGTTCTCTCGGTTGCAGCCCAGCAAATTTC | |
| | CATTATTCTGACATGTAAAAAGGAGCACAAAAAGTCTTTTATC | |
| | TTTACTGATGGAGATAATGTGACTATGAACCCTGAATTTGGGC | |
| | TTTTCTTAACCATGAATCCTGGCTATGCCGGACGGCAGGAACT | |
| | CCCTGAAAACTTGAAGATTAATTTCCGCTCAGTGGCCATGATG | |
| | GTGCCTGACCGTCAGATTATCATAAGGGTGAAGTTGGCTAGTT | |
| | GTGGCTTCATTGACAACGTTGTTTTGGCCAGGAAGTTTTTCAC | |
| | GCTCTACAAACTGTGTGAGGAGCAGCTTTCTAAGCAGGTTCAT | |
| | TATGACTTTGGCCTGCGTAACATTCTGTCAGTTCTTCGGACCT | |
| | TGGGAGCAGCAAAAAGAGCCAATCCAATGGATACGGAGTCCAC | |
| | GATTGTCATGCGTGTACTACGGGACATGAATCTTTCTAAACTG | |
| | ATTGATGAGGATGAACCCTTGTTTTTGAGTTTGATTGAAGATC | |
| | TCTTTCCAAATATTCTTCTGGACAAGGCAGGTTACCCTGAACT | |
| | GGAAGCAGCAATTAGTAGACAGGTTGAAGAAGCTGGTTTAATC | |
| | AACCATCCTCCTTGGAAACTGAAGGTCATCCAGCTATTCGAAA | |
| | CGCAGAGAGTGCGACATGGGATGATGACTCTGGGGCCCAGTGG | |
| | GGCTGGGAAGACCACCTGCATCCACACCTTGATGAGAGCCATG | |
| | ACAGATTGTGGAAAACCACATCGGGAAATGAGGATGAATCCCA | |
| | AAGCGATTACTGCCCCACAGATGTTTGGTCGGCTGGACGTTGC | |
| | CACAAATGACTGGACTGATGGGATATTTTCTACGCTTTGGAGG | |
| | AAAACATTAAGAGCAAAGAAAGGGGAACATATCTGGATAATTC | |
| | TTGATGGTCCAGTAGATGCCATCTGGATTGAAAATCTGAATTC | |
| | TGTTTTGGATGATAACAAAACTCTAACCCTTGCCAATGGTGAT | |
| | CGGATTCCCATGGCTCCAAACTGCAAGATCATTTTCGAGCCTC | |
| | ATAACATTGACAATGCTTCTCCTGCCACCGTCTCAAGAAATGG | |
| | AATGGTTTTCATGAGCTCTTCTATCCTTGATTGGAGTCCTATT | |
| | CTTGAGGGTTTTCTTAAGAAACGCTCACCTCAAGAAGCAGAAA | |
| | TTCTTCGTCAGCTGTACACCGAGTCTTTCCCAGACTTGTATCG | |
| | CTTCTGTATCCAGAACTTAGAATACAAGATGGAGGTGCTGGAG | |
| | GCCTTTGTCATCACACAGAGCATTAACATGCTTCAAGGCCTGA | |
| | TTCCTCTGAAGGAGCAAGGCGGGGAGGTGAGCCAGGCTCACCT | |
| | GGGGCGGCTGTTCGTGTTCGCGCTGCTGTGGAGCGCGGGGGCG | |
| | GCGCTGGAGCTGGACGGACGGCGCCGCCTGGAGCTCTGGCTGC | |
| | GCTCTCGGCCCACAGGGACGCTGGAGCTGCCGCCGCCAGCGGG | |
| | GCCCGGGGACACCGCCTTCGACTACTATGTGGCGCCCGATGGT | |
| | ACATGGACGCACTGGAACACGCGTACCCAGGAATACCTGTATC | |
| | CGTCTGATACCACCCCAGAGTATGGTTCTATTCTGGTGCCAAA | |
| | TGTTGACAATGTGAGGACTGACTTTCTAATTCAAACCATTGCT | |
| | AAACAGGGCAAGGCTGTGCTATTAATTGGTGAACAAGGAACAG | |
| | CCAAAACAGTAATAATTAAAGGATTTATGTCAAAATATGATCC | |
| | TGAATGTCACATGATCAAGAGTCTGAATTTTTCTTCTGCAACC | |
| | ACCCCACTGATGTTCCAGAGGACGATAGAGAGCTATGTGGATA | |
| | AACGAATGGGTACAACATATGGCCCTCCTGCGGGAAAGAAGAT | |
| | GACTGTTTTTATTGATGATGTGAATATGCCAATAATCAATGAG | |
| | TGGGGAGATCAGGTTACGAATGAGATAGTGCGACAGCTGATGG | |
| | AACAAAATGGATTCTATAATCTAGAGAAGCCTGGGGAGTTCAC | |
| | CAGCATCGTGGACATCCAGTTTTTGGCAGCCATGATCCATCCT | |
| | GGTGGTGGACGCAATGACATACCCCAAAGACTCAAGAGGCAGT | |
| | TCTCTATATTTAATTGCACGTTGCCCTCTGAAGCTTCTGTGGA | |
| | CAAGATCTTTGGTGTGATTGGGGTAGGCCACTACTGTACTCAG | |
| | AGGGGTTTCTCAGAAGAAGTGAGAGATTCTGTGACAAAATTGG | |
| | TGCCTCTGACACGCCGACTATGGCAGATGACCAAGATTAAAAT | |
| | GCTTCCTACCCCTGCAAAATTCCATTATGTGTTTAACCTACGA | |
| | GATCTTTCTCGGGTCTGGCAGGGAATGCTGAACACTACTTCAG | |
| | AGGTCATCAAGGAACCAAATGATCTGTTAAAGCTGTGGAAGCA | |
| | TGAGTGTAAACGTGTTATAGCTGACCGTTTCACAGTGTCCAGT | |
| | GATGTGACCTGGTTTGATAAGGCTTTAGTAAGTTTGGTAGAGG | |
| | AGGAGTTTGGTGAAGAGAAAAAACTCTTGGTGGATTGTGGAAT | |
| | TGACACATATTTTGTGGATTTCTTGAGAGATGCACCTGAAGCT | |
| | GCAGGTGAAACATCTGAAGAGGCTGATGCTGAAACACCTAAAA | |
| | TTTATGAGCCAATTGAATCTTTTAGTCACCTAAAAGAGCGTCT | |
| | GAATATGTTCCTGCAGCTCTATAATGAGAGCATCCGTGGCGCC | |
| | GGCATGGACATGGTGTTCTTTGCAGATGCCATGGTTCACTTAG | |
| | TCAAGATCTCTCGTGTCATTCGTACTCCTCAGGGAAATGCCCT | |
| | CCTGGTCGGGGTGGGCGGATCAGGAAAGCAGAGCCTGACGAGG | |
| | TTGGCTTCATTCATTGCTGGCTACGTTTCCTTCCAGATCACTC | |
| | TGACGAGATCCTACAACACATCAAATCTGATGGAAGATCTGAA | |
| | GGTTTTGTATCGAACAGCTGGTCAGCAAGGCAAAGGAATCACT | |
| | TTTATTTTCACAGACAATGAGATTAAAGATGAGTCATTTTTGG | |
| | AATATATGAACAATGTTTTATCATCAGGTGAGGTCTCTAACCT | |
| | ATTTGCTCGAGATGAAATTGATGAAATTAATAGCGACCTGGCA | |
| | TCAGTCATGAAAAAAGAATTCCCCAGGTGCCTTCCTACCAATG | |
| | AGAACCTGCACGACTACTTCATGAGTCGGGTCCGACAGAACCT | |
| | TCATATTGTGCTCTGCTTCTCGCCAGTGGGGGAGAAATTTCGA | |

TABLE 9-continued

Exemplary sequences of genes related to lung diseases

| Gene | Sequence | SEQ ID NO |
|---|---|---|
| | AACAGAGCTTTGAAGTTCCCTGCCCTAATTTCAGGATGCACAA | |
| | TTGACTGGTTCAGCCGATGGCCCAAAGATGCTTTAGTTGCTGT | |
| | GTCTGAACACTTCCTCACTTCCTATGATATTGACTGCAGTTTG | |
| | GAAATCAAGAAGGAGGTGGTCCAATGCATGGGCTCCTTCCAGG | |
| | ATGGGGTGGCTGAGAAGTGTGTTGATTATTTTCAGAGATTCCG | |
| | ACGTTCTACCCACGTGACGCCCAAATCATACCTCTCCTTTATT | |
| | CAGGGCTATAAGTTCATATATGGAGAAAAGCATGTGGAGGTGC | |
| | GGACCCTGGCCAACAGAATGAATACTGGATTGGAAAAGCTCAA | |
| | AGAAGCTTCAGAGTCTGTTGCAGCCTTGAGTAAAGAACTGGAA | |
| | GCGAAAGAAAAGGAGCTACAAGTGGCCAACGATAAAGCCGACA | |
| | TGGTCTTAAAAGAAGTGACAATGAAAGCACAGGCTGCTGAAAA | |
| | GGTCAAGGCTGAGGTACAGAAGGTGAAGGACAGGGCCCAGGCC | |
| | ATTGTGGACAGCATCTCTAAAGACAAAGCCATTGCTGAAGAAA | |
| | AACTGGAAGCAGCAAAACCAGCTTTAGAAGAGGCAGAAGCTGC | |
| | ATTGCAGACCATCAGGCCTTCGGACATCGCCACTGTTCGCACG | |
| | TTGGGCCGCCCCCCTCACCTCATCATGCGGATCATGGATTGCG | |
| | TACTGCTGCTGTTTCAAAGGAAAGTCAGTGCTGTGAAAATTGA | |
| | CCTGGAAAAAAGCTGTACCATGCCCTCCTGGCAGGAATCCTTA | |
| | AAATTGATGACTGCAGGGAACTTTTTACAGAACTTACAGCAAT | |
| | TCCCAAAAGACACAATCAATGAAGAGGTGATAGAATTTTTGAG | |
| | TCCTTACTTTGAAATGCCTGACTATAACATCGAAACTGCTAAA | |
| | CGCGTATGTGGAAATGTAGCTGGTCTTTGTTCCTGGACGAAAG | |
| | CTATGGCTTCCTTCTTTTCTATAAACAAAGAAGTACTGCCTCT | |
| | GAAGGCCAACTTGGTGGTGCAAGAGAATCGCCATCTCCTGGCC | |
| | ATGCAGGATCTGCAGAAAGCCCAGGCCGAGTTGGATGACAAGC | |
| | AGGCGGAACTTGACGTGGTGCAGGCTGAGTATGAACAGGCCAT | |
| | GACTGAAAAGCAGACCTTGCTTGAAGATGCAGAGCGATGCAGA | |
| | CACAAGATGCAGACAGCTTCCACGCTCATCAGTGGCTTGGCAG | |
| | GTGAAAAAGAAAGATGGACAGAGCAAAGCCAAGAGTTTGCTGC | |
| | ACAAACTAAAAGACTTGTAGGGGATGTACTGTTGGCTACAGCT | |
| | TTTCTATCTTATTCTGGTCCATTTAACCAAGAGTTTCGTGATC | |
| | TTCTGTTAAATGACTGGCGGAAGGAAATGAAAGCCCGGAAAAT | |
| | TCCATTTGGAAAGAACCTAAATCTCAGTGAGATGTTGATTGAT | |
| | GCTCCTACTATTAGTGAATGGAACCTCCAAGGTCTGCCAAATG | |
| | ATGACTTGTCCATTCAAAATGGAATTATTGTCACGAAGGCATC | |
| | TCGTTACCCTTTGTTAATTGATCCACAGACTCAAGGCAAGATC | |
| | TGGATTAAAAATAAAGAAAGCCGAAATGAACTCCAGATCACGT | |
| | CTTTAAATCACAAGTACTTCAGAAACCACCTGGAAGACAGCCT | |
| | TTCTCTTGGAAGGCCTTTGCTTATTGAAGATGTTGGAGAGGAA | |
| | CTAGATCCAGCACTAGATAATGTTTTGGAAAGAAACTTCATTA | |
| | AAACTGGGTCTACCTTTAAGGTGAAAGTTGGTGACAAGGAAGT | |
| | AGATGTGTTGGATGGCTTTAGACTCTACATTACCACCAAATTG | |
| | CCTAACCCAGCCTACACCCCTGAGATAAGTGCCCGTACCTCCA | |
| | TCATTGACTTCACTGTCACCATGAAAGGTCTAGAAGATCAGTT | |
| | ACTGGGGAGGGTCATTCTCACAGAGAAGCAGGAATTGGAGAAA | |
| | GAAAGAACTCATCTGATGGAAGATGTAACTGCAAACAAAAGAA | |
| | GGATGAAGGAACTAGAAGATAACTTGCTTTACCGCCTGACAAG | |
| | TACCCAGGGGTCCCTGGTAGAAGATGAAAGTCTCATTGTCGTG | |
| | CTGAGTAACACAAAAAGGACAGCCGAGGAGGTGACACAGAAGC | |
| | TAGAAATTTCTGCTGAGACAGAAGTTCAAATTAACTCAGCCCG | |
| | GGAGGAATACAGACCTGTGGCTACGCGGGGCAGCATCCTCTAC | |
| | TTCCTCATTACTGAGATGCGCTTGGTTAATGAGATGTATCAGA | |
| | CTTCGCTTCGCCAGTTTCTGGGCTTATTTGACCTTTCCTTAGC | |
| | CAGGTCTGTCAAGAGCCCGATTACAAGCAAGAGGATTGCTAAT | |
| | ATCATCGAGCACATGACCTACGAGGTTTATAAGTATGCTGCCC | |
| | GAGGGCTGTACGAGGAGCACAAATTCCTGTTCACCTTGTTGCT | |
| | TACCCTAAAGATTGACATCCAGAGGAACCGAGTCAAGCATGAA | |
| | GAGTTTCTCACTCTTATTAAAGGAGGTGCCTCATTAGACCTTA | |
| | AAGCTTGTCCTCCAAAACCATCAAAATGGATCCTGGACATAAC | |
| | ATGGCTGAATTTGGTGGAACTTAGCAAACTCAGACAGTTTTCA | |
| | GATGTCCTTGACCAGATATCGAGAAATGAGAAAATGTGGAAAA | |
| | TTTGGTTTGATAAGGAAAACCCGGAGGAGGAACCTCTTCCAAA | |
| | TGCCTATGATAAATCTCTTGACTGCTTCAGACGTCTTCTCCTT | |
| | ATTAGATCCTGGTGTCCTGACAGAACCATCGCCCAGGCCCGCA | |
| | AGTACATCGTGGACTCCATGGGAGAAAAATATGCCGAAGGTGT | |
| | TATTTTAGACTTGGAGAAGACGTGGGAGGAATCTGATCCACGG | |
| | ACGCCACTCATCTGTCTCCTGTCTATGGGCTCAGACCCCACAG | |
| | ATTCCATCATTGCCTTGGGGAAGAGATTAAAAATAGAAACCCG | |
| | TTATGTGTCCATGGGCCAGGGCCAGGAAGTCCATGCTCGGAAG | |
| | CTCTTGCAGCAGACCATGGCGAACGGAGGATGGGCACTTCTGC | |
| | AGAACTGCCATCTGGGACTTGATTTCATGGATGAGCTGATGGA | |
| | CATAATCATAGAAACTGAGCTTGTACATGATGCGTTCCGCCTC | |
| | TGGATGACCACCGAGGCTCATAAGCAGTTTCCCATTACACTCC | |
| | TTCAGATGTCCATTAAATTTGCCAACGATCCTCCACAAGGACT | |
| | CCGGGCAGGACTGAAAAGAACATATAGTGGTGTCAGCCAAGAC | |

TABLE 9-continued

Exemplary sequences of genes related to lung diseases

| Gene | Sequence | SEQ ID NO |
|---|---|---|
| | CTGCTGGACGTGAGCTCTGGGTCCCAGTGGAAGCCCATGCTGT<br>ACGCAGTGGCTTTCCTGCACTCCACTGTCCAGGAGAGGCGCAA<br>GTTCGGTGCCCTGGGGTGGAATATCCCCTACGAATTTAACCAA<br>GCGGACTTTAATGCCACTGTGCAGTTCATCCAAAACCACTTGG<br>ATGACATGGATGTCAAAAAGGGTGTCTCCTGGACCACCATCCG<br>CTACATGATAGGAGAGATTCAATATGGAGGCAGAGTCACTGAC<br>GACTATGATAAGAGATTGTTGAACACATTTGCTAAGGTTTGGT<br>TCAGTGAAAATATGTTTGGACCAGATTTCAGTTTTTACCAAGG<br>ATACAATATTCCAAAATGCAGCACAGTGGATAACTATCTTCAG<br>TATATCCAGAGTTTGCCTGCCTATGACAGCCCTGAGGTGTTTG<br>GGCTGCACCCCAATGCTGACATCACCTACCAGAGCAAGCTGGC<br>CAAGGACGTGCTGGACACCATCCTAGGCATCCAACCCAAGGAC<br>ACCTCTGGTGGAGGGGATGAGACCCGGGAGGCGGTGGTGGCCC<br>GGCTGGCTGATGATATGCTGGAGAAGCTGCCCCCAGACTATGT<br>CCCCTTTGAAGTAAAAGAGAGGCTGCAGAAGATGGGGCCATTC<br>CAGCCTATGAACATTTTCCTCAGGCAGGAAATAGACAGAATGC<br>AAAGGGTACTCAGCCTTGTCCGCAGCACCCTCACTGAGCTGAA<br>ACTTGCTATTGATGGCACCATCATCATGAGCGAAAATCTGCGA<br>GATGCATTGGATTGCATGTTTGATGCTAGAATCCCTGCTTGGT<br>GGAAAAAAGCTTCTTGGATTTCTAGTACACTGGGTTTCTGGTT<br>TACTGAACTTATAGAAAGAAACAGCCAGTTTACCTCGTGGGTT<br>TTCAATGGCCGACCTCACTGCTTTTGGATGACGGGTTTTTTA<br>ACCCCCAGGGATTTTTAACTGCAATGCGACAGGAAATAACTCG<br>GGCCAACAAAGGCTGGGCTCTGGACAATATGGTGCTTTGCAAT<br>GAAGTCACCAAATGGATGAAGGACGACATTTCTGCCCCTCCCA<br>CAGAGGGTGTCTATGTCTATGGCTTATATCTTGAAGGTGCTGG<br>CTGGGACAAGAGGAACATGAAACTCATTGAATCAAAGCCAAAA<br>GTGCTCTTTGAGTTGATGCCTGTCATAAGGATTTATGCAGAAA<br>ACAATACTTTACGAGATCCTCGGTTTTACTCCTGTCCCATCTA<br>TAAGAAGCCAGTTCGAACGGACTTGAACTACATTGCCGCTGTG<br>GATCTCAGGACAGCCCAGACCCCTGAACACTGGGTGCTCCGTG<br>GGGTTGCCCTTCTGTGTGATGTCAAGTAA | |
| AAT | ATGCCGTCTTCTGTCTCGTGGGGCATCCTCCTGCTGGCAGGCC<br>TGTGCTGCCTGGTCCCTGTCTCCCTGGCTGAGGATCCCCAGGG<br>AGATGCTGCCCAGAAGACAGATACATCCCACCATGATCAGGAT<br>CACCCAACCTTCAACAAGATCACCCCCAACCTGGCTGAGTTCG<br>CCTTCAGCCTATACCGCCAGCTGGCACACCAGTCCAACAGCAC<br>CAATATCTTCTTCTCCCCAGTGAGCATCGCTACAGCCTTTGCA<br>ATGCTCTCCCTGGGGACCAAGGCTGACACTCACGATGAAATCC<br>TGGAGGGCCTGAATTTCAACCTCACGGAGATTCCGGAGGCTCA<br>GATCCATGAAGGCTTCCAGGAACTCCTCCGTACCCTCAACCAG<br>CCAGACAGCCAGCTCCAGCTGACCACCGGCAATGGCCTGTTCC<br>TCAGCGAGGGCCTGAAGCTAGTGGATAAGTTTTTGGAGGATGT<br>TAAAAAGTTGTACCACTCAGAAGCCTTCACTGTCAACTTCGGG<br>GACACCGAAGAGGCCAAGAAACAGATCAACGATTACGTGGAGA<br>AGGGTACTCAAGGGAAAATTGTGGATTTGGTCAAGGAGCTTGA<br>CAGAGACACAGTTTTTGCTCTGGTGAATTACATCTTCTTTAAA<br>GGCAAATGGGAGAGACCCTTTGAAGTCAAGGACACCGAGGAAG<br>AGGACTTCCACGTGGACCAGGTGACCACCGTGAAGGTGCCTAT<br>GATGAAGCGTTTAGGCATGTTTAACATCCAGCACTGTAAGAAG<br>CTGTCCAGCTGGGTGCTGCTGATGAAATACCTGGGCAATGCCA<br>CCGCCATCTTCTTCCTGCCTGATGAGGGGAAACTACAGCACCT<br>GGAAAATGAACTCACCCACGATATCATCACCAAGTTCCTGGAA<br>AATGAAGACAGAAGGTCTGCCAGCTTACATTTACCCAAACTGT<br>CCATTACTGGAACCTATGATCTGAAGAGCGTCCTGGGTCAACT<br>GGGCATCACTAAGGTCTTCAGCAATGGGGCTGACCTCTCCGGG<br>GTCACAGAGGAGGCACCCCTGAAGCTCTCCAAGGCCGTGCATA<br>AGGCTGTGCTGACCATCGACGAGAAAGGGACTGAAGCTGCTGG<br>GGCCATGTTTTTAGAGGCCATACCCATGTCTATCCCCCCCGAG<br>GTCAAGTTCAACAAACCCTTTGTCTTCTTAATGATTGAACAAA<br>ATACCAAGTCTCCCCTCTTCATGGGAAAAGTGGTGAATCCCAC<br>CCAAAAATAA | 4 |
| ARMC4 | ATGGGTGTGGCTCTGAGGAAATTGACGCAGTGGACTGCTGCCG<br>GACATGGAACTGGAATCCTCGAAATCACCCCTCTAAATGAAGC<br>GATATTGAAAGAAATTATTGTGTTTGTGGAGAGTTTTATCTAT<br>AAACATCCTCAAGAGGCAAAATTTGTTTTTGTGGAACCACTTG<br>AATGGAACACAAGTTTGGCGCCCTCAGCATTTGAATCAGGTTA<br>TGTTGTCAGTGAAACAACAGTCAAATCAGAAGAAGTTGATAAA<br>AATGGACAGCCTTTGCTATTTCTCTCTGTACCACAAATTAAAA<br>TTAGGAGCTTTGGGCAGCTGTCACGCTTGTTACTTATTGCCAA<br>AACTGGGAAGTTGAAGGAAGCCCAAGCATGTGTTGAAGCTAAC<br>AGAGACCCCATAGTAAAAATCCTGGGCTCTGATTATAATACAA<br>TGAAAGAAAACTCAATTGCATTAAATATTCTTGGCAAAATTAC | 5 |

TABLE 9-continued

Exemplary sequences of genes related to lung diseases

| Gene | Sequence | SEQ ID NO |
|---|---|---|
| | CAGAGATGATGATCCTGAAAGTGAAATTAAGATGAAGATTGCT | |
| | ATGCTGCTTAAGCAATTGGATCTGCACCTCCTCAATCATTCTC | |
| | TAAAACATATTTCATTAGAAATAAGTTTAAGTCCCATGACGGT | |
| | GAAGAAGGATATAGAACTGCTCAAACGTTTCTCAGGAAAAGGA | |
| | AACCAAACAGTCTTGGAATCTATTGAATATACCTCAGATTATG | |
| | AATTTTCAAATGGATGTCGAGCCCCACCGTGGAGACAAATTCG | |
| | TGGGGAAATTTGTTATGTGCTGGTGAAACCTCACGATGGTGAG | |
| | ACTCTGTGCATTACTTGCAGTGCAGGAGGAGTATTTTTAAATG | |
| | GTGGCAAAACAGATGATGAAGGGGACGTTAATTATGAGAGAAA | |
| | AGGTTCAATTTATAAAAACCTTGTCACATTTTTAAGAGAAAAA | |
| | TCACCAAAATTTTCAGAAAATATGTCTAAATTGGGAATTAGCT | |
| | TCAGTGAAGACCAGCAAAAGGAAAAGGATCAGCTTGGCAAAGC | |
| | CCCCAAGAAGGAAGAAGCAGCTGCCCTCCGCAAAGACATTTCT | |
| | GGTTCAGACAAAAGGTCACTGGAGAAGAACCAAATTAATTTTT | |
| | GGAGGAATCAAATGACCAAGAGATGGGAACCAAGCTTAAACTG | |
| | GAAGACCACTGTTAATTACAAAGGCAAAGGCTCAGCAAAAGAA | |
| | ATCCAAGAGGACAAACACACAGGAAAACTTGAAAAACCAAGAC | |
| | CATCTGTTTCACACGGAAGAGCACAATTACTTCGGAAGAGTGC | |
| | TGAAAAGATTGAGGAAACTGTTAGCGATAGCTCCTCAGAAAGT | |
| | GAGGAAGATGAAGAACCACCTGACCATCGTCAGGAAGCAAGTG | |
| | CAGATTTGCCATCAGAATATTGGCAAATTCAGAAGCTGGTGAA | |
| | ATATTTAAAGGGAGGAAATCAAACAGCTACAGTGATTGCGTTG | |
| | TGTTCAATGAGGGATTTCAGCTTAGCTCAAGAAACCTGCCAGT | |
| | TGGCCATCAGAGATGTTGGAGGCCTGGAAGTGCTGATAAATTT | |
| | GCTTGAAACCGATGAAGTCAAATGTAAGATTGGTTCATTAAAA | |
| | ATACTGAAGGAAATCAGTCATAATCCTCAAATCAGACAGAATA | |
| | TTGTTGACCTTGGGGGCTTACCAATTATGGTGAATATACTTGA | |
| | TTCTCCACACAAGAGTCTAAAATGTTTGGCAGCCGAGACTATC | |
| | GCGAATGTTGCCAAGTTTAAAAGAGCACGGCGGGTGGTGAGGC | |
| | AGCACGGGGGTATCACCAAACTGGTTGCTCTACTAGACTGTGC | |
| | ACATGATTCCACAAAACCTGCCCAATCGAGTCTGTATGAGGCC | |
| | AGAGACGTGGAAGTGGCTCGCTGTGGGGCACTGGCCCTGTGGA | |
| | GCTGCAGTAAGAGTCATACGAATAAAGAAGCCATCCGCAAAGC | |
| | TGGGGGCATTCCTCTGTTGGCTCGGCTGCTGAAGACTTCTCAT | |
| | GAAAACATGCTAATTCCAGTGGTGGGGACATTGCAAGAGTGTG | |
| | CATCAGAGGAAAACTACCGGGCTGCAATCAAAGCAGAAAGGAT | |
| | CATTGAAAACCTTGTCAAGAACCTAAATAGTGAGAATGAGCAG | |
| | CTGCAGGAGCACTGCGCCATGGCCATTTACCAGTGTGCTGAAG | |
| | ATAAGGAAACCCGGGACCTCGTTAGGCTGCACGGAGGACTTAA | |
| | GCCCTTGGCCAGTCTACTCAATAACACTGACAATAAAGAGCGG | |
| | TTAGCTGCTGTCACAGGGGCTATATGGAAATGTTCCATCAGCA | |
| | AAGAGAATGTTACCAAGTTTCGGGAATACAAAGCCATTGAAAC | |
| | CTTGGTGGGACTTCTAACAGATCAGCCTGAAGAAGTACTTGTG | |
| | AATGTGGTTGGGGCCTTGGGAGAATGCTGCCAAGAACGTGAAA | |
| | ACCGAGTCATTGTCCGGAAATGTGGTGGCATTCAACCACTTGT | |
| | GAACCTCCTTGTTGGAATAAACCAAGCTCTTCTTGTGAATGTT | |
| | ACAAAAGCAGTTGGTGCTTGTGCAGTAGAACCTGAAAGTATGA | |
| | TGATAATTGATCGCTTAGATGGAGTTCGTTTGTTGTGGTCCCT | |
| | GCTGAAAAATCCTCACCCAGACGTGAAGGCCAGCGCAGCATGG | |
| | GCACTCTGTCCATGCATCAAAAATGCAAAGGATGCTGGGGAAA | |
| | TGGTTCGTTCCTTTGTTGGTGGTTTGGAACTTATTGTCAATTT | |
| | ACTGAAATCAGATAACAAAGAAGTTCTGGCAAGTGTATGTGCT | |
| | GCCATTACCAACATAGCAAAAGATCAAGAAAATTTAGCTGTTA | |
| | TCACAGATCATGGAGTTGTTCCTTTATTGTCCAAACTGGCAAA | |
| | TACAAATAACAATAAATTGAGACATCATCTAGCAGAAGCTATT | |
| | TCACGTTGCTGTATGTGGGGCAGGAATAGAGTGGCCTTCGGTG | |
| | AGCACAAAGCAGTGGCTCCACTAGTGCGTTATCTGAAATCAAA | |
| | TGACACCAACGTGCATCGGGCGACAGCTCAGGCCTTGTACCAA | |
| | CTCTCAGAAGACGCCGATAACTGCATCACCATGCATGAGAATG | |
| | GTGCAGTAAAGCTTCTACTGGATATGGTTGGGTCCCCTGACCA | |
| | GGATCTCCAGGAAGCTGCAGCTGGTTGTATATCCAATATCCGC | |
| | AGGCTGGCTCTTGCTACAGAGAAGGCAAGATACACTTGA | |
| DNAAF1 | ATGCACCCTGAGCCCTCGGAGCCTGCGACAGGTGGTGCAGCAG | 6 |
| | AGCTGGATTGCGCGCAGGAGCCCGGCGTGGAGGAGTCTGCGGG | |
| | TGACCACGGGAGCGCAGGCCGAGGGGGCTGCAAGGAAGAAATT | |
| | AATGATCCTAAGGAAATATGTGTGGGTTCTTCTGACACATCCT | |
| | ACCACAGCCAGCAGAAACAGAGTGGTGATAATGGGTCAGGTGG | |
| | TCACTTCGCACACCCAAGAGAAGACAGGGAAGATCGGGGCCCC | |
| | AGAATGACTAAAAGTTCCCTGCAAAAACTCTGCAAGCAGCACA | |
| | AGCTTTATATTACCCCAGCATTGAATGATACGCTGTATTTACA | |
| | CTTTAAAGGTTTTGATCGCATTGAGAACCTGGAAGAGTACACA | |
| | GGGCTGCGCTGTCTCTGGCTGCAGAGCAATGGAATACAGAAAA | |
| | TCGAAAACCTGGAGGCCCAAACTGAGTTGCGTTGCCTCTTCTT | |
| | GCAAATGAACTTGCTCCGTAAAATTGAGAACCTGGAACCTCTG | |

TABLE 9-continued

| Gene | Sequence | SEQ ID NO |
|---|---|---|
| | CAGAAACTGGATGCTCTTAACCTCAGCAACAATTACATCAAGA<br>CCATTGAAAACCTCTCCTGCCTCCCAGTCCTGAACACATTGCA<br>GATGGCCCACAATCACCTGGAGACCGTGGAGGACATTCAGCAT<br>CTACAAGAGTGTTTGAGGCTTTGTGTCCTTGACCTTTCGCACA<br>ACAAGCTGAGTGACCCGGAGATCCTGAGCATTCTGGAAAGCAT<br>GCCCGATTTGCGTGTACTGAATTTGATGGGAAACCCGGTTATC<br>AGACAGATTCCTAATTACAGAAGGACAGTCACTGTACGACTAA<br>AGCACTTAACATACCTGGATGATAGACCAGTGTTTCCAAAGGA<br>CAGAGCTTGTGCGGAGGCCTGGGCTAGGGGAGGGTACGCAGCT<br>GAAAAGGAGGAGAGACAGCAGTGGGAGAGCAGGGAGCGGAAGA<br>AGATCACAGACAGCATTGAAGCCTTGGCCATGATCAAGCAGCG<br>GGCAGAGGAGAGGAAAAGACAGAGAGAGAGTCAAGAGAGAGGG<br>GAGATGACATCTTCAGATGATGGTGAGAATGTGCCCGCCAGTG<br>CGGAAGGCAAGGAGGAGCCTCCCGGGGACAGAGAAACAAGGCA<br>GAAGATGGAGCTATTTGTTAAGGAAAGCTTTGAGGCCAAGGAC<br>GAGCTCTGCCCGGAAAAGCCAAGTGGAGAGGAGCCGCCTGTGG<br>AGGCTAAAAGAGAGGATGGAGGTCCAGAGCCAGAGGGGACCCT<br>CCCAGCTGAGACCCTGCTACTGTCGTCACCTGTGGAGGTTAAA<br>GGAGAGGACGGAGATGGAGAGCCAGAGGGGACCCTCCCAGCTG<br>AGGCCCCACCACCCCCGCCACCTGTGGAGGTTAAAGGAGAGGA<br>TGGAGATCAAGAGCCAGAGGGGACCCTCCCAGCTGAGACCCTG<br>CTACTGTCACCGCCTGTGAAGGTTAAAGGAGAGGATGGAGATC<br>GAGAGCCAGAGGGGACCCTCCCAGCTGAGGCCCCACCACCACC<br>GCCCCTGGGAGCTGCCAGGGAAGAACCGACTCCCCAGGCTGTG<br>GCCACTGAGGGTGTATTCGTTACAGAACTTGATGGAACGAGAA<br>CGGAAGATTTAGAAACCATTAGACTGGAGACAAAGGAGACATT<br>CTGCATTGATGACCTACCTGACTTGGAAGATGATGATGAAACA<br>GGCAAATCTCTGGAAGACCAGAATATGTGCTTTCCGAAGATTG<br>AGGTCATCTCGAGCTTGAGTGATGACAGTGACCCTGAACTGGA<br>CTACACGTCACTCCCTGTGCTGGAAAACCTCCCCACAGACACT<br>CTGTCAAATATATTTGCAGTCTCTAAAGACACCTCAAAGGCGG<br>CTCGGGTGCCCTTCACAGACATCTTTAAAAAAGAAGCTAAGAG<br>GGACTTGGAAATCCGAAAACAAGACACCAAGTCCCCAAGACCC<br>CTGATCCAGGAGCTCAGCGACGAGGACCCCTCTGGCCAGCTAC<br>TGATGCCCCCCACCTGCCAAAGAGATGCTGCACCACTCACTTC<br>CAGTGGAGACAGGGACAGCGACTTCCTTGCAGCCTCTTCTCCG<br>GTGCCGACTGAGAGCGCCGCCACACCCCCAGAGACGTGTGTCG<br>GAGTTGCCCAGCCCAGCCAAGCTCTGCCCACGTGGGACCTCAC<br>TGCATTCCCAGCACCGAAAGCATCATAG | |
| DNAAF2 | ATGGCCAAAGCGGCGGCCTCCTCGTCGCTGGAGGACTTGGACC<br>TGAGCGGAGAGGAGGTCCAGCGGCTCACCTCCGCCTTCCAGGA<br>CCCGGAGTTCCGGCGAATGTTCTCCCAGTACGCCGAGGAGCTC<br>ACCGACCCGGAGAACCGGCGGCGCTACGAGGCGGAGATCACCG<br>CGCTAGAGCGTGAGCGCGGGGTGGAAGTGCGGTTCGTGCACCC<br>GGAGCCCGGCCATGTGCTGCGCACCAGCCTGGACGGGGCGCGG<br>CGCTGCTTTGTGAATGTCTGCAGCAACGCGTTGGTGGGCGCGC<br>CCAGCAGCCGGCCCGGCTCCGGTGGCGACCGGGGCGCAGCTCC<br>TGGCAGCCACTGGTCCCTGCCCTACAGCCTGGCGCCCGGCCGC<br>GAGTACGCGGGGCGCAGCAGCAGCCGCTACATGGTCTACGACG<br>TGGTCTTCCATCCAGACGCGCTTGCGCTGGCCCGGCGGCACGA<br>GGGCTTCCGCCAGATGCTGGACGCCACGGCCCTGGAGGCCGTC<br>GAGAAGCAGTTCGGCGTGAAGCTGGACCGCAGGAATGCCAAGA<br>CCCTGAAGGCCAAGTATAAGGGGACCCCAGAGGCTGCGGTGCT<br>GCGCACGCCCCTGCCCGGGGTCATCCCCGCAAGGCCTGACGGG<br>GAGCCGAAGGGTCCTCTCCCGGACTTCCCCTACCCTTACCAGT<br>ACCCGGCAGCCCCCGGGCCCCGGGCGCCCTCCCCTCCGGAAGC<br>GGCCTTGCAGCCCGCCCCCACCGAGCCTCGCTACAGCGTGGTG<br>CAGCGCCACCACGTGGACCTCCAGGATTACCGCTGCTCCAGGG<br>ACTCAGCCCCGAGCCCCGTGCCCCATGAGCTGGTGATCACCAT<br>CGAACTGCCGCTGTTGCGCTCGGCCGAGCAGGCGGCGCTGGAG<br>GTAACGAGAAAGCTGCTGTGCCTCGACTCGAGGAAACCTGACT<br>ACCGGCTGCGGCTCTCGCTCCCGTACCCAGTGGACGATGGCCG<br>CGGCAAGGCACAATTCAACAAGGCCCGGCGGCAGCTGGTGGTT<br>ACGCTGCCAGTGGTGCTGCCGGCCGCGCGCCGGGAGCCCGCTG<br>TCGCCGTCGCCGCCGCCGCGCCGGAAGAGTCCGCGGACCGGTC<br>CGGAACTGACGGCCAGGCCTGCGCTTCCGCTCGCGAGGGGGAG<br>GCGGGACCCGCGAGGAGTCGCGCGGAGGACGGAGGCCACGATA<br>CCTGCGTGGCTGGGGCTGCGGGCTCCGGGGTCACCACCCTGGG<br>CGACCCGGAGGTGGCGCCTCCGCCGGCCGCAGCTGGAGAGGAG<br>CGTGTCCCCAAGCCGGGGGAGCAGGACTTGAGCAGGCACGCGG<br>GGTCACCGCCGGGCAGCGTGGAGGAGCCATCTCCTGGAGGAGA<br>AAACTCACCTGGTGGCGGAGGCTCCCCTTGTTTGTCCTCCCGG<br>AGCCTGGCGTGGGGTTCTTCTGCGGGAAGAGAGAGTGCGCGCG<br>GAGATAGCAGTGTGGAAACACGCGAGGAGTCGGAGGGCACGGG | 7 |

TABLE 9-continued

Exemplary sequences of genes related to lung diseases

| Gene | Sequence | SEQ ID NO |
|---|---|---|
| | CGGCCAGCGCTCAGCCTGCGCCATGGGTGGTCCCGGGACCAAG AGCGGGGAGCCTTTGTGTCCTCCGTTACTGTGTAATCAGGACA AAGAAACCTTGACTCTGCTCATTCAGGTGCCTCGGATCCAGCC GCAAAGTCTTCAAGGAGATTTGAATCCCCTCTGGTACAAATTA CGCTTCTCCGCACAAGACTTAGTTTATTCCTTCTTTTTGCAAT TTGCTCCAGAGAATAAATTGAGTACCACAGAACCTGTGATTAG CATTTCTTCAAACAATGCAGTGATAGAACTGGCAAAATCTCCA GAGAGCCATGGACATTGGAGAGAGTGGTATTATGGTGTAAACA ACGATTCTTTGGAGGAAAGGTTATTTGTCAATGAAGAAAATGT TAATGAGTTTCTTGAAGAGGTCCTGAGCTCTCCATTCAAACAG TCTATGTCCTTGACCCCACCATTAATTGAAGTTCTTCAAGTTA CTGATAATAAGATTCAAATTAATGCAAAGTTGCAAGAATGTAG TAACTCTGATCAGCTACAAGGAAAGGAGGAAAGAGTAAATGAA GAAAGTCATCTAACTGAAAAGGAATATATAGAACATTGTAACA CCCCTACAACTGATTCTGATTCATCTATAGCAGTTAAAGCACT ACAAATAGATAGCTTTGGTTTAGTTACATGCTTTCAACAAGAG TCTCTTGATGTTTCTCAAATGATACTTGGAAAATCTCAGCAAC CTGAGTCAAAAATGCAATCTGAATTTATAAAAGAAAAAAGTGC TACTTGTTCAAATGAGGAAAAAGATAACTTAAACGAGTCAGTA ATAACTGAAGAGAAAGAAACAGATGGAGATCACCTATCTTCAT TACTGAACAAAACTACGGTTCACAATATACCTGGATTCGACAG CATAAAAGAAACCAATATGCAGGATGGTAGTGTGCAGGTCATT AAAGATCATGTGACCAATTGTGCATTCAGTTTTCAGAATTCTT TGCTATATGATTTGGATTAA | |
| DNAAF4 | ATGCCTCTTCAGGTTAGCGATTACAGCTGGCAGCAGACGAAGA CTGCGGTCTTTCTGTCTCTGCCCCTCAAAGGCGTGTGCGTCAG AGACACGGACGTGTTCTGCACGGAAAACTATCTGAAGGTCAAC TTTCCTCCATTTTTATTTGAGGCATTTCTTTATGCTCCCATAG ACGATGAGAGCAGCAAAGCAAAGATTGGGAATGACACCATTGT CTTCACCTTGTATAAAAAAGAAGCGGCCATGTGGGAGACCCTT TCTGTGACGGGTGTTGACAAAGAGATGATGCAAAGAATTAGAG AAAAATCTATTTTACAAGCACAAGAGAGAGCAAAAGAAGCTAC AGAAGCAAAAGCTGCAGCAAAGCGGGAAGATCAAAAATACGCA CTAAGTGTCATGATGAAGATTGAAGAAGAAGAGAGGAAAAAAA TAGAAGATATGAAAGAAAATGAACGGATAAAAGCCACTAAAGC ATTGGAAGCCTGGAAAGAATATCAAAGAAAAGCTGAGGAGCAA AAAAAAATTCAGAGAGAAGAGAAATTATGTCAAAAAGAAAAGC AAATTAAAGAAGAAAGAAAAAAAATAAAATATAAGAGTCTTAC TAGAAATTTGGCATCTAGAAATCTTGCTCCAAAAGGGAGAAAT TCAGAAAATATATTTACTGAGAAGTTAAAGGAAGACAGTATTC CTGCTCCTCGCTCTGTTGGCAGTATTAAAATCAACTTTACCCC TCGAGTATTCCCAACAGCTCTTCGTGAATCACAAGTAGCAGAA GAGGAGGAGTGGCTACACAAACAAGCTGAGGCACGAAGAGCAA TGAATACTGACATAGCTGAACTTTGCGATTTAAAAGAAGAAGA AAAGAACCCAGAATGGTTGAAGGATAAAGGAAACAAATTGTTT GCAACGGAAAACTATTTGGCAGCTATCAATGCATATAATTTAG CCATAAGACTAAATAATAAGATGCCACTATTGTATTTGAACCG GGCTGCTTGCCACCTAAAACTAAAAAACTTACACAAGGCTATT GAAGATTCTTCTAAGGCACTGGAATTATTGATGCCACCTGTTA CAGACAATGCTAATGCAAGAATGAAGGCACATGTACGACGTGG AACAGCATTCTGTCAACTAGAATTGTATGTAGAAGGCCTACAG GATTATGAAGCGGCACTTAAGATTGATCCATCCAACAAAATTG TACAAATTGATGCTGAGAAGATTCGGAATGTAATTCAAGGAAC AGAACTAAAATCTTAA | 8 |
| ZMYND10 | ATGGGAGACCTGGAACTGCTGCTGCCCGGGGAAGCTGAAGTGC TGGTGCGGGGTCTGCGCAGCTTCCCCGCTACGCGAGATGGGCTC CGAAGGGTGGAACCAGCAGCATGAGAACCTGGAGAAGCTGAAC ATGCAAGCCATCCTCGATGCCACAGTCAGCCAGGGCGAGCCCA TTCAGGAGCTGCTGGTCACCCATGGGAAGGTCCCAACACTGGT GGAGGAGCTGATCGCAGTGGAGATGTGGAAGCAGAAGGTGTTC CCTGTGTTCTGCAGGGTGGAGGACTTCAAGCCCCAGAACACCT TCCCCATCTACATGGTGGTGCACCACGAGGCCTCCATCATCAA CCTCTTGGAGACAGTGTTCTTCCACAAGGAGGTGTGTGAGTCA GCAGAAGACACTGTCTTGGACTTGGTAGACTATTGCCACCGCA AACTGACCCTGCTGGTGGCCCAGAGTGGCTGTGGTGGCCCCCC TGAGGGGGAGGGATCCCAGGACAGCAACCCCATGCAGGAGCTG CAGAAGCAGGCAGAGCTGATGGAATTTGAGATTGCACTGAAGG CCCTCTCAGTACTACGCTACATCACAGACTGTGTGGACAGCCT CTCTCTCAGCACCTTGAGCCGTATGCTTAGCACACACAACCTG CCCTGCCTCCTGGTGGAACTGCTGGAGCATAGTCCCTGGAGCC GGCGGGAAGGAGGCAAGCTGCAGCAGTTCGAGGGCAGCCGTTG GCATACTGTGGCCCCCTCAGAGCAGCAAAAGCTGAGCAAGTTG GACGGGCAAGTGTGGATCGCCCTGTACAACCTGCTGCTAAGCC | 9 |

TABLE 9-continued

Exemplary sequences of genes related to lung diseases

| Gene | Sequence | SEQ ID NO |
|---|---|---|
| | CTGAGGCTCAGGCGCGCTACTGCCTCACAAGTTTTGCCAAGGG | |
| | ACGGCTACTCAAGCTTCGGGCCTTCCTCACAGACACACTGCTG | |
| | GACCAGCTGCCCAACCTGGCCCACTTGCAGAGTTTCCTGGCCC | |
| | ATCTGACCCTAACTGAAACCCAGCCTCCTAAGAAGGACCTGGT | |
| | GTTGGAACAGATCCCAGAAATCTGGGAGCGGCTGGAGCGAGAA | |
| | AACAGAGGCAAGTGGCAGGCAATTGCCAAGCACCAGCTCCAGC | |
| | ATGTGTTCAGCCCCTCAGAGCAGGACCTGCGGCTGCAGGCGCG | |
| | AAGGTGGGCTGAGACCTACAGGCTGGATGTGCTAGAGGCAGTG | |
| | GCTCCAGAGCGGCCCCGCTGTGCTTACTGCAGTGCAGAGGCTT | |
| | CTAAGCGCTGCTCACGATGCCAGAATGAGTGGTATTGCTGCAG | |
| | GGAGTGCCAAGTCAAGCACTGGGAAAAGCATGGAAAGACTTGT | |
| | GTCCTGGCAGCCCAGGGTGACAGAGCCAAATGA | |
| CCDC39 | ATGAGTAGCGAATTCCTGGCTGAGCTGCACTGGGAGGATGGGT | 10 |
| | TCGCCATCCCGGTGGCGAACGAGGAGAACAAGCTACTGGAAGA | |
| | TCAGTTGTCAAAGCTGAAGGATGAAAGAGCAAGCTTGCAAGAT | |
| | GAGTTACGTGAGTATGAAGAGCGAATTAATTCTATGACTTCTC | |
| | ACTTCAAAAATGTTAAGCAAGAGCTCTCAATTACACAGTCTCT | |
| | TTGCAAAGCAAGGGAGCGTGAGACTGAAAGTGAAGAACATTTT | |
| | AAGGCCATTGCTCAAAGAGAATTGGGACGAGTGAAAGATGAAA | |
| | TTCAACGGCTGGAAAATGAGATGGCTTCAATACTGGAAAAGAA | |
| | AAGTGATAAAGAAAATGGCATATTTAAAGCCACTCAAAAATTG | |
| | GATGGTTTGAAATGTCAAATGAACTGGGACCAGCAAGCATTGG | |
| | AGGCCTGGTTAGAAGAATCAGCTCATAAAGATAGTGATGCTCT | |
| | CACTCTCCAGAAGTATGCACAACAAGATGATAATAAAATCAGG | |
| | GCACTGACTCTGCAATTAGAAAGACTAACTTTGGAATGTAATC | |
| | AGAAAAGAAAGATACTTGACAACGAACTTACAGAGACTATAAG | |
| | CGCACAGTTAGAATTGGATAAAGCAGCACAAGATTTTCGTAAG | |
| | ATTCATAATGAAAGACAAGAACTCATTAAACAATGGGAGAACA | |
| | CAATAGAACAGATGCAGAAGAGGGATGGAGACATAGATAACTG | |
| | TGCTTTGGAATTAGCAAGGATAAAGCAGGAAACGAGAGAAAAA | |
| | GAAAATTTGGTTAAAGAAAAGATCAAGTTTTTGGAAAGTGAGA | |
| | TTGGGAATAACACAGAGTTTGAGAAAAGAATTTCTGTGGCTGA | |
| | TCGTAAACTTTTAAAATGTAGAACGGCATATCAGGACCATGAA | |
| | ACTAGTAGAATTCAGCTGAAGGGTGAGCTGGATTCTTTAAAAG | |
| | CCACTGTGAATAGAACTTCCAGTGATTTAGAAGCTCTGAGGAA | |
| | AAATATTTCCAAGATAAAGAAGGACATTCATGAAGAAACAGCA | |
| | AGGTTACAAAAAACTAAAAATCATAATGAGATAATACAAACAA | |
| | AATTAAAGGAGATAACTGAGAAAACCATGTCTGTAGAAGAGAA | |
| | AGCTACTAATTTGGAAGATATGCTAAAGGAGGAGGAAAAAGAT | |
| | GTGAAGGAAGTAGATGTTCAACTGAACCTCATAAAAGGTGTGC | |
| | TGTTTAAGAAAGCTCAGGAGTTACAGACTGAGACAATGAAAGA | |
| | AAAAGCTGTTTTATCAGAAATTGAAGGAACTCGTTCCTCTCTG | |
| | AAACATCTCAACCATCAGTTACAAAAACTGGATTTTGAAACCT | |
| | TGAAGCAGCAAGAAATTATGTACAGCCAGGATTTTCACATTCA | |
| | ACAAGTGGAACGGAGAATGTCACGGTTAAAGGGAGAAATTAAT | |
| | TCAGAAGAAAAACAAGCGCTTGAAGCAAAAATTGTTGAACTTA | |
| | GGAAGTCTTTGGAAGAGAAAAAATCTACATGTGGCCTTTTGGA | |
| | AACACAGATCAAGAAGCTTCATAATGATCTTTATTTTATCAAG | |
| | AAGGCACATAGTAAAAACAGTGATGAAAAACAGTCCCTTATGA | |
| | CCAAAATAAATGAACTAAACCTTTTCATCGACAGATCAGAGAA | |
| | AGAACTTGATAAAGCCAAAGGTTTTAAGCAGGATTTGATGATA | |
| | GAGGACAATCTTTTAAAACTTGAAGTTAAGCGTACTCGAGAAA | |
| | TGCTTCACAGTAAGGCAGAAGAAGTTCTTTCCCTAGAAAAAAG | |
| | AAAACAGCAATTATACACAGCAATGGAAGAGCGAACTGAAGAA | |
| | ATCAAGGTTCATAAAACAATGCTTGCGTCACAAATAAGATATG | |
| | TTGATCAAGAACGGGAAAACATAAGCACTGAGTTTCGCGAGCG | |
| | GCTAAGTAAAATTGAGAAGCTGAAGAATAGATATGAAATTCTG | |
| | ACTGTTGTTATGCTGCCTCCTGAAGGAGAAGAGGAGAAAACAC | |
| | AGGCCTATTATGTAATAAAGGCTGCTCAAGAAAAAGAAGAACT | |
| | TCAAAGGGAAGGTGACTGTTTGGATGCCAAGATCAACAAAGCT | |
| | GAAAAAGAAATCTACGCTCTAGAAAATACCCTTCAAGTGCTGA | |
| | ACAGCTGTAACAACAATTATAAGCAATCTTTTAAAAAAGTGAC | |
| | TCCATCTAGTGATGAGTATGAGCTAAAAATTCAACTAGAAGAA | |
| | CAAAAAAGAGCTGTTGATGAAAAATACAGATACAAACAAAGAC | |
| | AAATCAGAGAACTTCAAGAAGACATCCAGAGCATGGAAAATAC | |
| | ATTAGATGTTATAGAACATTTGGCAAATAATGTTAAAGAAAAG | |
| | TTATCAGAGAAGCAGGCTTATTCATTTCAACTAAGTAAAGAAA | |
| | CGGAGGAGCAGAAGCCAAAATTAGAAAGAGTGACCAAACAGTG | |
| | TGCAAAACTCACAAAGGAAATCCGTCTTTTGAAAGACACAAAA | |
| | GATGAAACAATGGAAGAACAAGACATCAAACTTCGTGAAATGA | |
| | AACAGTTTCACAAAGTTATTGATGAAATGTTAGTTGATATCAT | |
| | AGAAGAAAATACTGAGATCCGTATTATCCTTCAAACATACTTT | |
| | CAACAGAGTGGGTTAGAACTACCTACAGCTAGCACAAAAGGCA | |
| | GTCGTCAGAGCTCTAGATCTCCTTCACATACTTCACTATCAGC | |

TABLE 9-continued

Exemplary sequences of genes related to lung diseases

| Gene | Sequence | SEQ ID NO |
|---|---|---|
| | AAGGTCATCTAGGAGTACAAGTACATCTACTTCTCAGTCTTCA<br>ATTAAAGTACTGGAGCTTAAATTCCCGGCCTCCTCTTCACTAG<br>TAGGCAGCCCTTCTAGGCCATCTAGTGCTAGTAGTAGCTCTAG<br>TAATGTTAAGAGCAAAAAGAGCAGCAAATAA | |
| CCDC40 | ATGGCGGAACCGGGCGGCGCGGCGGGCCGGTCCCATCCGGAAG<br>ATGGATCGGCTTCTGAGGGAGAGAAGGAAGGGAATAATGAAAG<br>CCACATGGTGTCACCACCAGAGAAGGATGATGCCAGAAAGGTG<br>AAGAAGCTGTCGGTAGCACAGAGCATCCTGAGGAAGTCACAAC<br>CCAAGCGGAAGCTGCAATTGAAGAGGGGGAGGTGGAGACAGAA<br>GGGGAAGCAGCAGTGGAAGGGGAAGAGGAGGCTGTGTCCTATG<br>GAGATGCTGAAAGCGAAGAGGAATATTACTATACAGAAACTTC<br>ATCCCCGGAAGGGCAAATCAGTGCTGCAGATACGACTTACCCG<br>TATTTCAGTCCTCCTCAGGAACTGCCTGGAGAGGAGGCATACG<br>ATAGTGTTAGCGGGGAGGCTGGTCTCCAAGGCTTCCAGCAAGA<br>GGCCACCGGTCCACCAGAATCCAGAGAAAGGAGGGTCACCTCC<br>CCAGAGCCATCCCACGGAGTCTTAGGCCCGTCGGAGCAAATGG<br>GCCAGGTCACCTCTGGGCCAGCAGTGGGCAGATTGACAGGATC<br>CACAGAGGAGCCCCAGGGGCAGGTGCTCCCAATGGGCGTCCAG<br>CACCGCTTCCGGCTGAGCCACGGGAGCGACATCGAGTCCTCAG<br>ACCTGGAGGAGTTCGTCTCGCAGGAGCCAGTGATCCCCCCAGG<br>GGTGCCCGATGCCCACCCCAGGGAAGGAGACCTGCCAGTGTTC<br>CAGGACCAGATCCAGCAGCCCAGCACCGAGGAGGGGGCCATGG<br>CAGAGAGAGTGGAGTCCGAGGGGAGTGACGAGGAAGCAGAAGA<br>CGAAGGGTCCCAGCTGGTGGTTTTGGACCCAGACCACCCCCTG<br>ATGGTAAGATTCCAGGCTGCCCTGAAGAACTACCTGAACCGAC<br>AGATCGAAAAGTTGAAGCTGGACCTCCAAGAGCTGGTTGTGGC<br>TACCAAGCAGAGCCGAGCCCAGCGGCAGGAGCTGGGGGTGAAT<br>CTCTATGAGGTGCAGCAGCACCTGGTACACCTGCAGAAGCTGC<br>TGGAGAAGAGTCACGACCGCCACGCAATGGCCTCGAGCGAGCG<br>CAGGCAGAAGGAGGAGGAGCTGCAGGCCGCCCGCGCTCTCTAC<br>ACCAAGACCTGCGCAGCCGCCAACGAGGAGCGCAAAAAGTTGG<br>CGGCTCTGCAGACTGAGATGGAGAACTTGGCCCTGCATCTCTT<br>CTACATGCAGAACATCGACCAGGACATGCGTGACGACATCCGC<br>GTGATGACACAAGTGGTAAAGAAGGCCGAGACGGAGAGGATCC<br>GGGCAGAAATCGAGAAGAAAAAGCAGGACCTGTATGTGGACCA<br>GCTCACCACTCGAGCCCAGCAACTGGAAGAAGACATTGCCCTG<br>TTTGAGGCTCAGTACTTGGCCCAAGCTGAGGACACCCGGATTT<br>TAAGGAAAGCAGTGAGTGAGGCCTGCACCGAGATCGACGCCAT<br>CAGCGTGGAGAAGAGGCGCATCATGCAGCAATGGGCCAGCAGC<br>CTGGTGGGCATGAAGCACCGCGACGAGGCGCACAGGGCGGTGC<br>TGGAGGCGCTCAGAGGATGCCAGCATCAAGCCAAATCCACCGA<br>CGGCGAGATTGAGGCCTATAAGAAATCCATCATGAAGGAGGAA<br>GAAAAGAACGAGAAGCTGGCGAGCATCCTGAACCGGACAGAGA<br>CGGAAGCCACACTGCTGCAGAAGCTCACCACCCAGTGCCTGAC<br>CAAGCAGGTGGCCCTGCAGAGCCAGTTCAATACCTACAGGCTC<br>ACCCTGCAGGACACAGAGGATGCCCTCAGCCAGGACCAGCTGG<br>AACAAATGATACTCACGGAGGAGTTGCAGGCCATCCGCCAAGC<br>CATCCAGGGCGAGCTGGAGCTCAGGAGGAAGACGGATGCTGCC<br>ATCCGGGAGAAGCTGCAGGAGCACATGACCTCCAACAAGACCA<br>CCAAATACTTCAACCAGCTCATCCTGAGGCTGCAGAAGGAGAA<br>GACCAACATGATGACACATCTTTCCAAAATCAACGGTGACATT<br>GCCCAGACCACCCTGGACATCACACACACCAGCAGCAGGCTGG<br>ACGCACACCAGAAGACCCTGGTGGAGCTGGACCAGGACGTGAA<br>GAAAGTCAACGAGCTCATCACCAACAGCCAGAGCGAGATCTCC<br>CGGCGCACGATCCTGATCGAGAGGAAGCAAGGGCTCATCAACT<br>TCCTCAACAAGCAGCTGGAGCGGATGGTCTCCGAGCTGGGGGG<br>GGAAGAAGTGGGGCCCCTGGAGCTTGAAATCAAAAGGCTGAGC<br>AAGCTGATCGACGAGCACGATGGCAAGGCGGTCCAGGCCCAGG<br>TGACCTGGCTGCGCCTGCAGCAGGAGATGGTCAAGGTGACACA<br>GGAGCAGGAGGAGCAGCTGGCCTCCCTGGACGCATCCAAGAAG<br>GAGCTCCACATCATGGAGCAGAAGAAACTACGAGTAGAAAGCA<br>AGATTGAGCAGGAGAAGAAGGAGCAGAAGGAGATCGAGCACCA<br>CATGAAGGACCTGGACAACGACCTGAAGAAGCTCAACATGTTG<br>ATGAATAAAAACCGGTGCAGCTCGGAGGAGCTGGAGCAGAACA<br>ACCGGGTGACAGAGAATGAGTTCGTGCGCTCGCTGAAGGCCTC<br>TGAGAGGGAGACCATCAAGATGCAGGACAAGCTGAACCAGCTC<br>AGCGAGGAGAAGGCGACCCTCCTGAATCAACTGGTGGAAGCAG<br>AACACCAGATTATGCTTTGGGAGAAAAAAATCCAACTGGCAAA<br>AGAGATGCGTTCCTCAGTGGATTCCGAGATCGGCCAGACGGAG<br>ATCCGGGCCATGAAGGGCGAGATCCACAGGATGAAGGTCAGGC<br>TCGGGCAGCTGCTGAAGCAGCAGGAGAAGATGATCCGTGCCAT<br>GGAGTTGGCGGTTGCCCGCAGAGAGACCGTCACCACCCAGGCC<br>GAGGGGCAGCGCAAGATGGACAGGAAGGCGCTCACCCGCACCG<br>ACTTCCACCACAAGCAGCTTGAGCTGCGCCGGAAAATCAGGGA | 11 |

TABLE 9-continued

| Gene | Sequence | SEQ ID NO |
|---|---|---|
| | CGTTCGCAAGGCCACCGATGAGTGCACCAAAACCGTCCTGGAA<br>CTGGAAGAAACACAAAGAAATGTGAGCAGCTCCCTCCTAGAGA<br>AGCAGGAAAAGCTGTCGGTGATTCAGGCAGACTTCGACACACT<br>CGAGGCCGACCTCACCCGGCTTGGGGCCCTCAAACGACAGAAC<br>CTTTCAGAGATCGTGGCCCTGCAGACACGCCTTAAGCACCTGC<br>AGGCTGTGAAGGAGGGGCGCTACGTGTTCCTGTTCCGCTCCAA<br>GCAGTCCCTAGTGCTGGAGCGCCAGCGCCTGGACAAGCGACTG<br>GCTCTCATCGCCACCATCCTGGACCGCGTGCGGGACGAGTACC<br>CCCAGTTCCAGGAGGCCCTGCACAAGGTCAGCCAGATGATCGC<br>CAACAAGCTCGAGTCACCAGGGCCCTCCTAG | |

Exemplary sequences of genes related to lung diseases

In some embodiments, the mRNA encoding CFTR comprises a polynucleotide sequence at least 85% identical, at least 90% identical, at least 95% identical, at least 98% identical, or at least 99% identical to SEQ ID NO: 1. In some embodiments, the mRNA encoding DNAI1 comprises a polynucleotide sequence at least 85% identical, at least 90% identical, at least 95% identical, at least 98% identical, or at least 99% identical to SEQ TD NO: 2. In some embodiments, the mRNA encoding DNAH5 comprises a polynucleotide sequence at least 85% identical, at least 90% identical, at least 95% identical, at least 98% identical, or at least 99% identical to SEQ ID NO: 3. In some embodiments, the mRNA encoding AAT comprises a polynucleotide sequence at least 85% identical, at least 900% identical, at least 95% identical, at least 98% identical, or at least 99% identical to SEQ TD NO: 4. In some embodiments, the mRNA encoding ARMC4 comprises a polynucleotide sequence at least 85% identical, at least 90% identical, at least 95% identical, at least 98% identical, or at least 99% identical to SEQ ID NO: 5. In some embodiments, the mRNA encoding DNAAF1 comprises a polynucleotide sequence at least 85% identical, at least 900% identical, at least 95% identical, at least 98% identical, or at least 99% identical to SEQ TD NO: 6. In some embodiments, the mRNA encoding DNAAF2 comprises a polynucleotide sequence at least 85% identical, at least 90% identical, at least 95% identical, at least 98% identical, or at least 99% identical to SEQ ID NO: 7. In some embodiments, the mRNA encoding DNAAF4 comprises a polynucleotide sequence at least 85% identical, at least 90% identical, at least 95% identical, at least 98% identical, or at least 99% identical to SEQ ID NO: 8. In some embodiments, the mRNA encoding ZMYND10 comprises a polynucleotide sequence at least 85% identical, at least 90% identical, at least 95% identical, at least 98% identical, or at least 99% identical to SEQ ID NO: 9. In some embodiments, the mRNA encoding CCDC39 comprises a polynucleotide sequence at least 85% identical, at least 90% identical, at least 95% identical, at least 98% identical, or at least 99% identical to SEQ ID NO: 10. In some embodiments, the mRNA encoding CCDC40 comprises a polynucleotide sequence at least 85% identical, at least 90% identical, at least 95% identical, at least 98% identical, or at least 99% identical to SEQ ID NO: 11.

Polynucleotide sequences can be optimized for expression in various cells and tissues by adjusting codon usage. Codon usage optimization is known in the art, for example at world wide web owpgenomes.urv.es/OPTIMIZER/. In some embodiments, the codon usage of the polynucleotide is optimized for expression in a cell, for example a human cell.

Modified Polynucleotides

In some embodiments, the polynucleotide comprises one or more modifications selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyladenosine, 2-methylthio-N6-threonylcarbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

In some embodiments, a polynucleotide of the disclosure comprises a modified pyrimidine, such as a modified uridine. In some cases a uridine analogue is selected from pseudouridine (Ψ), 1-methylpseudouridine ($m^1P$), 2-thiouridine ($s^2U$), 5-methyluridine ($m^5U$), 5-methoxyuridine ($mo^5U$), 4-thiouridine ($s^4U$), 5-bromouridine ($Br^5U$), 2'O-methyluridine (U2'm), 2'-amino-2'-deoxyuridine (U2'$NH_2$), 2'-azido-2'-deoxyuridine (U2'$N_3$), and 2'-fluoro-2'-deoxyuridine (U2'F).

Modification in Untranslated Regions

In some embodiments, a polynucleotide such as a nucleic acid construct, a vector, or a polyribonucleotide of the disclosure can comprise one or more untranslated regions. An untranslated region can comprise any number of modified or unmodified nucleotides. Untranslated regions (UTRs) of a gene are transcribed but not translated into a polypeptide. In some cases, an untranslated sequence can increase the stability of the polynucleotide and the efficiency of translation. The regulatory features of a UTR can be incorporated into the modified mRNA molecules of the present disclosure, for instance, to increase the stability of the molecule. The specific features can also be incorporated to ensure controlled down-regulation of the transcript in case they are misdirected to undesired organ sites. Some 5' UTRs play roles in translation initiation. A 5' UTR can comprise a Kozak sequence which is involved in the process by which the ribosome initiates translation of many genes. Kozak sequences can have the consensus GCC(R)CCAUGG, where R is a purine (adenine or guanine) that is located three bases upstream of the start codon (AUG). 5' UTRs may form secondary structures which are involved in binding of translation elongation factor. In some cases, one can increase the stability and protein production of the polynucleotide molecule of the disclosure, by engineering the features typically found in abundantly expressed genes of specific target organs. For example, introduction of 5'UTR of liver-expressed mRNA, such as albumin, serum amyloid A, Apolipoprotein A/B/E, transferrin, alpha fetoprotein, erythropoietin, or Factor VIII, can be used to increase expression of an polynucleotide in a liver. Likewise, use of 5' UTR from muscle proteins (MyoD, Myosin, Myoglobin, Myogenin, Herculin), for endothelial cells (Tie-1, CD36), for myeloid cells (C/EBP, AML1, G-CSF, GM-CSF, CD1 lb, MSR, Fr-1, i-NOS), for leukocytes (CD45, CD18), for adipose tissue (CD36, GLUT4, ACRP30, adiponectin) and for lung epithelial cells (SP-A/B/C/D) can be used to increase expression of a polynucleotide in a desired cell or tissue.

Other non-UTR sequences can be incorporated into the 5' (or 3' UTR) UTRs of the polynucleotides of the present disclosure. The 5' and/or 3' UTRs can provide stability and/or translation efficiency of polynucleotides. For example, introns or portions of intron sequences can be incorporated into the flanking regions of a polynucleotide. Incorporation of intronic sequences can also increase the rate of translation of the polynucleotide.

In some embodiments, 3' UTRs may have stretches of Adenosines and Uridines embedded therein. These AU rich signatures are particularly prevalent in genes with high rates of turnover. Based on their sequence features and functional properties, the AU rich elements (AREs) can be separated into classes: Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and T F-α. Class III ARES are less well defined. These U rich regions do not contain an AUUUA motif c-Jun and Myogenin are two well-studied examples of this class. Proteins binding to the AREs may destabilize the messengerRNA (mRNA), whereas members of the ELAV family, such as HuR, may increase the stability of mRNA. HuR may bind to AREs of all the three classes. Engineering the HuR specific binding sites into the 3' UTR of polynucleotide molecules can lead to HuR binding and thus, stabilization of the message in vivo. Engineering of 3' UTR AU rich elements (AREs) can be used to modulate the stability of a polynucleotide. One or more copies of an ARE can be engineered into a polynucleotide to modulate the stability of a polynucleotide. AREs can be identified, removed or mutated to increase the intracellular stability and thus increase translation and production of the resultant protein. Transfection experiments can be conducted in relevant cell lines, using polynucleotides and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

In some embodiments, a polynucleotides such as a nucleic acid construct, a vector, a polyribonucleotide, or compositions of the disclosure can comprise an engineered 5' cap structure, or a 5'-cap can be added to a polynucleotide intracellularly. The 5'cap structure of an mRNA can be involved in binding to the mRNA Cap Binding Protein (CBP), which is responsible for mRNA stability in the cell and translation competency through the association of CBP with poly(A) binding protein to form the mature pseudo-circular mRNA species. The 5'cap structure can also be involved in nuclear export, increases in mRNA stability, and in assisting the removal of 5' proximal introns during mRNA splicing.

In some embodiments, a polynucleotides such as a nucleic acid construct, a vector, or a polynucleotide can be 5'-end capped generating a 5'-GpppN-3'-triphosphate linkage between a terminal guanosine cap residue and the 5'-terminal transcribed sense nucleotide of the mRNA molecule. The cap-structure can comprise a modified or unmodified 7-methylguanosine linked to the first nucleotide via a 5'-5' triphosphate bridge. This 5'-guanylate cap can then be methylated to generate an N7-methyl-guanylate residue (Cap-0 structure). The ribose sugars of the terminal and/or anteterminal transcribed nucleotides of the 5'end of the mRNA may optionally also be 2'-O-methylated (Cap-1 structure). 5'-decapping through hydrolysis and cleavage of the guanylate cap structure may target a polynucleotide molecule, such as an mRNA molecule, for degradation. In some cases, a cap can comprise further modifications, including the methylation of the 2' hydroxy-groups of the first 2 ribose sugars of the 5' end of the mRNA. For instance, an eukaryotic cap-1 has a methylated 2'-hydroxy group on the first ribose sugar, while a cap-2 has methylated 2'-hydroxy groups on the first two ribose sugars. The 5' cap can be chemically similar to the 3'end of an RNA molecule (the 5'carbon of the cap ribose is bonded, and the free 3'-hydroxyls on both 5'- and 3'-ends of the capped transcripts. Such double modification can provide significant resistance to 5' exonucleases. Non-limiting examples of 5' cap structures that can be used with a polynucleotide include, but are not limited to, $m^7G(5')ppp(5')N$(Cap-0), $m^7G(5')ppp(5')$N1mpNp (Cap-1), and $m^7G(5')$-ppp(5')N1mpN2mp (Cap-2).

Modifications to the modified mRNA of the present disclosure may generate a non-hydrolyzable cap structure preventing decapping and thus increasing mRNA half-life while facilitating efficient translation. Because cap structure hydrolysis requires cleavage of 5'-ppp-5' triphosphate linkages, modified nucleotides may be used during the capping reaction. For example, a Vaccinia Capping Enzyme from New England Biolabs (Ipswich, MA) may be used with guanosine α-thiophosphate nucleotides according to the manufacturer's instructions to create a phosphorothioate linkage in the 5'-ppp-5' cap. Additional modified guanosine nucleotides may be used such as α-methyl-phosphonate and seleno-phosphate nucleotides. Additional modifications include, but are not limited to, 2'-O-methylation of the ribose sugars of 5'-terminal and/or 5'-anteterminal nucleotides of the mRNA on the 2'-hydroxyl group of the sugar ring. Multiple distinct 5'-cap structures can be used to generate the 5'-cap of a polynucleotide.

The modified mRNA may be capped post-transcriptionally. According to the present disclosure, 5' terminal caps may include endogenous caps or cap analogues. According to the present disclosure, a 5' terminal cap may comprise a guanine analogue. Useful guanine analogues include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

In some embodiments, an untranslated region can comprise any number of nucleotides. An untranslated region can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. An untranslated region can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length.

In some embodiments, a polynucleotide of the disclosure can comprise a polyA sequence. A polyA sequence (e.g., polyA tail) can comprise any number of nucleotides. A polyA sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. In some examples, a polyA sequence is at least about 100, 110, 120, 130, 140, 150, 160, 170, 180, 190, or 200 nucleotides in length. A polyA sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length. A polyA sequence can comprise a length of at most 100 bases or base pairs, 90 bases or base pairs, 80 bases or base pairs, 70 bases or base pairs, 60 bases or base pairs, 50 bases or base pairs, 40 bases or base pairs, 30 bases or base pairs, 20 bases or base pairs, 10 bases or base pairs, or 5 bases or base pairs.

Gene Editing Payload

The LNPs of the present disclosure can comprise one or more components for gene editing, such as, but not limited to, a guide RNA, a tracr RNA, a sgRNA, an mRNA encoding a gene or base editing protein, a zinc-finger nuclease (ZFN), a transcription activator-like effector nuclease (TALEN), a clustered regularly interspaced short palindromic repeats (CRISPR) nuclease (e.g., Cas9), a DNA template for gene editing, or a combination thereof. In some embodiments, the payload of the LNPs can be suitable for a genome editing technique. In some embodiments, the genome editing technique can be CRISPR or TALEN. In some embodiments, the LNPs can comprise one or more mRNAs, which can encode a gene editing or base editing protein. In some embodiments, the LNPs can comprises both a gene- or base-editing protein encoding mRNA and one or more guide RNAs. In some embodiments, the LNPs can comprise at least one nucleic acid suitable for a genome editing technique, such as a CRISPR RNA (crRNA), a trans-activating crRNA (tracrRNA), a guide RNA (gRNA), and a DNA repair template. In some embodiments, CRISPR nucleases can have altered activity, for example, modifying the nuclease so that it can be a nickase instead of making double-strand cuts or so that it can bind the sequence specified by the guide RNA but has no enzymatic activity. In some embodiments, the base editing protein can be a fusion protein comprising a deaminase domain and a sequence-specific DNA binding domain, such as an inactive CRISPR nuclease.

Gene Editing Methods

The presently described LNPs or pharmaceutical composition can comprise a payload of any conventional gene editing methods. In some embodiments, gene editing components can be selectively delivered to the cells of target organ. In some embodiments, the target organ can be lungs. In some embodiments, the cells of target organ can be lung cells. In some embodiments, the cells can be ciliated cells, goblet cells, secretory cells, club cells, basal cells or ionocytes.

In some embodiments, the gene editing can be targeted editing. Targeted editing can be achieved either through a nuclease-independent approach or through a nuclease-dependent approach.

The nuclease-independent targeted editing, such as base-editing and/or prime editing, can involve precise modifications to DNA sequences without creating double-strand breaks. Homologous recombination can be guided by homologous sequences flanking an exogenous polynucleotide to be introduced into an endogenous sequence through the enzymatic machinery of the cells of target organ.

Base editing can allow for the conversion of one DNA base pair into another at a specific target site. In some embodiments, the nuclease can be a fusion of a deaminase enzyme to a modified Cas9 protein (dCas9) or other engineered Cas variants. In some embodiments, base editing can change C (cytosine) to T (thymine) or A (adenine) to G (guanine) in the endogenous DNA. A guide RNA can be designed to target the specific genomic location of interest in the cells of target organ.

Prime editing can allow for more complex and precise DNA modifications, including insertions, deletions, and all 12 possible base-to-base conversions (A, C, G, T) without double-strand breaks. A prime editing guide RNA, which can consist of a guide sequence and a template for the desired edit, can be designed. The prime editor protein (PE2), which can combine a reverse transcriptase and a Cas9 variant, can be guided to the target site by the prime editing guide RNA. The Cas9 variant can generate a single-strand break (nick) in the DNA. The reverse transcriptase then can use the prime editing guide RNA's template sequence to copy the desired changes into the nicked strand of DNA. Subsequently, the cellular repair machinery of the cells of target organ can repair the nick, incorporating the edited sequence, via homology-directed repair (HDR).

The nuclease-dependent approach can achieve targeted editing with higher frequency through the specific introduction of double strand breaks (DSBs) by specific rare-cutting nucleases (e.g., endonucleases). Such nuclease-dependent targeted editing can also utilize DNA repair mechanisms, for example, non-homologous end joining (NHEJ), which can occur in response to DSBs. In some embodiments, DNA repair by NHEJ can lead to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which can result in targeted integration of the exogenous genetic material. In some embodiments, a nuclease of the nuclease-dependent targeted editing can include, but not limited to, CRISPR-Cas9, CRISPR-Cas12 (Cpf1), CRISPR-Cas13, C2c2, C2c6, NgAgo, and/or TALEN.

Methods of using CRISPR-Cas gene editing technology to create a genomic deletion in a cell (e.g., to knock out a gene in a cell) are well-known techniques. See for example, Bauer et al., *J Vis Exp.* 95:e52118 (2015). Available endonucleases capable of introducing specific and targeted DSBs can include, but not limited to, ZFN, TALEN, and CRISPR/Cas9.

In some embodiments, targeted gene editing can be achieved via dual integrase cassette exchange (DICE) system utilizing phiC31 and Bxb1 integrases.

CRISPR-Cas9 Gene Editing System

The CRISPR-Cas9 system is a naturally occurring defense mechanism in prokaryotes that has been repurposed as an RNA-guided DNA-targeting platform used for gene editing. It can rely on the DNA nuclease Cas9, and two noncoding RNAs, crisprRNA (crRNA) and transactivating RNA (tracrRNA), to target the cleavage of DNA. CRISPR is a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA can be used by the prokaryote to detect and destroy similar foreign DNA upon re-introduction, for example, from similar viruses during subsequent attacks. Transcription of the CRISPR locus can result in the formation of an RNA molecule comprising the spacer sequence, which can associate with and target Cas (CRISPR-associated) proteins able to recognize and cut the foreign, exogenous DNA. Numerous types and classes of CRISPR/Cas systems have been described in e.g., Koonin et al., *Curr Opin Microbiol* 37:67-78 (2017).

crRNA can drive sequence recognition and specificity of the CRISPR-Cas9 complex through Watson-Crick base pairing typically with about 20 nucleotide sequence in the target DNA. Changing the sequence of the 5' 20 nucleotides in the crRNA can allow targeting of the CRISPR-Cas9 complex to specific loci. The CRISPR-Cas9 complex can only bind DNA sequences that contain a sequence match to the first 20 nucleotides of the crRNA, if the target sequence is followed by a specific short DNA motif (with the sequence NGG) referred to as a protospacer adjacent motif (PAM).

tracrRNA can hybridize with the 3' end of crRNA to form an RNA-duplex structure that can be bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, cells can use two main DNA repair pathways to repair the DSB: non-homologous end joining (NHEJ) and homology-directed repair (HDR). NHEJ is a repair mechanism that is highly active in the majority of cell types, including non-dividing cells. NHEJ can be error-prone and can often result in the removal or addition of between one and several hundred nucleotides at the site of the DSB, though such modifications can typically be less than 20 nucleotides. The resulting insertions and deletions (indels) can disrupt coding or noncoding regions of genes. Alternatively, HDR can use a long stretch of homologous donor DNA, provided endogenously or exogenously, to repair the DSB with high fidelity. HDR is active only in dividing cells and can occur at a relatively low frequency in most cell types.

CRISPR Endonuclease: In some embodiments, Cas9 endonuclease can be used in a CRISPR method for genetically engineering cells of the target organ of the LNPs described herein. In some embodiments, Cas9 enzyme can be from *Streptococcus pyogenes*, although other Cas9 homologs can also be used. In some embodiments, the Cas9 enzyme can be wild-type Cas9. In some embodiments, the Cas9 enzyme can be a modified version of Cas9 (e.g., evolved versions of Cas9, or Cas9 orthologues or variants). In some embodiments, Cas9 can be substituted with another RNA-guided endonuclease, such as Cpf1 (class II CRISPR/Cas system).

In some embodiments, the CRISPR/Cas system can comprise components derived from a Type-I, Type-II, or Type-III system. In some embodiments, the CRISPR/Cas system can comprise components derived from Class 1 and Class 2 CRISPR/Cas systems, having Types I to V or Types II, V, and VI, respectively (Makarova et al., *Nat Rev Microbiol* 13(11):722-36 (2015); Shmakov et al., *Mol Cell* 60:385-397 (2015)).

Class 2 CRISPR/Cas systems can have single protein effectors. Cas proteins of Types II, V, and VI can be single-protein, RNA-guided endonucleases, herein called Class 2 Cas nucleases. Class 2 Cas nucleases can include, for example, but not limited to, Cas9, Cpf1, C2c1, C2c2, and C2c3 proteins. The Cpf1 nuclease is homologous to Cas9 and contains a RuvC-like nuclease domain.

In some embodiments, the Cas nuclease can be from a Type-II CRISPR/Cas system (e.g., a Cas9 protein from a CRISPR/Cas9 system). In some embodiments, the Cas nuclease can be from a Class 2 CRISPR/Cas system (a single-protein Cas nuclease, such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, which is further explained infra.

In some embodiments, a Cas nuclease can comprise more than one nuclease domain. In some embodiments, a Cas9 nuclease can comprise at least one RuvC-like nuclease domain (e.g., Cpf1) and at least one HNH-like nuclease domain (e.g., Cas9). In some embodiments, the Cas9 nuclease can introduce a DSB in the target sequence. In some embodiments, the Cas9 nuclease can be modified to contain only one functional nuclease domain. For example, the Cas9 nuclease can be modified such that one of the nuclease domains can be mutated or fully or partially deleted to reduce its nucleic acid cleavage activity. In some embodiments, the Cas9 nuclease can be modified to contain no functional RuvC-like nuclease domain. In other embodiments, the Cas9 nuclease can be modified to contain no functional HNH-like nuclease domain. In some embodiments in which only one of the nuclease domains can be functional, the Cas9 nuclease can be a nickase that can introduce a single-stranded break (nick) into the target sequence. In some embodiments, a conserved amino acid within a Cas9 nuclease domain can be substituted to reduce or alter a nuclease activity. In some embodiments, the Cas nuclease nickase can comprise an amino acid substitution in the RuvC-like nuclease domain. Exemplary amino acid substitutions in the RuvC-like nuclease domain can include D10A (based on the *S. pyogenes* Cas9 nuclease). In some embodiments, the nickase can comprise an amino acid substitution in the HNH-like nuclease domain. Exemplary amino acid substitutions in the HNH-like nuclease domain can include, but not limited to, E762A, H840A, N863A, H983A, and D986A (based on the *S. pyogenes* Cas9 nuclease).

In some embodiments, the Cas nuclease can be from a Type-I CRISPR/Cas system. In some embodiments, the Cas nuclease can be a component of the Cascade complex of a Type-I CRISPR/Cas system. For example, the Cas nuclease can be a Cas3 nuclease. In some embodiments, the Cas nuclease can be derived from a Type-III CRISPR/Cas system. In some embodiments, the Cas nuclease can be derived from Type-IV CRISPR/Cas system. In some embodiments, the Cas nuclease can be derived from a Type-V CRISPR/Cas system. In some embodiments, the Cas nuclease can be derived from a Type-VI CRISPR/Cas system.

A Type I CRISPR/Cas system can utilize a large effector complex known as Cascade (CRISPR-associated complex for antiviral defense) for target binding and interference. The Cascade complex can contain multiple Cas proteins, including Cas3, which can be responsible for the destruction of the target DNA. A Type II CRISPR/Cas system, particularly the CRISPR-Cas9 system, can utilize a single Cas9 protein, guided by a synthetic guide RNA (sgRNA), to introduce double-strand breaks in target DNA for subsequent repair or modification. A Type III CRISPR/Cas system can utilize a Csm (CRISPR-Cas subtype multiprotein) or Cmr (CRISPR-Cas subtype ribonucleoprotein) complex for interference. Type III CRISPR/Cas system can target RNA molecules in addition to DNA. A Type V CRISPR/Cas system, including Cpf1 (also known as Cas12) and C2c2 (also known as Cas13), can utilize a single effector protein to perform interference. A Type VI CRISPR/Cas system can utilize a single Cas protein, such as C2c2 (also known as Cas13), to target and cleave RNA molecules, making it useful for RNA editing and manipulation.

Guide RNAs (gRNAs): The CRISPR technology can involves the use of a genome-targeting nucleic acid that can direct one or more endonucleases to a specific target sequence within a target gene for gene editing at the specific target sequence. The genome-targeting nucleic acid can be an RNA. A genome-targeting RNA is referred to as a “guide RNA” or “gRNA” herein. A guide RNA can comprise at least one spacer sequence that can hybridize to a target nucleic acid sequence within a target gene for editing, and a CRISPR repeat sequence.

In Type II systems, the gRNA can also comprise a second RNA called the tracrRNA sequence. In the Type II gRNA, the CRISPR repeat sequence and tracrRNA sequence can hybridize to each other to form a duplex. In the Type V gRNA, the crRNA can form a duplex. In both systems, the duplex can bind a site-directed polypeptide, such that the guide RNA and site-direct polypeptide can form a complex. In some embodiments, the genome-targeting nucleic acid can provide target specificity to the complex by virtue of its association with the site-directed polypeptide. The genome-targeting nucleic acid can thus direct the activity of the site-directed polypeptide.

As is understood by the person of ordinary skill in the art, each guide RNA can be designed to include a spacer sequence complementary to its genomic target sequence. See Jinek et al., *Science* 337:816-821 (2012); Deltcheva et al., *Nature* 471:602-607 (2011).

In some embodiments, the genome-targeting nucleic acid (e.g., gRNA) can be a double-stranded guide RNA, comprising two strands of RNA molecules. The first strand can comprise in the 5' to 3' direction, an optional spacer extension sequence, a spacer sequence, and a minimum CRISPR repeat sequence. The second strand can comprise a minimum tracrRNA sequence (complementary to the minimum CRISPR repeat sequence), a 3' tracrRNA sequence, and an optional tracrRNA extension sequence.

In some embodiments, the genome-targeting nucleic acid (e.g., gRNA) can be a single-molecule guide RNA (sgRNA). sgRNA in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence, and an optional tracrRNA extension sequence. The optional tracrRNA extension can comprise elements that can contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins. A single-molecule guide RNA in a Type V system can comprise, in the 5' to 3' direction, a minimum CRISPR repeat sequence and a spacer sequence.

A spacer sequence in a gRNA is a sequence (e.g., a 20-nucleotide sequence) that can define the target sequence (e.g., a DNA target sequences, such as a genomic target sequence) of a target gene of interest (e.g., DNAI1 or CFTR). In some embodiments, the spacer sequence can range from 15 to 30 nucleotides. For example, the spacer sequence can contain 15, 16, 17, 18, 19, 29, 21, 22, 23, 24, 25, 26, 27, 28, 29, or 30 nucleotides. In some embodiments, a spacer sequence can contain 20 nucleotides.

The target sequence is in a target gene (e.g., DNAI1 or CFTR) that can be adjacent to a PAM sequence and can be the sequence to be modified by an RNA-guided nuclease (e.g., Cas9). The target sequence is on the PAM strand in a target nucleic acid, which is a double-stranded molecule containing the PAM strand and a complementary non-PAM strand. One of skill in the art recognizes that the gRNA spacer sequence can hybridize to the complementary sequence located in the non-PAM strand of the target nucleic acid of interest. Thus, the gRNA spacer sequence can be the RNA equivalent of the target sequence. The spacer of a gRNA can interact with a target nucleic acid of interest in a sequence-specific manner via hybridization (i.e., base pairing). The nucleotide sequence of the spacer thus can vary depending on the target sequence of the target nucleic acid of interest.

In a CRISPR/Cas system, the spacer sequence can be designed to hybridize to a region of the target nucleic acid that is located 5' of a PAM recognizable by a Cas9 enzyme used in the system. The spacer can perfectly match the target sequence or can have mismatches. Each Cas9 enzyme can have a particular PAM sequence that it can recognize in a target DNA. For example, *S. pyogenes* can recognize in a target nucleic acid a PAM that comprises the sequence 5'-NRG-3', where R can comprise either A or G, where N can be any nucleotide and N can be immediately 3' of the target nucleic acid sequence targeted by the spacer sequence.

In some embodiments, the target nucleic acid sequence can have about 20 nucleotides in length. In some embodiments, the target nucleic acid can have less than about 20 nucleotides in length. In some embodiments, the target nucleic acid can have more than about 20 nucleotides in length. In some embodiments, the target nucleic acid can have at least 5, 10, 15, 16, 17, 18, 19, 20, 21, 22, 23, 24, 25, 30 or more nucleotides in length. In some embodiments, the target nucleic acid can have at most 5, 10, 15, 16, 17, 18, 19, 20, 21, 22, 23, 24, 25, 30 or more nucleotides in length. In some embodiments, the target nucleic acid sequence can have 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence can be the *S. pyogenes* PAM.

The guide RNA can target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene can be 100% complementary. In other embodiments, the spacer sequence of the guide RNA and the target sequence in the target gene can contain up to 10 mismatches, e.g., up to 9, up to 8, up to 7, up to 6, up to 5, up to 4, up to 3, up to 2, or up to 1 mismatch.

The length of the spacer sequence in gRNAs can depend on the CRISPR/Cas9 system and components used for editing any of the target genes (e.g., DNAI1 or CFTR). For example, different Cas9 proteins from different bacterial species can have varying optimal spacer sequence lengths. Accordingly, the spacer sequence can have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence can have 18-24 nucleotides in length. In some embodiments, the targeting sequence can have 19-21 nucleotides in length. In some embodiments, the spacer sequence can comprise 20 nucleotides in length.

In some embodiments, the gRNA can be an sgRNA, which can comprise a 20-nucleotide spacer sequence at the 5' end of the sgRNA sequence. In some embodiments, the sgRNA can comprise a less than 20 nucleotide spacer sequence at the 5' end of the sgRNA sequence. In some embodiments, the sgRNA can comprise a more than 20 nucleotide spacer sequence at the 5' end of the sgRNA sequence. In some embodiments, the sgRNA can comprise a variable length spacer sequence with about 17-30 nucleotides at the 5' end of the sgRNA sequence.

In some embodiments, the gRNAs can comprise unmodified ribonucleic acid. In some embodiments, the gRNAs can comprise modified ribonucleic acid. Various types of RNA modifications can be introduced during or after chemical synthesis and/or enzymatic generation of RNAs, e.g., modifications that can enhance stability, reduce the likelihood or degree of innate immune response, and/or enhance other attributes, as described in the art. In some embodiments, non-natural modified nucleobases can be introduced into any of the gRNAs during synthesis or post-synthesis. In some embodiments, modifications can be on internucleoside linkages, purine or pyrimidine bases, or sugar. In some embodiments, a modification can be introduced at the terminal of a gRNA with chemical synthesis or with a polymerase enzyme.

In some embodiments, more than one guide RNAs can be used with a CRISPR/Cas nuclease system. Each guide RNA can contain a different targeting sequence, such that the CRISPR/Cas system can cleave more than one target nucleic acid. In some embodiments, one or more guide RNAs can have the same or differing properties, such as activity or stability within the Cas9 RNP complex. Where more than one guide RNA can be used, each guide RNA can be encoded on the same or on different vectors. The promoters used to drive expression of the more than one guide RNA can be the same or different.

In some embodiments, enzymatic or chemical ligation methods can be used to conjugate polynucleotides or their regions with different functional moieties, such as targeting or delivery agents, fluorescent labels, liquids, nanoparticles, and the like.

In some embodiments, the CRISPR/Cas nuclease system can contain multiple gRNAs, for example, 2, 3, or 4 gRNAs. Such multiple gRNAs can target different sites in a same target gene. Alternatively, the multiple gRNAs can target different genes. In some embodiments, the guide RNA(s) and the Cas protein can form a ribonucleoprotein (RNP), e.g., a CRISPR/Cas complex. The guide RNAs can guide the Cas protein to a target sequence(s) on one or more target genes (e.g., DNAI1 and CFTR), where the Cas protein can cleave the target gene at the target site. In some embodiments, the CRISPR/Cas complex can be a Cpf1/guide RNA complex. In some embodiments, the CRISPR complex can be a Type-II CRISPR/Cas9 complex. In some embodiments, the Cas protein can be a Cas9 protein. In some embodiments, the CRISPR/Cas9 complex can be a Cas9/guide RNA complex.

In some embodiments, the indel frequency (editing frequency) of a particular CRISPR/Cas nuclease system, comprising one or more specific gRNAs, can be determined using a TIDE analysis, which can be used to identify highly efficient gRNA molecules for editing a target gene. In some embodiments, a highly efficient gRNA can yield a gene editing frequency of higher than 80%. For example, a gRNA can be considered to be highly efficient if it can yield a gene editing frequency of at least 80%, at least 85%, at least 90%, at least 95%, or 100%.

Other Gene Editing Methods

Besides the CRISPR system disclosed herein, additional gene editing systems as known in the art can also be used as a payload of the LNPs described herein. In some embodiments, the additional gene editing system can comprise zinc finger nuclease (ZFN), transcription activator-like effector nucleases (TALEN), restriction endonucleases, meganucleases homing endonucleases, or the like.

ZFNs are targeted nucleases comprising a nuclease fused to a zinc finger DNA binding domain (ZFBD), which can be a polypeptide domain that can bind DNA in a sequence-specific manner through one or more zinc fingers. A zinc finger can be a domain of about 30 amino acids within the zinc finger binding domain whose structure can be stabilized through coordination of a zinc ion. Examples of zinc fingers include, but not limited to, C2H2 zinc fingers, C3H zinc fingers, and C4 zinc fingers. A designed zinc finger domain can be a domain not occurring in nature whose design/composition results principally from rational criteria, e.g., application of substitution rules and computerized algorithms for processing information in a database storing information of existing ZFP designs and binding data. A selected zinc finger domain can be a domain not found in nature whose production can result primarily from an empirical process such as phage display, interaction trap or hybrid selection. In some embodiments, a ZFN can be a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins can be secreted by plant pathogens of the genus *Xanthomonas* during infection. These proteins can enter the nucleus of the plant cell, bind effector-specific DNA sequences via their DNA binding domain, and activate gene transcription at these sequences via their transactivation domains. TAL effector DNA binding domain specificity can depend on an effector-variable number of imperfect 34 amino acid repeats, which can comprise polymorphisms at select repeat positions called repeat variable-diresidues (RVD). In some embodiments, a TALEN can be a fusion polypeptide of the FokI nuclease to a TAL effector DNA binding domain.

Additional examples of targeted nucleases suitable for use can include, but not limited to, Bxb1, phiC31, PhiBT1, and WO/SPBc/TP901-1, whether used individually or in combination. The Bxb1 nuclease, also known as the Bxb1 integrase, is a site-specific recombinase enzyme derived from the mycobacteriophase Bxb1. The Bxb1 integrase can catalyze site-specific recombination between two specific DNA sequences, referred to as attachment (att) sites. The Bxb1 integrase can recognize a specific 48 base-pair sequence within the attachment sites. The phiC31 nuclease, also known as the phiC31 integrase, is derived from the bacteriophage phiC31. The phiC31 nuclease can catalyze site-specific recombination between two specific DNA sequences, referred to as attB (attachment site in bacteriophage) and attP (attachment site in the phage). The phiC31 nuclease can promote integration of a DNA fragment flanked by attB and attP into the genome in cells of target organ. The phiBT1 nuclease can integrate into a different attachment site than phiC31. The WO/SPBc/TP901-1 nuclease, also known as bacteriophage P2 Bxb1 Cre nuclease, is a site-specific recombination enzyme derived from the temperate bacteriophage P2.

Pharmaceutical Composition

The disclosure also provides pharmaceutical compositions comprising the LNP composition described herein and a pharmaceutically acceptable excipient and/or diluent. Such compositions can be used for the treatment of a lung disease as described herein in a patient or subject. The pharmaceutical compositions of the disclosure may include a pharmaceutically acceptable carrier, and a thorough discussion of such carriers is available in Chapter 30 of *Remington: The Science and Practice of Pharmacy* (23$^{rd}$ ed., 2021).

In some embodiments, the composition comprises Tris buffer, optionally at a pH from 6-9. In some embodiments, the composition comprises sucrose, optionally at 5-15%. In some embodiments, the composition comprises citrate buffer, optionally at a pH 4-6. In some embodiments, the composition comprises 15 mM Tris buffer, optionally at a pH from 6-9, and/or 5-15% sucrose. In some embodiments, the composition comprises 10 mM citrate buffer, optionally at a pH from 4-6.

In some embodiments, the pharmaceutical compositions include one or more of a poloxamer (e.g., Poloxamer 188) polyethylene glycol ("PEG"), sucrose, and a buffer, wherein the buffer comprises a citrate buffer, an acetate buffer, or a Tris buffer.

In some embodiments, the composition comprises a citrate buffer. For example, the citrate buffer is at a pH from 4 to 8. In some embodiments, the buffer is an acetate buffer and has a pH from 4 to 8. In another embodiments, the composition comprises a Tris buffer, and the Tris buffer has a pH from 4 to 8.

In some embodiments, the composition comprises sucrose. In some embodiments, the sucrose is at a concentration from 1% to 15% w/v, 5% to 15% w/v, 1% to 10% w/v, or 5% to 10% w/v.

In some embodiments, pharmaceutical compositions can also include excipients and/or additives. Examples of these are surfactants, stabilizers, complexing agents, antioxidants, or preservatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In some embodiments, preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E, salts or esters thereof.

In some embodiments, one or more tonicity agents may be added to provide the desired ionic strength. Tonicity agents for use herein include those which display no or only negligible pharmacological activity after administration. Both inorganic and organic tonicity adjusting agents may be used.

Method of Treatment

In some embodiments, the LNP compositions and pharmaceutical compositions described herein can be employed to treat or prevent a lung disease or disorder, including but not limited to a disease or disorder from the following: Acute Interstitial Pneumonia (AlP), alpha-1 antitrypsin deficiency, asthma, bronchiectasis, Bronchiolitis obliterans with Organizing Pneumonia (BOOP), bronchitis, Chronic Obstructive Pulmonary Disease (COPD), coronavirus, cystic fibrosis, Desquamative Interstitial Pneumonia (DIP), emphysema, Idiopathic Interstitial Pneumonia (IIP), influenza, Interstitial Lung Disease (ILD), Interstitial Pulmonary Fibrosis (IPF), Legionnaire's disease, lung cancer, Non-Specific Interstitial Pneumonia (NSIP), pleurisy, pneumonia, Primary Ciliary Dyskinesia (PCD), pulmonary arterial hypertension, pulmonary edema, pulmonary fibrosis, pulmonary hypertension, Respiratory Bronchiolitis-associated Interstitial Lung Disease (RBILD), restrictive lung disease, sarcoidosis, Severe Acute Respiratory Syndrome, and tuberculosis.

In another aspect, the disclosure provides a method for treating and/or preventing a lung disease in a subject in need thereof, wherein the method comprises administering the composition described herein to the subject by intravenous injection.

In some embodiments, the payload is a messenger RNA (mRNA) and the method results in delivery of the payload to the lung in an amount effective to increase expression and/or function of a gene encoded by the mRNA.

In some embodiments, the method results in expression of a polypeptide in a lung of the subject, wherein the expression is 10%, 20%, 30%, 40%, 50%, 60%, 70%, 80%, or 90% increased compared to the polypeptide expression prior to delivery.

In some embodiments, the method results in expression of the polypeptide in the lung of the subject between 10 min and 24 hours after administration of the composition to the subject.

In another aspect, the disclosure provides a method of delivering a payload to a cell in a lung of a subject, wherein the method comprising administering to the subject, by intravenous injection, the LNP composition described herein.

In another aspect, the disclosure provides a kit including the composition described herein. In another aspect, the disclosure provides use of the LNP composition described herein for treatment of a lung disease by intravenous injection.

Method of Administration

In another aspect, the disclosure provides a method of delivering a payload to a cell in a lung of a subject, wherein the method comprising administering to the subject, by intravenous injection, the composition disclosed herein. In another aspect, the disclosure provides a kit comprising the composition disclosed herein.

In some embodiments, the administering to the subject is done by intravenous (I.V.) delivery. In some embodiments, the administering to the subject is done by intrathecal (I.T.) delivery. In some embodiments the administering to the subject is done by intramuscular (I.M.) delivery. In some embodiments, the administering to the subject is done by intradermal (I.D.) delivery. In some embodiments of the method, the administering to the subject is done by intranasal delivery.

In some embodiments, the administration is single administration. In some embodiments, the administration is a multiple administration. In some embodiments, the multiple administrations occur three times a day, twice a day, once a day, every other day, every third day, weekly, biweekly, every three weeks, every four weeks, or monthly.

Method of Quantification of Capped mRNA

In another aspect, the disclosure provides a method for quantifying an amount of capped messenger RNA (mRNA) in an mRNA sample, the method comprising steps of providing an mRNA sample comprising capped mRNA and uncapped mRNA, contacting mRNA in the sample with two or more of a nuclease, an alkaline phosphatase, and a polynucleotide kinase, separating the capped mRNA and the uncapped mRNA, identifying an amount of separated, capped mRNA and an amount of separated, uncapped mRNA, and comparing the amount of separated, capped mRNA to the amount of separated, uncapped mRNA; comparing the amount of separated, capped mRNA to the amount of total mRNA in the sample; and/or comparing the amount of separated, capped mRNA to a standard mRNA sample, thereby quantifying the amount of capped mRNA in the mRNA sample.

In some embodiments, the mRNA in the sample is contacted with each of the nuclease, the alkaline phosphatase, and the polynucleotide kinase. In some embodiments, the mRNA in the sample is contacted with the nuclease under conditions sufficient to create 5' end fragments of mRNA. In some embodiments, the mRNA in the sample is contacted with the alkaline phosphatase under conditions sufficient to remove a triphosphate group and/or a 3' linear phosphate group from an mRNA molecule. In some embodiments, the mRNA in the sample is contacted with the polynucleotide kinase under conditions sufficient to remove a cyclic phosphate group from the 3' end of an mRNA molecule. In some embodiments, the mRNA in the sample is contacted with the nuclease and the alkaline phosphatase sequentially or simultaneously. In some embodiments, the mRNA in the sample is contacted with the nuclease before the alkaline phosphatase. In some embodiments, the mRNA in the sample is contacted with polynucleotide kinase after contacting the mRNA with the nuclease and with the alkaline phosphatase.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, separating the capped mRNA and the uncapped mRNA occurs using chromatography. In some embodiments, the chromatography comprises liquid chromatography. In some embodiments, the liquid chromatography comprises liquid chromatography-mass spectrometry (LC-MS) or high-performance liquid chromatography (HPLC), e.g., HPLC-UV.

In some embodiments, the amount of total mRNA in the mRNA sample is known. In some embodiments, the accuracy of the quantifying in greater than the accuracy obtained from a method that does not comprise nuclease, the alkaline phosphatase, and/or the polynucleotide kinase.

In some embodiments, the mRNA is in vitro transcribed. In some embodiments, the mRNA was contacted with a vaccinia capping enzyme, a guanine-N7 methyltransferase, and/or a 2'-O-methyltransferase during in vitro transcription or after in vitro transcription. In some embodiments, the vaccinia capping enzyme comprises an RNA triphosphatase and/or an RNA guanyl transferase. In some embodiments, the standard mRNA sample comprises a known amount of capped mRNA and/or uncapped mRNA.

In another aspect, the disclosure provides a method for collecting capped messenger RNA (mRNA) from an mRNA sample comprising capped mRNA and uncapped mRNA, the method comprising steps of providing an mRNA sample comprising capped mRNA and uncapped mRNA, contacting mRNA in the sample with two or more of a nuclease, an alkaline phosphatase, and a polynucleotide kinase, separating the capped mRNA and the uncapped mRNA, and collecting the capped mRNA.

In some embodiments, the mRNA in the sample is contacted with each of the nuclease, the alkaline phosphatase, and the polynucleotide kinase.

In some embodiments, the mRNA in the sample is contacted with the nuclease under conditions sufficient to create 5' end fragments of mRNA. In some embodiments, the mRNA in the sample is contacted with the alkaline phosphatase under conditions sufficient to remove a triphosphate group and/or a 3' linear phosphate group from an mRNA molecule. In some embodiments, the mRNA in the sample is contacted with the polynucleotide kinase under conditions sufficient to remove a cyclic phosphate group from the 3' end of an mRNA molecule. In some embodiments, the mRNA in the sample is contacted with the nuclease and the alkaline phosphatase sequentially. In some embodiments, the mRNA in the sample is contacted with the nuclease before the alkaline phosphatase. In some embodiments, the mRNA in the sample is contacted with polynucleotide kinase after contacting the mRNA with the nuclease and with the alkaline phosphatase.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, separating the capped mRNA and the uncapped mRNA occurs using chromatography. In some embodiments, the chromatography comprises liquid chromatography. In some embodiments, the liquid chromatography comprises liquid chromatography-mass spectrometry (LC-MS) or high-performance liquid chromatography (HPLC), e.g., HPLC-UV.

In some embodiments, the amount of total mRNA in the mRNA sample is known. In some embodiments, the accuracy of the quantifying in greater than the accuracy obtained from a method that does not comprise nuclease, the alkaline phosphatase, and/or the polynucleotide kinase.

In some embodiments, the mRNA is in vitro transcribed. In some embodiments, the mRNA was contacted with a vaccinia capping enzyme, a guanine-N7 methyltransferase, and/or a 2'-O-methyltransferase during in vitro transcription or after in vitro transcription. In some embodiments, the vaccinia capping enzyme comprises an RNA triphosphatase and/or an RNA guanyl transferase. In some embodiments, the standard mRNA sample comprises a known amount of capped mRNA and/or uncapped mRNA.

In another aspect, the disclosure provides a method for collecting Cap G messenger RNA (mRNA), Gap 0 mRNA, and/or Cap 1 mRNA from an mRNA sample comprising uncapped mRNA and one or more of Cap G mRNA, Gap 0 mRNA, and Cap 1 mRNA, the method comprising steps of providing an mRNA sample comprising uncapped mRNA and one or more of Cap G mRNA, Gap 0 mRNA, and Cap 1 mRNA, contacting mRNA in the sample with two or more of a nuclease, an alkaline phosphatase, and a polynucleotide kinase, separating the uncapped mRNA from the Cap G mRNA, the Gap 0 mRNA, and/or the Cap 1 mRNA, and collecting one or more of the Cap G mRNA, Gap 0 mRNA, and Cap 1 mRNA.

In some embodiments, the mRNA in the sample is contacted with each of the nuclease, the alkaline phosphatase, and the polynucleotide kinase. In some embodiments, the mRNA in the sample is contacted with the nuclease under conditions sufficient to create 5' end fragments of mRNA. In some embodiments, the mRNA in the sample is contacted with the alkaline phosphatase under conditions sufficient to remove a triphosphate group and/or a 3' linear phosphate group from an mRNA molecule. In some embodiments, the mRNA in the sample is contacted with the polynucleotide kinase under conditions sufficient to remove a cyclic phosphate group from the 3' end of an mRNA molecule. In some embodiments, the mRNA in the sample is contacted with the nuclease and the alkaline phosphatase sequentially. In some embodiments, the mRNA in the sample is contacted with the nuclease before the alkaline phosphatase. In some embodiments, wherein the mRNA in the sample is contacted with polynucleotide kinase after contacting the mRNA with the nuclease and with the alkaline phosphatase.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, separating the uncapped mRNA from the Cap G mRNA, the Gap 0 mRNA, and/or the Cap 1 mRNA occurs using chromatography. In some embodiments, the chromatography comprises liquid chromatography. In some embodiments, the liquid chromatography comprises liquid chromatography-mass spectrometry (LC-MS) or high-performance liquid chromatography (HPLC), e.g., HPLC-UV.

In some embodiments, the amount of total mRNA in the mRNA sample is known. In some embodiments, the accuracy of the quantifying in greater than the accuracy obtained from a method that does not comprise nuclease, the alkaline phosphatase, and/or the polynucleotide kinase.

In some embodiments, the mRNA is in vitro transcribed. In some embodiments, the mRNA was contacted with a vaccinia capping enzyme, a guanine-N7 methyltransferase, and/or a 2'-O-methyltransferase during in vitro transcription or after in vitro transcription. In some embodiments, the vaccinia capping enzyme comprises an RNA triphosphatase and/or an RNA guanyl transferase. In some embodiments, the standard mRNA sample comprises a known amount of uncapped mRNA, a known amount of Cap G mRNA, a known amount of Gap 0 mRNA, and/or a known amount of Cap 1 mRNA.

In another aspect, the disclosure provides a kit for quantifying an amount of capped messenger RNA (mRNA) in an mRNA sample, the kit comprising two or more of a nuclease, an alkaline phosphatase, and a polynucleotide kinase. In some embodiments, the kit further comprising a standard mRNA sample comprising a known amount of capped mRNA and/or uncapped mRNA.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK). In some embodiments, the kit further comprising a vaccinia capping enzyme, a guanine-N7 methyltransferase, and/or a 2'-O-methyltransferase. In some embodiments, the vaccinia capping enzyme comprises an RNA triphosphatase and/or an RNA guanyl transferase. In some embodiments, the kit further comprising instructions for use.

In another aspect, the disclosure provides a kit for quantifying an amount of Cap G messenger RNA (mRNA), Gap 0 mRNA, and/or Cap 1 mRNA in an mRNA sample, the kit comprising two or more of a nuclease, an alkaline phosphatase, and a polynucleotide kinase. In some embodiments, the kit further comprising a standard mRNA sample comprising a known amount of uncapped mRNA, a known amount of Cap G mRNA, a known amount of Gap 0 mRNA, and/or a known amount of Cap 1 mRNA.

In some embodiments, the nuclease is a ribozyme or a DNAzyme. In some embodiments, the alkaline phosphatase is a shrimp alkaline phosphatase (SAP), a calf-intestinal alkaline phosphatase (CIP), or a placental alkaline phosphatase (PLAP). In some embodiments, the polynucleotide kinase is a T4 Polynucleotide Kinase (T4PNK).

In some embodiments, the kit further comprising a vaccinia capping enzyme, a guanine-N7 methyltransferase, and/or a 2'-O-methyltransferase. In some embodiments, the vaccinia capping enzyme comprises an RNA triphosphatase and/or an RNA guanyl transferase. In some embodiments, the kit further comprising instructions for use.

EXAMPLES

Example 1. Methods

Preparation of lipid nanoparticles: For formation of LNP composition, mRNA was dissolved in 1×PBS or citrate buffer (10 mM, pH 4.0), and mixed rapidly into ethanol containing ionizable lipids, DOPE, cholesterol, DMG-PEG and 16:0 EPC, fixing the weight ratio of 40:1 (total lipid: mRNA) and volume ratio of 3:1 (lipids:mRNA). Exemplary LNP composition are shown in Table 10. LNPs were loaded with luciferase (Fluc) mRNA as indicated.

TABLE 10

Exemplary LNP compositions

| Composition | Dendrimer (%) | | SORT (%) | | DOPE (%) | Cholesterol (%) | DMG-PEG (%) | Lipid:mRNA (wt/wt) |
|---|---|---|---|---|---|---|---|---|
| A | 4A3-SC7 | 16.67 | 16:0 EPC | 30 | 16.67 | 33.33 | 3.33 | 40 |
| B | 4A3-SC7 | 16.67 | 16:0 EPC | 30 | 16.67 | 33.33 | 3.33 | 30 |
| C | 4A3-SC7 | 14.29 | 16:0 EPC | 40 | 14.29 | 28.57 | 2.86 | 30 |
| D | 4A3-SC7 | 11.9 | 16:0 EPC | 50 | 11.9 | 23.81 | 2.38 | 30 |
| E | 4A3-SC7 | 19.05 | 16:0 EPC | 20 | 19.05 | 38.09 | 3.81 | — |
| F | 4A3-SC7 | 23.81 | 16:0 EPC | 0 | 23.81 | 47.62 | 4.76 | — |
| G | 4A3-SC7 | 21.43 | 16:0 EPC | 10 | 21.43 | 42.85 | 4.29 | — |
| H | D-Lin-MC3-DMA | 50 | — | — | 10 DSPC | 38.5 | 1.5 | 20.6 |
| I | 4A3-SC7 | 19.05 | DODAP | 20 | 19.05 | 38.09 | 3.81 | 40 |
| J | 5A2-SC8 | 11.9 | DOTAP | 50 | 11.9 | 23.82 | 2.38 | 40 |

LNP characterization: The different LNP compositions were characterized by size, polydispersity index (PDI), and zeta-potential as assessed by Dynamic Light Scattering (DLS, Malvern, 173° Scattering angle). DLS measures the scattering of light that results from subjecting a sample to a light source. PDI, as determined from DLS measurements, represents the distribution of particle size (at or around the mean particle diameter) in a population, with a perfectly uniform population having a PDI of zero. The encapsulation efficacy (EE %) was tested using RiboGreen RNA Assay (Zhao et al., 2016).

Aerosol delivery: Formulations are mixed on benchtop Ignite using 10 mM sodium citrate buffer at pH 4. Formulations are diluted to 1:1 with 1×PBS after 30-minute maturation then buffer is exchanged using PD10. Formulation is concentrated using Amicon concentrators to 1 mg/ml, stored in 15 mM Tris, 10% sucrose, pH 7.5.

DSI Tower Setup Parameters

| |
|---|
| 3 subjects with a flow rate of 0.5 L/min per port |
| RTX0215 concentration 0.5 mg/ml |
| Aerogen Solo nebulizer |
| Nebulizer ER (nebulizer flow rate) 0.11 ml/min |
| Total of 4.95 mg required |
| Dosed 1.2375 mg/animal |
| Nebulization delivery time 90 minutes |

IVIS image: Subjects were intravenously or intrathecally injected with mRNA containing LNP compositions at a given dose. At the given time point, subjects were injected intraperitoneal (TP) with D-Luciferin and incubated for 5 min Luciferase expression of whole body and ex vivo images were imaged by IVIS Lumina system (Perkin Elmer®). Images were processed using Living Image analysis software (Perkin Elmer®).

LC-MS Methods for Lipids Distribution

| Methods | |
|---|---|
| Extraction | Add 10 µL/mg lysis solution to sample<br>(solution: can/Water = 33:7)<br>No phospholipid removal cartridges were used<br>Tissue mass to Final Lysate Volume: 10 mg/100 µL (m/v) |
| HPLC | Run time: 12 minutes each<br>Mobile Phase A: Water/DFA (100:0.05 v/v) with 0.5 mM Ammonium acetate<br>Mobile Phase B: Methanol/Acetonitrile/DFA (80:20:0.05 v/v) with 0.5 mM Ammonium acetate<br>Gradient: 80% B to 100% B in 7 minutes |
| MS | Selective Multiple reaction monitoring (MRM) method for each lipids.<br>One fragment of each lipid was monitored. |

Example 2. Lung Specific LNP Delivery In Vivo

This example describes the determination of organ specificity of Composition E at different doses in vivo.

Figure 1B:
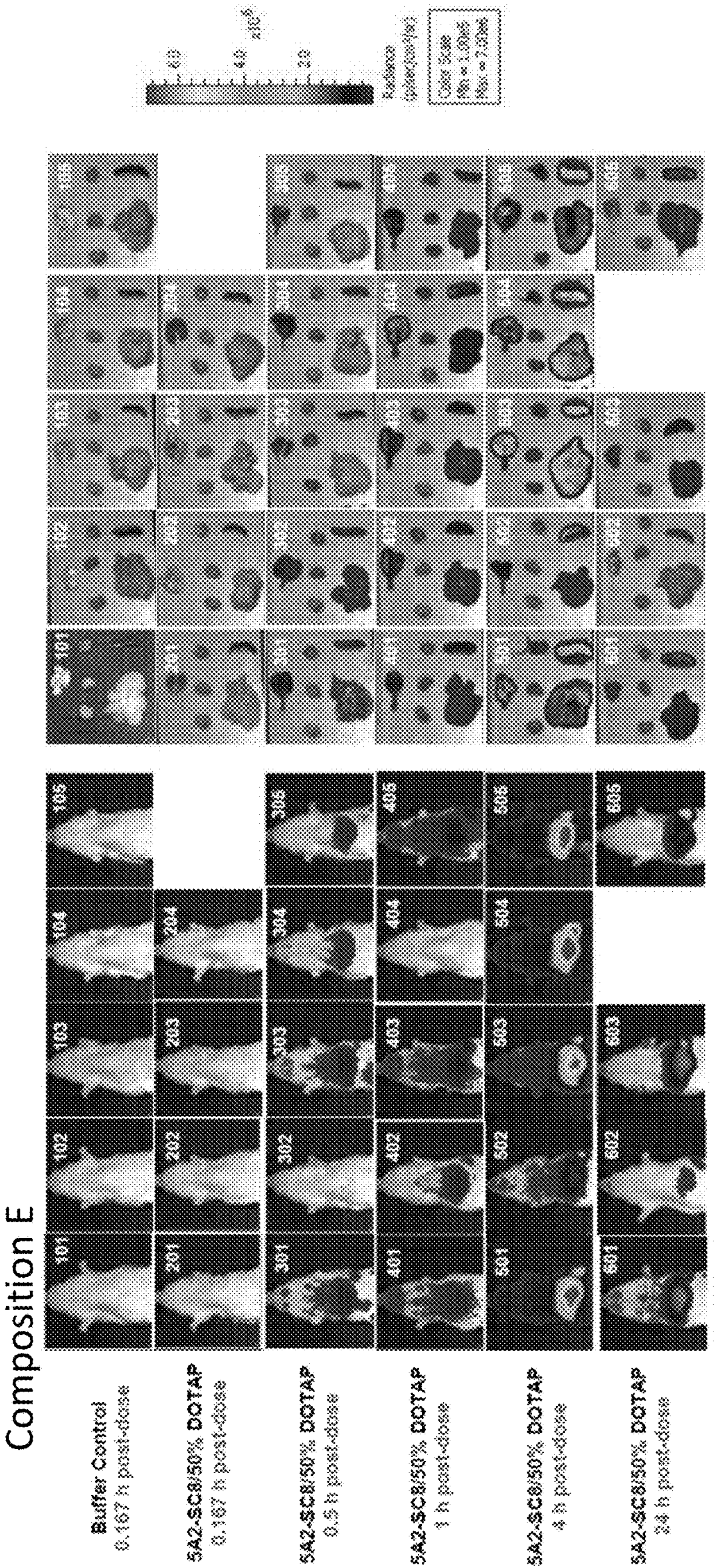
FIG. 1 B shows whole body in vivo imaging (IVIS®) of rats at different time course.
FIG. 1C shows a summary of LNP composition characterization (size, PDI, EE %) for LNPs comprising different amounts of DOTAP.
FIG. 1D shows whole body in vivo imaging (IVIS®) of rats dosed with LNP in different DOTAP molar percentages (%).

Briefly, rats were injected with 0.3 mg/kg, 0.1 mg/kg, 0.03 mg/kg, 0.01 mg/kg, and 0.003 mg/kg LNP composition E with mRNA encoding luciferase. A second cohort of rats were injected with 0.3 mg/kg of LNP composition E and imaged at 0.167 h, 0.5 h, 1 h, 4 h, and 24 hrs post dose. The subjects were imaged and distribution of the LNP composition was determined. The results show that the LNPs composition was targeted to the lung (FIG. 1A). Furthermore, organ tropism was not related to dose level between 0.3 mg/kg and 0.1 mg/kg. Further experiments were conducted to evaluate a time course to Formulation J following IV administration in rats. The in vivo imaging showed that the luciferase signal appeared first in lung tissue before spleen and liver. The peak response was observed at 4 h post dose (FIG. 1B).

Example 3. Impact of Different SORT Lipids on Lung Delivery

Figure 1D:
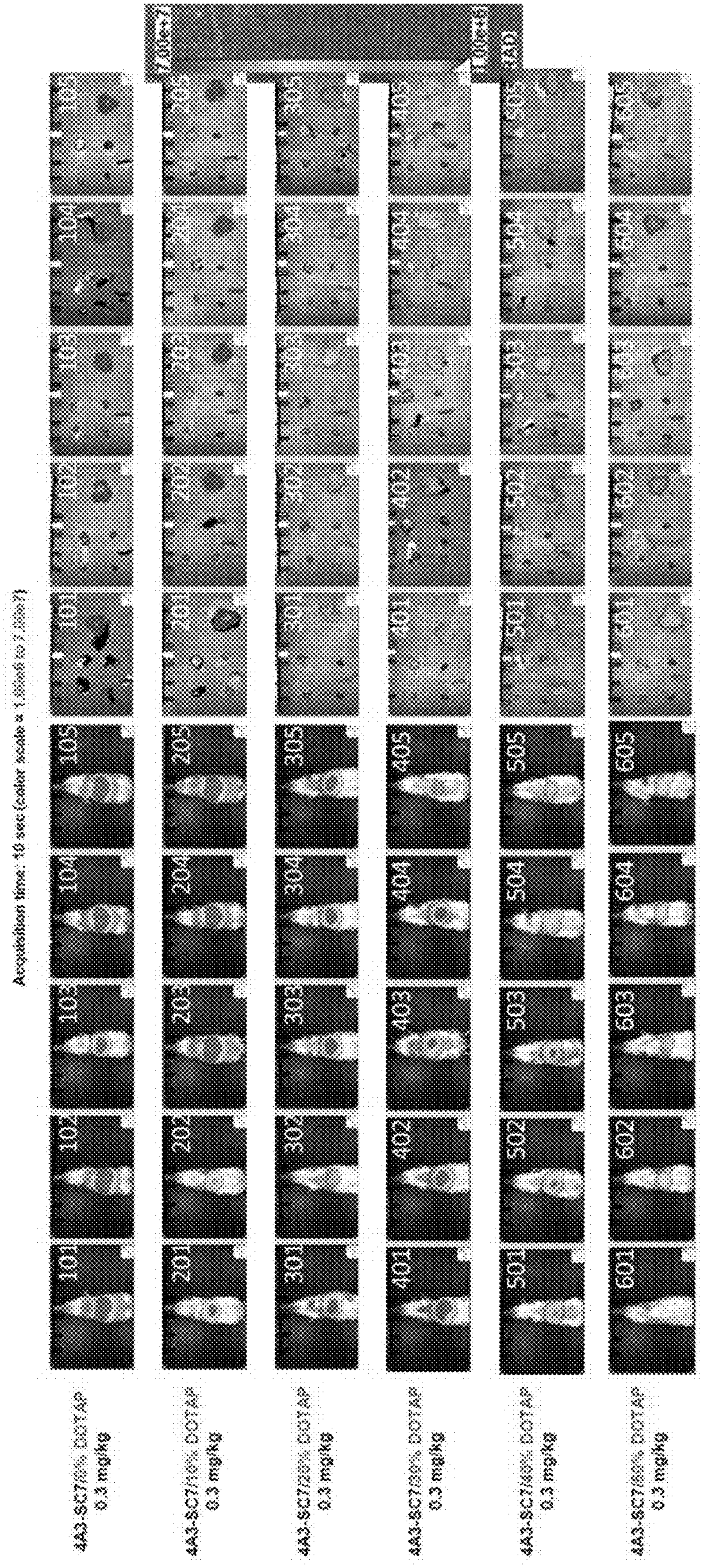

This example describes the evaluation of the impact of the concentration of 1,2-Dioleoyl-3-trimethylammonium-propane (DOTAP) on the delivery of mRNA to the lung in rat. LNPs with different concentrations of DOTAP (0%, 10%, 20%, 30%, 40% and 50%) and 4A3-SC7, DOPE, Cholesterol, and DMG-PEG were produced and characterized as described in Example 1. FIG. 1C shows similar particle size (nm), polydispersity index (PDI), and encapsulation efficiency (EE, %) on each lipid nanoparticle composition containing different molar percentages of DOTAP. The LNP compositions were then assayed in mice for organ targeting at 0.3 mg/kg. The results show the strongest lung signal at 30% DOTAP (FIG. 1D).

Figure 2A:
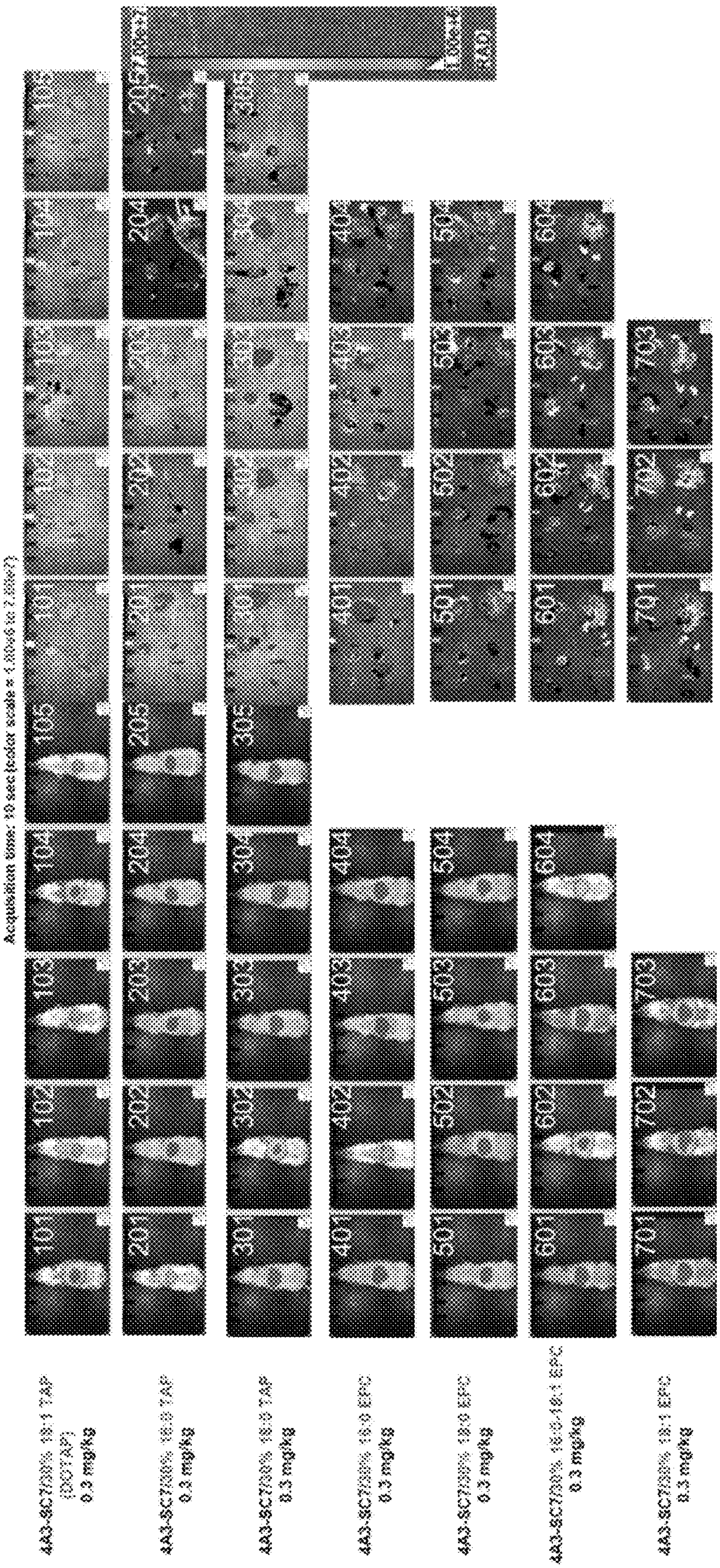
FIG. 2A shows whole body in vivo imaging (IVIS®) of rat dosed with DOTAP alternatives (30% molar %).
Figure 2B:
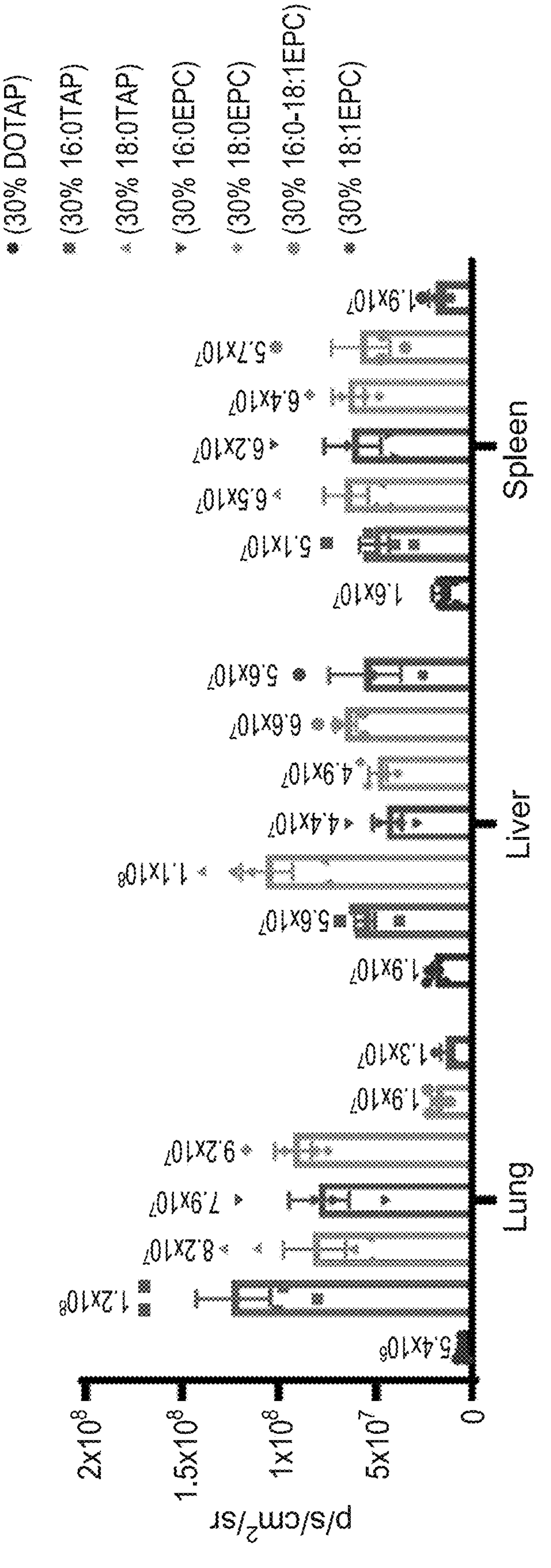
FIG. 2B shows quantitative results of whole body in vivo imaging (IVIS®) of rat dosed with DOTAP alternatives (30% molar %).

Additionally, DOTAP alternatives were tested for lung delivery of lipid nanoparticles. The tested lipids in the LNPs replacing DOTAP were: 30% 1,2-dipalmitoyl-3-trimethylammonium-propane (16:0 TAP), 30% 1,2-stearoyl-3-trimethylammonium-propane (18:0 TAP), 30% 1,2-dipalmitoyl-sn-glycero-3-ethylphosphocholine (16:0 EPC), or 30% 1,2-distearoyl-sn-glycero-3-ethylphosphocholine (18:0 EPC)-based. The results show that the LNP compositions with DOTAP alternatives showed greater lung targeting activity than a 30% DOTAP-based LNP composition (top row) (FIG. 2A). LNPs were targeting primarily the lung, and to a lower degree the liver and spleen (FIG. 2B).

Example 4. Effect of 16:0 EPC for Lung Delivery

This example describes the determination of the organ targeting activity of LNPs with 16:0 EPC compositions. To assess the effect of lipid:mRNA ratio on the delivery of mRNA to the lung, Composition 2A (high lipid:mRNA ratio) and Composition 2B (low lipid:mRNA ratio) lipid nanoparticles were delivered intravenously (IV).

Figure 3:
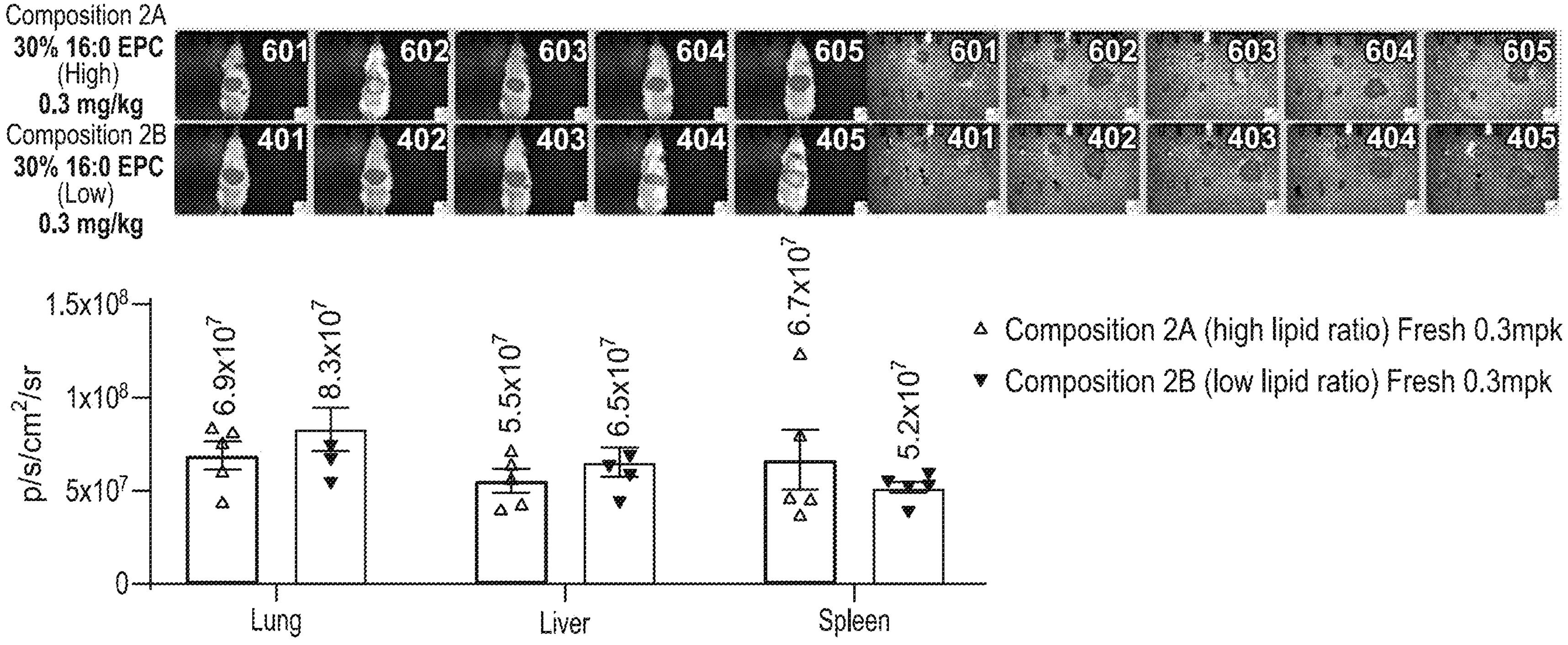
FIG. 3 shows whole body in vivo imaging (IVIS®) of rat dosed with 16:0 EPC with different lipid:mRNA ratio and its quantitative results.
Figure 4:
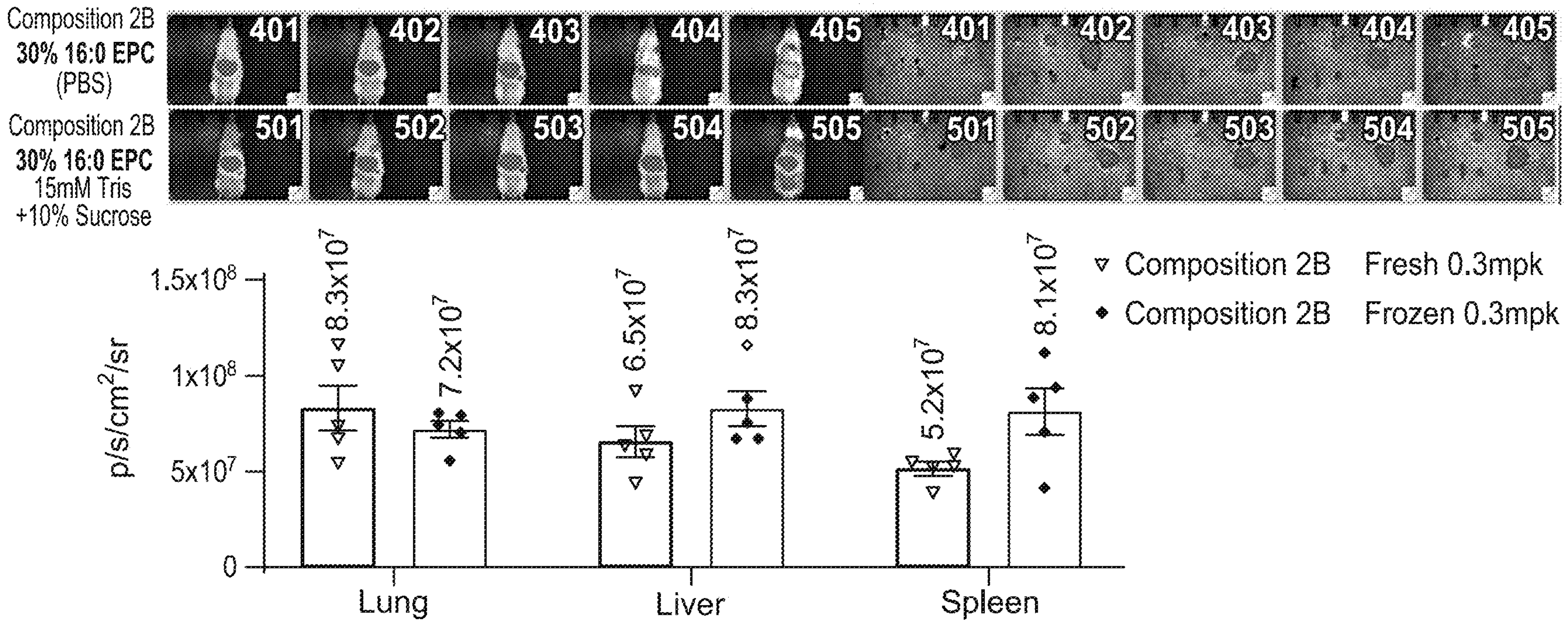
FIG. 4 shows whole body in vivo imaging (IVIS®) of rat dosed with Formulation B in different buffer and its quantitative results.

Briefly, rats were injected intravenously with Compositions A and B at 0.3 mg/kg and the uptake in the lung, liver and spleen was monitored. 16:0 EPC in EPC SORT formulations had shown tolerability limitations. The result show that both Formulation A and Formulation B had comparable lung signal (FIG. 3). To evaluate IV lung SORT lipid nanoparticle storage conditions suitable for in vivo testing, Composition 2B lipid nanoparticles were either stored in PBS or 15 mM Tris containing 10% sucrose, stored frozen, and delivered intravenously to mice. Whole body in vivo imaging and ex vivo bioluminescence images showed good stability of lipid nanoparticles in 15 mM Tris pH 7.5 with 10% sucrose and strong lung signal, liver, and spleen (FIG. 4).

Figure 5A:
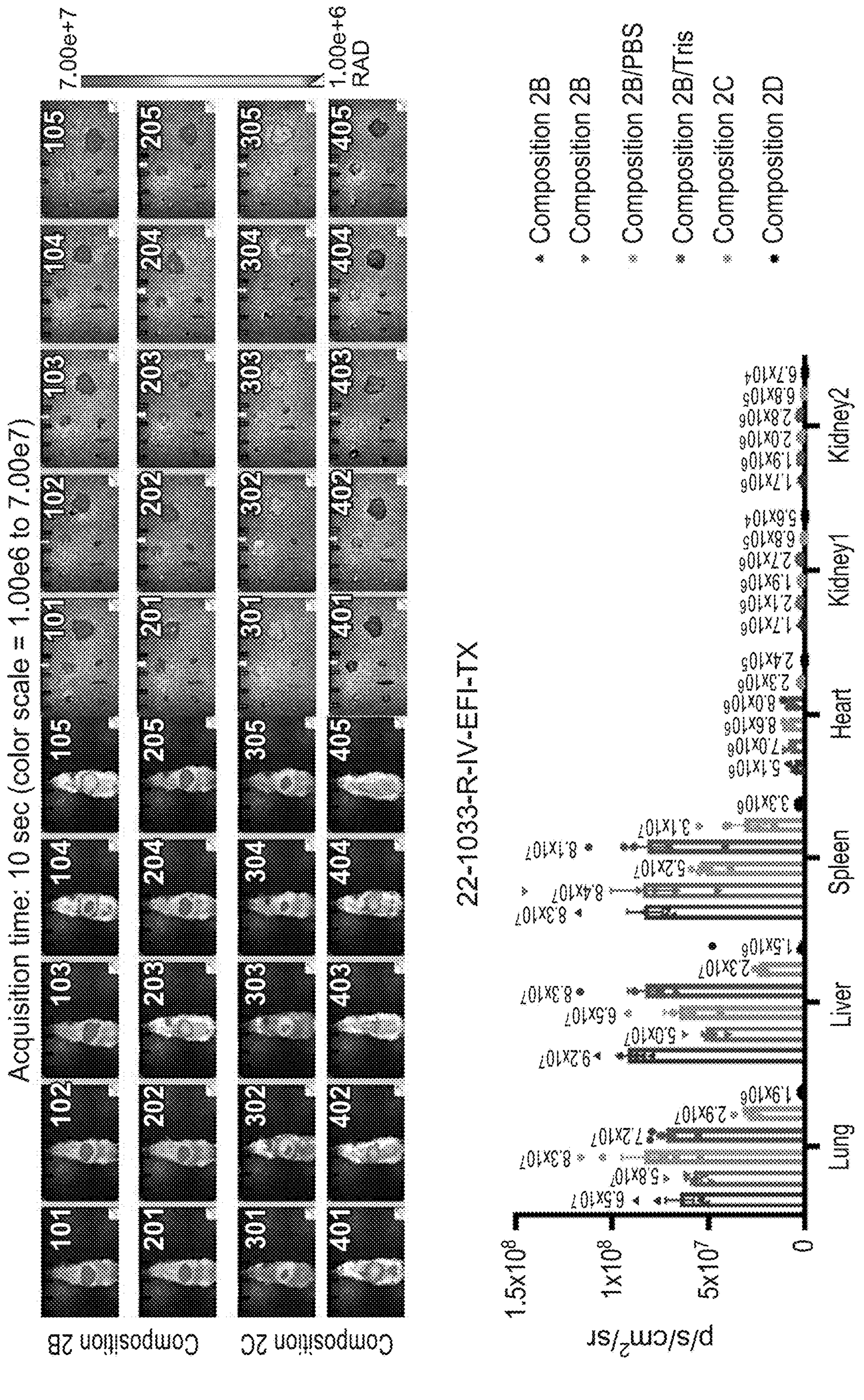
FIG. 5A shows whole body in vivo imaging (IVIS®) of rat dosed with different 16:0 EPC molar %.

Additional lipid nanoparticle compositions were prepared to assess the effect of different molar percentages of 16:0 EPC on the delivery of mRNA to the lung. Sprague Dawley rats were intravenously administered with lipid nanoparticle compositions containing either 30% (Composition 2B), 40% (Composition 2C), or 50% (Composition 2D) 16:0 EPC. After 4 h, rats were intraperitoneal (IP) injected with D-Luciferin and imaged by an IVIS Lumina system (Perkin Elmer). Selected organs (liver, spleen, kidneys, heart and lungs) were harvested after rats were transcardially perfused with PBS, soaked in luciferin (30 mg/mL) for 1 minute, and imaged (FIG. 5A). The quantification results showed 30% 16:0 EPC produced the highest lung signal as compared to 40% or 50% 16:0 EPC. There were no significant differences observed in Composition 2B organ tropism and bioluminescence activity across studies or batches. The characterization of each LNP composition are shown in FIG. 5B.

Figure 5C:
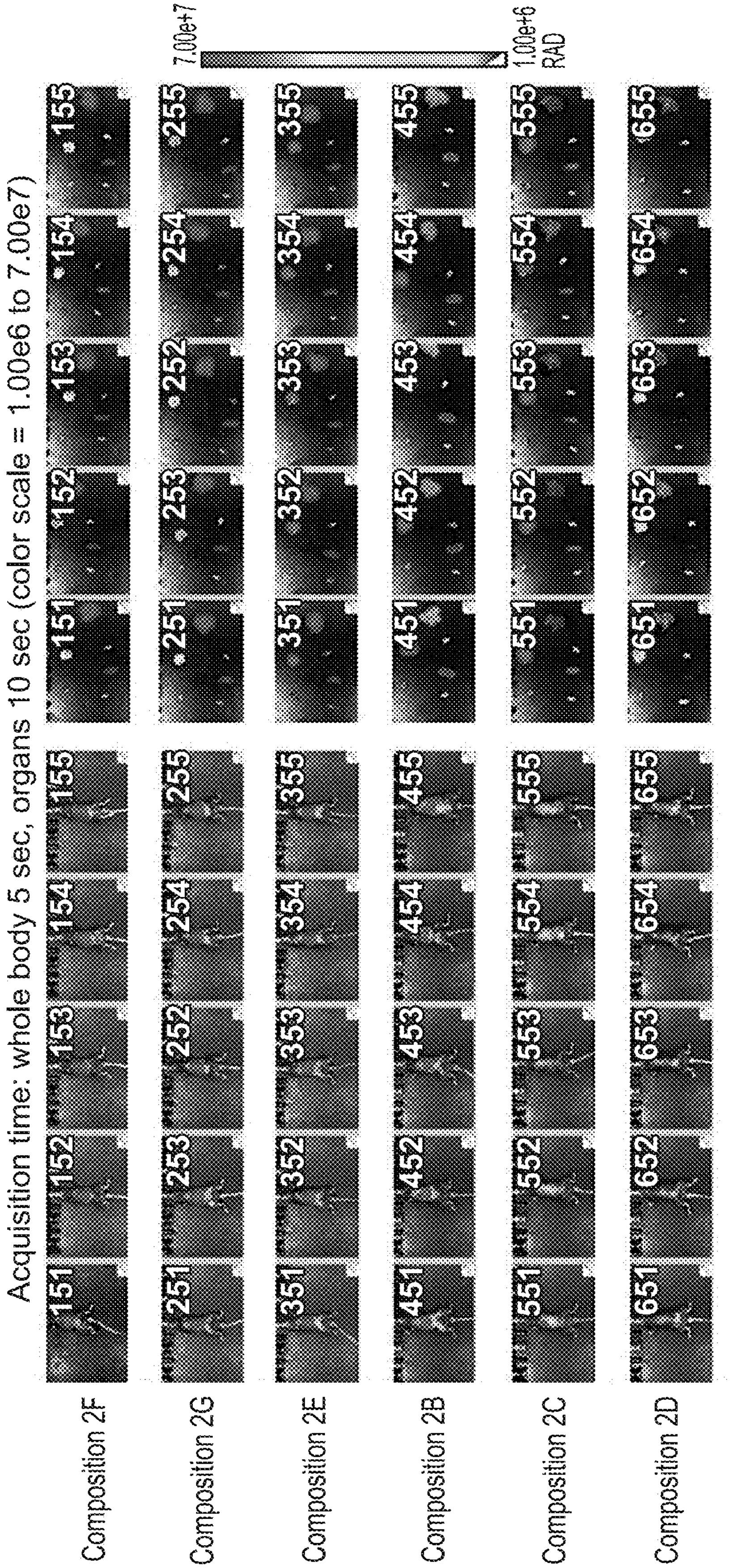
FIG. 5C shows whole body in vivo imaging (IVIS®) of mouse dosed with different 16:0 EPC molar %.
Figure 5C:
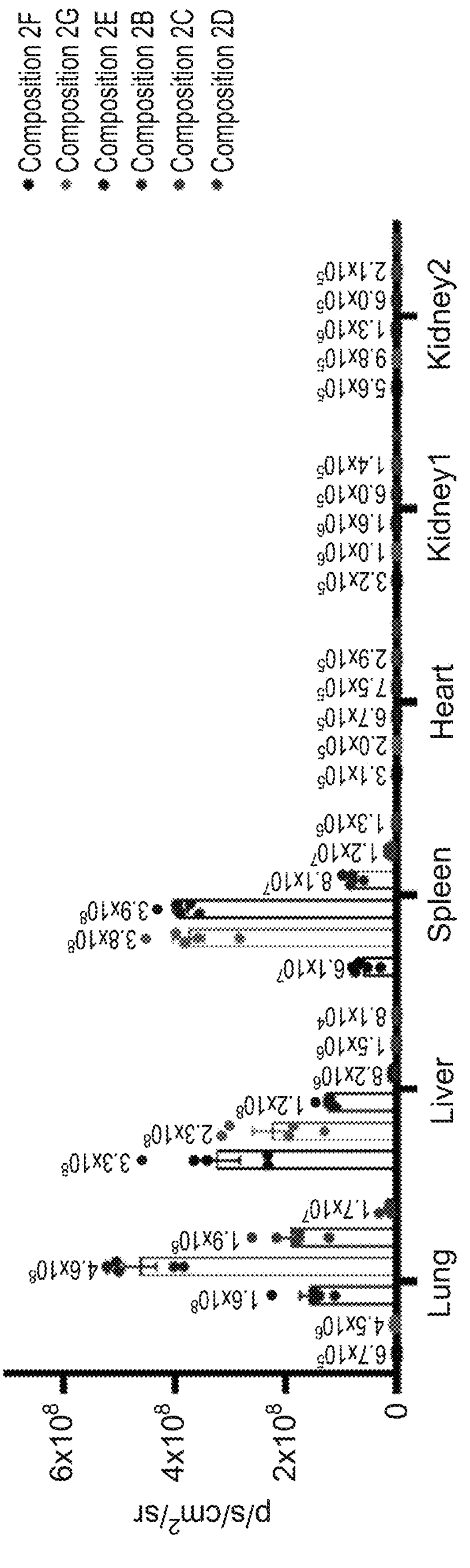

Further studies were conducted in mice to confirm the effect of 16:0 EPC on lung delivery. C87BL6J mice were intravenously administered with different LNP compositions containing 0% (Composition 2F), 10% (Composition 2G), 20% (Composition 2E), 30% (Composition 2B) 40%, (Composition 2C), or 50% (Composition 2D) 16:0 EPC. After 4 h, mice were imaged IVIS Lumina system (Perkin Elmer) and harvested organs (liver, spleen, kidneys, heart and lungs) were re-imaged (FIG. 5C). Similar to the results in rats, 30% 16:0 EPC produced the highest lung signal in mice as compared to 40% (Composition 2C) or 50% (Composition 2D). Composition 2B had greater lung specificity (lung:liver=56; lung:spleen-5.7) compared to the rat where lung organ tropism is less selective (lung:liver=~2; lung:spleen=~2) at the same dose level (shown in Table 11). The characterization of each LNP compositions are shown in FIG. 5D.

TABLE 11

| LNP compositions | Lung:Liver signal | Lung:Spleen signal |
|---|---|---|
| Composition 2F (0% EPC) | 0.002 | 0.01 |
| Composition 2G (10% EPC) | 0.02 | 0.01 |
| Composition 2E (20% EPC) | 1.25 | 0.4 |
| Composition 2B (30% EPC) | 56 | 5.7 |
| Composition 2C (40% EPC) | 128.1 | 2.38 |
| Composition 2D (50% EPC) | 209.9 | 13.1 |

Figure 6:
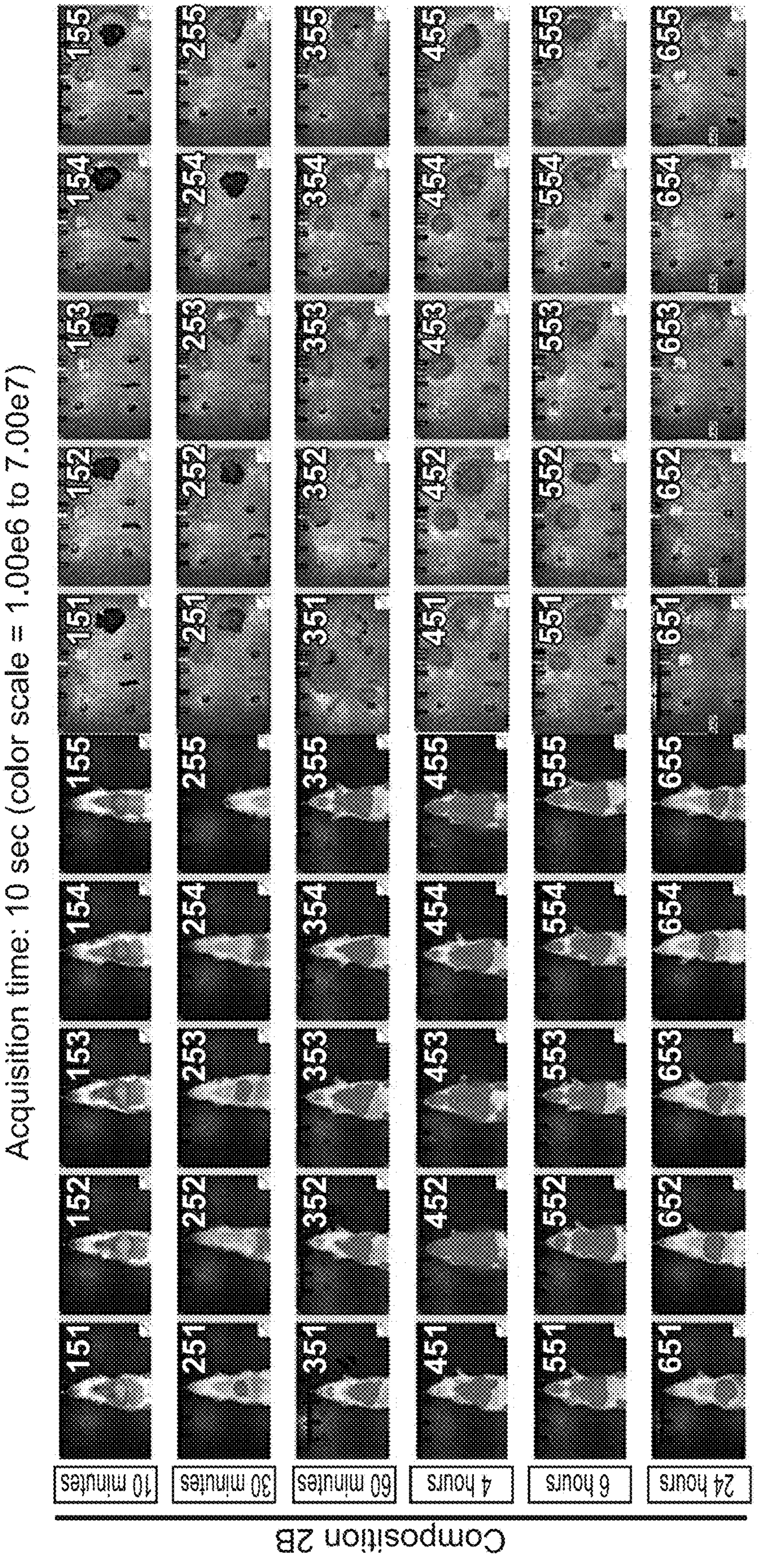
FIG. 6 shows whole body in vivo imaging (IVIS®) of rat at different time course.
Figure 6:
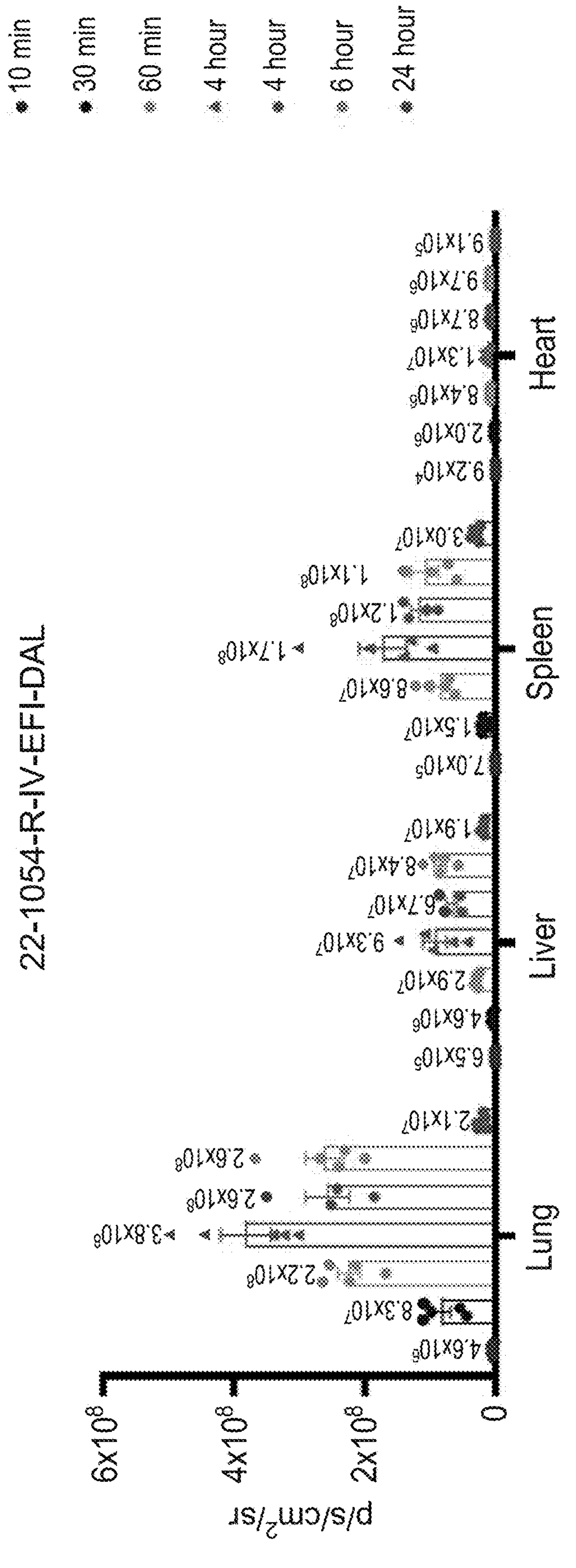

Further experiments were conducted to evaluate a time course to Formulation B following IV administration in rats. Sprague Dawley rats were intravenously administered with Composition 2B and imaged by IVIS Lumina system (Perkin Elmer) at 10 minute, 30 minutes, 60 minutes, 4 hours, 6 hours, and 24 hours post injection (FIG. 6). The results showed that the signals were observed at the earliest time point of 10 min and 4 hour time point showed the highest bioluminescence signal. The bioluminescence signal appeared first in lung before it appeared in liver and spleen. Also, selectivity for lung over liver and spleen peaked at 30 minutes post IV administration (shown in Table 12).

TABLE 12

| Group | Lung:liver signal | Lung:spleen signal |
|---|---|---|
| 10 minutes | 7.1 | 6.6 |
| 30 minutes | 18.2 | 5.6 |
| 60 minutes | 7.8 | 2.6 |
| 4 hours | 4.1 | 2.2 |
| 4 hours different batch | 3.9 | 2.2 |
| 6 hours | 3.1 | 2.4 |
| 24 hours | 1.1 | 0.9 |

Figure 7:
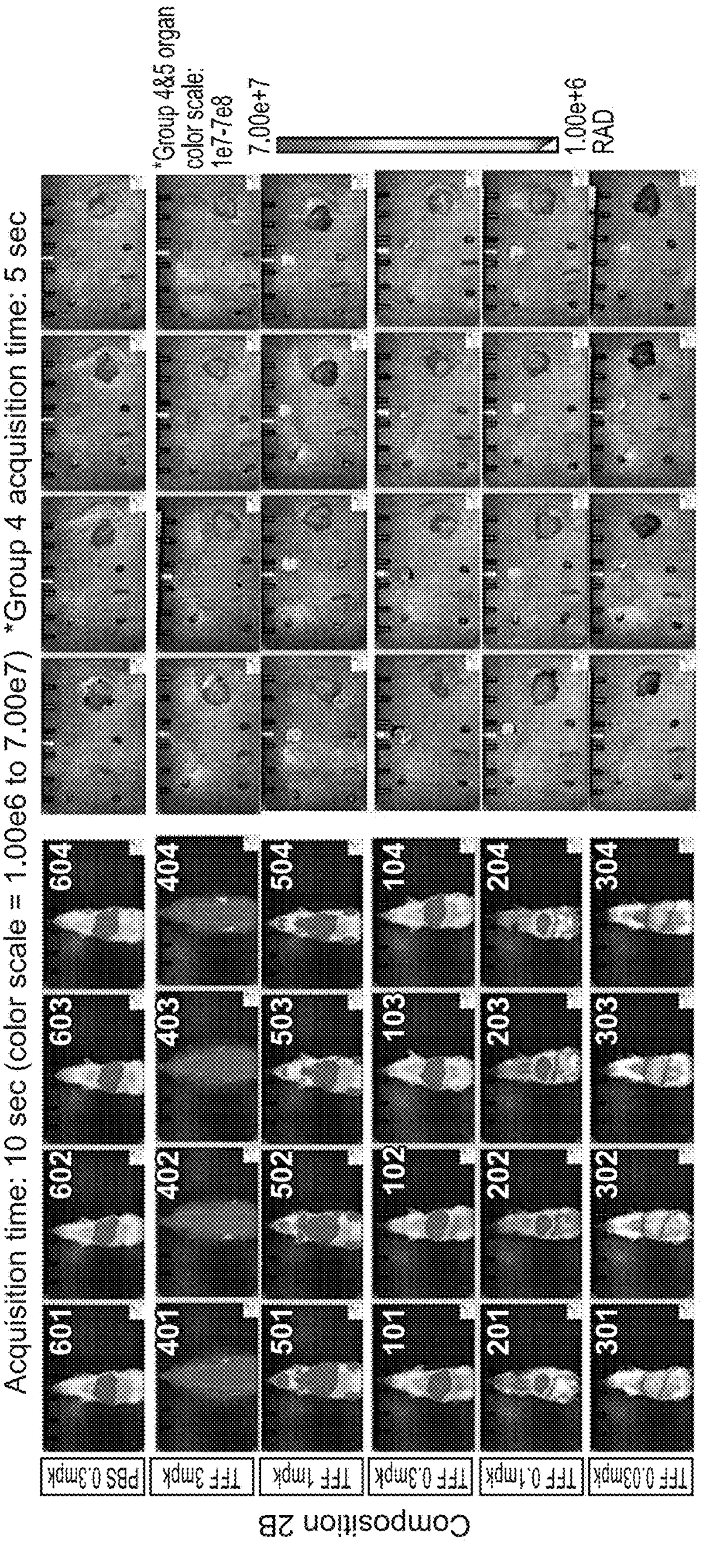
FIG. 7 shows whole body in vivo imaging (IVIS®) of rat with different dose.

Further experiments were conducted to evaluate a dose response to Composition 2B following IV administration in rats. Sprague Dawley rats were intravenously administered with Composition 2B lipid nanoparticles containing different doses (0.03-3mpk). After 4 h post-injection, rats were intraperitoneal (TP) injected with D-Luciferin and imaged by an IVIS Lumina system (Perkin Elmer). Selected organs (liver, spleen, kidneys, heart, and lungs) were harvested after rats were transcardially perfused with PBS, soaked in luciferin (30 mg/mL) for 1 minute, and imaged (FIG. 7). The quantification results showed that the lung signal continued to increase exponentially with dose dependency while the liver and spleen signal was more linear. Lung specificity appeared dose dependent in rats. The selectivity for lung over liver and spleen peaked at the high dose of 3 mpk (shown in Table 13).

TABLE 13

| LNP composition | Lung:Liver signal | Lung:Spleen signal |
|---|---|---|
| PBS 0.3 mpk | 2.3 | 2.0 |
| TFF 3 mpk | 5.9 | 5.2 |
| TFF 1 mpk | 3.9 | 2.2 |
| TFF 0.3 mpk | 1.3 | 1.0 |
| TFF 0.1 mpk | 1.2 | 0.7 |
| TFF 0.03 mpk | 0.5 | 0.8 |

Example 5. Lipid Distribution in Organs

This example shows the determination of the lipid distribution in organ in vivo.

Figure 8A:
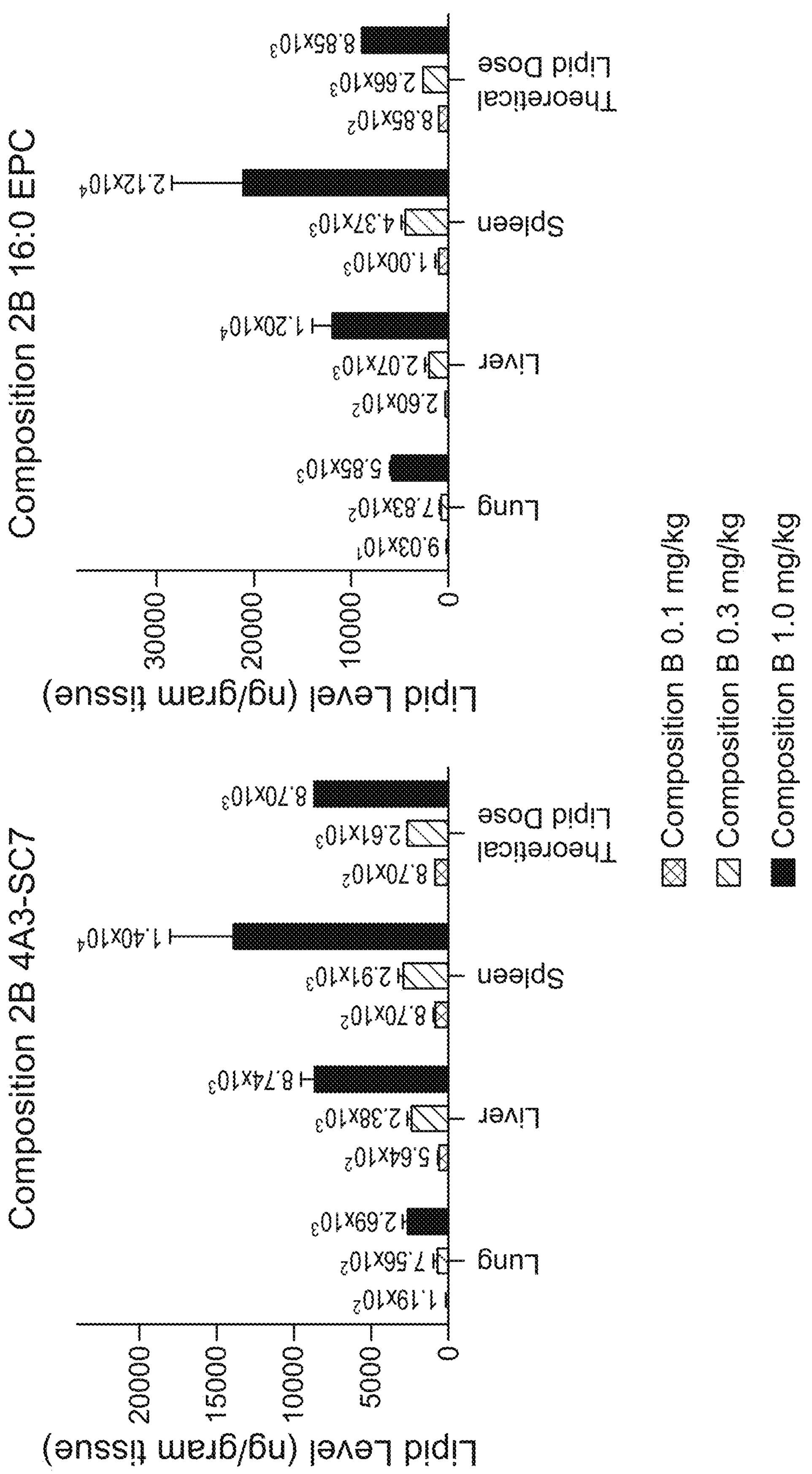
FIGS. 8A-8B show the evaluation of lipids distributions in rat organs.
Figure 8A:
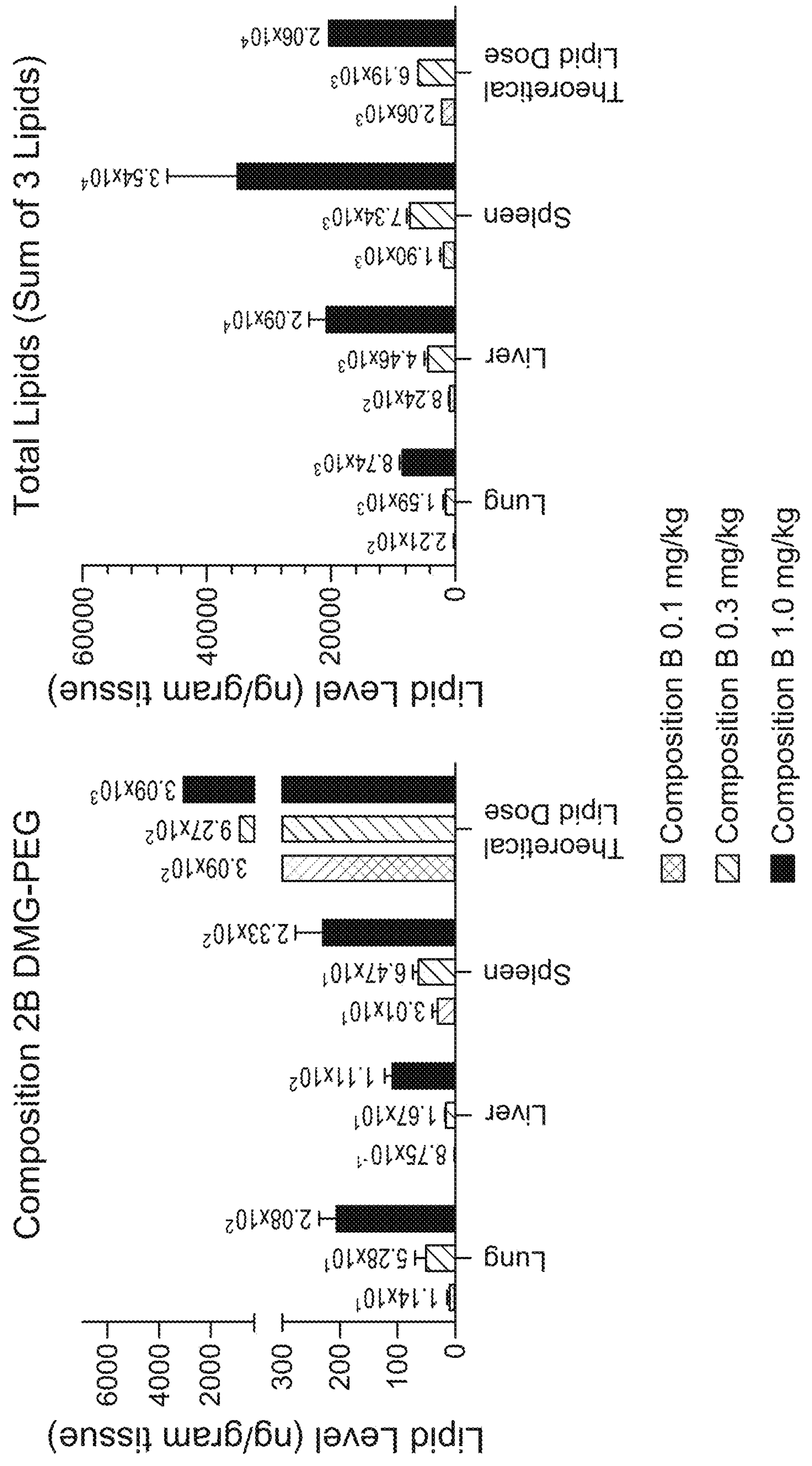
Figure 8B:
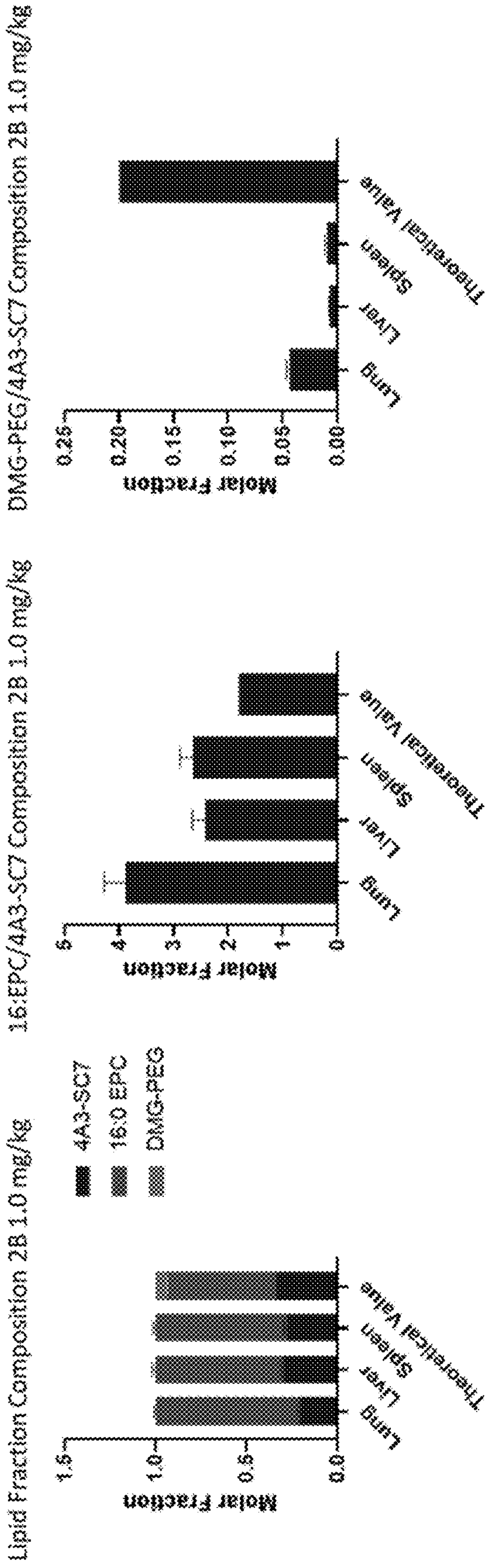

Briefly, rats were injected with Composition 2B at 0.1 mg/kg, 0.3 mg/kg, and 1.0 mg/kg and the lipid distribution for 4A3-SC7, 16:0 EPC, and DMG-PEG in lung, liver, spleen were determined using LC-MS as described in Example 1. The results of the lipid distribution are shown in FIG. 8A. The results show that Composition 2B and its lipids were localized the most in spleen and least in lung. The result for lipid ratios is shown in FIG. 8B. The molar fraction of DMG-PEG/4A3-SC7 in every organ were lower than the theoretical value.

Figure 9A:
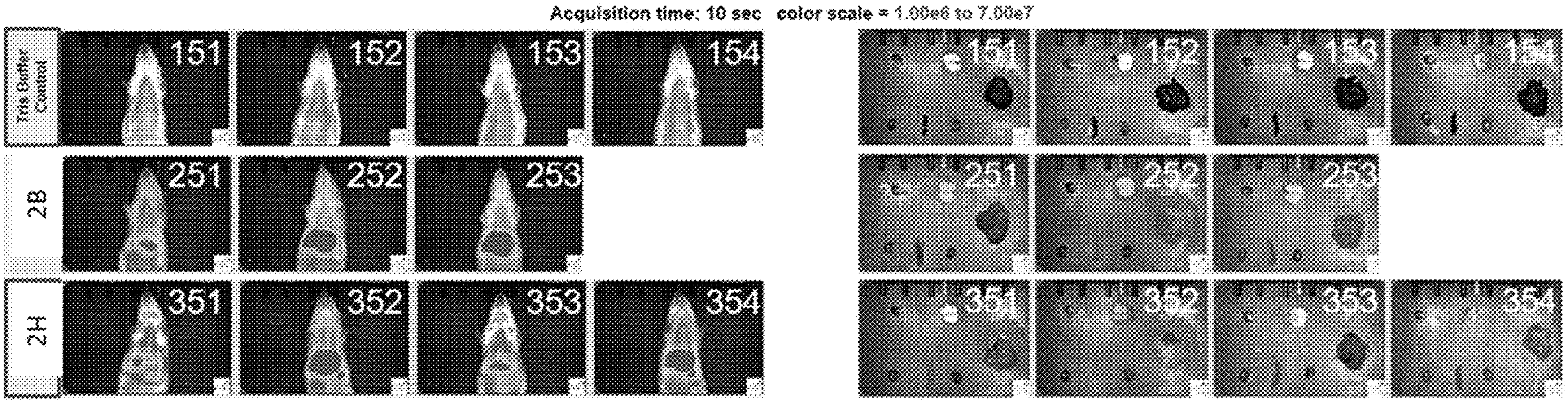
FIG. 9A shows whole body in vivo imaging (IVIS®) of rat with 6 week repeat dosing.
Figure 9B:
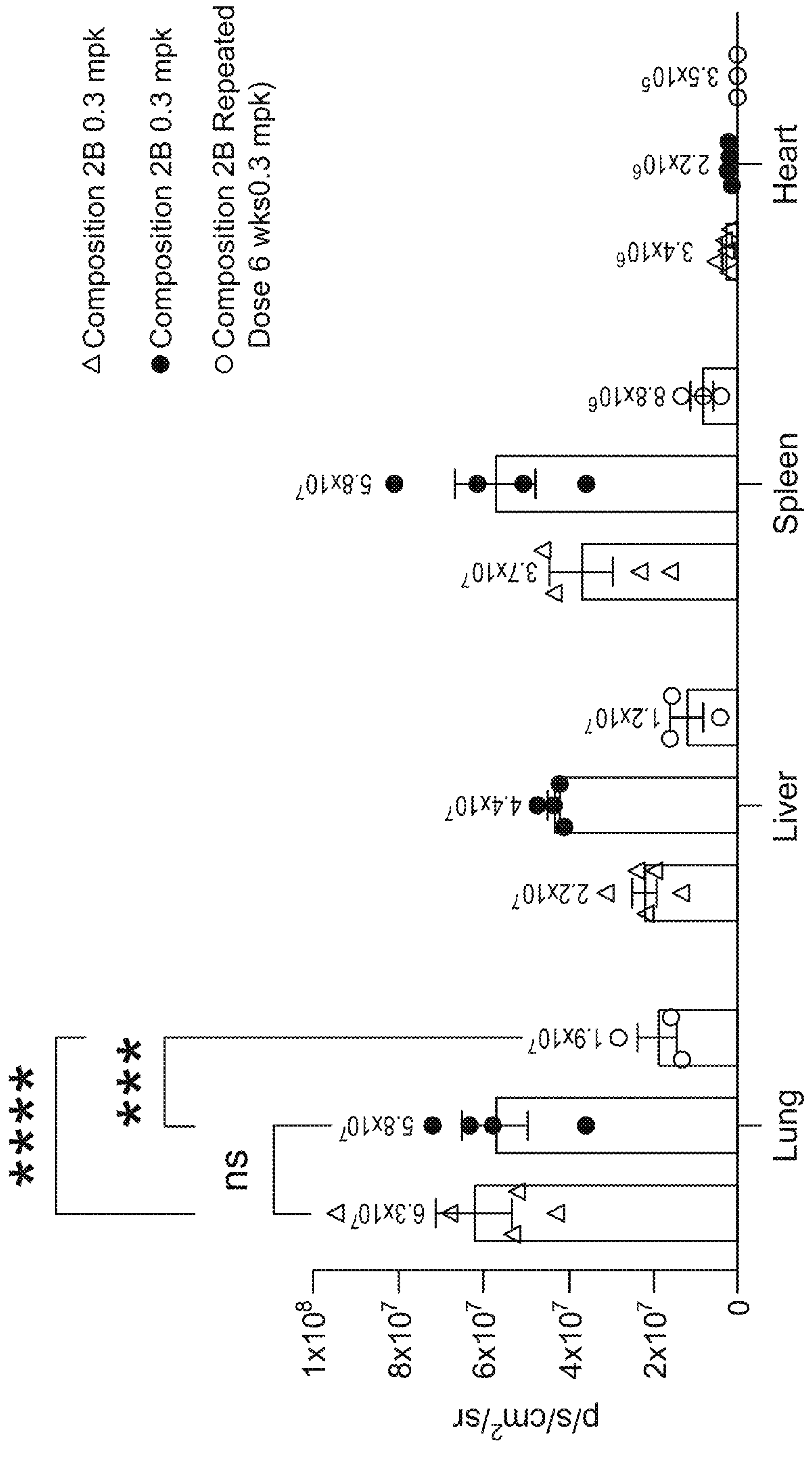
FIG. 9B shows quantitative results of whole body in vivo imaging (IVIS®) of rat with 6 week repeat dosing.

Further studies were conducted to evaluate repeat dosing tolerability following IV administration. Sprague Dawley rats were intravenously administered with either Composition 2B or Composition W once a week for 6 weeks. At 4 h after the $6^{th}$ dose, rats were intraperitoneal (IP) injected with D-Luciferin and imaged by an IVIS Lumina system (Perkin Elmer). Selected organs (liver, spleen, kidneys, heart, and lungs) were harvested after perfusion with PBS and imaged. FIGS. 9A and B showed a significant drop of bioluminescence signals in all organs after repeated dosing, which was similar to that observed in Non Human Primates (NHP) Example 5. Selectivity for lung over liver and spleen remained relatively unchanged (Table 14).

TABLE 14

| LNP composition | Lung:Liver signal | Lung:Spleen signal |
|---|---|---|
| Composition 2B Single Dose | 2.8 | 1.7 |
| Composition 2B Single Dose | 1.3 | 1.0 |
| Composition 2B TFF Multi Dose | 1.6 | 2.2 |

Clinical observations were taken daily and body weight were measured once a week. There was no significant body weight changes for any treatment group. For clinical observations, 3 of 4 animals showed no changes in behavior, body weight, or activity. 1 of 4 animals was euthanized due to mobility impairment, which unlikely the clinical signs were LNP administration related. There was a multifocal minimal to mild periportal nonsuppurative inflammation in liver considered to be related to treatment. There was minimal to mild multifocal interstitial inflammation in the lungs of control and treated animals. The immediate cause of the inflammation was not discernable but could be related to the repeated brief exposure to isoflurane anesthesia. The inflammation was not made more or less severe due to the treatment with Composition 2B.

Figure 10A:
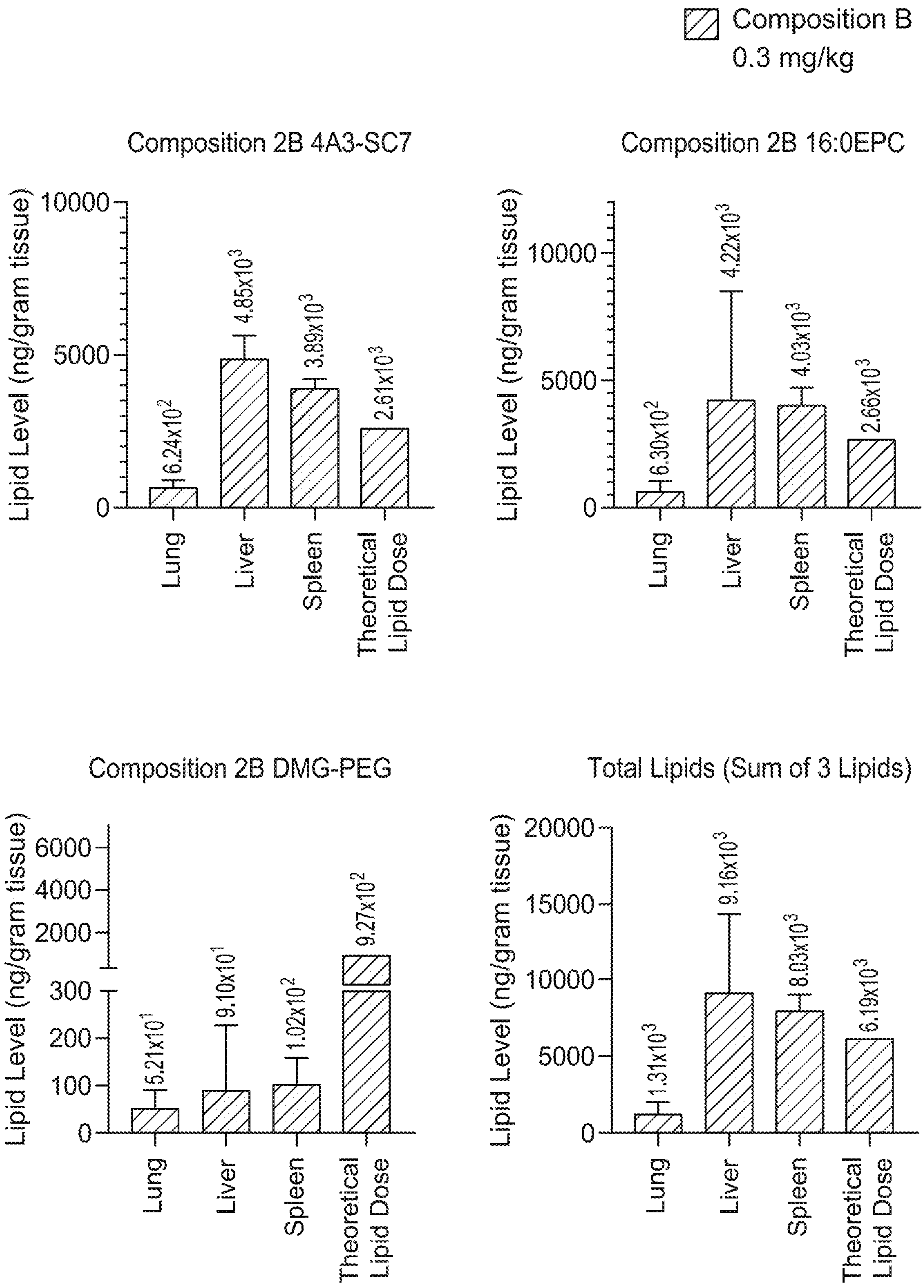
FIGS. 10A-10C show the evaluation of lipids distribution in rat organs.
Figure 10A:
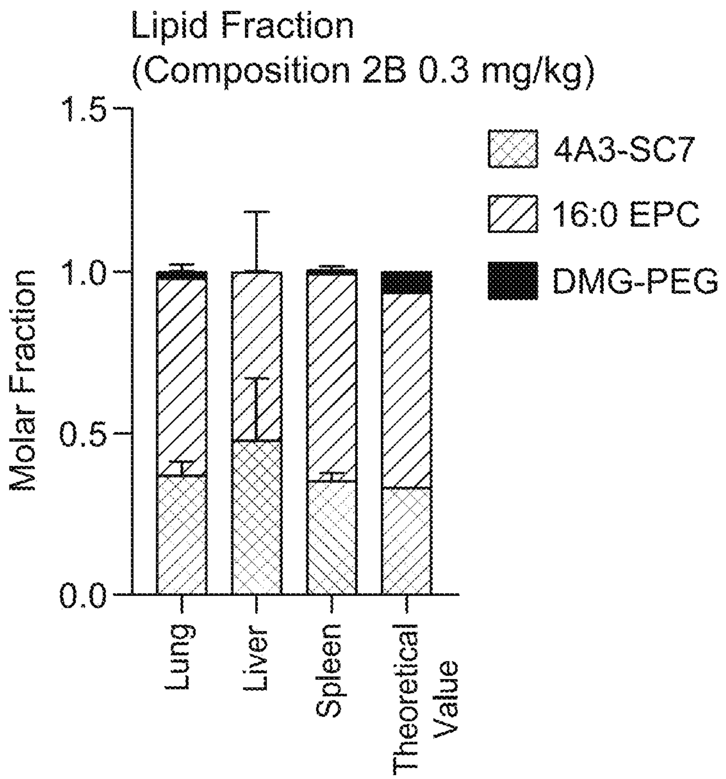
Figure 10A:
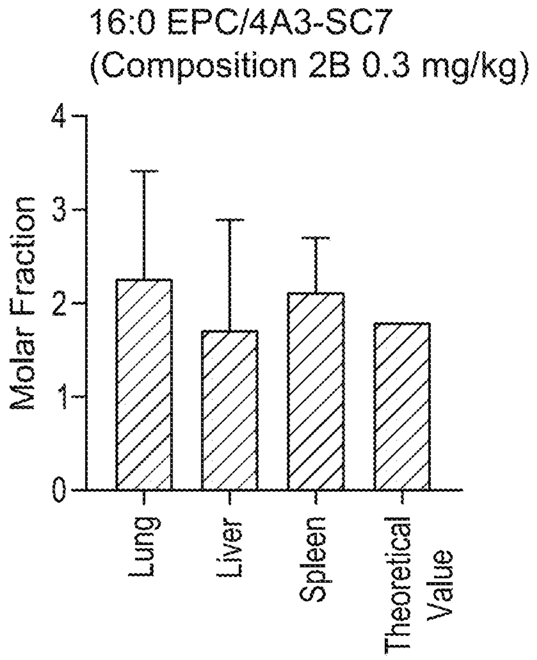
Figure 10A:
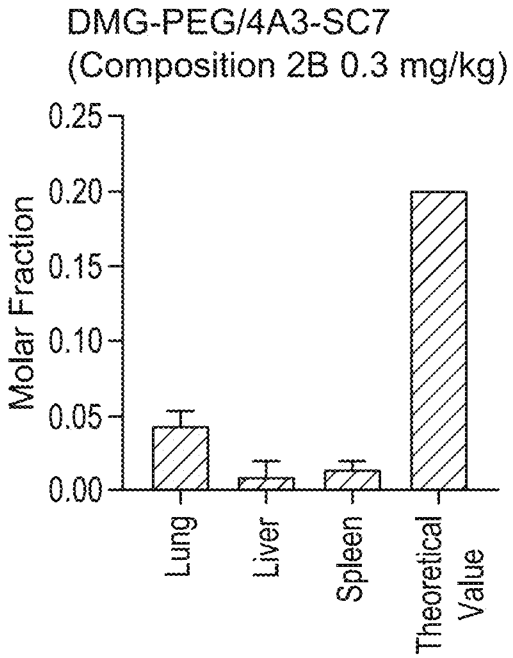
Figure 10B:
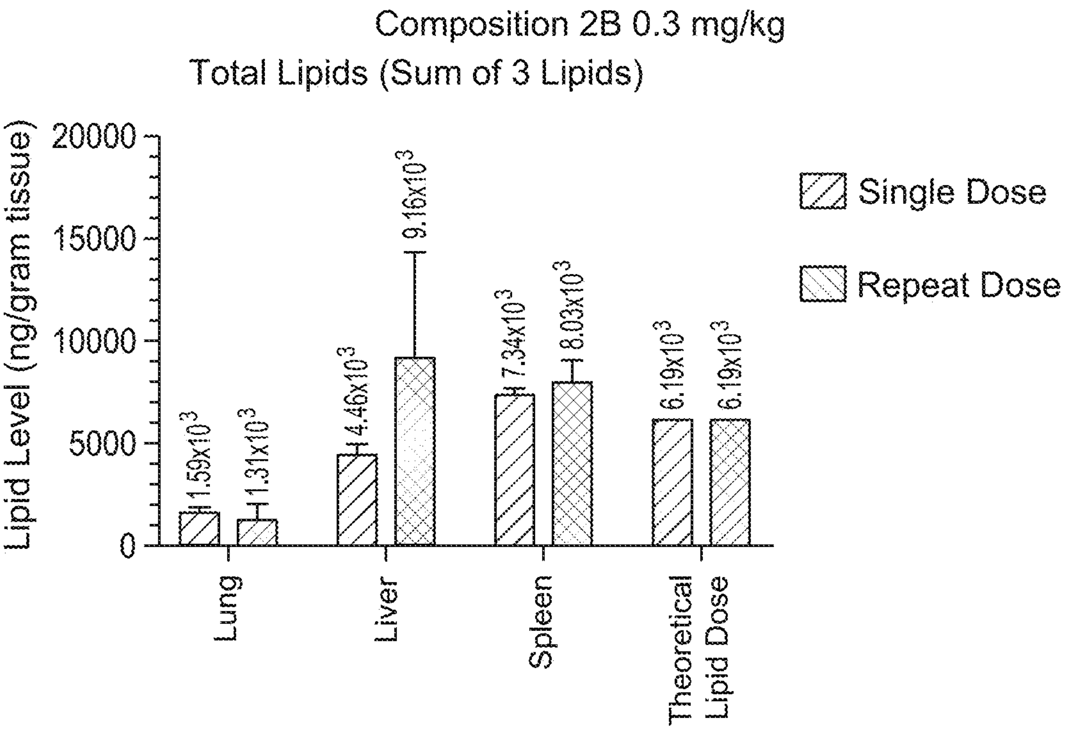
Figure 10B:
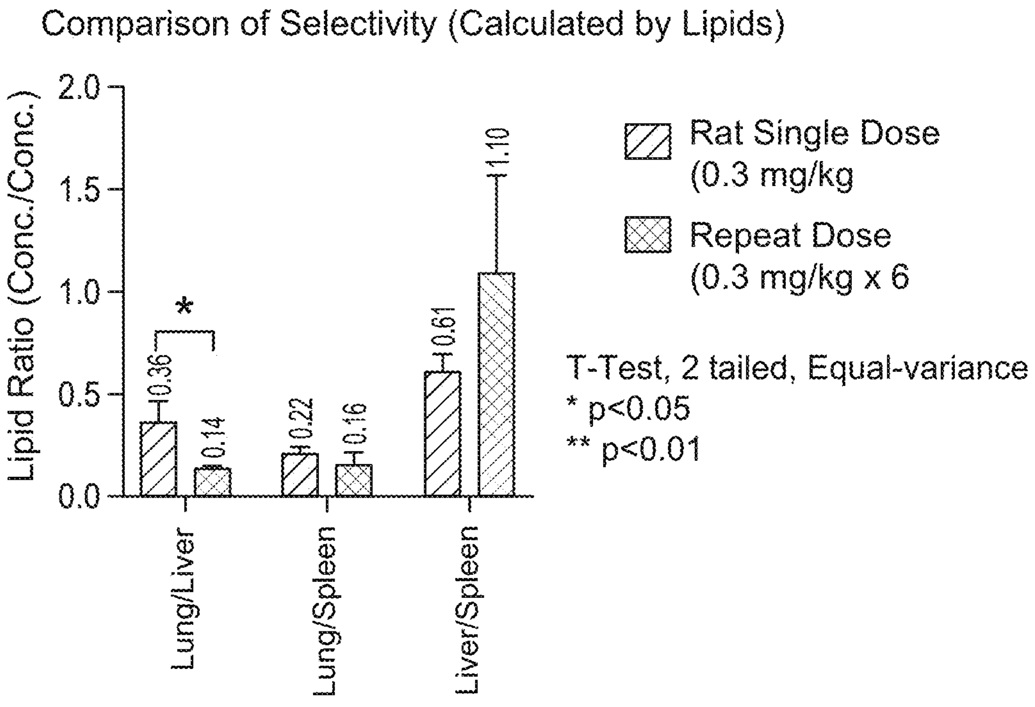
Figure 10C:
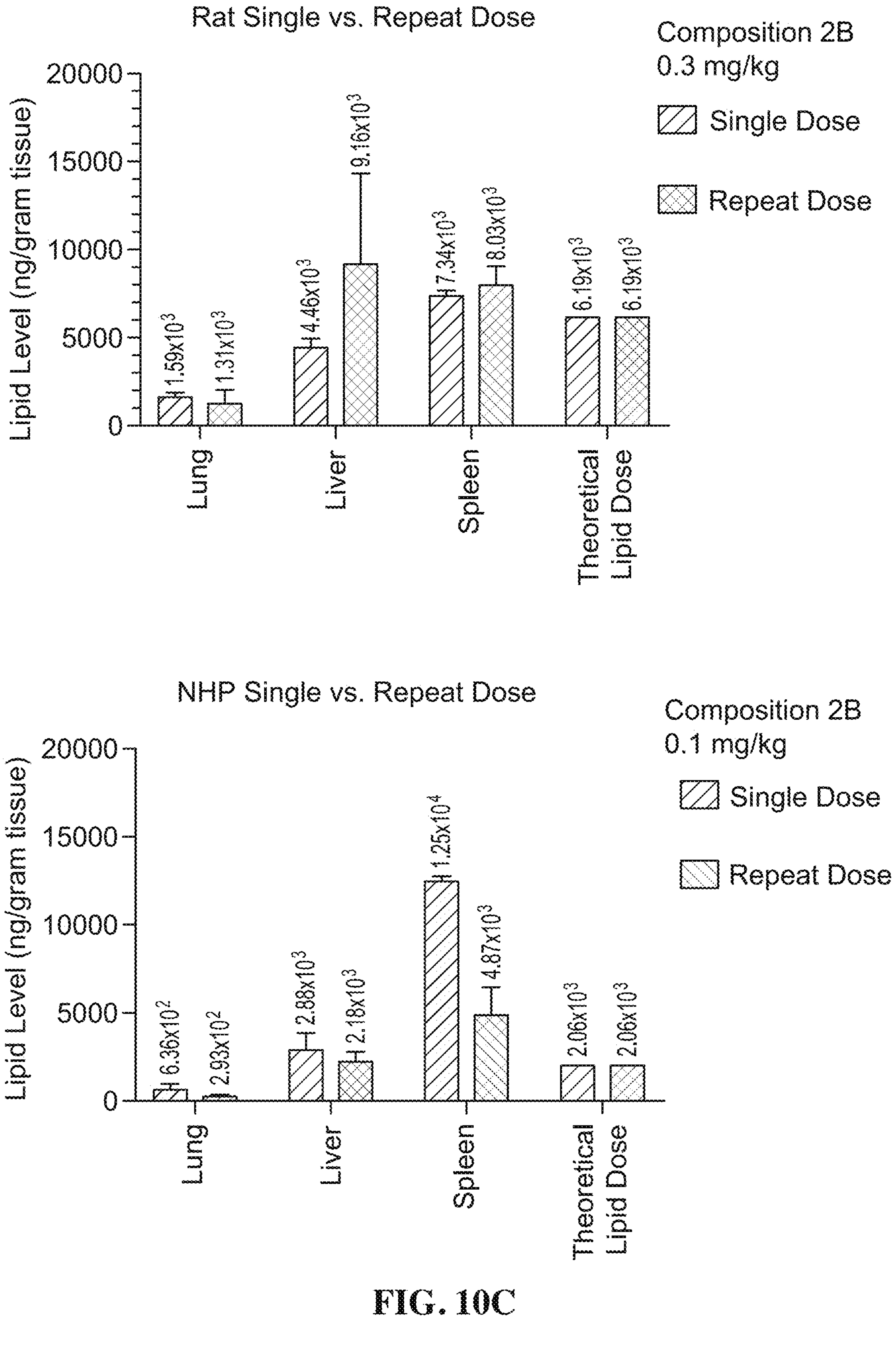
Figure 10C:
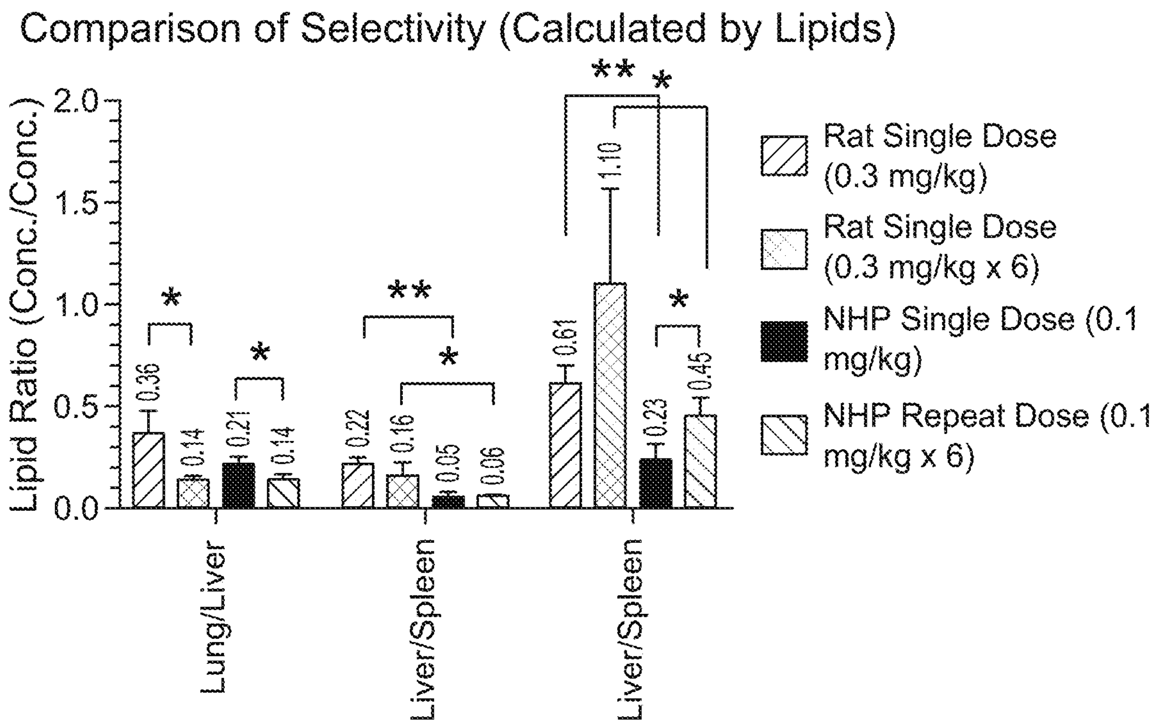
Figure 10C:
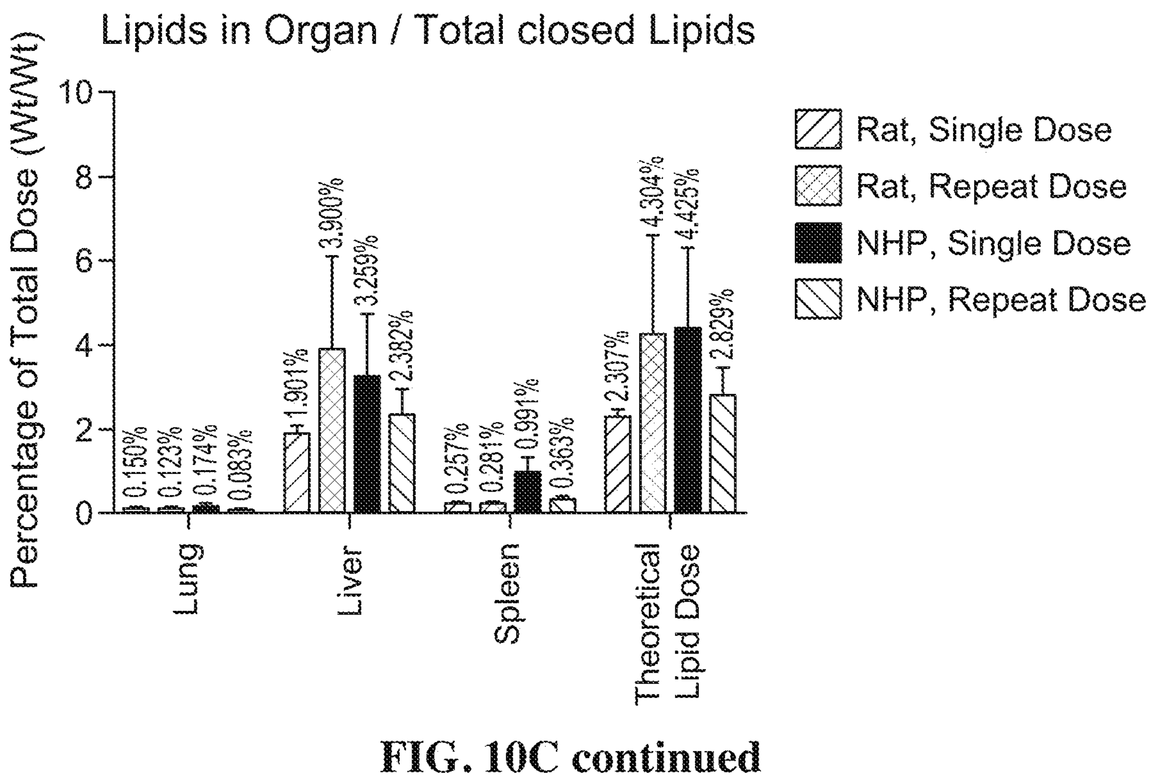
Figure 11A:
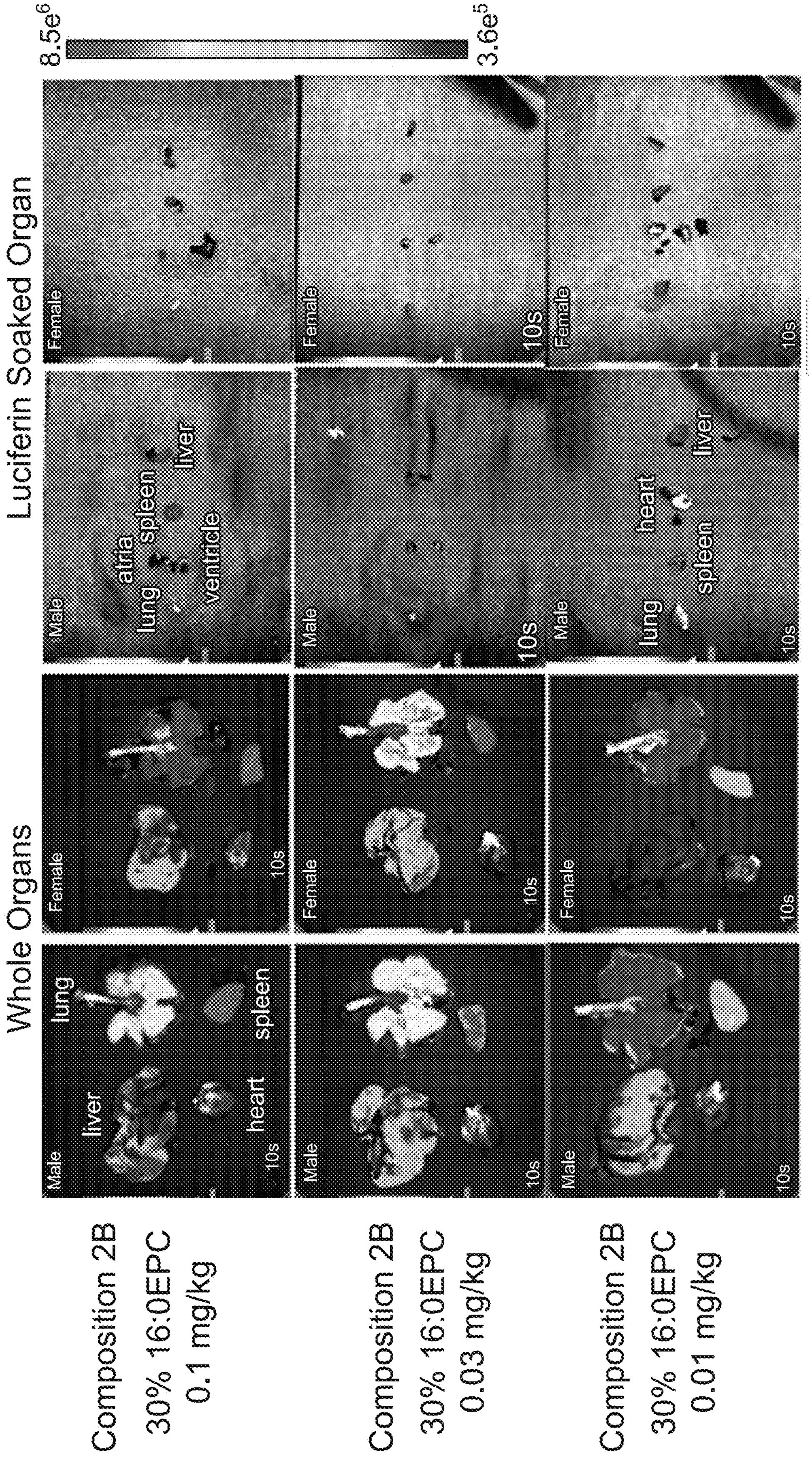
FIG. 11A show ex vivo bioluminescence image of NHP dosed with Formulation B and the evaluation of lipid distribution.
Figure 11A:
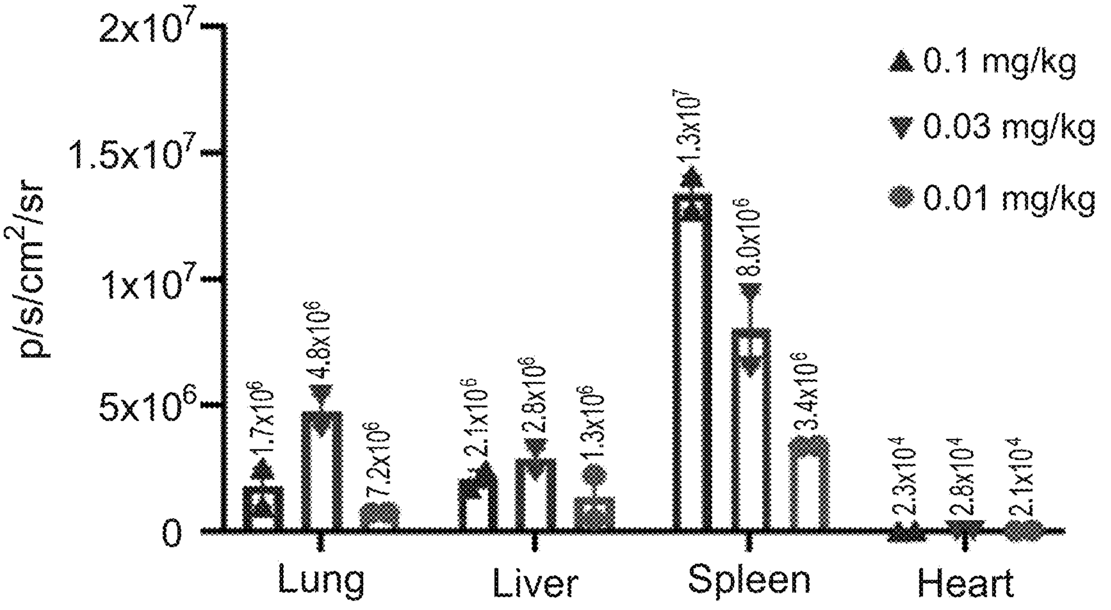
Figure 11A:
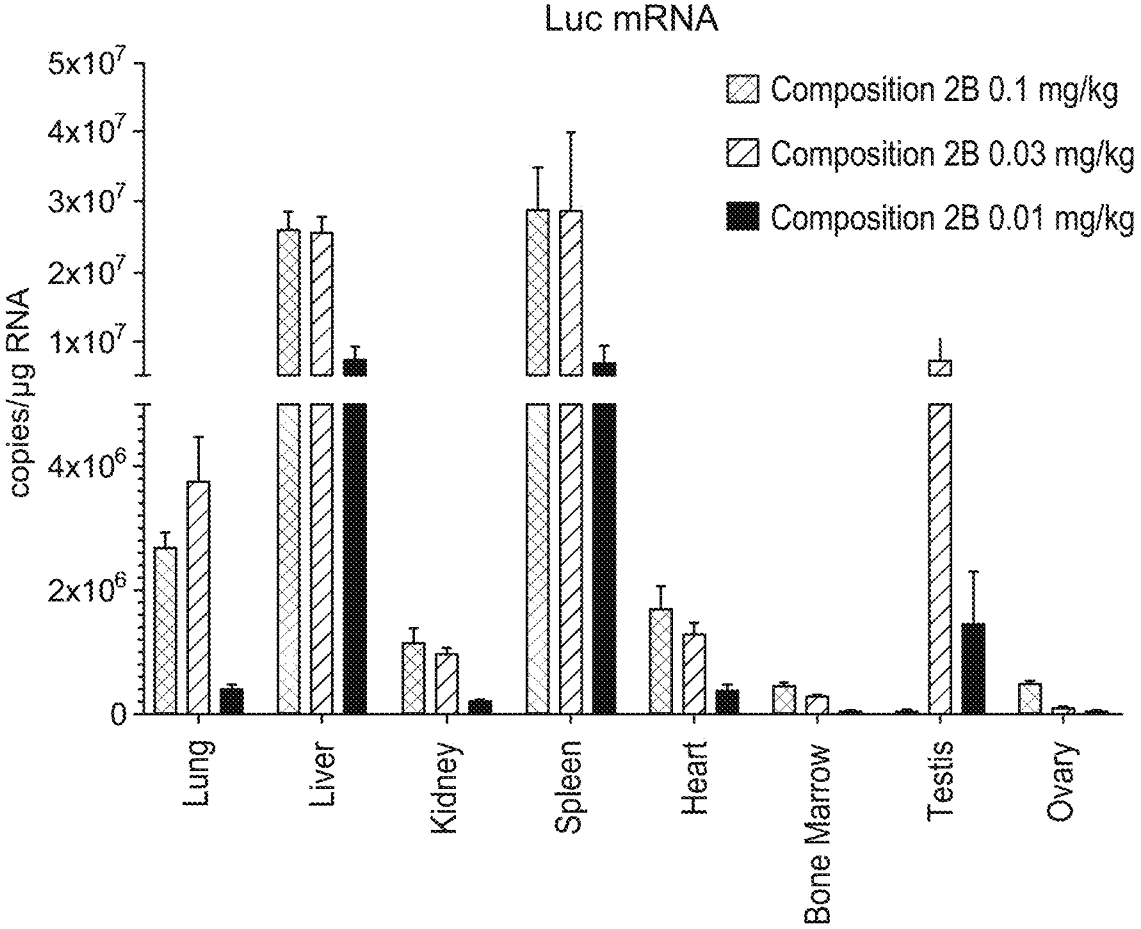
Figure 11B:
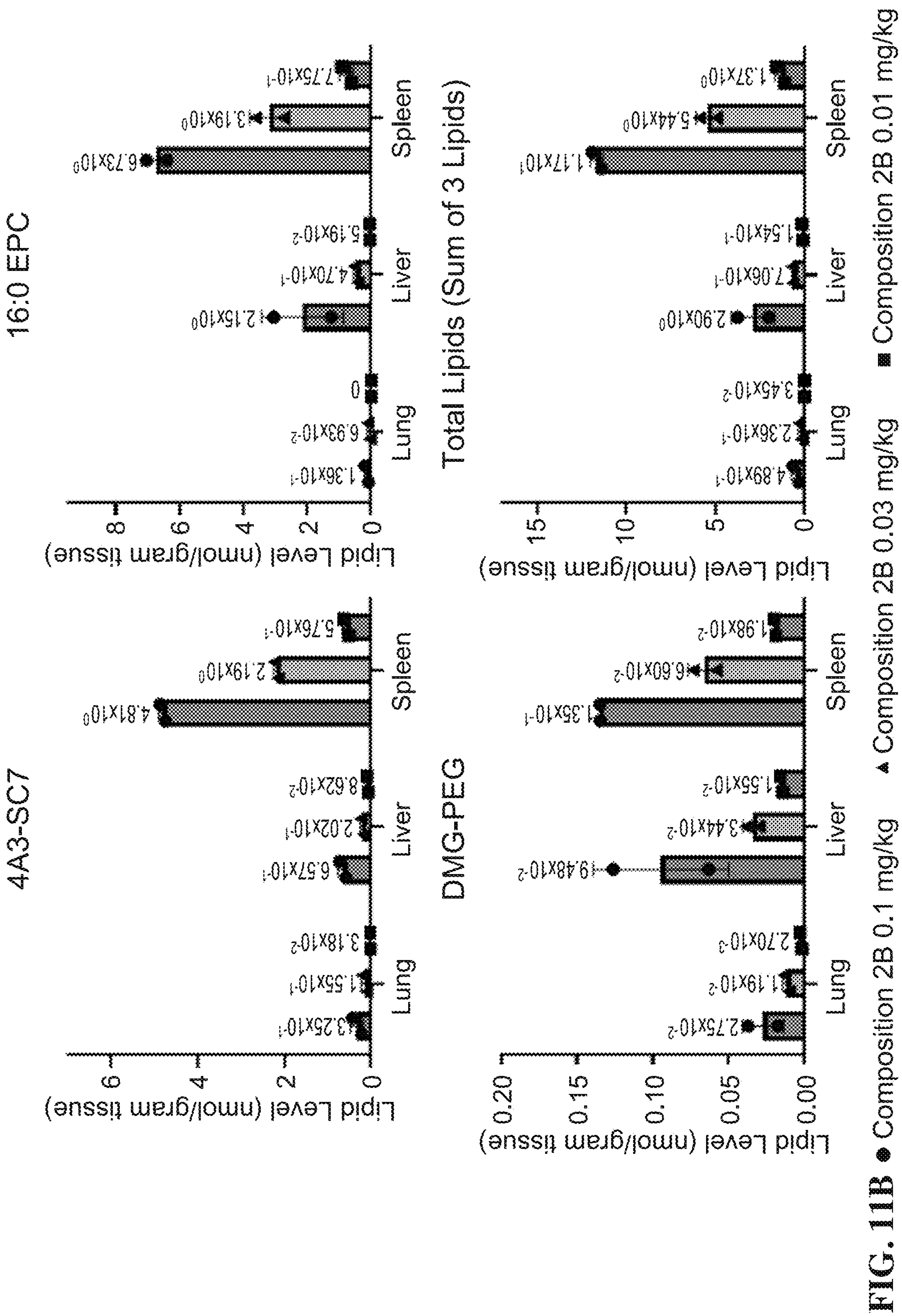
FIG. 11B shows the evaluation of lipid distribution of NHP dosed with Formulation B.
Figure 11B:
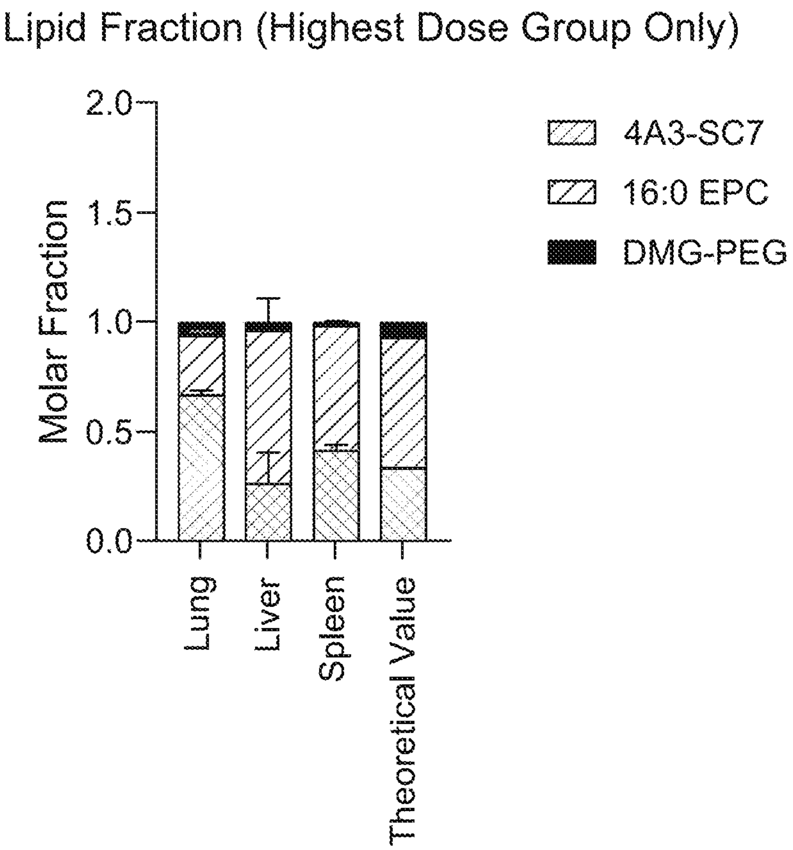
Figure 12A:
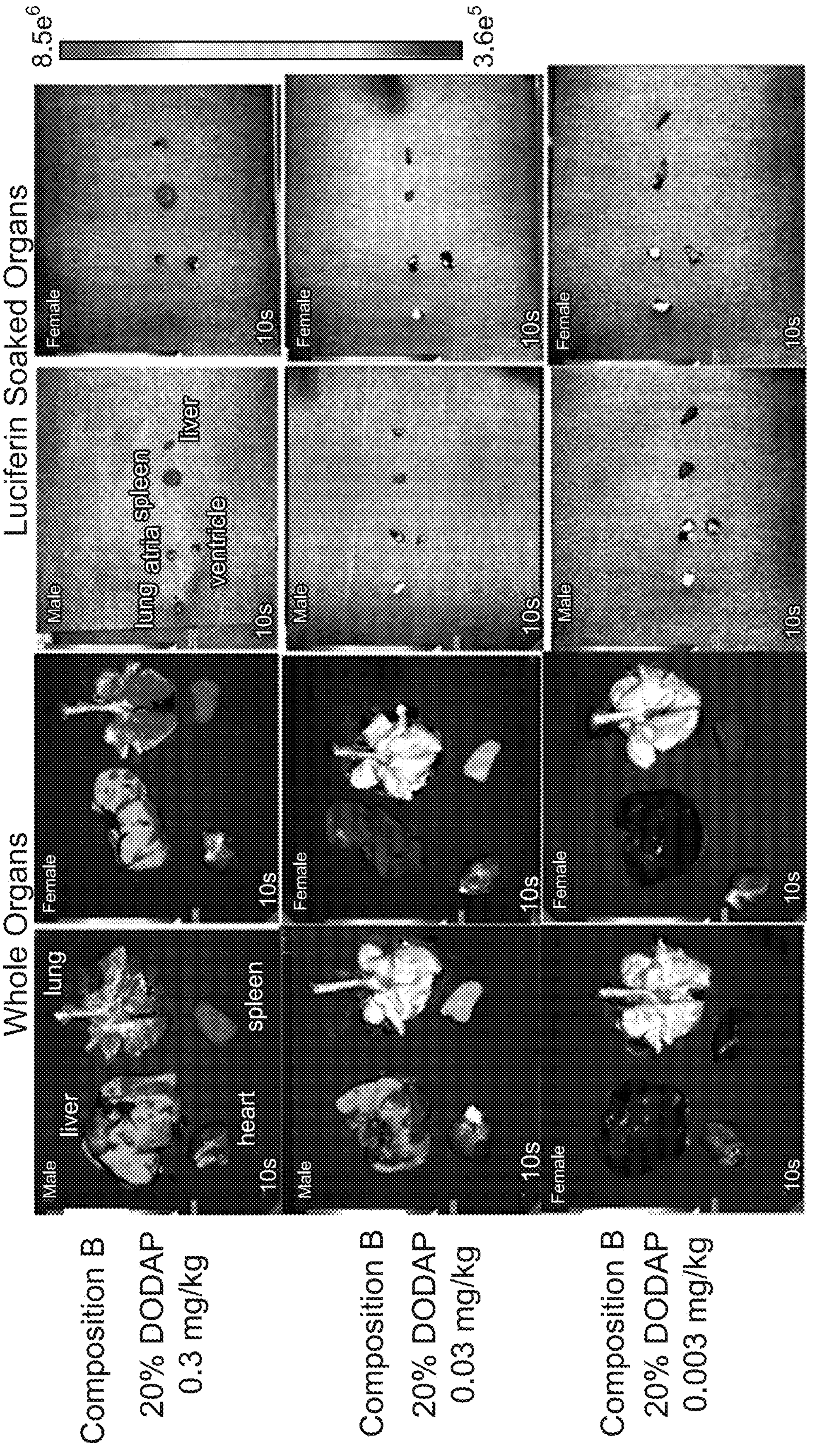
FIG. 12A shows ex vivo bioluminescence image of NHP dosed with Formulation I and the evaluation of lipid distribution.
Figure 12A:
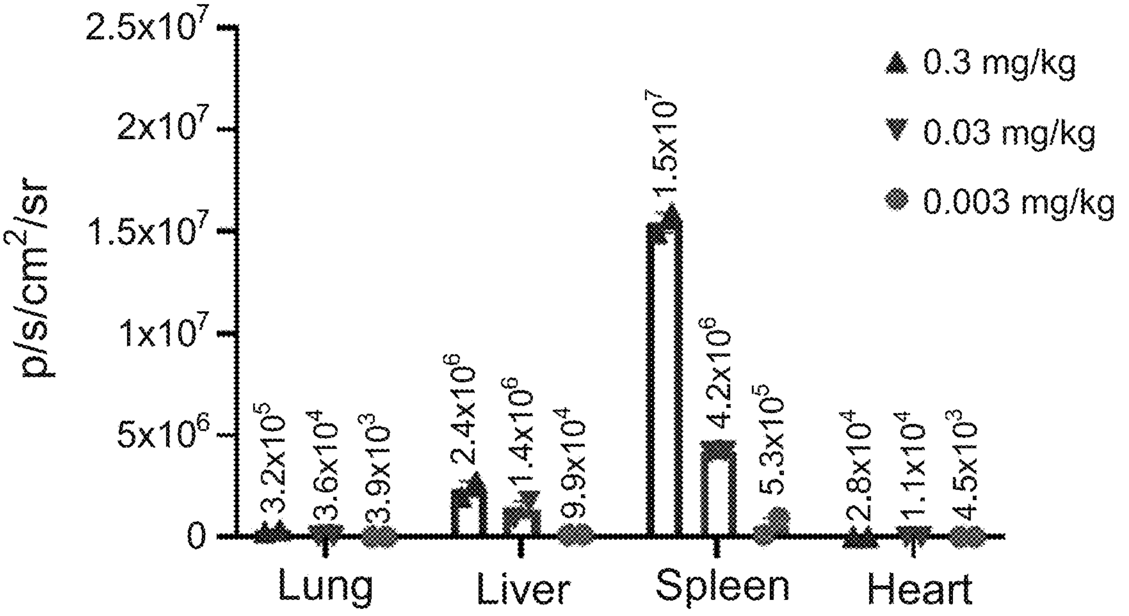
Figure 12A:
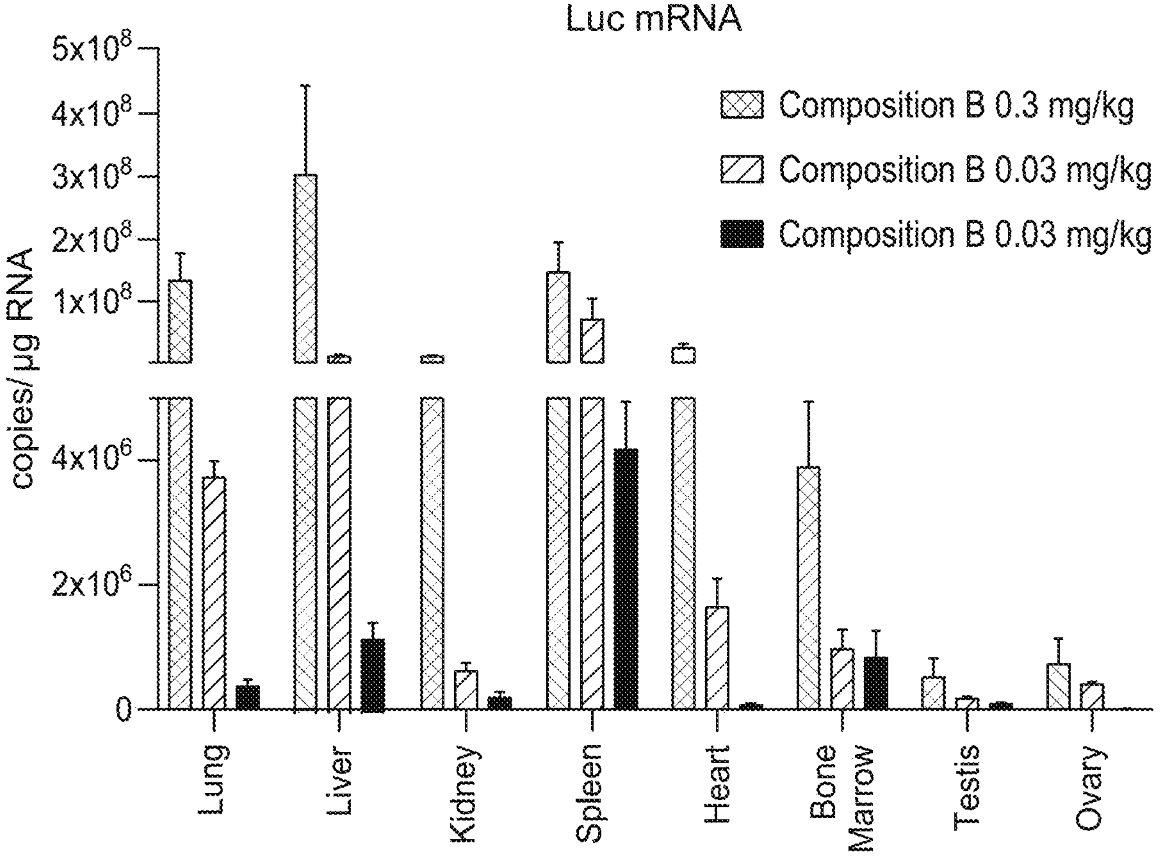
Figure 12B:
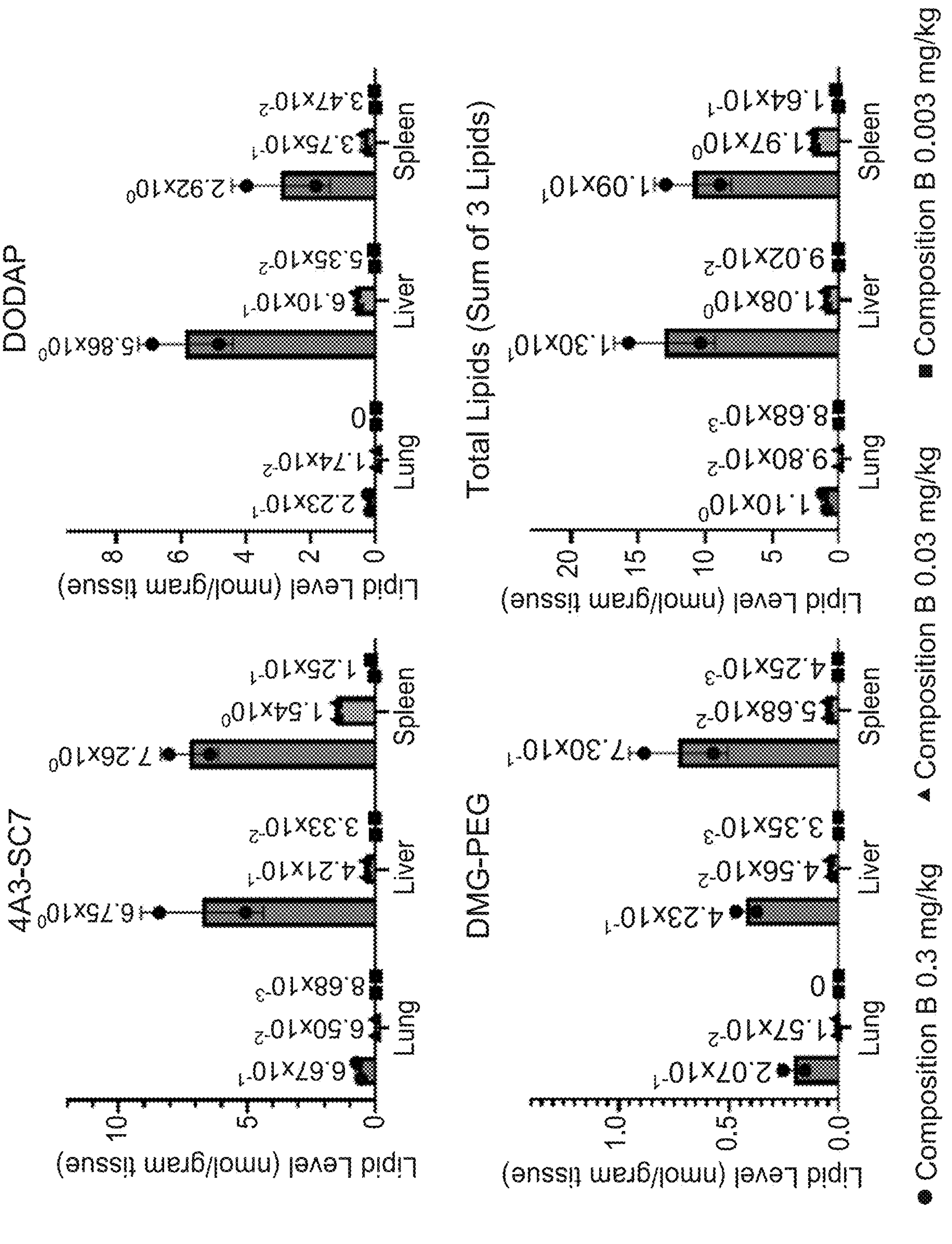
FIG. 12B shows the evaluation of lipid distribution of NHP dosed with Formulation I.
Figure 12B:
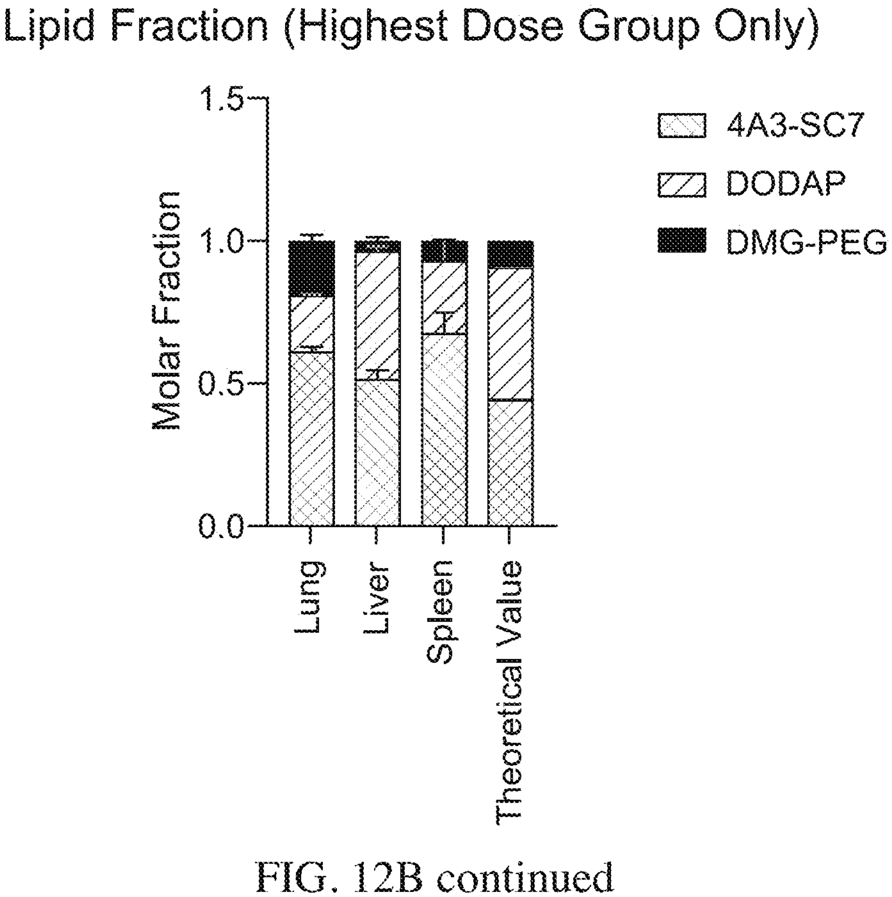

Lipid distribution in rat organs was evaluated after repeat dosing. The result of lipid distribution is shown in FIG. 10A and showed that Composition 2B was similarly distributed in both spleen and liver and less distributed in the lung. The lipid ratio in rat was similar as that in single dose study shown in FIGS. 8A and 8B. The comparison result of lipid distribution in FIG. 10B showed that lipid level in liver was higher after 6 weeks of repeat dose comparing to that in single dose study. Furthermore, Lung/Liver ratio was decreased significantly in repeat dose study compared to single dose study. Comparison results between rat and NHP showed that spleen lipid levels were higher in NHP compared to rat (FIG. 10C), see also Example 6.

Example 6. Effect of Lung Delivery of LNP on Nonhuman Primates

Further studies were conducted in Non-human primates (NHPs). Cynomolgus monkey (*Macaca fascicularis*) were intravenously administrated with either Composition 2B or Composition B. Each LNP composition was formulated in 15 mM Tris (pH 7.5) containing 10% sucrose and mixed with mRNA with mixing buffer (10 mM Citrate, pH 4.0). Characterization of lipid nanoparticles were shown in Table 15.

TABLE 15

| LNP compositions | SORT lipid (Mol %) | Lipid:mRNA (wt/wt) | Size (nm) | PDI | EE % |
|---|---|---|---|---|---|
| Composition 2B | 16:0 EPC (30) | 30 | 72.8 | 0.13 | 96.5 |
| Composition B | DODAP (40) | 40 | 76.8 | 0.17 | 88.3 |

Figure 13:
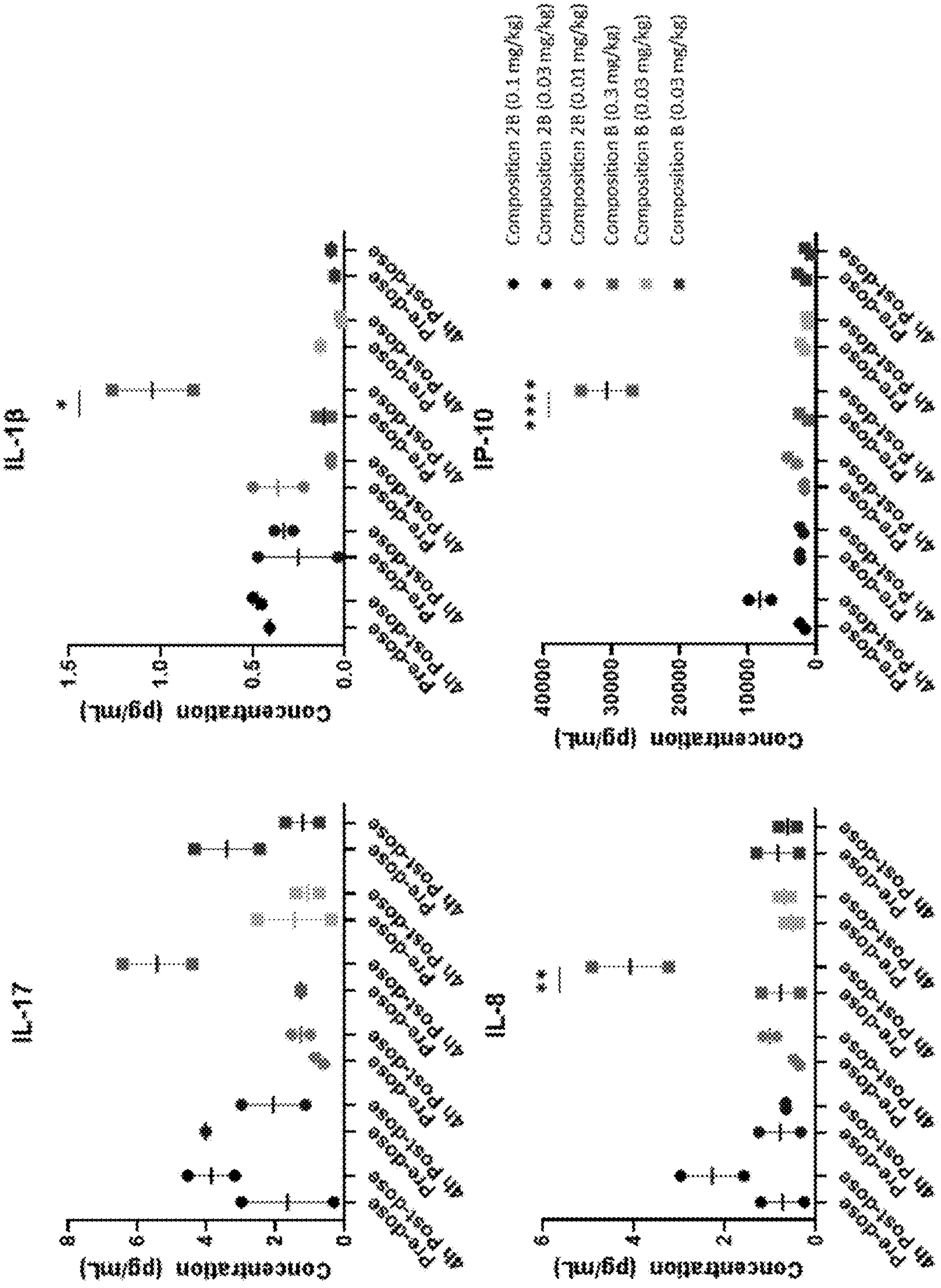
FIG. 13 shows concentration of plasma cytokines.
Figure 13:
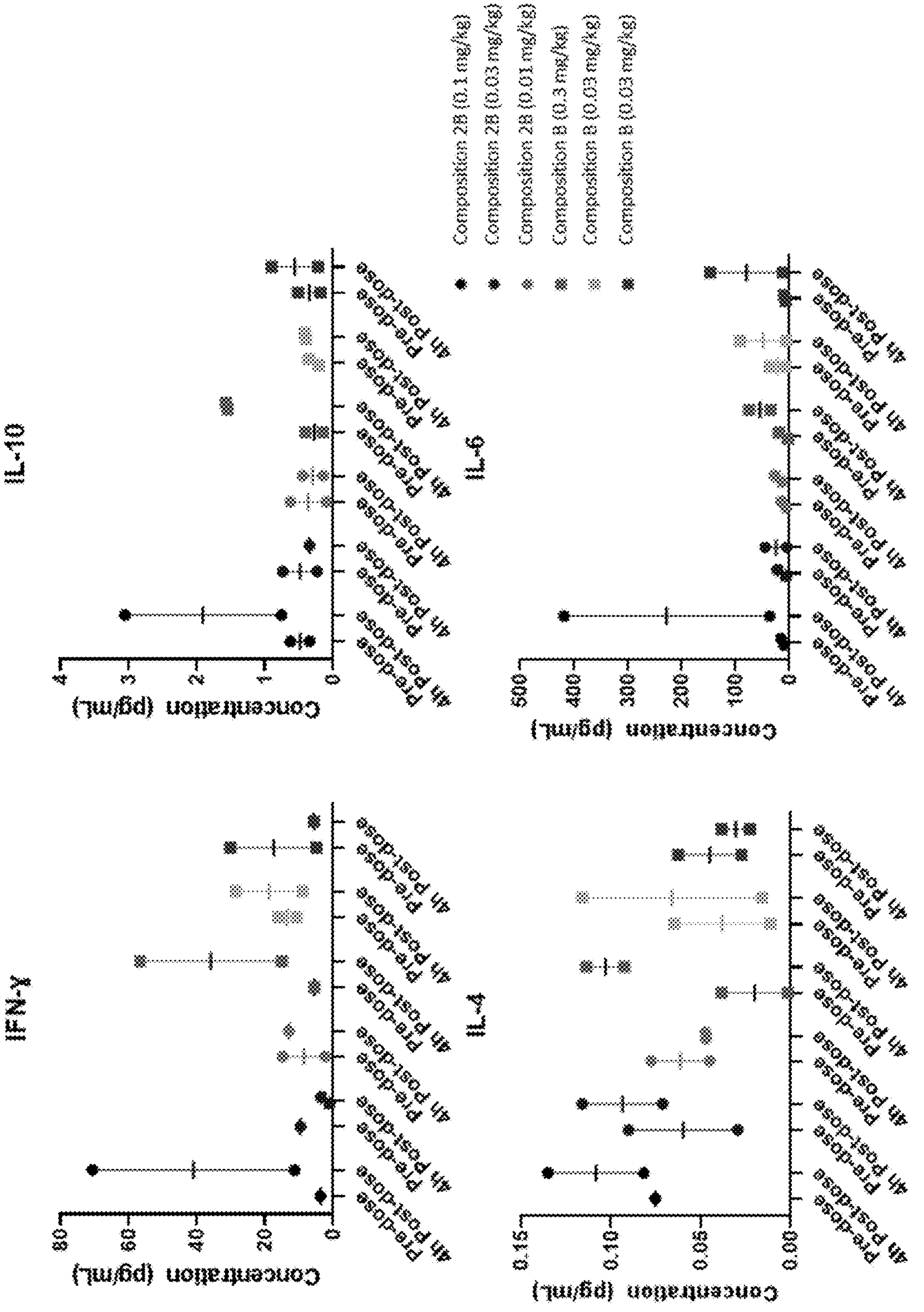
Figure 13:
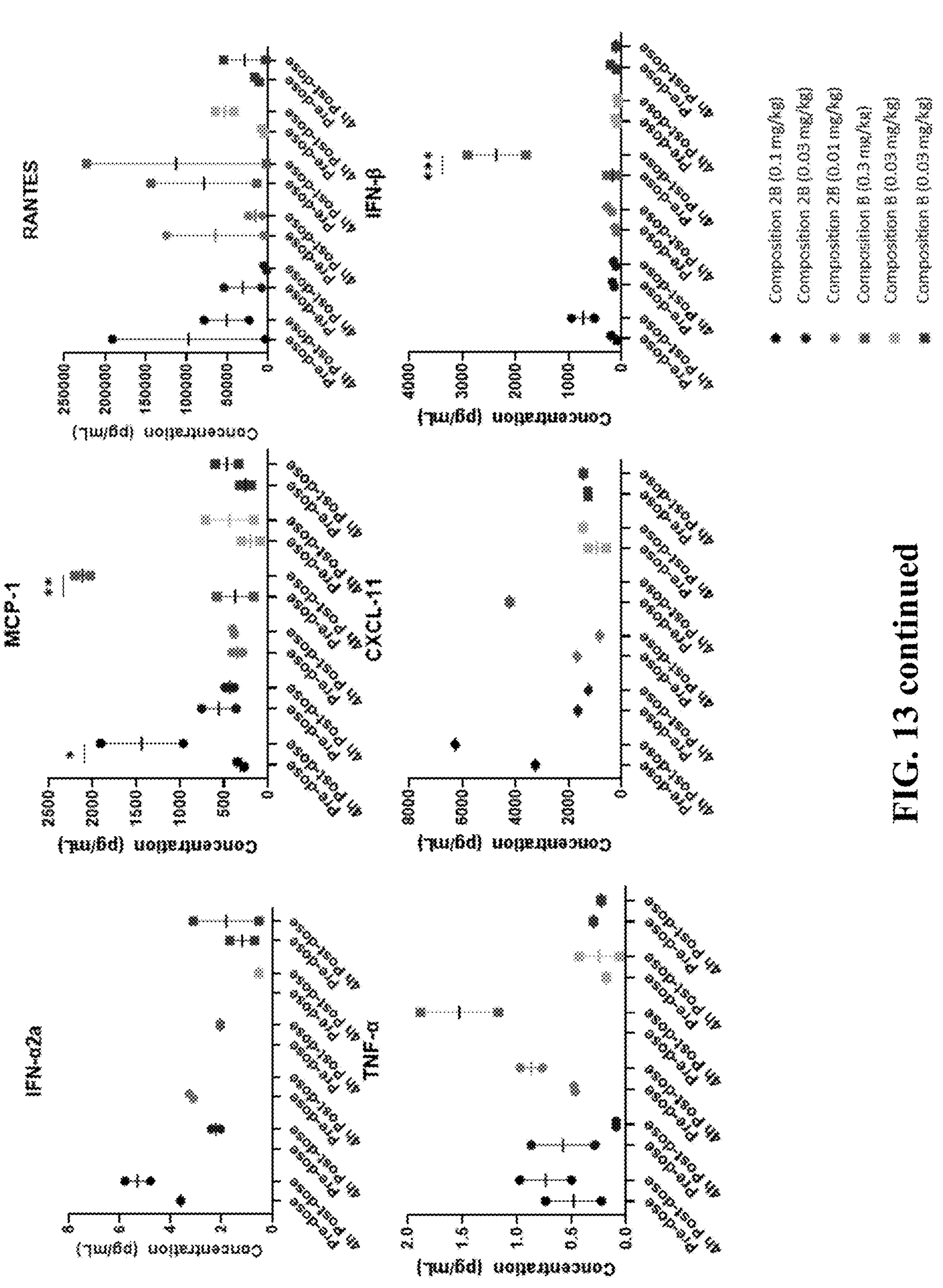

4 h post-injection, selected organs (lung, liver, spleen, kidney, heart, and testes/ovaries) were harvested, weighed, and imaged. Each organ was sectioned in 2-3 cm pieces, soaked in luciferin (10 mg/mL) for 1 minute, and then imaged. Composition 2B-injected NHPs showed moderate lung signal (FIG. 11 A). 200 mg pieces of each organ (lung, liver, spleen, kidney, heart, testes/ovaries, and bone marrow) were frozen for lipid analysis and 100 mg pieces of each organ were submerged in RNAlater for mRNA analysis. The results of lipid distribution in tissues showed that lipids were distributed the most in spleen and the least in lung. Levels of all lipids in all organs were roughly proportional to the three different dosing levels. DMG-PEG fractions in liver and spleen were lower than that in lung and theoretical value. 16:0 EPC fraction was lower in lung than that in liver and spleen and much lower than theoretical value. Three measured lipids (4A3-SC7, 16:0 EPC, and DMG-PEG) had different metabolic/clearance rates and varied in different tissues (FIG. 11 B). Composition B-injected NHPs observed moderate liver signal, including dose-dependent response at all organs (FIG. 12 A). The results of the lipid distribution in tissues showed that lipids were equally distributed in spleen and liver, and the least in lung. Levels of all lipids in all organs were roughly proportional to the three different dosing levels. DMG-PEG fractions in liver and spleen were lower than that in lung and theoretical value. DMG-PEG fractions were higher than the theoretical value in lung. DODAP fraction was lower in lung and spleen than that in liver theoretical value. Three measured lipids had different metabolic/clearance rates and varies in different tissues (FIG. 12 B). Blood samples were collected before, 0.5 h, and 4 h post injection for complements (C3a, C8b-9), cytokines, and clinical pathology analysis. Plasma cytokines were measured and shown in FIG. 13.

Further studies were conducted to evaluate repeat dosing tolerability following IV administration in NHPs. Cynomolgus monkey (*Macaca fascicularis*) were intravenously administrated with either Composition 2B, Composition B, or Composition W once a week for 6 weeks. At 4 h after $6^{th}$ dose, selected organs (lung, liver, spleen, kidney, heart, testes/ovaries, and femur) were harvested and weighted before it was imaged. Then each organ was sectioned in 2-3 cm pieces, soaked in luciferin (10 mg/mL) for 1 minute and imaged. Blood collection schedules for further analysis are shown in Table 16.

TABLE 16

| | Week | Time |
|---|---|---|
| Clinical pathology, Lipids, mRNA | week 1 and week 5<br>week 6 | 4, 24, 72, 168 h<br>4 h |
| Complements serum | week 1 and week 5 | Pre-dose and 4 h |
| Cytokine plasma, Anti-PEG | week 1-6 | Pre-dose |

Figure 14:
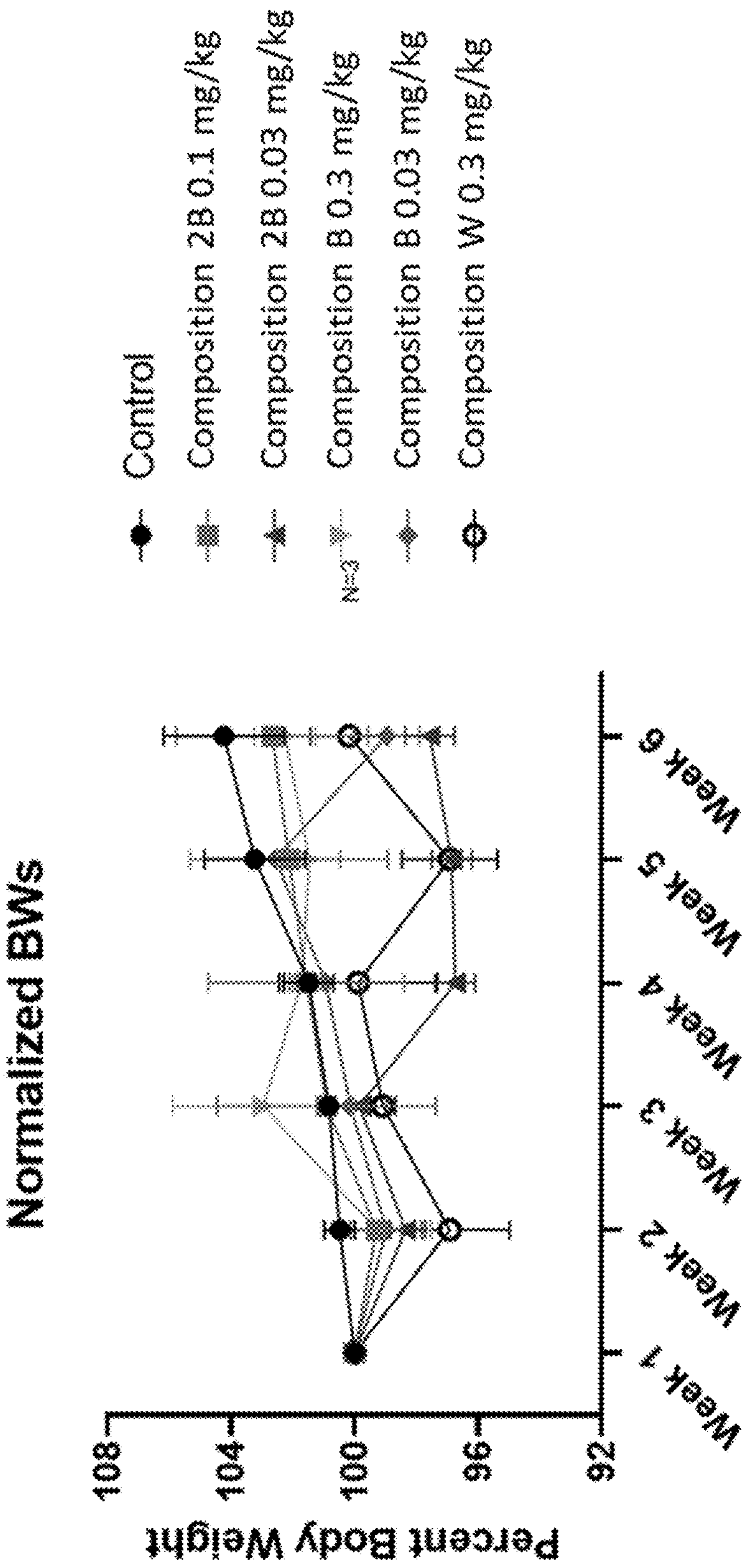
FIG. 14 shows percent body weight following.
Figure 15A:
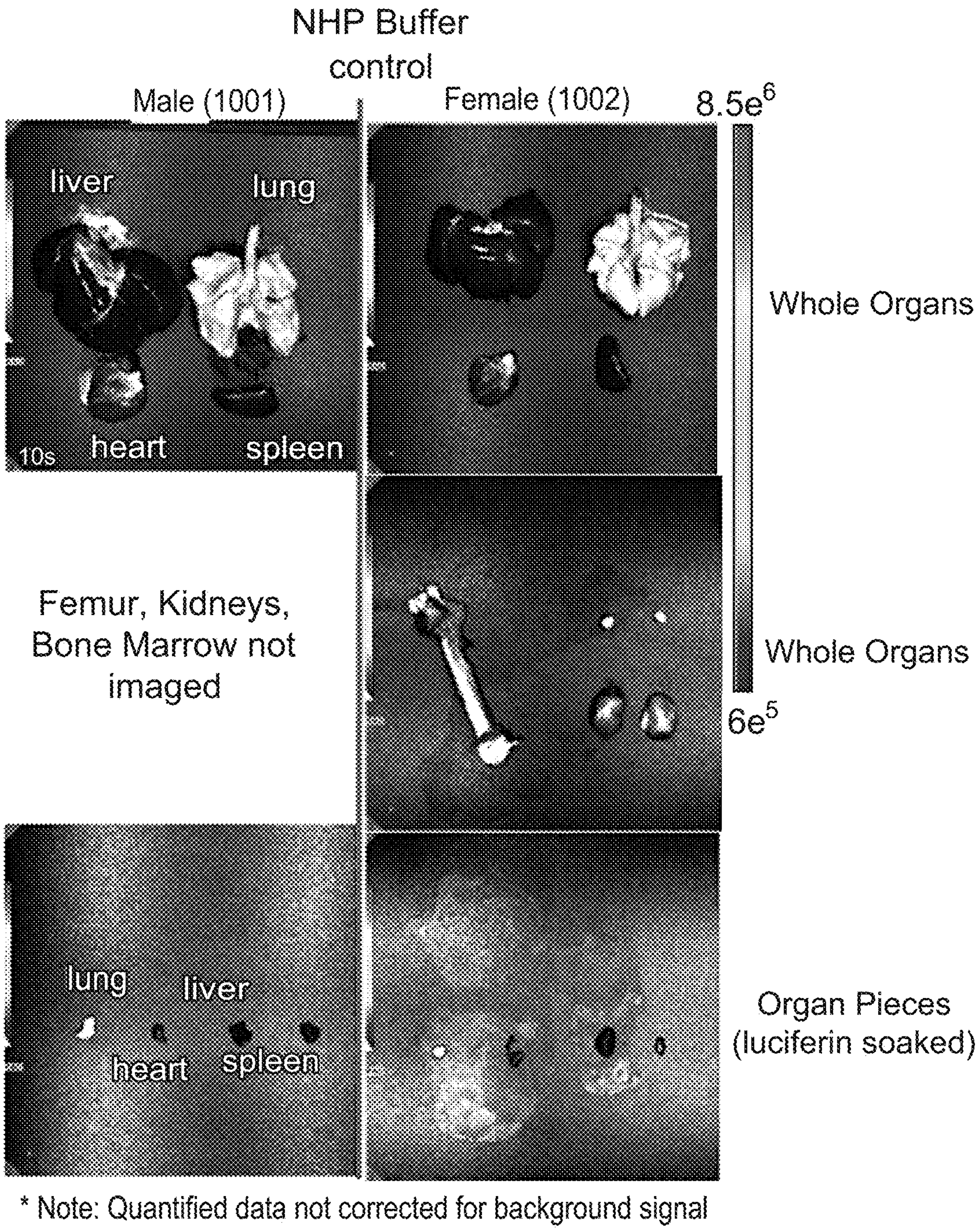
FIG. 15A shows ex vivo bioluminescence image of NHP dosed with Buffer control and its quantitative results.
Figure 15A:
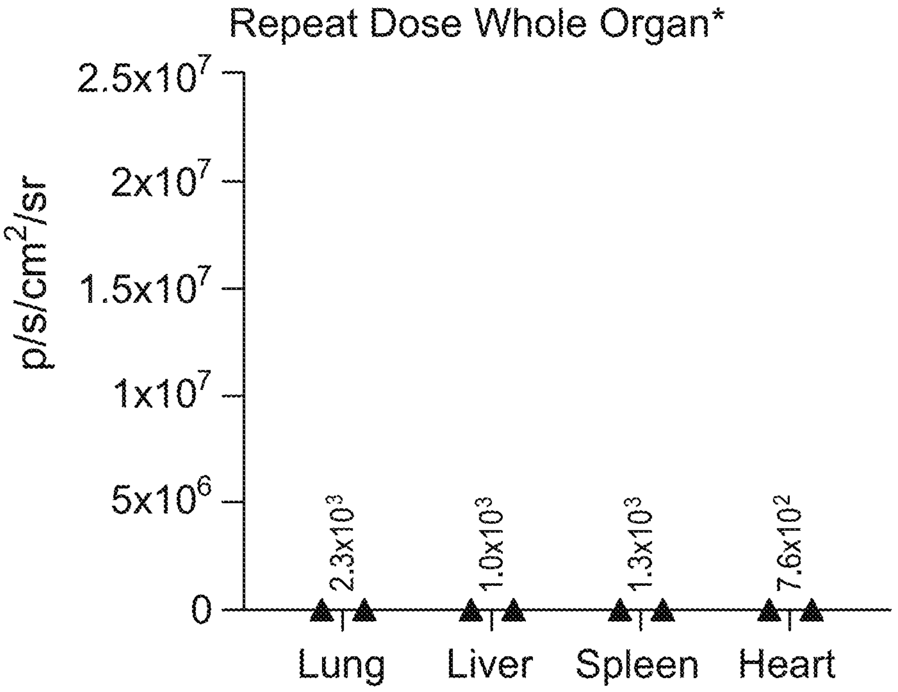
Figure 15A:
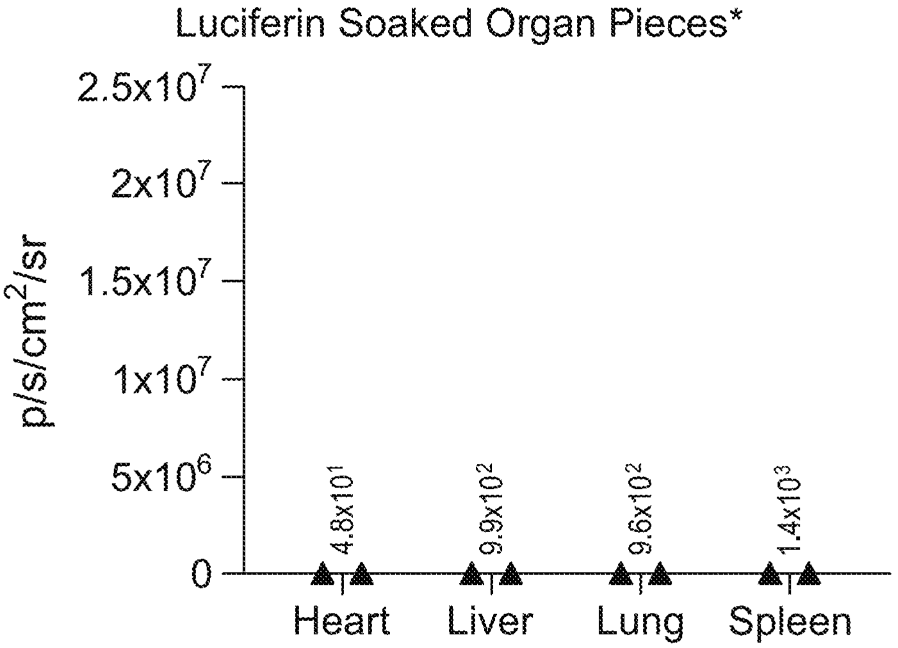
Figure 15B:
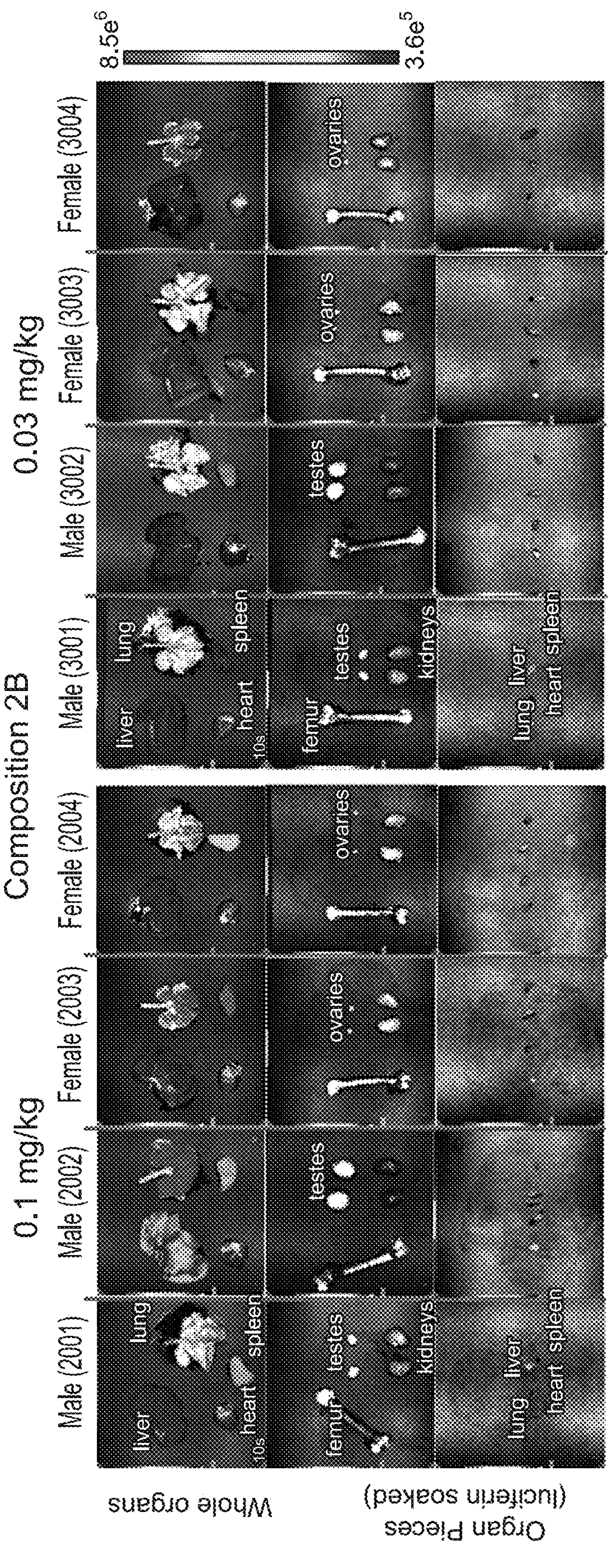
FIG. 15B shows ex vivo bioluminescence image of NHP dosed with Formulation B repeatedly and its quantitative results.
Figure 15B:
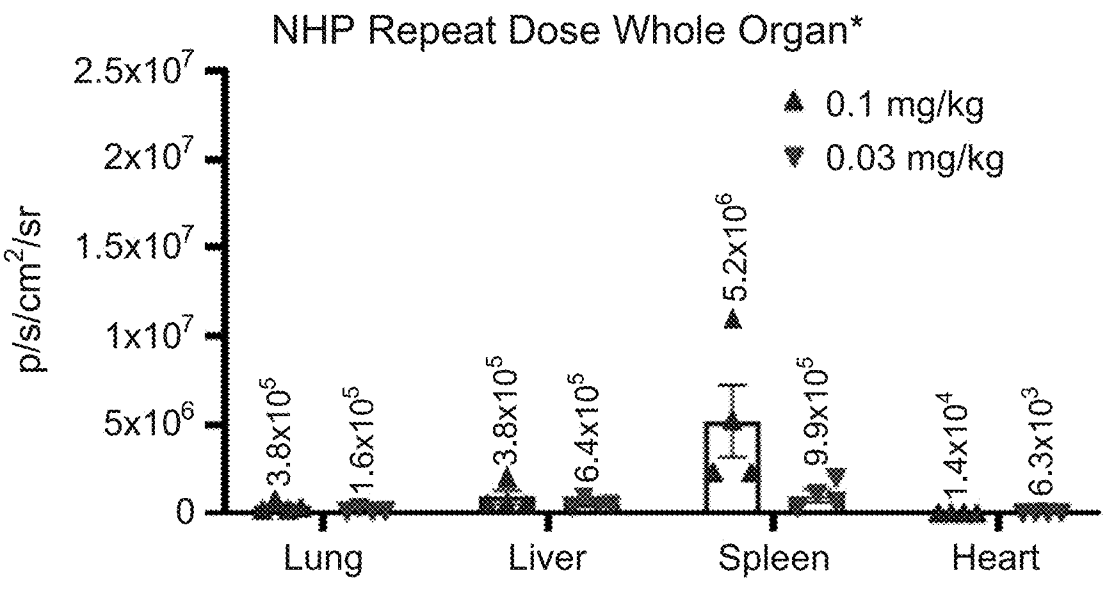
Figure 15B:
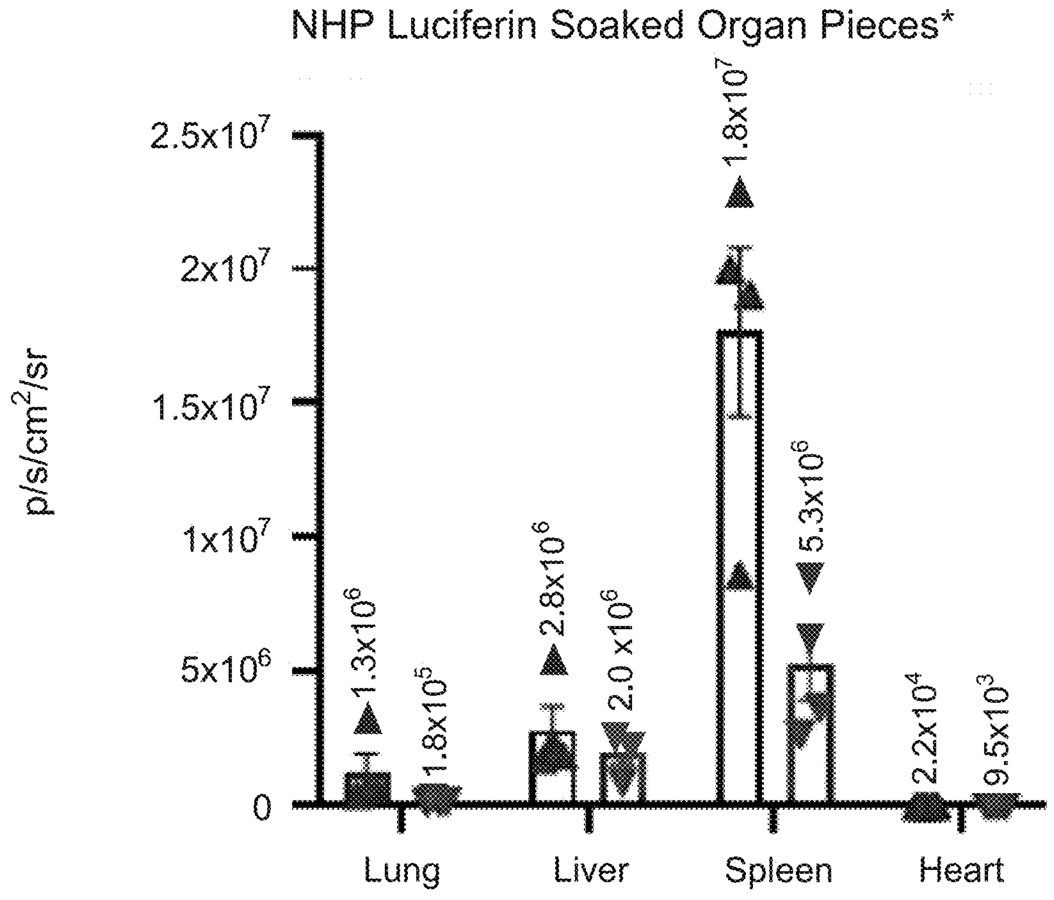
Figure 15C:
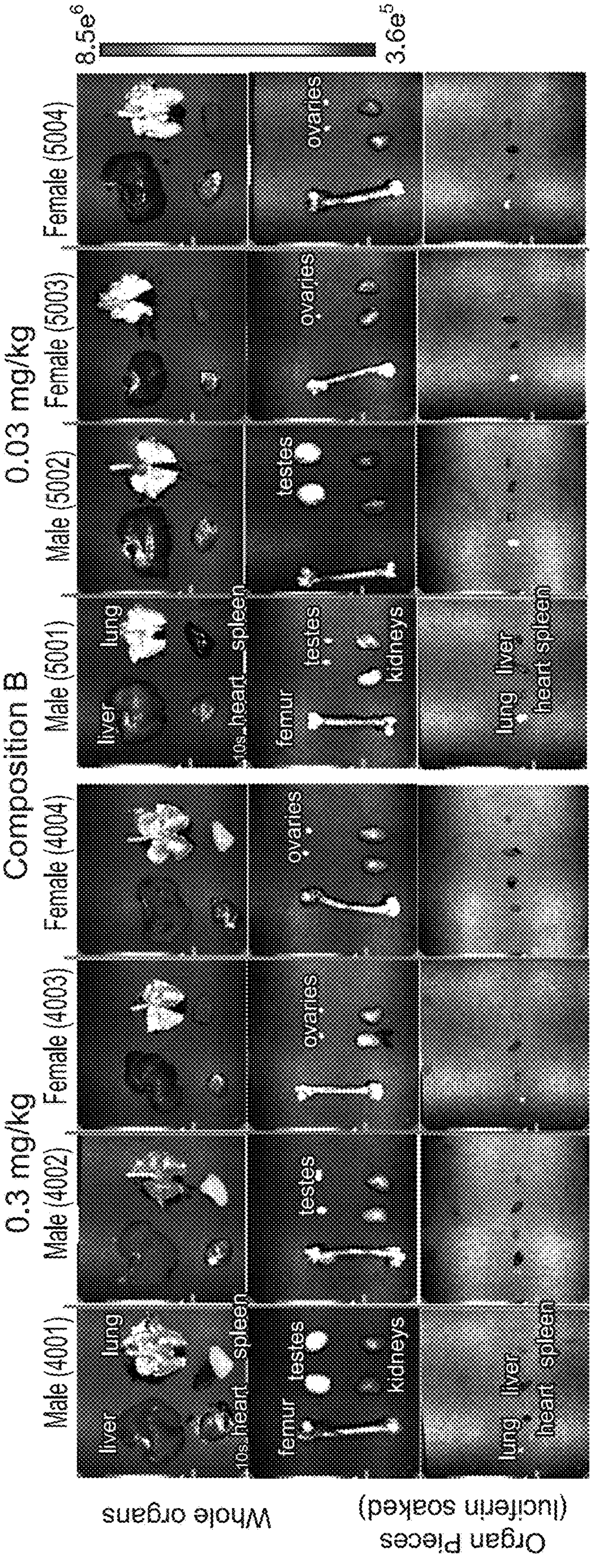
FIG. 15C shows ex vivo bioluminescence image of NHP dosed with Formulation I repeatedly and its quantitative results.
Figure 15C:
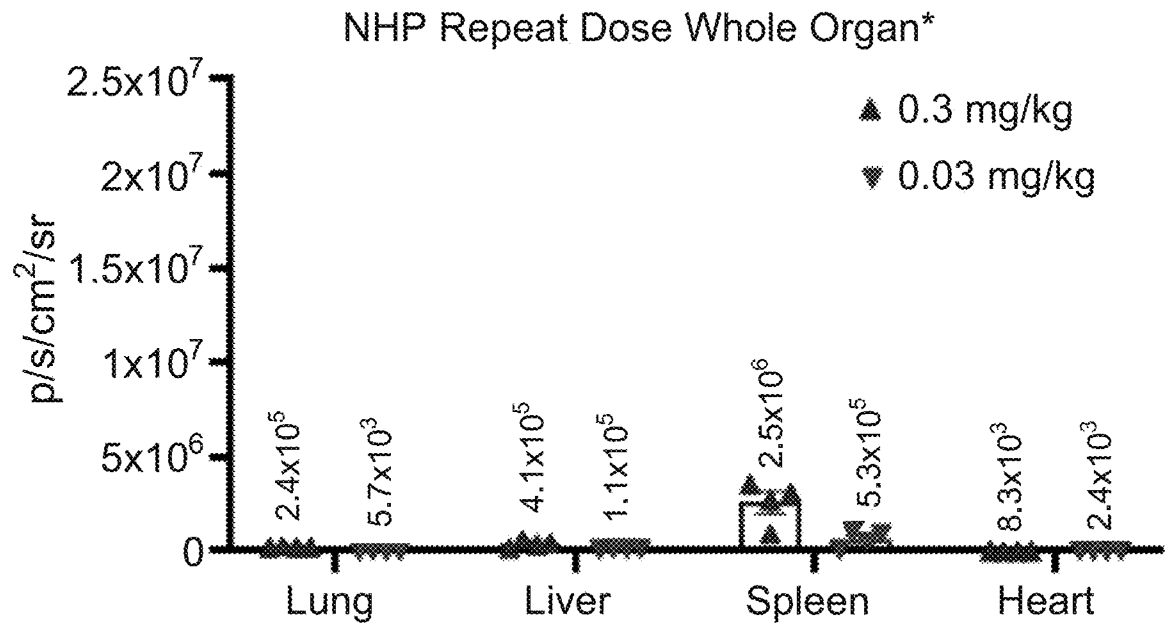
Figure 15C:
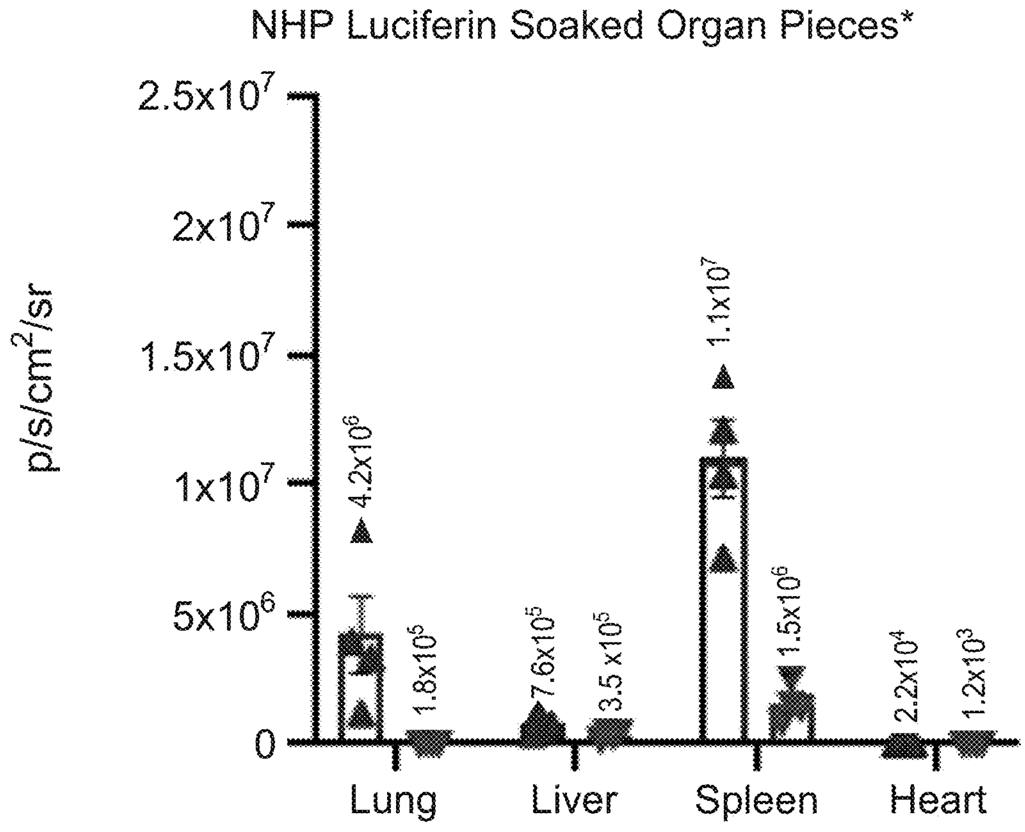
Figure 15D:
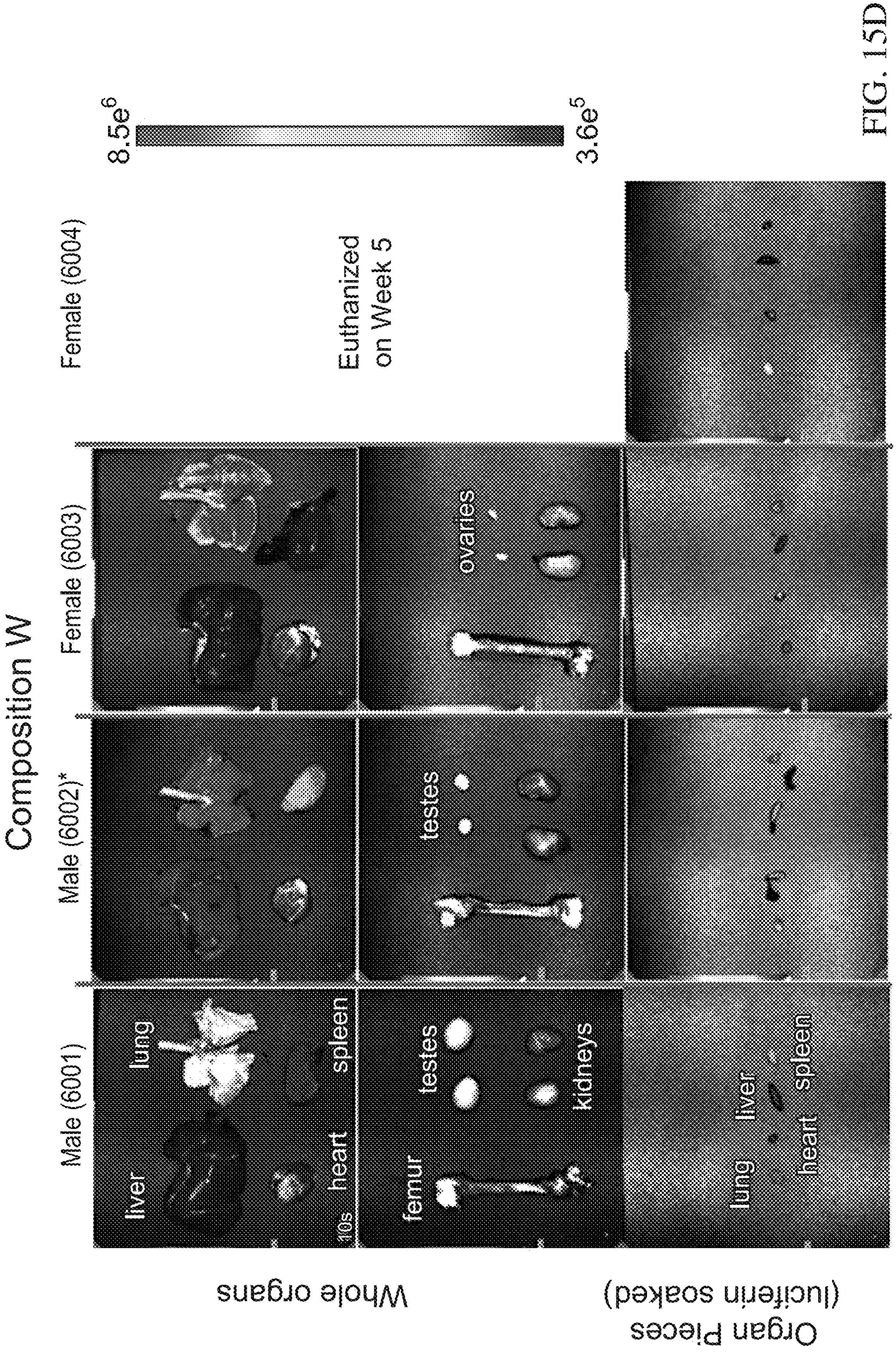
FIG. 15D shows ex vivo bioluminescence image of NHP dosed with Formulation H repeatedly and its quantitative results.
Figure 15D:
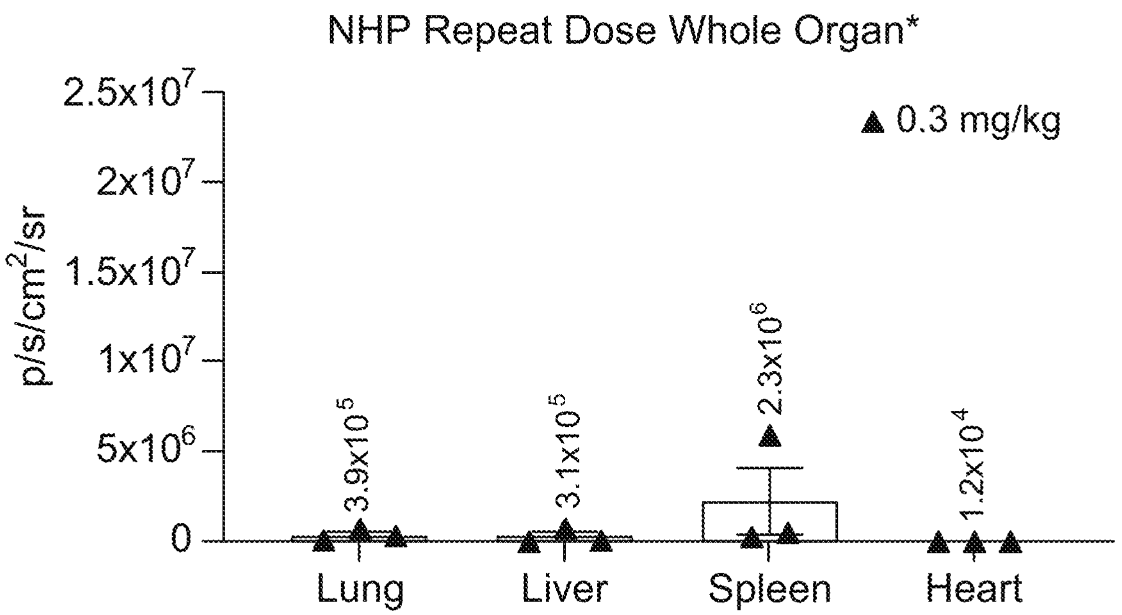
Figure 15D:
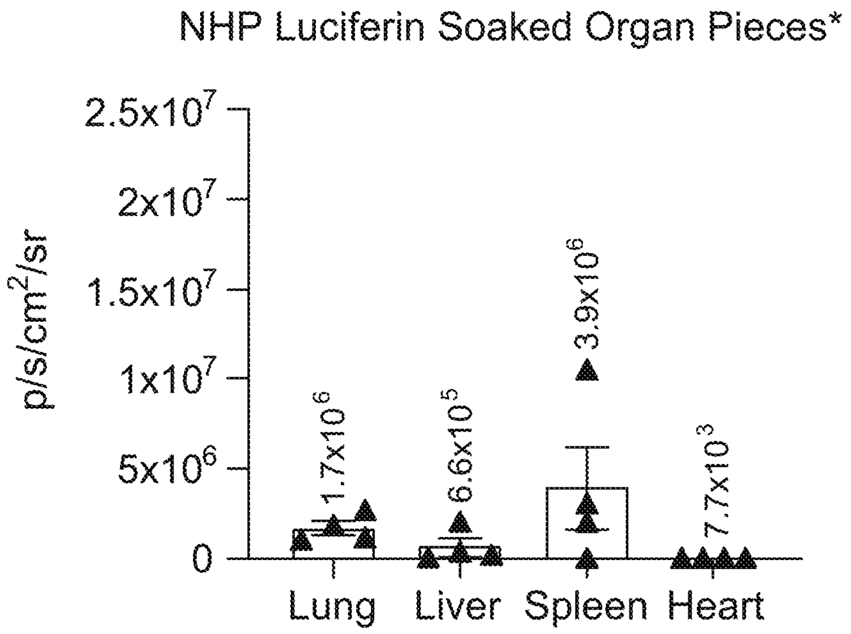

There was no significant changes for body weight (FIG. 14) and body temperature for any treatment group. For Composition 2B and Composition B group, there were no significant clinical observations. For Composition W treated group, one female showed signs of a reaction, vocalized, and lost consciousness during week 5 administration. Histopathology data showed repeat administration of Composition 2B showed no gross necropsy and histopathological changes. Bioluminescence data on NHPs dosed with Composition 2B lipid nanoparticles showed lower whole organ signal following repeat dosing compared to single dose. Also it showed weak signal in lung and the strongest signal in spleen (FIG. 15B). Bioluminescence data on NHPs dosed with Composition B lipid nanoparticles showed lower overall whole organ signal following repeat dosing compared to single dose. Also, it showed weak signal in liver, compared to the single dose study (FIG. 15C). Bioluminescence data on NHPs dosed with Formulation H lipid nanoparticles showed different organ tropism between rat and NHPs (FIG. 15D).

Figure 16A:
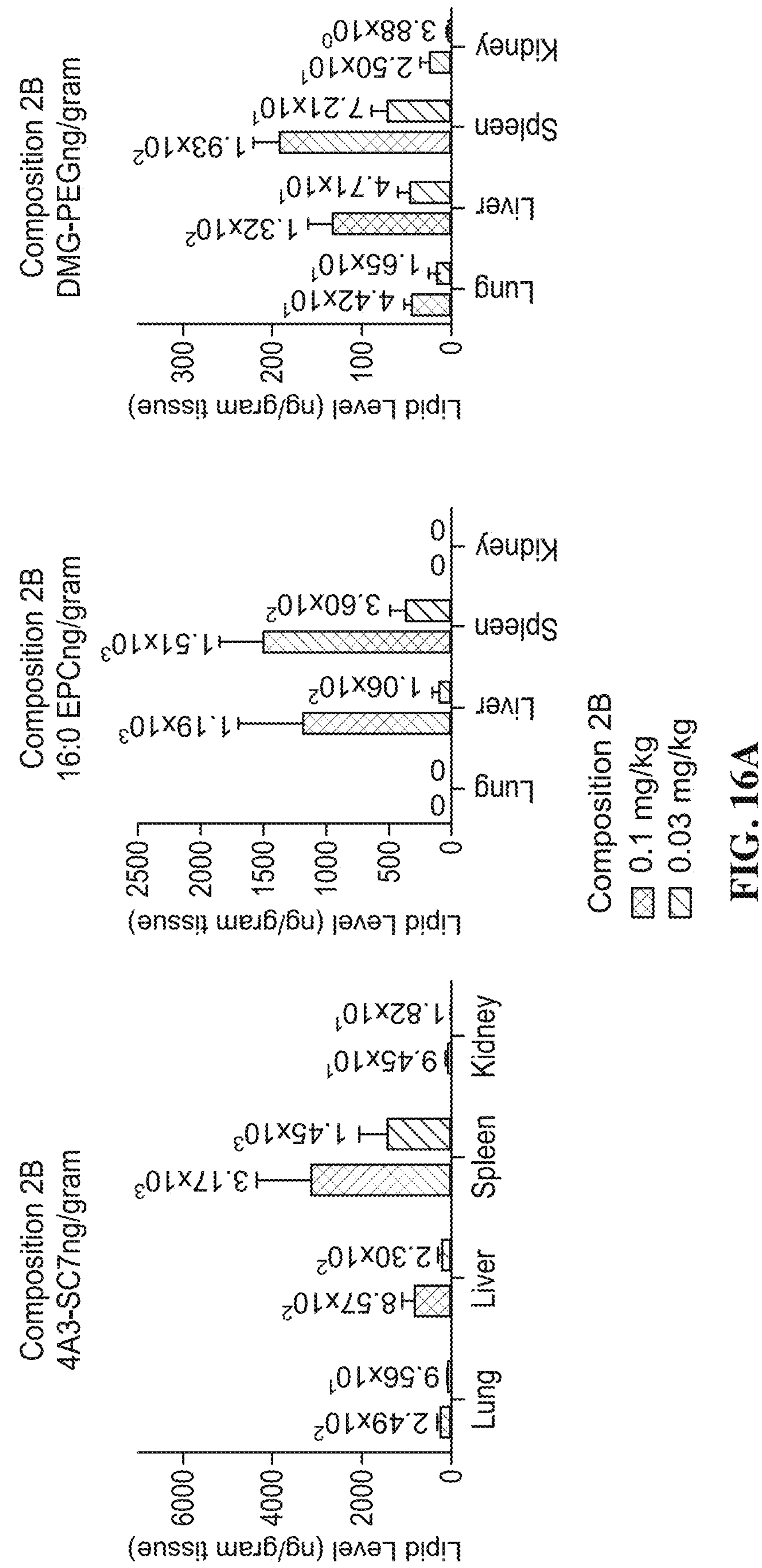
FIG. 16A shows the evaluation of lipid tissue distribution.
Figure 16A:
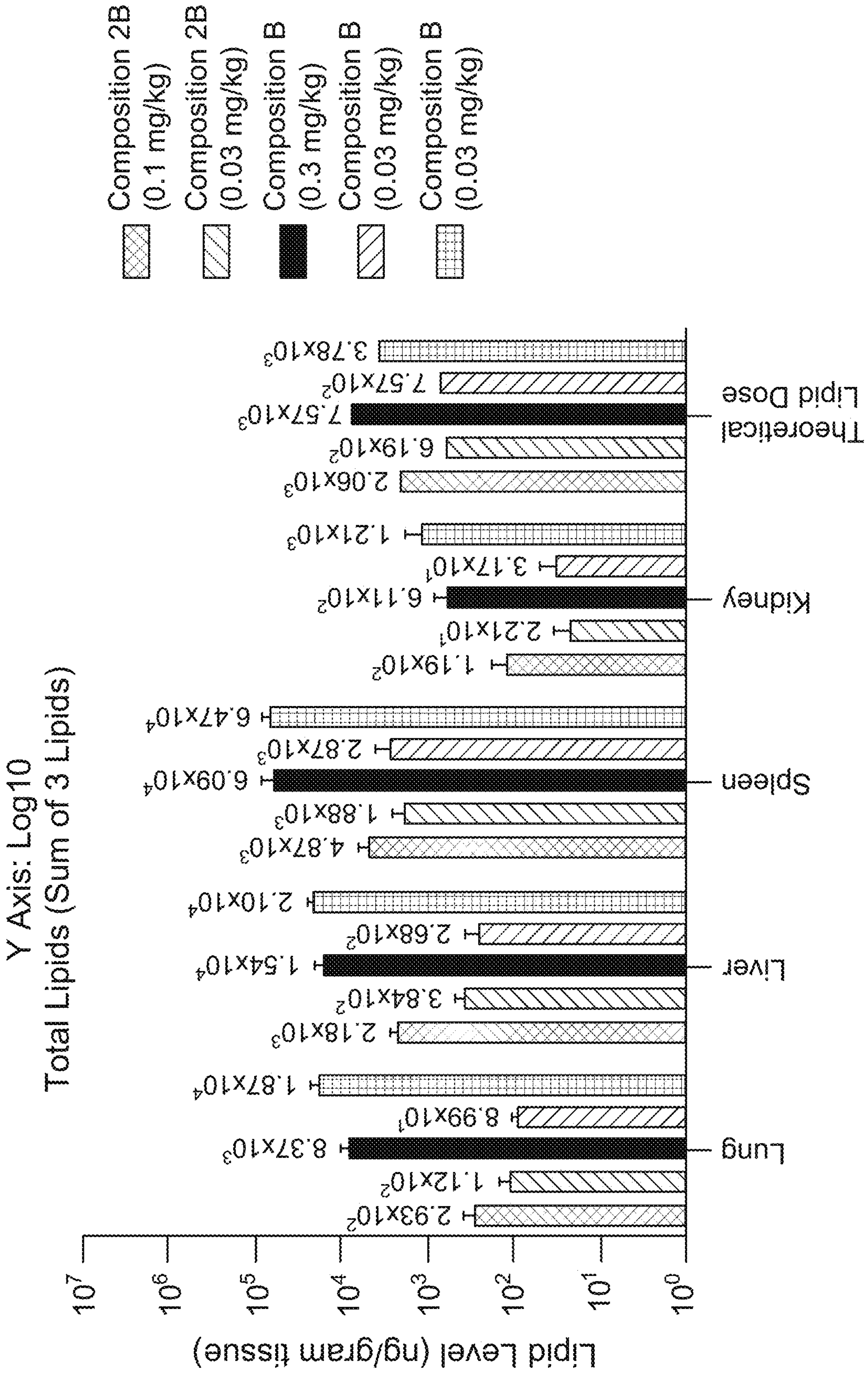
Figure 16A:
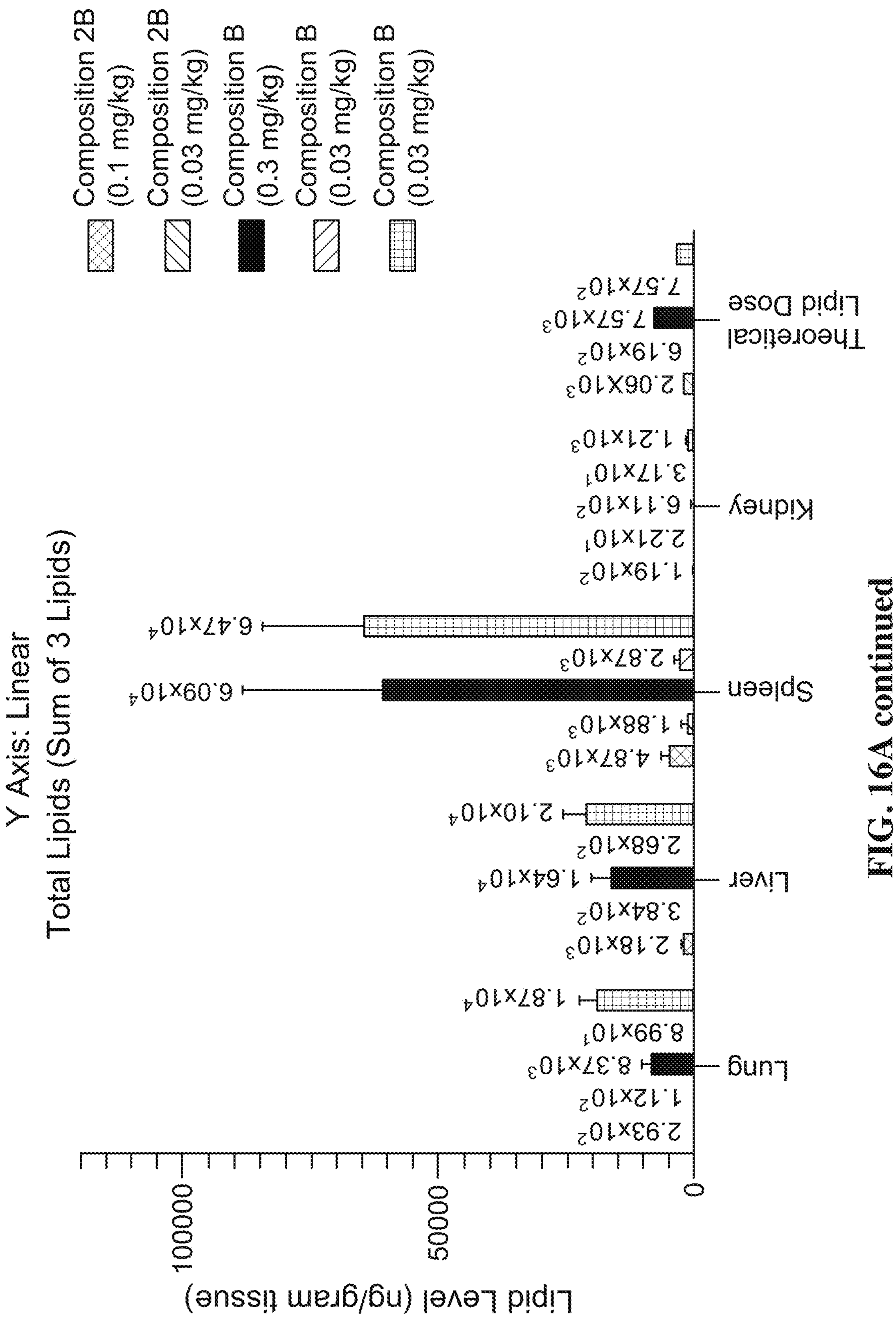
Figure 16B:
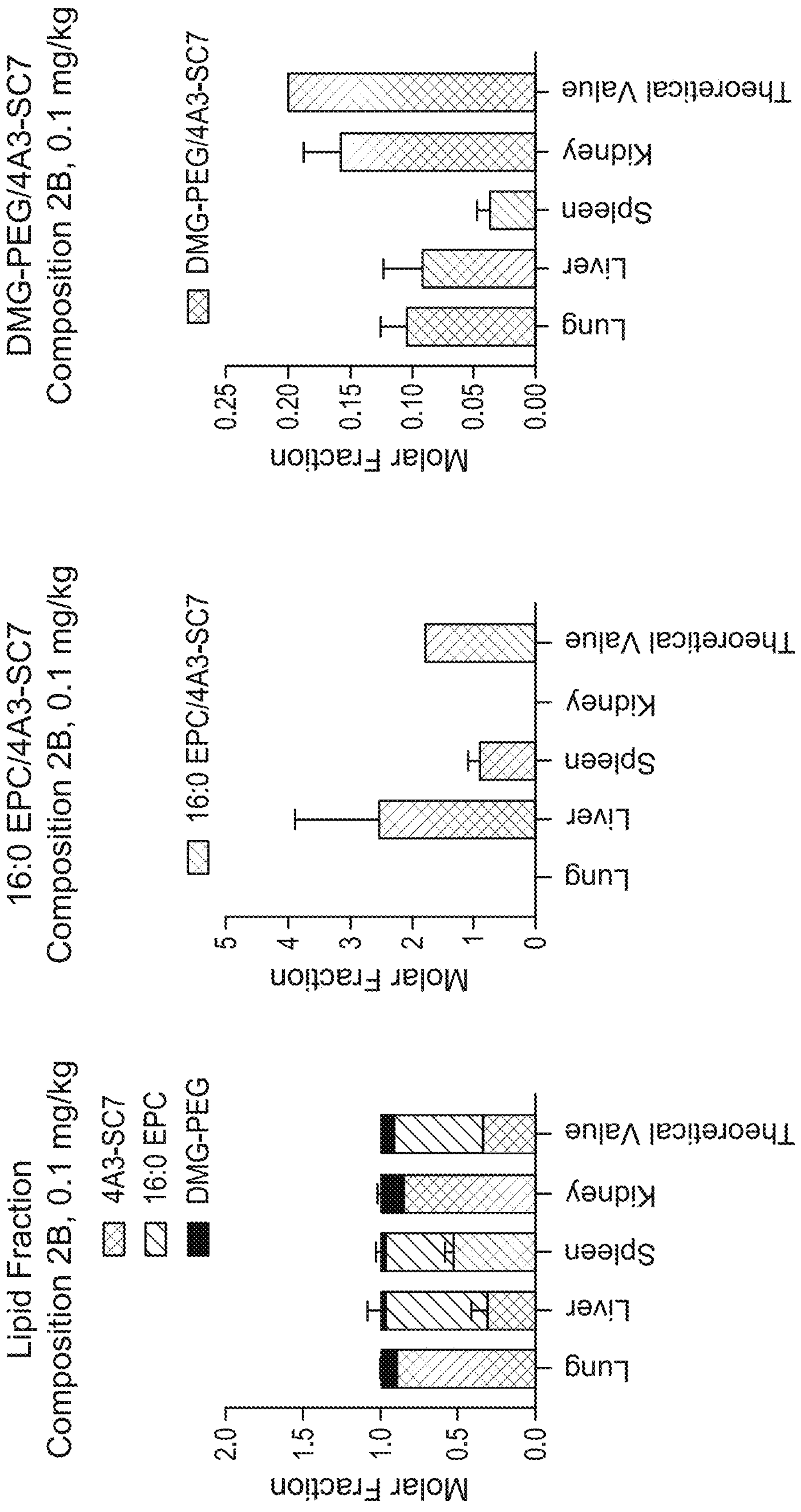
FIG. 16B shows lipid ratio.
Figure 17A:
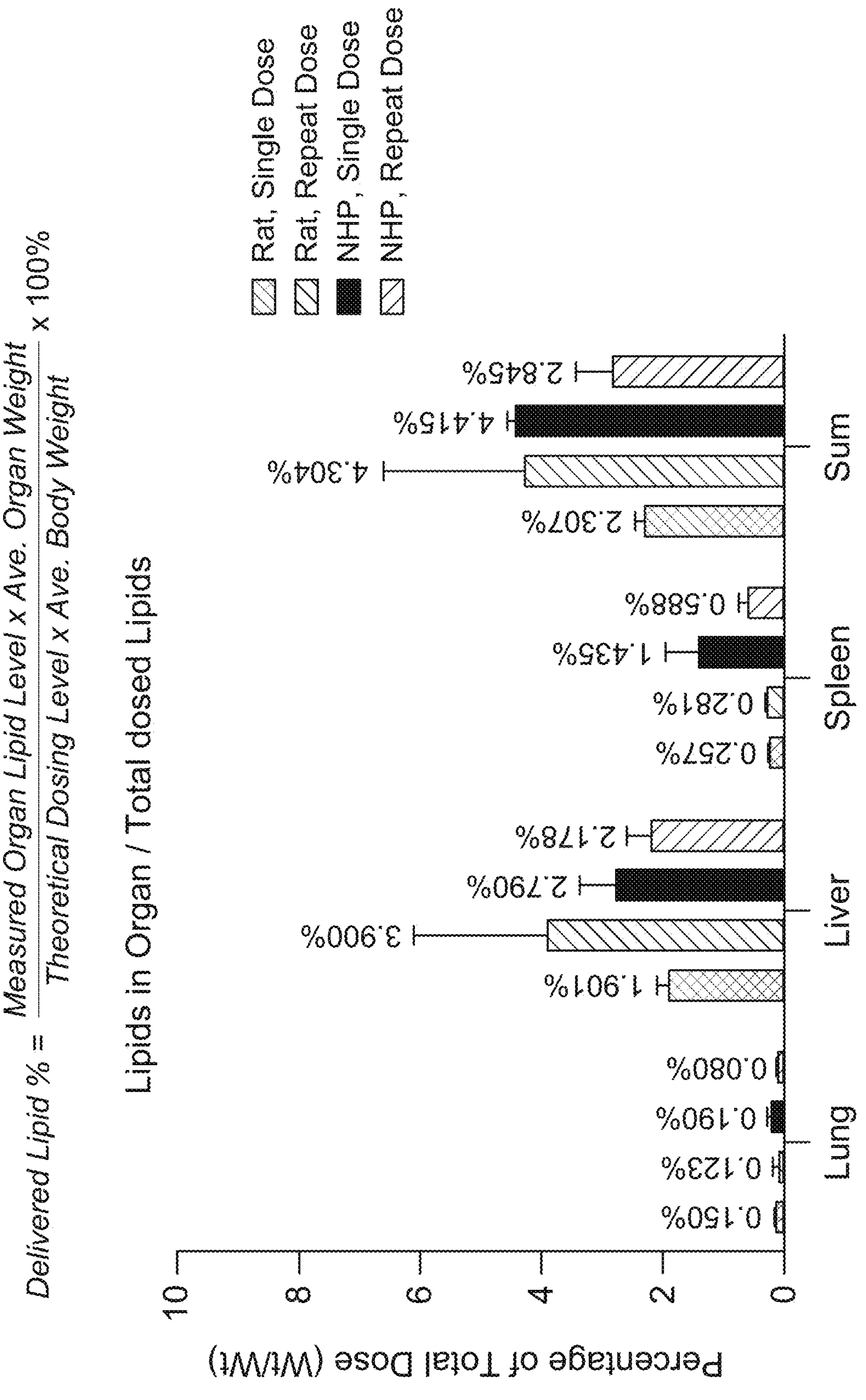
FIG. 17A shows estimated percentage of lipids delivered in each organ.
Figure 18:
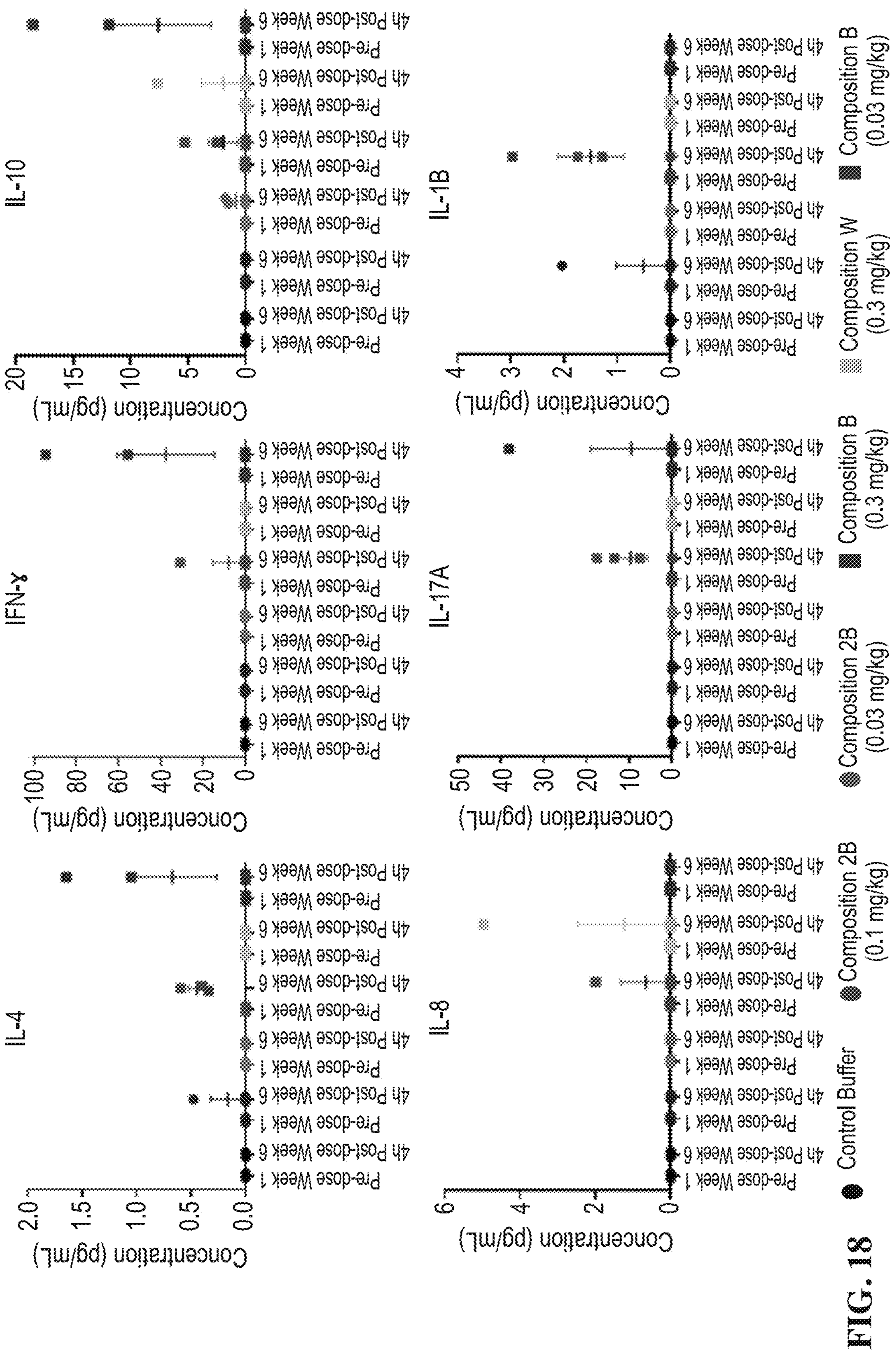
FIG. 18 shows concentration of plasma cytokines.
Figure 18:
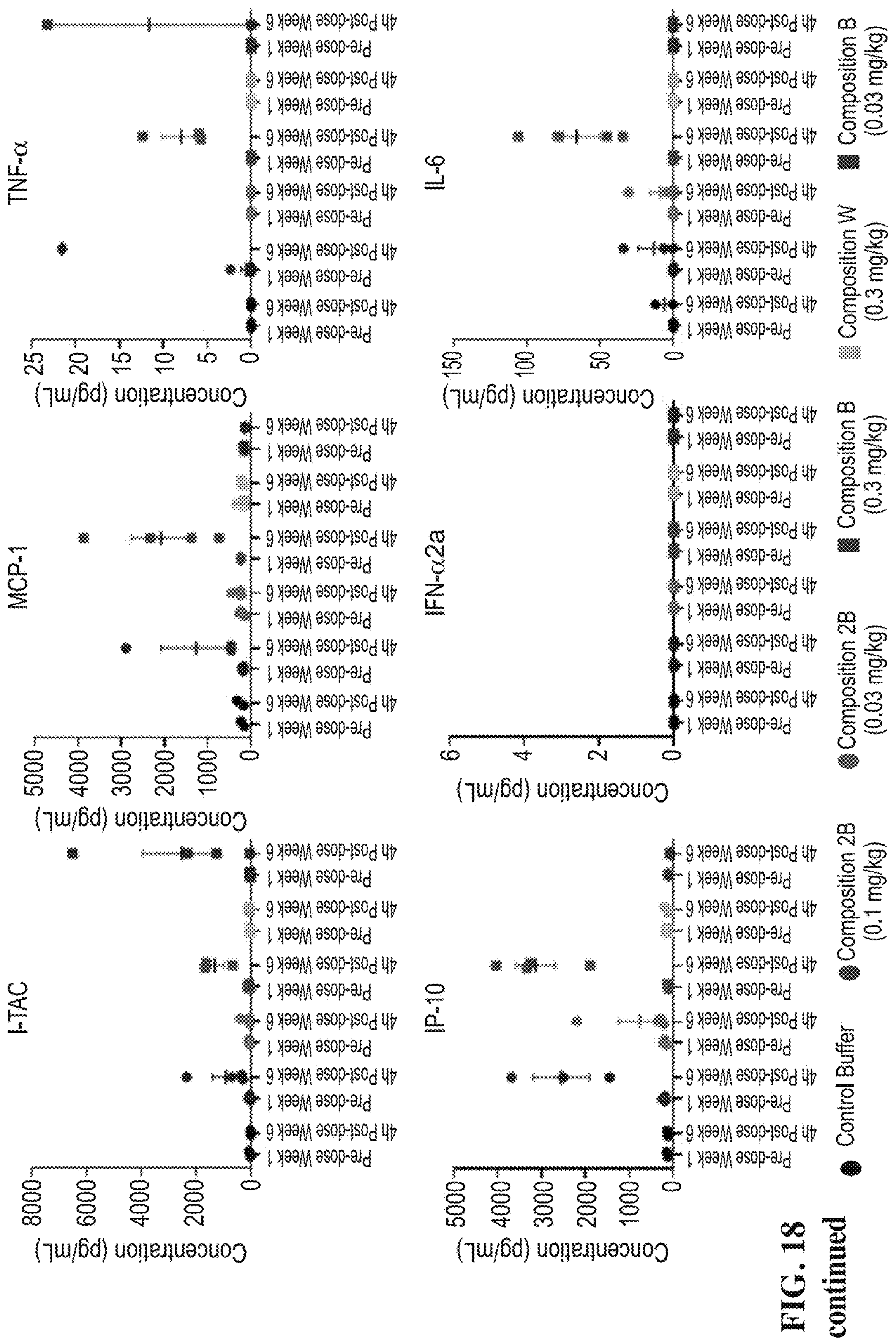

Lipid distribution in NHPs was evaluated. It showed similar results as single dose study (spleen>liver>lung) (FIG. 16A). Unlike the single dose study, levels of lipids in the repeat dose study were not proportional to the different dosing levels. Lipid ratios measured in tissue were not proportional to the theoretical values in most cases (FIG. 16C). Estimated percentage of lipids delivered in each organ were calculated. NHP data was calculated by using actual body and organ weight of the samples while rat data was estimated based on literature reported body weight and organ weight of young adult rats. The results show that only 2.3% to 4.4% percent of dosed lipids were found in lung, liver, and spleen combined 4 hours after injection. Repeat dosing with a frequency of one dose per week did not significantly increase lipid level in these three organs both in rat and NHP (FIG. 17). Plasma cytokines were measured and shown in FIG. 18.

Figure 19:
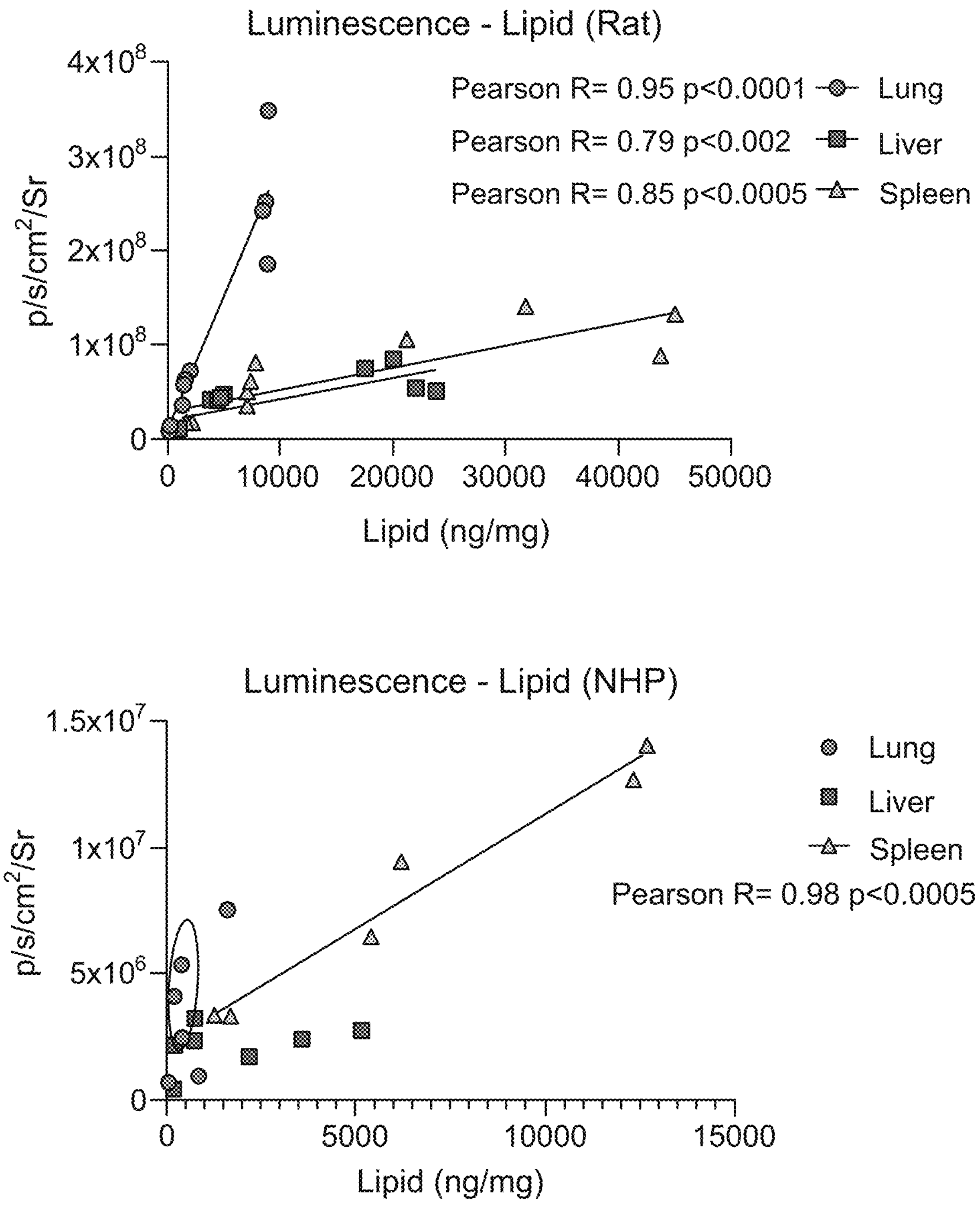
FIG. 19 shows correlation between lipid concentration and protein expression (luminescence).
Figure 19:
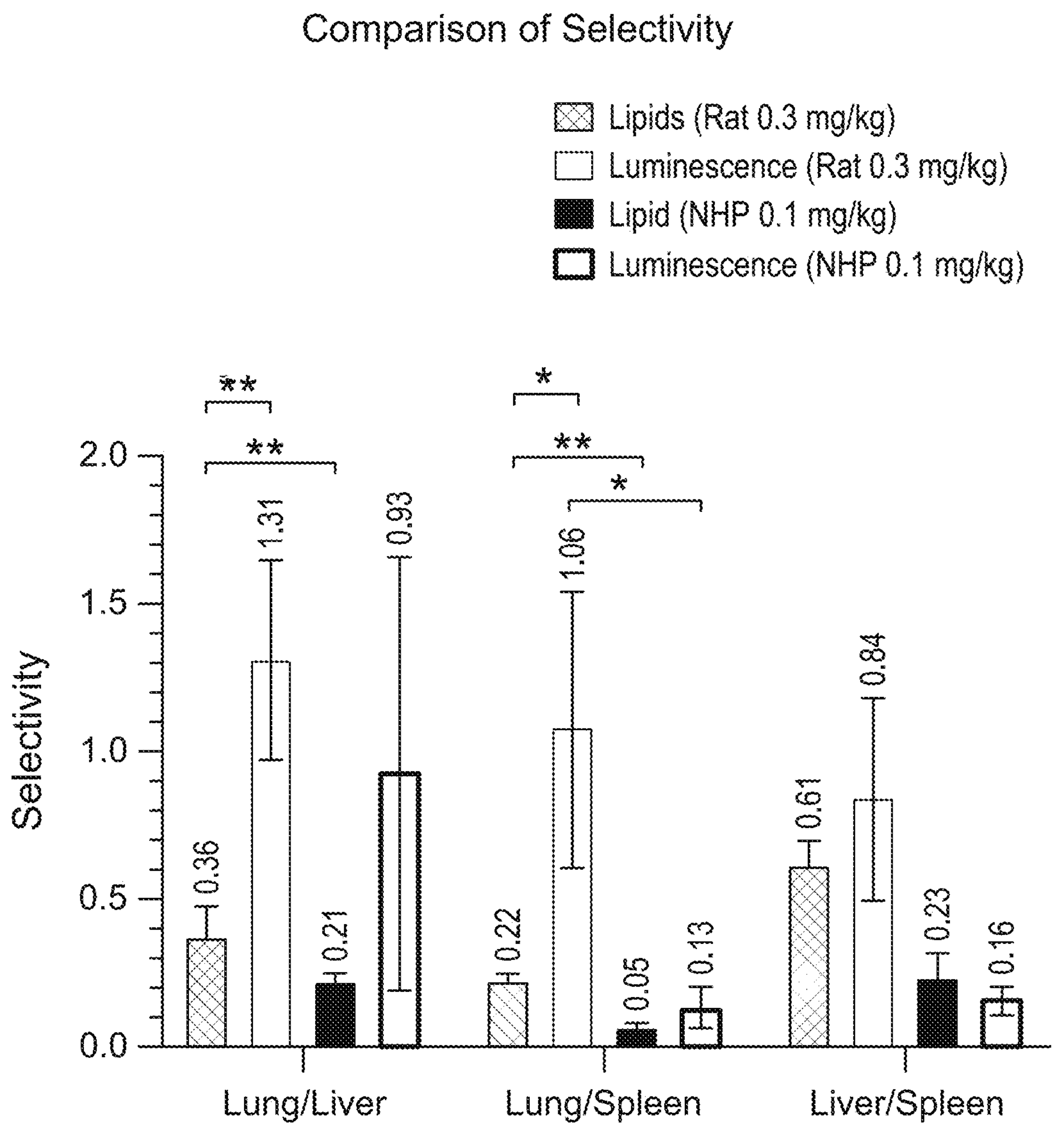

Correlation between lipid concentration and protein expression by the mRNA (luminescence) in rat and NHP were evaluated in FIG. 19. In the Rat single dose study, protein expression was significantly correlated with lipid concentration. However, the slopes of Luminescence-Lipid curves were different for lung, liver, and spleen. If same amount of LNP was delivered, the luciferase expression level in lung would be higher than liver and spleen. In the NHP single dose study, the protein expression in spleen was significantly correlated with lipid concentration. There was not enough data to establish correlation between protein and lipid concentration in lung and liver. However, the trend in NHP was similar to that in Rat.

Example 7. Development of a LC-MS Method for the Analysis of mRNA 5' Capping Efficiency This example describes the development of a method to determine mRNA capping efficiency. Proper mRNA 5' cap structure (Cap 1) is important for mRNA stability, translation efficiency, and to avoid immune responses in vivo.

Both enzymatic and co-transcriptional capping may lead to incomplete positioning of the cap on newly synthesized mRNA molecules. For example, capping after in vitro transcription (IVT) with vaccinia capping enzyme and 2'-O-methyltransferase results in four different states of capping: uncapped mRNA, G cap mRNA, Cap 0 mRNA, and Cap 1 (fully capped) mRNA. Capping during in vitro transcription (IVT) results in two capping states: uncapped mRNA, and cap mRNA. Assays that allow for fast and simple quantitative measurements of the capping efficiency are needed. Current analysis methods use, for example a Ribozyme or a DNAzyme cleavage and subsequent LC-MS analysis to determine mRNA capping efficiency (e.g., I. Vlatkovic et al., Pharmaceutics (2022) 14(2): 328). However, this method generates cyclic phosphate as well as linear phosphates resulting in non-uniform 3' ends of the cut fragment. Moreover, the triphosphate group of the uncapped fragment binds to metal ions thus creating multiple ion adducts which makes the quantitation of the uncapped fragment more challenging.

Figure 20A:
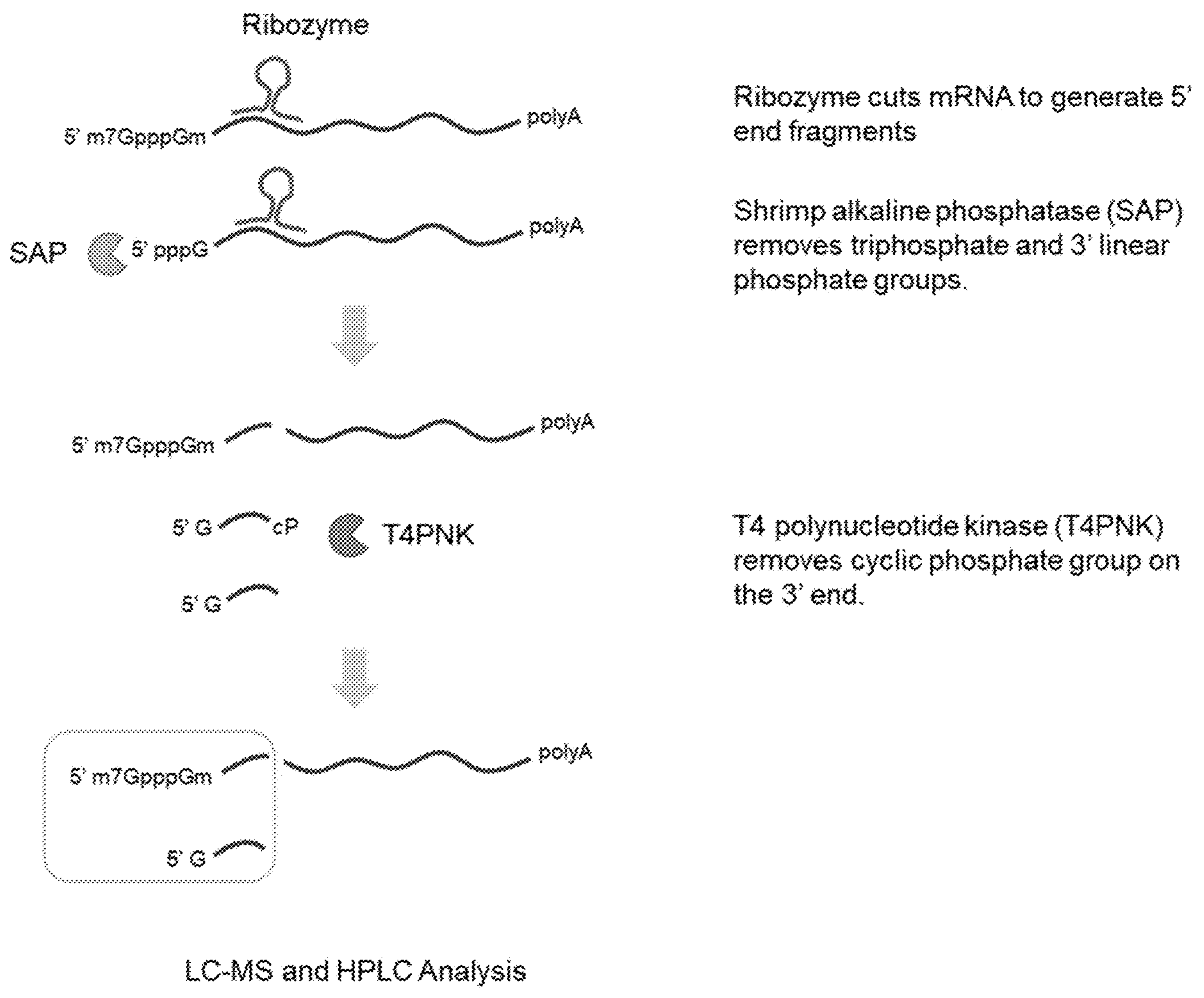
FIG. 20A shows schematic method of LC-MS method for the analysis of mRNA 5' capping efficiency.
Figure 20B:
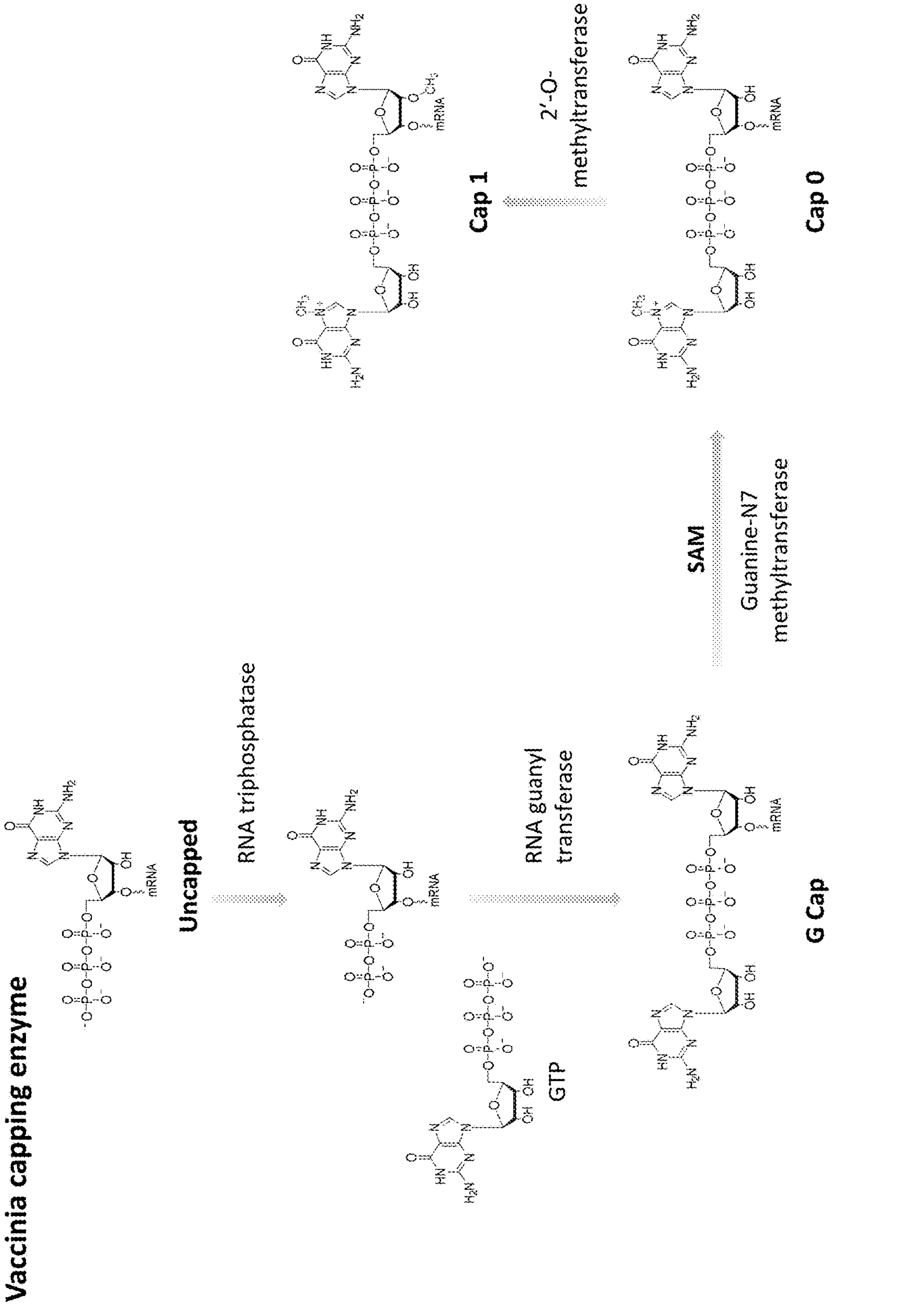
FIG. 20B shows schematic diagram of Vaccine capping enzyme system.

In this example, a new method is developed to determine mRNA capping using Ribozyme cleavage, followed by shrimp alkaline phosphatase (SAP) and T4 polynucleotide kinase (T4PNK). Briefly, Ribozyme is added to in vitro produced mRNA to generate 5' end fragments. Then, shrimp alkaline phosphatase (SAP) is added to remove triphosphate and 3' linear phosphate groups. Finally, T4 polynucleotide kinase (T4PNK) is added to remove any cyclic phosphate groups on the 3' end. This results in only fully capped fragments (5' m7GpppGm) and triphosphate-removed fragments (5' G). Samples are then analyzed using LC-MS and HPLC analysis (FIGS. 20A and B).

Briefly, samples were prepared in a 100 μL reaction in a microtube with Tris buffer, mRNA and Ribozyme. Then samples were annealed at 65° C. for 2 minutes, the samples were cooled to room temperature for 5 min, and $MgCl_2$ and SAP were added. Samples were incubated at 37° C. for 1 hour. Then T4PNK was added to the tube and incubated for another 30 minutes at 37° C. Finally, 10 μL of 0.5 M EDTA was added to quench the reaction. Each solution used in the procedure is shown in Table 17.

TABLE 17

| Solution | 100 μL |
|---|---|
| 2 mg/mL DNAI1, uncapped | 16 μL (42 pmol) |
| 1M Tris, pH 8.0 | 2 μL |
| 1M $MgCl_2$ | 1 μL |
| 100 μM Ribozyme | 2 μL |
| SAP | 20 μL |
| Water | 51 μL |
| T4PNK | 8 μL |

Figure 21A:
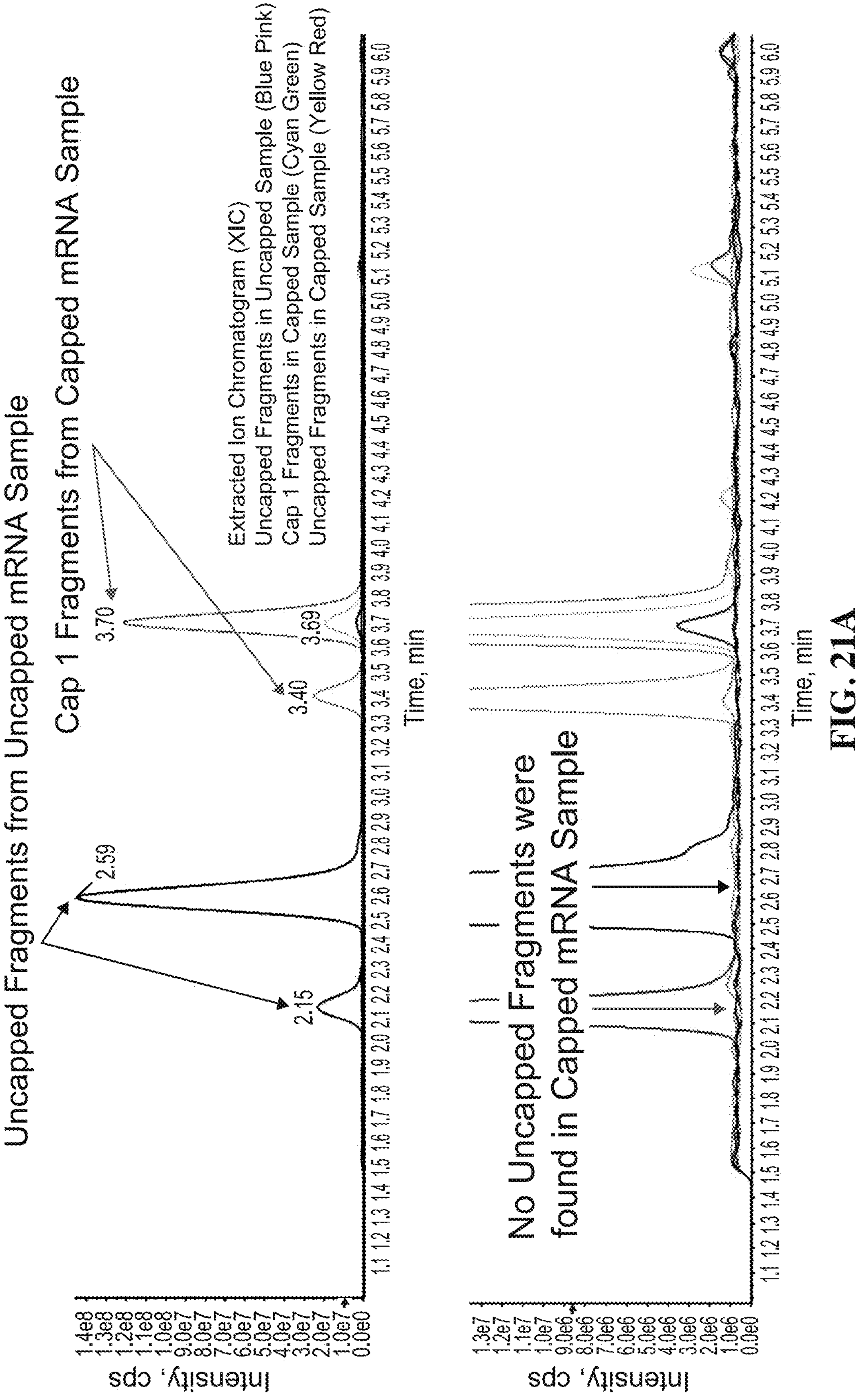
FIG. 21A shows LC-MS data to detect uncapped structure in capped mRNA sample after Ribozyme/SAP Digestion.
Figure 21B:
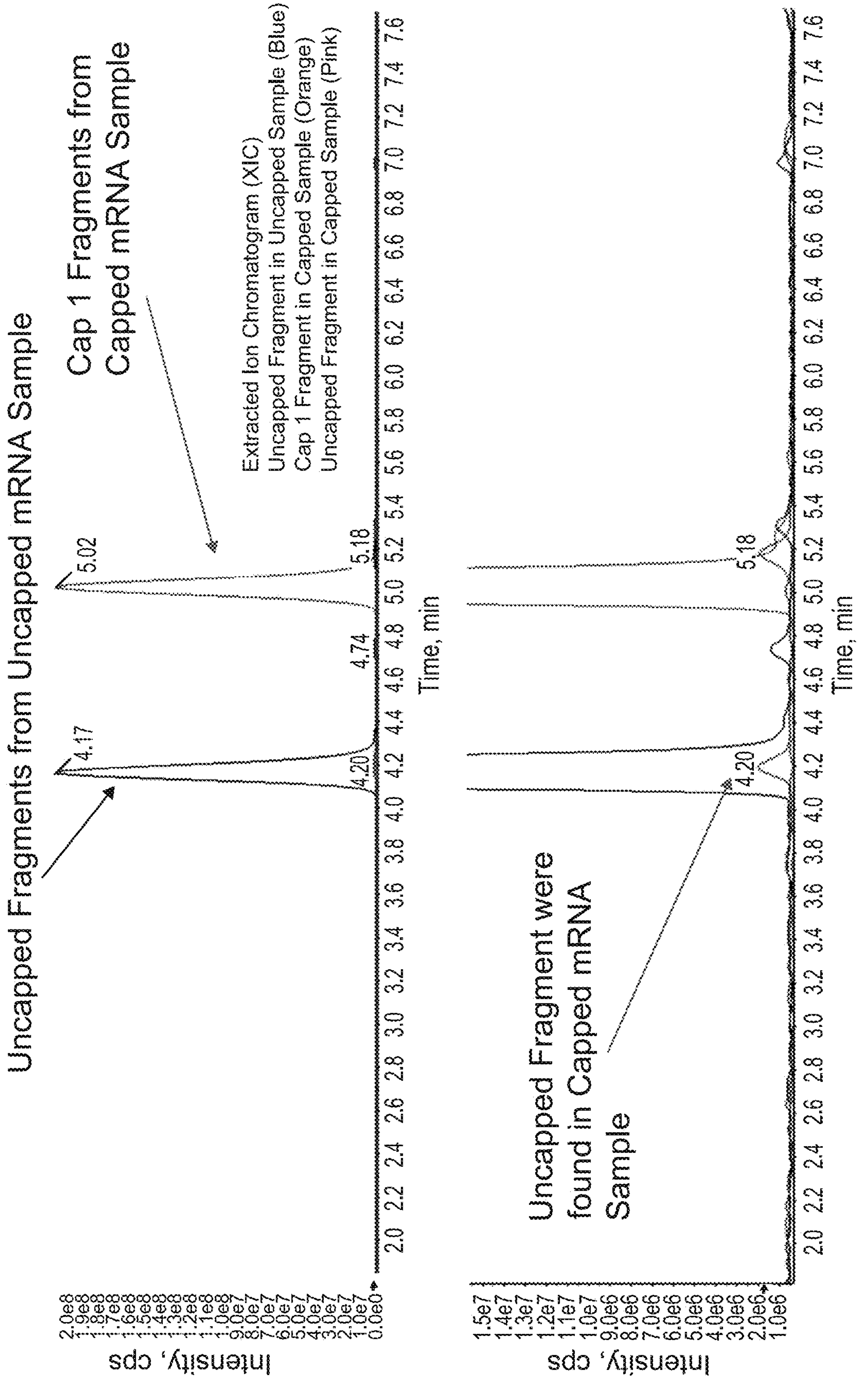
FIG. 21B shows LC-MS to detect uncapped structure in capped mRNA sample after Ribozyme/SAP and T4 PNK digestion.
Figure 22:
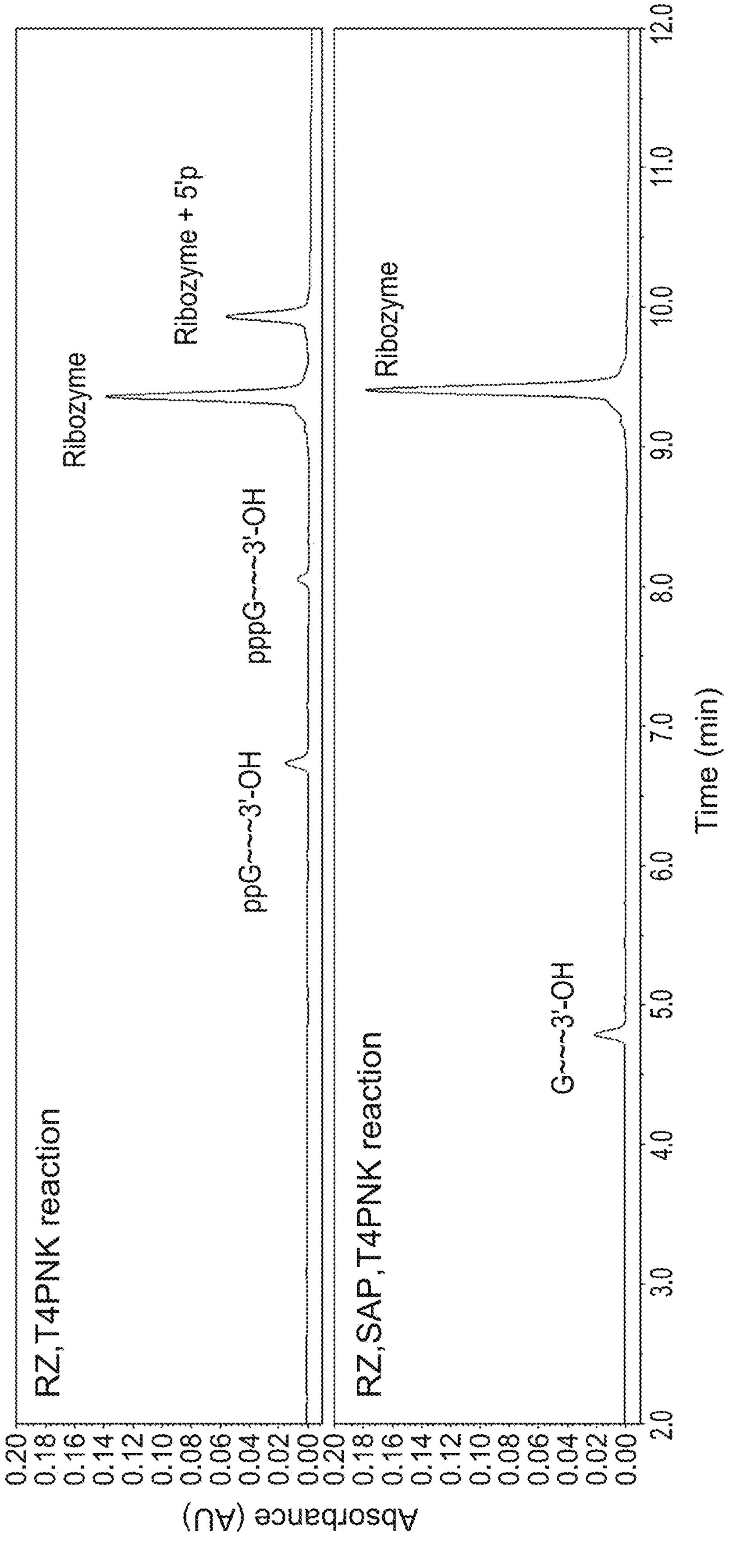
FIG. 22 shows LC-MS to detect uncapped structure in capped mRNA sample after Ribozyme and T4PNK digestion.

When samples were digested with only Ribozyme and SAP, two fragments from each mRNA species were observed, resulting in lower sensitivity (FIG. 21A). However, samples digested with Ribozyme/SAP and T4PNK showed one fragment from each mRNA species, resulting in better sensitivity (FIG. 21B). When samples were digested with Ribozyme (RZ) and T4PNK, several peaks were observed in the LC-MS analysis, showing that T4PNK does not remove all phosphate groups at the 5' end (FIG. 22). The combination of Ribozyme, Alkaline phosphatase, and T4PNK results in clean 5' fragments which results in cleaner chromatogram which helps with separation and accurate quantitation. This method shows higher sensitivity with both UV and MS and better quantitation of uncapped fragments.

The Ribozyme sequence used in the experiment was (sequences binds to mRNA 5' UTR region are underlined/bold):

(SEQ ID NO: 12)
5'-AAACGCCUGAUGAGGCCGUGAGGCCGAAAGCCAGCUUG-3'

The targeted mRNA sequence was:

(SEQ ID NO: 13)
5'-CAAGCUGGCUA"GCGUUU-3' (the cleavage site is denoted with a ")

For quantification, synthetic RNA standards were generated and used to determine the concentration of standards.

Figure 23:
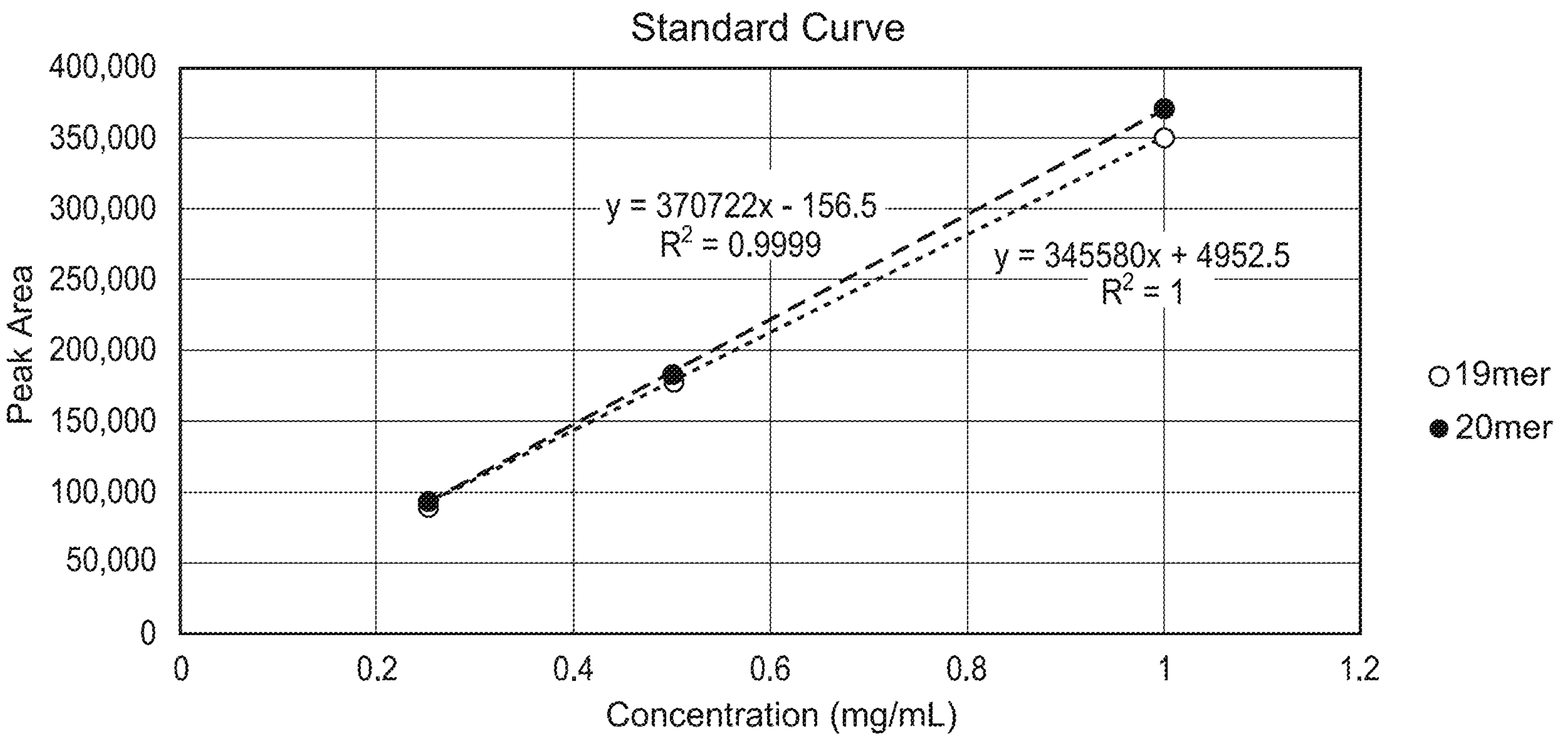
FIG. 23 shows a concentration of standard to measure quantitation of mRNA 5' fragment and measurement of mRNA 5' fragments quantitation.

The 19mer sequence and the 20mer sequence having an extra G for the quantification were used as standards, because ribozyme used in the experiment generates a 19mer fragment when the mRNA is not capped and the capped species have an extra guanine. Based on the standard, the concentration of each mRNA 5' capping structures were measured (FIG. 23).

Example 8. Delivery of Gene Editing Cargos

Figure 24A:
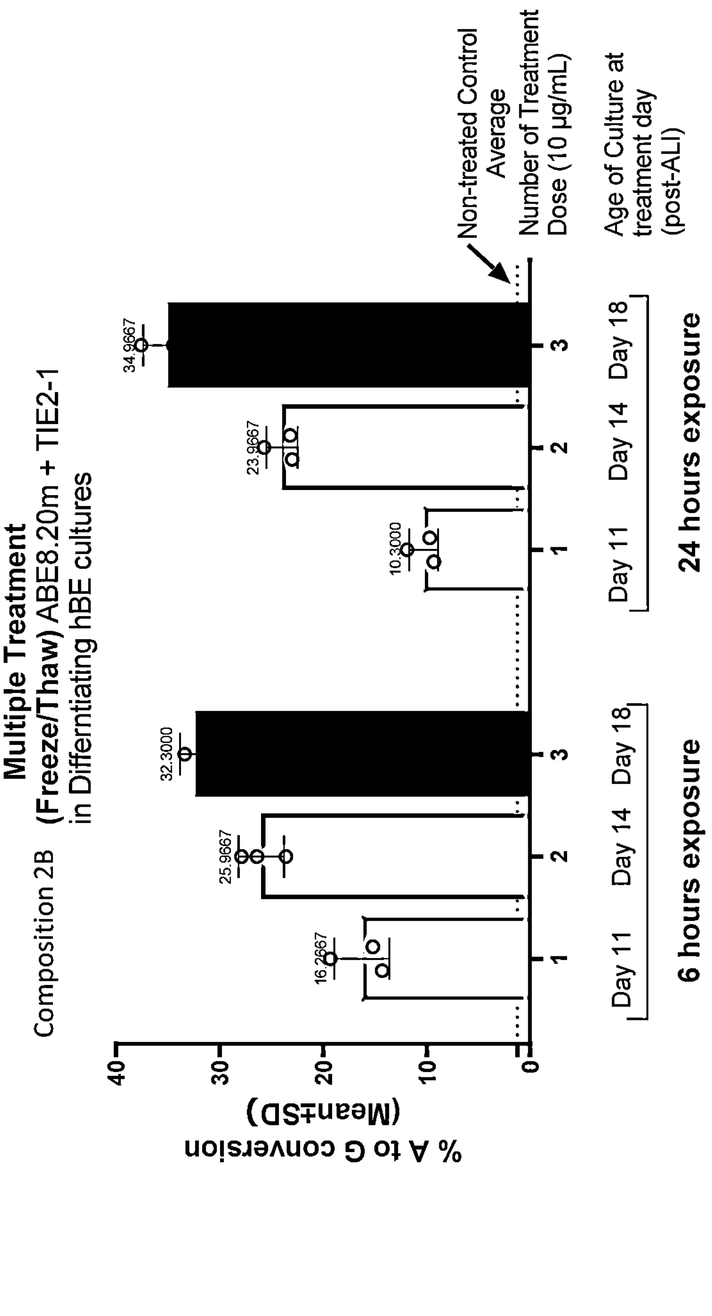
FIG. 24A shows % A to G conversion in differentiating hBE culture cells dosed with ABE8.20m+TIE2-1 Composition 2B.
Figure 24B:
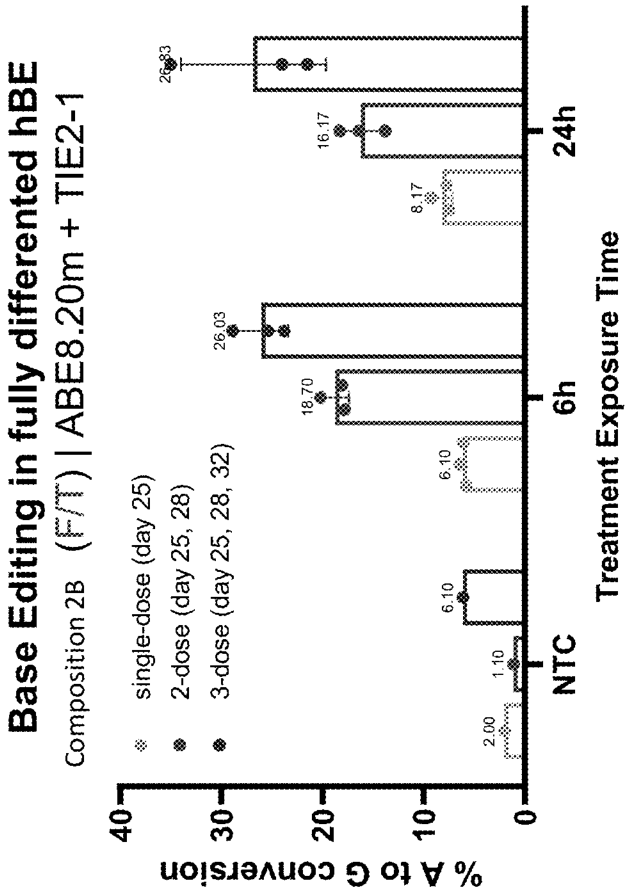
FIG. 24B shows % A to G conversion in fully differentiated hBE culture cells dosed with ABE8.20m+TIE2-1 Composition 2B.
Figure 24C:
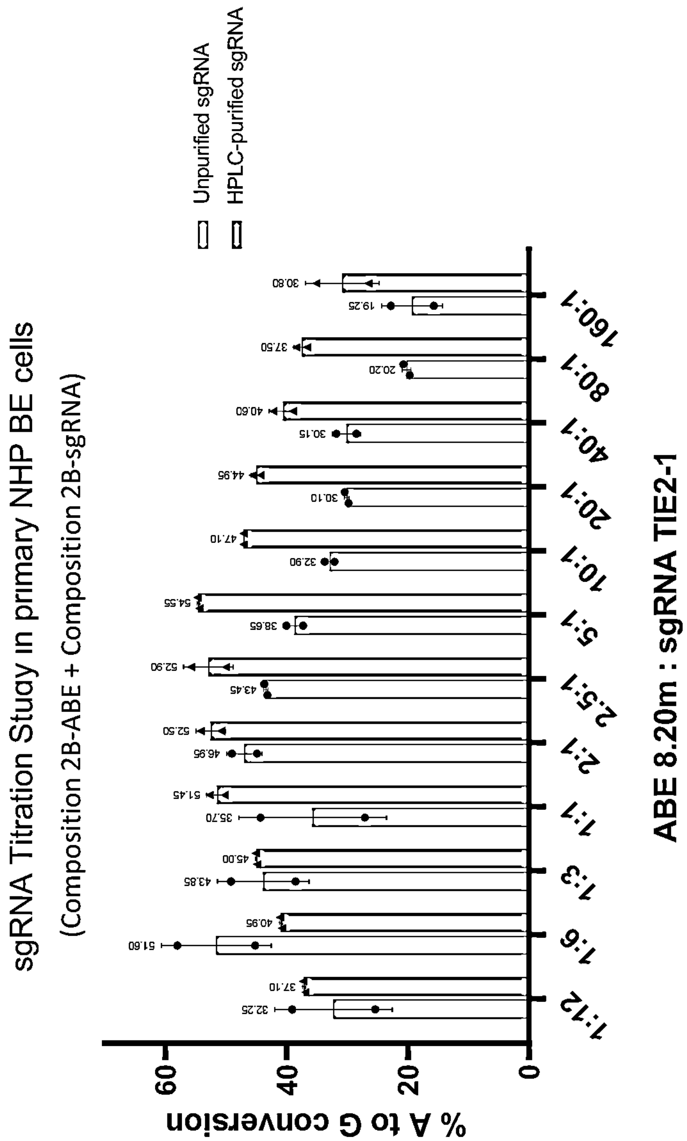
FIG. 24C shows % A to G conversion in primary NHP BE cells dosed with ABE8.20m+sgRNA Composition 2B.

This example demonstrates successful delivery of gene editing cargos by LNP to basal cells of bronchial epithelium to create TIE2 gene nucleotide conversion using Adenine Base Editors (ABEs).

hBE cells were dosed with adenine base editors (ABE 8.20m)/sgRNA TIE2-1 containing Composition 2B. Multiple treatment of Composition 2B in both primary differentiating hBE cells (FIG. 24A) and fully differentiated hBE cells (FIG. 24B) showed improved base editing efficiency. Furthermore, HPLC-purified sgRNA showed marked increase in editing rates in primary NHP BE cells (FIG. 24C).

ABBREVIATIONS

LNP lipid nanoparticle
NHP non-human primates
RIPA buffer Radioimmunoprecipitation assay buffer
BCA assay Bicinchoninic acid assay
CV coefficient of variance
HPLC High performance liquid chromatography
DFA Difluoroacetic acid
MS mass spectrometry
PBS phosphate-buffered saline
FBS Fetal bovine serum
IVIS in vivo imaging system

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

TABLE 18

| Two synthetic RNAs used as standards for quantification (HPLC purified) | |
|---|---|
| 19 mer | GGGAGACCCAAGCUGGCUA (use as standard for uncapped) (SEQ ID NO: 14) |
| 20 mer | GGGAGACCCAAGCUGGCUAG (use as standard for cap 1, cap 0 and G cap)[1] (SEQ ID NO: 15) |

[1]extra G was added at the 3' end since four consecutive Gs will promote G-quadruplexes

What is claimed is:

1. A method for quantifying amounts of capped and uncapped messenger RNA (mRNA) in an mRNA sample, the method comprising:

providing the mRNA sample comprising capped mRNA and uncapped mRNA;

contacting the mRNA sample with a nuclease wherein the nuclease is a Ribozyme, an alkaline phosphatase, and a polynucleotide kinase;

an amount of capped mRNA and an amount of uncapped mRNA, wherein the method quantifies uncapped fragments with more accuracy than a method comprising contacting the mRNA sample with the Ribozyme and without the alkaline phosphatase and the polynucleotide kinase, wherein the Ribozyme comprises a sequence according to nucleotides 7-29 of SEQ ID NO: 12.

2. The method of claim 1, wherein the mRNA is in vitro transcribed.

3. The method of claim 1, wherein the mRNA in the sample is contacted with the nuclease to create 5' end fragments of mRNA.

4. The method of claim 1, wherein the mRNA in the sample is contacted with the alkaline phosphatase to remove a triphosphate group and a 3' linear phosphate group from an mRNA molecule.

5. The method of claim 1, wherein the mRNA in the sample is contacted with the polynucleotide kinase to remove a cyclic phosphate group from the 3' end of an mRNA molecule.

6. The method of claim 1, wherein the mRNA in the sample is contacted with the nuclease before the alkaline phosphatase.

7. The method of claim 1, wherein the mRNA in the sample is contacted with the alkaline phosphatase after the nuclease but before the polynucleotide kinase.

8. The method of claim 1, wherein the mRNA in the sample is contacted with the polynucleotide kinase after the nuclease but before the alkaline phosphatase.

9. The method of claim 1, wherein the nuclease is a Ribozyme.

10. The method of claim 1, wherein the alkaline phosphatase is a shrimp alkaline phosphatase (SAP), a calf-intestinal alkaline phosphatase (CIP), or a placental alkaline phosphatase (PLAP).

11. The method of claim 1, wherein the polynucleotide kinase is a T4 Polynucleotide Kinase (T4PNK).

12. The method of claim 1, wherein the method comprises separating the capped mRNA and the uncapped mRNA occurs using chromatography.

13. The method of claim 12, wherein the chromatography comprises liquid chromatography.

14. The method of claim 13, wherein the liquid chromatography comprises liquid chromatography-mass spectrometry (LC-MS) or high-performance liquid chromatography (HPLC).

15. The method of claim 2, wherein the mRNA was contacted with a vaccinia capping enzyme, a guanine-N7 methyltransferase, and/or a 2'-O-methyltransferase during in vitro transcription or after in vitro transcription.

16. The method of claim 15, wherein the vaccinia capping enzyme comprises an RNA triphosphatase and/or an RNA guanyl transferase.

17. The method of claim 1, wherein the mRNA sample comprises Tris buffer.

18. The method of claim 17, wherein the Tris buffer has a pH of 8.0.

19. The method of claim 1, wherein the mRNA sample is contacted with the nuclease followed by the alkaline phosphatase and the polynucleotide kinase.

* * * * *

SEQUENCE LISTING

```
Sequence total quantity: 15
SEQ ID NO: 1            moltype = DNA  length = 4520
FEATURE                 Location/Qualifiers
source                  1..4520
                        mol_type = other DNA
                        organism = synthetic construct
SEQUENCE: 1
gggagaccca agctggctag cgtttaaact tcagcttggc aatccggtac tgttggtaaa  60
gccaccatgc agagaagccc cctggaaaag gccagcgtgg tgagcaagct gttcttcagc  120
tggacccggc ccatcctgcg gaagggctac agacagagac tggaactgag cgacatctac  180
cagatcccca gcgtggacag cgccgacaac ctgagcgaga agctggaaag agagtgggac  240
agagagctgg ccagcaagaa gaaccccaag ctgatcaacg ccctgcggcg gtgcttcttc  300
tggcggttca tgttctacgg catcttcctg tacctgggcg aagtgaccaa agccgtgcag  360
cccctgctgc tgggcagaat catcgccagc tacgaccccg acaacaaaga ggaacggagc  420
atcgccatct acctcggcat cggcctgtgc ctgctgttca tcgtcagaac cctgctgctg  480
caccccgcca tcttcggact gcaccacatc ggcatgcaga tgcggatcgc catgttcagc  540
ctgatctaca agaaaaccct gaagctgagc agcagagtgc tggacaagat cagcatcgga  600
cagctggtga gcctgctgag caacaacctg aacaagttcg acgaaggcct ggccctggcc  660
cacttcgtgt ggatcgcccc cctgcaagtg gccctgctga tgggcctgat ctgggaactg  720
ctgcaggcca gcgccttctg cggactggga ttcctgatcg tgctggccct gttccaggcc  780
ggactgggga gaatgatgat gaagtaccgg gaccagagag ccggcaagat cagcgagaga  840
ctggtcatca ccagcgagat gatcgagaac atccagagcg tgaaggccta ctgctgggaa  900
gaggccatgg aaaagatgat cgagaacctg cggcagaccg agctgaagct gacaagaaag  960
gccgcctacg tgcgctactt caacagcagc gccttcttct tcagcggctt cttcgtggtg  1020
ttcctgagcg tgctgcccta cgccctgatc aagggcatca tcctgagaaa gatcttcacc  1080
accatcagct tctgcatcgt gctgcggatg gccgtgacca gacagttccc ctgggccgtg  1140
cagacctggt acgacagcct gggcgccatc aacaagatcc aggacttcct gcagaagcaa  1200
gagtacaaga ccctcgagta caacctgacc accaccgagg tggtcatgga aaacgtgacc  1260
gccttctggg aggaaggctt cggcgagctg ttcgagaagg ccaagcagaa caacaacaac  1320
cgcaagacca gcaacggcga cgacagcctg ttcttcagca acttcagcct gctggggacc  1380
cccgtgctga aggacatcaa cttcaagatc gagcggggac agctgctggc cgtggccgga  1440
agcacaggcg ccggaaaaac cagcctgctc atggtcatca tgggcgagct ggaacccagc  1500
gagggcaaga tcaagcacag cggcaggatc agcttctgca gccagttcag ctggatcatg  1560
cccggcacca tcaaagagaa catcatcttc ggcgtgagct acgacgagta cagataccgc  1620
agcgtgatca aggcctgcca gctggaagag gacatcagca agttcgccga gaaggacaac  1680
atcgtgctcg gcgaaggcgg catcacactg agcggcggac agagggccag aatcagcctg  1740
gccagagccg tgtacaagga cgccgacctg tacctgctgg acagcccctt cggctacctg  1800
gacgtgctga ccgagaaaga gatcttcgag agctgcgtgt gcaagctgat ggccaacaag  1860
acccggatcc tggtcaccag caagatggaa cacctgaaga aggccgacaa gatcctgatc  1920
ctgcacgagg gcagcagcta cttctacggc accttcagcg agctgcagaa cctgcagccc  1980
gacttcagca gcaaactgat gggctgcgac agcttcgacc agttcagcgc cgagcggaga  2040
aacagcatcc tgacagagac actgcaccgg ttcagcctgg aaggcgacgc ccccgtgagc  2100
tggaccgaga caaagaagca gagcttcaag cagaccggcg agttcggcga gaagcggaag  2160
aacagcatcc tgaaccccat caacagcatc cggaagttca gcatcgtcca gaaaaccccc  2220
ctgcagatga acggcatcga agaggacagc gacgagcccc tggaaagacg gctgagcctg  2280
gtgcccgaca gcgaacaggg cgaagccatc ctgccccgga tcagcgtgat cagcacaggc  2340
cccacactgc aggcccggag aaggcagagc gtgctgaacc tgatgaccca cagcgtgaac  2400
cagggacaga acatccacag aaagaccacc gccagcacac ggaaagtgag cctggccccc  2460
caggccaacc tgactgagct ggacatctac agcagacggc tgagccaaga gacaggcctg  2520
gaaatcagcg aggaaatcaa cgaagaggac ctgaaagagt gcttcttcga cgacatggaa  2580
agcatccccg ccgtgacaac ctggaacacc tacctgcggt acatcaccgt gcacaagagc  2640
ctgatcttcg tgctgatctg gtgcctcgtg atcttcctgg ccgaagtggc cgccagcctg  2700
gtggtgctgt ggctgctcgg aaacaccccca ctgcaggaca agggcaacag cacccacagc  2760
cggaacaaca gctacgccgt gatcatcacc agcaccagca gctactacgt gttctacatc  2820
tacgtgggcg tcgccgacac tctgctcgcc atgggcttct tcagaggact gcccctggtg  2880
cacaccctga tcaccgtgag caagatcctg caccacaaga tgctgcacag cgtcctgcag  2940
gcccccatga gcacactgaa caccctgaaa gccggcggaa tcctgaacag attcagcaag  3000
gacatcgcca tcctggacga cctgctgccc ctgaccatct tcgacttcat ccagctgctg  3060
ctgatcgtga tcggcgccat cgccgtggtg gccgtgctgc agccctacat cttcgtggcc  3120
accgtgcccg tgatcgtggc cttcatcatg ctgcgggcct acttcctgca gaccagccag  3180
cagctgaagc agctcgagag cgagggcaga agccccatct tcacccacct cgtgaccagc  3240
ctgaaaggcc tgtggaccct gagagccttc ggcagacagc cctacttcga gacactgttc  3300
cacaaggccc tgaacctgca caccgccaac tggttcctgt acctgagcac cctgcggtgg  3360
ttccagatga ggatcgagat gatcttcgtc atcttcttca tcgccgtgac cttcatcagc  3420
atcctcacca ctggcgaagg cgagggcaga gtgggaatca tcctgaccct ggccatgaac  3480
atcatgagca cactccagtg ggccgtgaac agcagcatcg acgtggacag cctgatgcgg  3540
agcgtgagcc gggtgttcaa gttcatcgac atgcccacag agggcaagcc caccaagagc  3600
accaagccct acaagaacgg ccagctgagc aaagtcatga tcatcgagaa cagccacgtc  3660
aagaaggacg acatctggcc cagcggaggc cagatgaccg tgaaggacct gaccgccaag  3720
tacaccgaag gcggaaacgc catcctggaa aacatcagct tcagcatcag ccccggccag  3780
cgcgtgggac tcctgggaag aaccggaagc ggcaagagca ctctgctgag cgccttcctg  3840
agactgctga acaccgaggg cgagatccag atcgacgggg tgagctggga cagcatcacc  3900
ctgcaacaat ggcggaaggc cttcggcgtg atcccccaga aggtgttcat cttcagcggc  3960
acgttccgga agaacctgga cccctacgag cagtggagcg accaagagat ctggaaggtg  4020
gccgacgaag tgggactgag aagcgtgatc gagcagttcc ccggcaagct ggacttcgtg  4080
ctggtggacg gcggctgcgt gctgagccac ggacacaagc agctgatgtg cctggccaga  4140
agcgtgctga gcaaggccaa gatcctgctg ctcgacgagc ccagcgccca cctggacccc  4200
gtgacctacc agatcatccg gcggacactg aagcaggcct tcgccgactg caccgtgatc  4260
```

```
ctgtgcgagc acagaatcga ggccatgctg gaatgccagc agttcctggt gatcgaagag  4320
aacaaagtgc ggcagtacga cagcatccag aagctgctga acgagcggag cctgttcaga  4380
caggccatca gccccagcga cagagtgaag ctgttccccc accggaacag cagcaagtgc  4440
aagagcaagc cccagatcgc cgccctgaaa gaagaaaccg aggaagaggt gcaggacaca  4500
cggctgtgag aattctgcag                                              4520

SEQ ID NO: 2           moltype = DNA  length = 2177
FEATURE                Location/Qualifiers
source                 1..2177
                       mol_type = other DNA
                       organism = synthetic construct
SEQUENCE: 2
gggagaccca agctggctag cgtttaaact tcagcttggc aatccggtac tgttggtaaa  60
gccaccatga tcccagcaag cgccaaggca ccacacaagc agccccacaa gcagagcatc  120
agcatcggca ggggcacaag gaagagggac gaggacagcg gaaccgaagt gggagaggga  180
acagacgagt gggcacagag caaggcaacc gtgcgcccac ccgaccagct ggagctgaca  240
gacgccgagc tgaaggagga gttcaccagg atcctgacag ccaacaaccc acacgccccc  300
cagaacatcg tgcgctacag cttcaaggag ggcacataca agccaatcgg cttcgtgaac  360
cagctggccg tgcactacac ccaagtgggc aacctgatcc ccaaggacag cgacgagggc  420
cggagacagc actacaggga cgagctggtg gcaggaagcc aggagagcgt gaaagtgatc  480
agcgagaccg gcaacctgga ggaggacgag gagccaaagg agctggagac cgagccagga  540
agccagacag acgtgcccgc agcaggagca gcagagaagg tgaccgagga ggagctgatg  600
acacccaagc agccaaagga gcggaagctg accaaccagt tcaacttcag cgagagagcc  660
agccagacat acaacaaccc agtgcgggac agagagtgcc agaccgagcc acccccccaga  720
accaacttca gcgccacagc caaccagtgg gagatctacg acgcctacgt ggaggagctg  780
gagaagcagg agaagaccaa ggagaaggag aaggccaaga caccccgtggc caagaagagc  840
ggcaagatgg ccatgcggaa gctgaccagc atggagagcc agacagacga cctgatcaag  900
ctgagccagg ccgccaagat catggagaga atggtgaacc agaacaccta cgacgacatc  960
gcccaggact tcaagtacta cgacgacgca gcagacgagt acagggacca agtgggcaca  1020
ctgctgcccc tgtggaagtt ccagaacgac aaggccaaga ggctgagcgt gaccgccctg  1080
tgctggaacc caaagtacag ggacctgttc gcagtgggat acggaagcta cgacttcatg  1140
aagcagagca gaggcatgct gctgctgtac agcctgaaga accccagctt ccccgagtac  1200
atgttcagca gcaacagcgg cgtgatgtgc ctggacatcc acgtggacca cccctacctg  1260
gtggccgtgg gccactacga cggcaacgtg gccatctaca acctgaagaa gccccacagc  1320
cagcccagct tctgcagcag cgccaagagc ggcaagcaca gcgaccccgt gtggcaggtg  1380
aagtggcaga aggacgacat ggaccagaac ctgaacttct tcagcgtgag cagcgacggc  1440
aggatcgtga gctggaccct ggtgaagcgc aagctggtgc acatcgacgt gatcaagctg  1500
aaggtggagg gcagcaccac agaggtgcca gagggactgc agctgcaccc agtgggatgc  1560
ggcacagcct tcgacttcca caaggagatc gactacatgt tcctggtggg caccgaggag  1620
ggcaagatct acaagtgcag caagagctac agcagccagt tcctggacac atacgacgcc  1680
cacaacatga gcgtggacac cgtgagctgg aacccctacc acacaaaggt gttcatgagc  1740
tgcagcagcg actggaccgt gaagatctgg gaccacacca tcaagacacc catgttcatc  1800
tacgacctga acagcgccgt gggcgacgtg gcatgggcac catacagcag cacagtgttc  1860
gcagcagtga ccacagacgg caaggcacac atcttcgacc tggccatcaa caagtacgag  1920
gccatctgca accagcccgt ggccgccaag aagaacaggc tgacccacgt gcagttcaac  1980
ctgatccacc ccatcatcat cgtgggcgac gaccggggcc acatcatcag cctgaagctg  2040
agccccaacc tgagaaagat gcccaaggag aagaagggac aggaggtgca gaagggacca  2100
gcagtggaga tcgcaaagct ggacaagctg ctgaacctgg tgcgcgaggt gaagatcaag  2160
acctgagaat tctgcag                                                 2177

SEQ ID NO: 3           moltype = DNA  length = 13875
FEATURE                Location/Qualifiers
source                 1..13875
                       mol_type = other DNA
                       organism = unidentified
SEQUENCE: 3
atgtttagga ttgggaggag acagctctgg aagcatagcg tcactcgagt tttaacgcaa  60
agactgaagg gagagaagga agccaagcgg gctcttttgg atgcgaggca taactactta  120
tttgcaattg tggcttcctg tttggacctg aacaaaaccg aagtggagga tgccattctt  180
gaagggaatc agattgaaag aattgatcaa ctttttgctg ttggaggtct ccgacacctc  240
atgttttact atcaagatgt ggaggaagca gaaacaggac aacttggctc tctaggaggg  300
gtaaatcttg tttctggaaa gattaaaaaa cctaaggtgt tcgtgaccga gggaaacgat  360
gtggctctta ctggggtatg tgtgttcttc atcaggactg acccttccaa agccatcacc  420
cctgacaaca tccaccagga ggtgagtttt aacatgttag atgcggcaga tggaggcctg  480
ctcaacagtg tgagacgttt gctgtcggac atcttcattc ctgctctcag agccacgagc  540
catggctggg gcgagctcga gggccttcag gacgcagcta acattcgcca ggagttcttg  600
agctccctgg aaggctttgt gaacgtcctg tcgggtgcac aggagagtct gaaggagaag  660
gtgaaccttc gaaagtgtga catacttgaa ctgaaaaccc taaaggaacc tacggactac  720
ttgactctag caaataaccc tgagactttg ggaaaaatag aggattgcat gaaagtatgg  780
atcaaacaga cagaacaggt tcttgctgaa aacaatcagc tgctgaagga agcggatgac  840
gttgggccac gagcggagct ggagcactgg aaaaaaagac tctccaagtt taactacctt  900
ttggaacaat tgaaaagccc ggatgtgaag gctgtgctgg cagtgcttgc ggcggccaag  960
tcgaaactgc tgaagacttg gcgggagatg gatattcgaa tcactgatgc aactaatgaa  1020
gcaaaggaca atgtgaaata cttgtataca cttgaaaaat gttgtgaccc tttgtacagc  1080
agtgatcccc tatccatgat ggatgctatt cctacactta taaatgcaat taaaatgatc  1140
tatagtatct ctcattacta taatacctct gagaagatca catctctgtt tgtaaaggtg  1200
acaaatcaga ttatatctgc atgtaaagcc tatattacca ataatggaac cgcttccatc  1260
tggaaccagc cacaggatgt tgttgaagaa aaaatactat ctgcgattaa actgaaacag  1320
gaataccagc tctgctttca caagacaaaa caaaagctta aacaaaatcc aaatgcaaaa  1380
```

-continued

```
caatttgatt ttagcgagat gtatattttt ggaaaattcg aaacttttca ccgacgcctt  1440
gccaagataa tagacatctt tacaaccctc aagacgtatt cagtcctgca agattccaca  1500
attgaagggc tggaagacat ggccactaaa taccagggca ttgtggcaac cataaagaaa  1560
aaggaataca atttcctaga ccagcggaaa atggattttg accaagatta cgaagagttt  1620
tgcaagcaga ctaatgacct tcataacgag ttgcggaagt tcatggatgt tacatttgca  1680
aagattcaaa acacaaatca agctctaaga atgttgaaga aatttgaaag attgaatata  1740
cctaatcttg gtattgatga caaatatcaa cttatccttg agaactatgg ggctgacatt  1800
gatatgattt caaagctgta tacaaagcag aaatacgatc ctcctctggc tcgaaaccag  1860
cctcccatcg ctggaaagat tttgtgggcc cgccagctct tccataggat tcagcagccc  1920
atgcagcttt tccagcagca cccagctgtg ctaagcacgg cagaagccaa acctataatt  1980
cgcagttaca acaggatggc caaggtcctc ctggagtttg aggtcctctt ccacagggcg  2040
tggcttcggc aaattgaaga aattcatgta ggtcttgagg cttcattatt ggtgaaggct  2100
ccaggcacag ggaattgtt tgtaaacttt gaccctcaga tattaatctt atttagagaa  2160
acagagtgca tggcccagat gggtctggaa gtctctccac tggcaacttc cctcttccag  2220
aaacgagata gatacaaaag gaacttcagt aacatgaaga tgatgctagc tgaatatcag  2280
agagtgaagt caaaaaatacc tgctgccatt gagcaattga ttgtccctca cttggccaaa  2340
gtggatgaag ctctccaacc tggcttggct gcactgacct ggacatcact gaatattgag  2400
gcttatttag aaaacacttt tgcaaagatc aaggacctgg agttgctgct tgacagggtc  2460
aatgatttga ttgagttccg cattgatgcc attctagaag aaatgagcag cacgcctctt  2520
tgtcagcttc cccaggagga gccactaacc tgtgaagagt ttctccaaat gacaaaggat  2580
ctttgtgtaa atggtgcaca aatactacat tttaaaagct cattagtgga ggaggcagtc  2640
aatgagcttg taaatatgtt gctggatgtg gaagttttat ctgaagaaga aagtgaaaaa  2700
atatccaatg agaatagtgt taattacaaa aatgaaagtt cagcaaaaag agaagaagga  2760
aattttgaca ccttgacatc atctattaat gccagggcca atgccctgct tttgacgaca  2820
gtcacgagga aaaagaaaga aactgagatg ttaggggaag aagcccgcga gttactctct  2880
catttcaacc atcagaacat ggatgctctt ctgaaagtta caaggaatac actagaggcc  2940
attcgcaaac gtattcattc ctctcacaca attaacttcc gggacagtaa cagtgcctct  3000
aacatgaagc agaacagttt gcccattttc cgggcaagcg tcactctggc cattcccaac  3060
atcgtcatgg cccctgccct ggaagatgta cagcagaccc tgaacaaagc cgtggagtgc  3120
atcatcagtg tccctaaggg ggtcagacag tggagcagtg aactgttgtc caagaaaaag  3180
atacaagaaa gaaaaatggc tgctttgcag agtaatgaag acagtgattc tgatgttgaa  3240
atgggagaaa atgaacttca agataccttg gagatagcat ctgtaaattt acccattccc  3300
gtgcaaacca agaactatta taagaatgtt tctgaaaaca aagagattgt aaaattagtt  3360
tctgtgctta gcacaattat caactccacc aaaaaggaag ttattacatc catggattgc  3420
ttcaaacgct acaatcacat ttggcaaaag ggaaaagaag aagccattaa gacatttatt  3480
acacagagcc ccttgctttc tgaatttgag tcccagattc tctatttcca aaacctagag  3540
caggaaatta atgctgagcc tgaatatgtc tgtgtgggtt ccattgctct gtacacagct  3600
gacttgaagt tcgccctgac tgctgagaca aaggcctgga tggttgtcat tggacgccac  3660
tgtaacaaaa aataccggag tgagatggaa aacattttta tgcttattga agaattcaat  3720
aagaaactaa atcgtccaat taaggaccta gatgatattc ggattgcaat ggcagcgctg  3780
aaagaaataa gggaggagca aatctccatt gactttcaag taggacctat tgaggaatct  3840
tatgccctgc ttaacagata tggacttctg atagcaaggg aagagataga caaagttgat  3900
acactgcact atgcttggga gaagctgctg gcacgtgctg gcgaagtcca gaataaatta  3960
gtctcactgc agcccagttt caagaaagag cttattagtg ctgtggaggt attcctccaa  4020
gattgtcacc agttttatct ggactatgat ttgaatggtc caatggctag cggcttgaag  4080
ccccaggaag ccagtgacag gcttatcatg tttcagaatc aatttgataa tatctatcgg  4140
aaatacatca catatactgg aggagaggag ctttttggcc tgccagctac acagtatcct  4200
cagcttcttg aaataaagaa gcaactaaat cttctacaga aaatatatac tctgtacaac  4260
agtgtcatag aaactgtaaa tagctattat gatattcttt ggtcagaggt gaatattgaa  4320
aaaattaaca atgaactctt agaattccag aacagatgtc gaaagcttcc ccgggccttg  4380
aaggactggc aggctttttt ggacctgaag aagatcattg atgatttcag cgagtgttgc  4440
ccgctgctgg aatacatggc cagtaaagcc atgatggagc ggcactggga aaggataacc  4500
accctcaccg ggcacagtct ggatgtgggg aatgaaagct ttaagttaag aaatatcatg  4560
gaggcacctc ttctgaaata taaagaggaa atagaggaca tctgtatcag tgcggtgaaa  4620
gagagagaca ttgagcaaaa gctgaagcaa gtgattaatg aatgggacaa taaaacattc  4680
accttcggca gctttaaaac ccgtggagag ctcctcttga gaggagacag tacctcggaa  4740
atcatcgcca acatggagga cagcttgatg ttgctgggat ccctactgag caacaggtac  4800
aatatgccat tcaaagccca gattcaaaaa tgggtgcagt acctttccaa ctcaacagac  4860
atcatcgaga gctggatgac ggtgcaaaac ctgtggattt atttagaagc tgtctttgtg  4920
ggaggagaca ttgccaagca gctgcccaag gaagccaagc ggttttctaa catagataaa  4980
tcttgggtga agatcatgac tcgggcacat gaagtgccca gtgtagtcca gtgctgtgtt  5040
ggagatgaga ccctggggca gctgttacca cacttgctgg accagttgga aatatgccag  5100
aaatccctta ctgggtactt ggagaaaaaa cgactgtgct ttcctcggtt tttcttcgtc  5160
tcagatcctg cccttctaga gattctgggg caggcgtcgg actcccacac tatacaggcc  5220
catttgctga atgtgtttga caacattaaa tctgtcaagt tccacgaaaa gatctatgat  5280
cgaattctgt caatttcctc tcaagagggt gagacgattg aattggataa acctgtcatg  5340
gcagagggca atgtggaagt ttggcttaat tctcttttgg aagaatctca gtcctcattg  5400
catcttgtga ttcgccaggc agccgcaaat attcaagaaa caggtttcca actaactgaa  5460
tttctttcat ccttccctgc tcaggttgga ttattaggaa ttcagatgat atggacacgg  5520
gattcagaag aagcccttag aaatgccaag tttgataaaa aaatcatgca gaaaactaat  5580
caggctttcc tggagctact caatacattg atagacgtca ccacgaggga tctgagttcc  5640
acggaacgag tgaaatacga gactctgatt actattcatg tgcaccaaag ggatatcttt  5700
gatgacctgt gtcatatgca tatcaagagt cccatggact ttgagtggct gaaacagtgc  5760
agattttact ttaacgaaga ttctgacaag atgatgattc acatcacaga tgtggcgttc  5820
atataccaga atgaattttt aggctgcact gacaggcttg taataactcc acttacagac  5880
agatgttaca tcacgctggc tcaagctctg ggaatgagca tgggggggagc ccctgctgga  5940
cctgcaggca caggcaaaac agaaaccact aaagacatgg gacgatgcct cgggaaatac  6000
gtcgtggttt tcaattgttc agaccagatg gatttccgag gacttggacg gatttttaag  6060
ggactggcac agtctggatc ctggggttgt tttgatgaat ttaaccgtat tgatctacca  6120
```

-continued

```
gttctctcgg ttgcagccca gcaaatttcc attattctga catgtaaaaa ggagcacaaa  6180
aagtctttta tctttactga tggagataat gtgactatga accctgaatt tgggcttttc  6240
ttaaccatga atcctggcta tgccggacgg caggaactcc ctgaaaactt gaagattaat  6300
ttccgctcag tggccatgat ggtgcctgac cgtcagatta tcataagggt gaagttggct  6360
agttgtggct tcattgacaa cgttgttttg gccaggaagt tttcacgct ctacaaactg   6420
tgtgaggagc agctttctaa gcaggttcat tatgactttg gcctgcgtaa cattctgtca  6480
gttcttcgga ccttgggagc agcaaaaaga gccaatccaa tggatacgga gtccacgatt  6540
gtcatgcgtg tactacggga catgaatctt tctaaactga ttgatgagga tgaacccttg  6600
tttttgagtt tgattgaaga tctctttcca aatattcttc tggacaaggc aggttaccct  6660
gaactggaag cagcaattag tagacaggtt gaagaagctg gtttaatcaa ccatcctcct  6720
tggaaactga aggtcatcca gctattcgaa acgcagagag tgcgacatgg gatgatgact  6780
ctggggccca gtggggctgg gaagaccacc tgcatccaca ccttgatgag agccatgaca  6840
gattgtggaa aaccacatcg ggaaatgagg atgaatccca aagcgattac tgccccacag  6900
atgtttggtc ggctggacgt tgccacaaat gactggactg atgggatatt ttctacgctt  6960
tggaggaaaa cattaagagc aaagaaaggg gaacatatct ggataattct tgatggtcca  7020
gtagatgcca tctggattga aaatctgaat tctgttttgg atgataacaa aactctaacc  7080
cttgccaatg gtgatcggat tcccatggct ccaaaactgca agatcatttt cgagcctcat 7140
aacattgaca atgcttctcc tgccaccgtc tcaagaaatg gaatggtttt catgagctct  7200
tctatccttg attggagtcc tattcttgag ggtttttcta agaaacgctc acctcaagaa  7260
gcagaaattc ttcgtcagct gtacaccgag tctttcccag acttgtatcg cttctgtatc  7320
cagaacttag aatacaagat ggaggtgctg gaggcctttg tcatcacaca gagcattaac  7380
atgcttcaag gcctgattcc tctgaaggag caaggcgggg aggtgagcca ggctcacctg  7440
gggcggctgt tcgtgttcgc gctgctgtgg agcgcggggg cggcgctgga gctggacgga  7500
cggcgccgcc tggagctctg gctgcgctct cggcccacag ggacgctgga gctgccgccg  7560
ccagcggggc ccggggacac cgccttcgac tactatgtgg cgcccgatgg tacatggacg  7620
cactggaaca cgcgtaccca ggaatacctg tatccgtctg ataccacccc agagtatggt  7680
tctattctgg tgccaaatgt tgacaatgtg aggactgact ttctaattca aaccattgct  7740
aaacagggca aggctgtgct attaattggt gaacaaggaa cagccaaaac agtaataatt  7800
aaaggattta tgtcaaaata tgatcctgaa tgtcacatga tcaagagtct gaatttttct  7860
tctgcaacca ccccactgat gttccagagg acgatagaga gctatgtgga taaacgaatg  7920
ggtacaacat atggccctcc tgcgggaaag aagatgactg tttttattga tgatgtgaat  7980
atgccaataa tcaatgagtg gggagatcag gttacgaatg agatagtgcg acagctgatg  8040
gaacaaaatg gattctataa tctagagaag cctggggagt tcaccagcat cgtggacatc  8100
cagtttttgg cagccatgat ccatcctggt ggtggacgca atgacatacc ccaaagactc  8160
aagaggcagt tctctatatt taattgcacg ttgccctctg aagcttctgt ggacaagatc  8220
tttggtgtga ttggggtagg ccactactgt actcagaggg gtttctcaga agaagtgaga  8280
gattctgtga caaaattggt gcctctgaca cgccgactat ggcagatgac caagattaaa  8340
atgcttccta cccctgcaaa attccattat gtgtttaacc tacgagatct ttctcgggtc  8400
tggcagggaa tgctgaacac tacttcagag gtcatcaagg aaccaaatga tctgttaaag  8460
ctgtggaagc atgagtgtaa acgtgttata gctgaccgtt tcacagtgtc cagtgatgtg  8520
acctggtttg ataaggcttt agtaagtttg gtagaggagg agtttggtga agagaaaaaa  8580
ctcttggtgg attgtggaat tgacacatat tttgtggatt tcttgagaga tgcacctgaa  8640
gctgcaggtg aaacatctga agaggctgat gctgaaacac ctaaaattta tgagccaatt  8700
gaatctttta gtcacctaaa agagcgtctg aatatgttcc tgcagctcta taatgagagc  8760
atccgtggcg ccggcatgga catggtgttc tttgcagatg ccatggttca cttagtcaag  8820
atctctcgtg tcattcgtac tcctcaggga aatgccctcc tggtcggggt gggcggatca  8880
ggaaagcaga gcctgacgag gttggcttca ttcattgctg gctacgtttc cttccagatc  8940
actctgacga gatcctacaa cacatcaaat ctgatggaag atctgaaggt tttgtatcga  9000
acagctggtc agcaaggcaa aggaatcact tttatttca cagacaatga gattaaagat   9060
gagtcatttt tggaatatat gaacaatgtt ttatcatcag gtgaggtctc taacctattt  9120
gctcgagatg aaattgatga aattaatagc gacctggcat cagtcatgaa aaaagaattc  9180
cccaggtgcc ttcctaccaa tgagaacctg cacgactact tcatgagtcg ggtccgacag  9240
aaccttcata ttgtgctctg cttctcgcca gtgggggaga aatttcgaaa cagagctttg  9300
aagttccctg ccctaatttc aggatgcaca attgactggt tcagccgatg gcccaaagat  9360
gctttagttg ctgtgtctga acacttcctc acttcctatg atattgactg cagtttggaa  9420
atcaagaagg aggtggtcca atgcatgggc tccttccagg atggggtggc tgagaagtgt  9480
gttgattatt ttcagagatt ccgacgttct acccacgtga cgcccaaatc atacctctcc  9540
tttattcagg gctataagtt catatatgga gaaaagcatg tggaggtgcg gaccctggcc  9600
aacagaatga atactggatt ggaaaagctc aaagaagctt cagagtctgt tgcagccttg  9660
agtaaagaac tggaagcgaa agaaaaggag ctacaagtgg ccaacgataa agccgacatg  9720
gtcttaaaag aagtgacaat gaaagcacag gctgctgaaa aggtcaaggc tgaggtacag  9780
aaggtgaagg acagggccca ggccattgtg gacagcatct ctaaagacaa agccattgct  9840
gaagaaaaac tggaagcagc aaaaccagct ttagaagagg cagaagctgc attgcagacc  9900
atcaggcctt cggacatcgc cactgttcgc acgttgggcc gcccccctca cctcatcatg  9960
cggatcatgg attgcgtact gctgctgttt caaaggaaag tcagtgctgt gaaaattgac  10020
ctggaaaaaa gctgtaccat gccctcctgg caggaatcct taaaattgat gactgcaggg  10080
aactttttac agaacttaca gcaattccca aaagacacaa tcaatgaaga ggtgatagaa  10140
tttttgagtc cttactttga aatgcctgac tataacatcg aaactgctaa acgcgtatgt  10200
ggaaatgtag ctggtctttg ttcctggacg aaagctatgg cttccttctt ttctataaac  10260
aaagaagtac tgcctctgaa ggccaacttg gtggtgcaag agaatcgcca tctcctggcc  10320
atgcaggatc tgcagaaagc ccaggccgag ttggatgaca agcaggcgga acttgacgtg  10380
gtgcaggctg agtatgaaca ggccatgact gaaaagcaga ccttgcttga agatgcagag  10440
cgatgcagac acaagatgca gacagcttcc acgctcatca gtggcttggc aggtgaaaaa  10500
gaaagatgga cagagcaaag ccaagagttt gctgcacaaa ctaaaagact tgtaggggat  10560
gtactgttgg ctacagcttt tctatcttat tctggtccat ttaaccaaga gtttcgtgat  10620
cttctgttaa atgactggcg gaaggaaatg aaagcccgga aaattccatt tggaaagaac  10680
ctaaatctca gtgagatgtt gattgatgct cctactatta gtgaatggaa cctccaaggt  10740
ctgccaaatg atgacttgtc cattcaaaat ggaattattg tcacgaaggc atctcgttac  10800
cctttgttaa ttgatccaca gactcaaggc aagatctgga ttaaaaataa agaaagccga  10860
```

-continued

```
aatgaactcc agatcacgtc tttaaatcac aagtacttca gaaaccacct ggaagacagc  10920
ctttctcttg gaaggccttt gcttattgaa gatgttggag aggaactaga tccagcacta  10980
gataatgttt tggaaagaaa cttcattaaa actgggtcta cctttaaggt gaaagttggt  11040
gacaaggaag tagatgtgtt ggatggcttt agactctaca ttaccaccaa attgcctaac  11100
ccagcctaca cccctgagat aagtgcccgt acctccatca ttgacttcac tgtcaccatg  11160
aaaggtctag aagatcagtt actggggagg gtcattctca cagagaagca ggaattggag  11220
aaagaaagaa ctcatctgat ggaagatgta actgcaaaca aaagaaggat gaaggaacta  11280
gaagataact tgctttaccg cctgacaagt acccaggggt ccctggtaga agatgaaagt  11340
ctcattgtcg tgctgagtaa cacaaaaagg acagccgagg aggtgacaca gaagctagaa  11400
atttctgctg agacagaagt tcaaattaac tcagcccggg aggaatacag acctgtggct  11460
acgcggggca gcatcctcta cttcctcatt actgagatgc gcttggttaa tgagatgtat  11520
cagacttcgc ttcgccagtt tctgggctta tttgaccttt ccttagccag gtctgtcaag  11580
agcccgatta caagcaagag gattgctaat atcatcgagc acatgaccta cgaggtttat  11640
aagtatgctg cccgagggct gtacgaggag cacaaattcc tgttcacctt gttgcttacc  11700
ctaaagattg acatccagag gaaccgagtc aagcatgaag agtttctcac tcttattaaa  11760
ggaggtgcct cattagacct taaagcttgt cctccaaaac catcaaaatg gatcctggac  11820
ataacatggc tgaatttggt ggaacttagc aaactcagac agttttcaga tgtccttgac  11880
cagatatcga gaaatgagaa aatgtggaaa atttggtttg ataaggaaaa cccggaggag  11940
gaacctcttc caaatgccta tgataaatct cttgactgct tcagacgtct tctccttatt  12000
agatcctggt gtcctgacag aaccatcgcc caggcccgca agtacatcgt ggactccatg  12060
ggagaaaaat atgccgaagg tgttatttta gacttggaga agacgtggga ggaatctgat  12120
ccacggacgc cactcatctg tctcctgtct atgggctcag accccacaga ttccatcatt  12180
gccttgggga agagattaaa aatagaaacc cgttatgtgt ccatgggcca gggccaggaa  12240
gtccatgctc ggaagctctt gcagcagacc atggcgaacg gaggatgggc acttctgcag  12300
aactgccatc tgggacttga tttcatggat gagctgatgg acataatcat agaaactgag  12360
cttgtacatg atgcgttccg cctctggatg accaccgagg ctcataagca gtttcccatt  12420
acactccttc agatgtccat taaatttgcc aacgatcctc cacaaggact ccgggcagga  12480
ctgaaaagaa catatagtgg tgtcagccaa gacctgctgg acgtgagctc tgggtcccag  12540
tggaagccca tgctgtacgc agtggctttc ctgcactcca ctgtccagga gaggcgcaag  12600
ttcggtgccc tggggtggaa tatcccctac gaatttaacc aagcggactt taatgccact  12660
gtgcagttca tccaaaacca cttggatgac atggatgtca aaaagggtgt ctcctggacc  12720
accatccgct acatgatagg agagattcaa tatggaggca gagtcactga cgactatgat  12780
aagagattgt tgaacacatt tgctaaggtt tggttcagtg aaaatatgtt tggaccagat  12840
ttcagttttt accaaggata caatattcca aaatgcagca cagtggataa ctatcttcag  12900
tatatccaga gtttgcctgc ctatgacagc cctgaggtgt ttgggctgca ccccaatgct  12960
gacatcacct accagagcaa gctggccaag gacgtgctgg acaccatcct aggcatccaa  13020
cccaaggaca cctctggtgg aggggatgag acccgggagg cggtggtggc ccggctggct  13080
gatgatatgc tggagaagct gcccccagac tatgtcccct ttgaagtaaa agagaggctg  13140
cagaagatgg ggccattcca gcctatgaac attttcctca ggcaggaaat agacagaatg  13200
caaagggtac tcagccttgt ccgcagcacc ctcactgagc tgaaacttgc tattgatggc  13260
accatcatca tgagcgaaaa tctgcgagat gcattggatt gcatgtttga tgctagaatc  13320
cctgcttggt ggaaaaaagc ttcttggatt tctagtacac tgggtttctg gtttactgaa  13380
cttatagaaa gaaacagcca gtttacctcg tgggttttca atggccgacc tcactgcttt  13440
tggatgacgg gtttttttaa cccccaggga tttttaactg caatgcgaca ggaaataact  13500
cgggccaaca aaggctgggc tctggacaat atggtgcttt gcaatgaagt caccaaatgg  13560
atgaaggacg acatttctgc ccctcccaca gagggtgtct atgtctatgg cttatatctt  13620
gaaggtgctg gctgggacaa gaggaacatg aaactcattg aatcaaagcc aaaagtgctc  13680
tttgagttga tgcctgtcat aaggatttat gcagaaaaca atactttacg agatcctcgg  13740
ttttactcct gtcccatcta taagaagcca gttcgaacgg acttgaacta cattgccgct  13800
gtggatctca ggacagccca gacccctgaa cactgggtgc tccgtggggt tgcccttctg  13860
tgtgatgtca agtaa                                                  13875

SEQ ID NO: 4            moltype = DNA  length = 1257
FEATURE                 Location/Qualifiers
source                  1..1257
                        mol_type = other DNA
                        organism = unidentified
SEQUENCE: 4
atgccgtctt ctgtctcgtg gggcatcctc ctgctggcag gcctgtgctg cctggtccct  60
gtctccctgg ctgaggatcc ccagggagat gctgcccaga agacagatac atcccaccat  120
gatcaggatc acccaacctt caacaagatc acccccaacc tggctgagtt cgccttcagc  180
ctataccgcc agctggcaca ccagtccaac agcaccaata tcttcttctc cccagtgagc  240
atcgctacag cctttgcaat gctctccctg gggaccaagg ctgacactca cgatgaaatc  300
ctggagggcc tgaatttcaa cctcacggag attccggagg ctcagatcca tgaaggcttc  360
caggaactcc tccgtaccct caaccagcca gacagccagc tccagctgac caccggcaat  420
ggcctgttcc tcagcgaggg cctgaagcta gtggataagt tttggagga tgttaaaaag  480
ttgtaccact cagaagcctt cactgtcaac ttcggggaca ccgaagaggc caagaaacag  540
atcaacgatt acgtggagaa gggtactcaa gggaaaattg tggatttggt caaggagctt  600
gacagagaca cagtttttgc tctggtgaat tacatcttct ttaaaggcaa atgggagaga  660
ccctttgaag tcaaggacac cgaggaagag gacttccacg tggaccaggt gaccaccgtg  720
aaggtgccta tgatgaagcg tttaggcatg tttaacatcc agcactgtaa gaagctgtcc  780
agctgggtgc tgctgatgaa atacctgggc aatgccaccg ccatcttctt cctgcctgat  840
gaggggaaac tacagcacct ggaaaatgaa ctcacccacg atatcatcac caagttcctg  900
gaaaatgaag acagaaggtc tgccagctta catttaccca aactgtccat tactggaacc  960
tatgatctga agagcgtcct gggtcaactg ggcatcacta aggtcttcag caatggggct  1020
gacctctccg gggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tccccccga ggtcaagttc aacaaaccct ttgtcttctt aatgattgaa  1200
caaaatacca agtctcccct cttcatggga aaagtggtga atcccaccca aaaataa  1257
```

-continued

SEQ ID NO: 5 moltype = DNA length = 3135
FEATURE Location/Qualifiers
source 1..3135
mol_type = other DNA
organism = unidentified
SEQUENCE: 5
atgggtgtgg ctctgaggaa attgacgcag tggactgctg ccggacatgg aactggaatc 60
ctcgaaatca cccctctaaa tgaagcgata ttgaaagaaa ttattgtgtt tgtggagagt 120
tttatctata aacatcctca agaggcaaaa tttgtttttg tggaaccact tgaatggaac 180
acaagtttgg cgccctcagc atttgaatca ggttatgttg tcagtgaaac aacagtcaaa 240
tcagaagaag ttgataaaaa tggacagcct ttgctatttc tctctgtacc acaaattaaa 300
attaggagct ttgggcagct gtcacgcttg ttacttattg ccaaaactgg gaagttgaag 360
gaagcccaag catgtgttga agctaacaga gaccccatag taaaaatcct gggctctgat 420
tataatacaa tgaaagaaaa ctcaattgca ttaaatattc ttggcaaaat taccagagat 480
gatgatcctg aaagtgaaat taagatgaag attgctatgc tgcttaagca attggatctg 540
cacctcctca atcattctct aaaacatatt tcattagaaa taagtttaag tcccatgacg 600
gtgaagaagg atatagaact gctcaaacgt ttctcaggaa aaggaaacca aacagtcttg 660
gaatctattg aatatacctc agattatgaa ttttcaaatg gatgtcgagc ccccaccgtgg 720
agacaaattc gtggggaaat ttgttatgtg ctggtgaaac ctcacgatgg tgagactctg 780
tgcattactt gcagtgcagg aggagtattt ttaaatggtg gcaaaacaga tgatgaaggg 840
gacgttaatt atgagagaaa aggttcaatt tataaaaacc ttgtcacatt tttaagagaa 900
aaatcaccaa aattttcaga aaatatgtct aaattgggaa ttagcttcag tgaagaccag 960
caaaaggaaa aggatcagct tggcaaagcc cccaagaagg aagaagcagc tgccctccgc 1020
aaagacattt ctggttcaga caaaaggtca ctggagaaga accaaattaa tttttggagg 1080
aatcaaatga ccaagagatg ggaaccaagc ttaaactgga agaccactgt taattacaaa 1140
ggcaaaggct cagcaaaaga aatccaagag gacaaacaca caggaaaact tgaaaaacca 1200
agaccatctg tttcacacgg aagagcacaa ttacttcgga agagtgctga aaagattgag 1260
gaaactgtta gcgatagctc ctcagaaagt gaggaagatg aagaaccacc tgaccatcgt 1320
caggaagcaa gtgcagattt gccatcagaa tattggcaaa ttcagaagct ggtgaaatat 1380
ttaaagggag gaaatcaaac agctacagtg attgcgttgt gttcaatgag ggatttcagc 1440
ttagctcaag aaacctgcca gttggccatc agagatgttg gaggcctgga agtgctgata 1500
aatttgcttg aaaccgatga agtcaaatgt aagattggtt cattaaaaat actgaaggaa 1560
atcagtcata atcctcaaat cagacagaat attgttgacc ttgggggctt accaattatg 1620
gtgaatatac ttgattctcc acacaagagt ctaaaatgtt tggcagccga gactatcgcg 1680
aatgttgcca agtttaaaag agcacggcgg gtggtgaggc agcacggggg tatcaccaaa 1740
ctggttgctc tactagactg tgcacatgat tccacaaaac ctgcccaatc gagtctgtat 1800
gaggccagag acgtggaagt ggctcgctgt ggggcactgg ccctgtggag ctgcagtaag 1860
agtcatacga ataaagaagc catccgcaaa gctgggggca ttcctctgtt ggctcggctg 1920
ctgaagactt ctcatgaaaa catgctaatt ccagtggtgg ggacattgca agagtgtgca 1980
tcagaggaaa actaccgggc tgcaatcaaa gcagaaagga tcattgaaaa ccttgtcaag 2040
aacctaaata gtgagaatga gcagctgcag gagcactgcg ccatggccat ttaccagtgt 2100
gctgaagata aggaaacccg ggacctcgtt aggctgcacg gaggacttaa gcccttggcc 2160
agtctactca ataacactga caataaagag cggttagctg ctgtcacagg ggctatatgg 2220
aaatgttcca tcagcaaaga gaatgttacc aagtttcggg aatacaaagc cattgaaacc 2280
ttggtgggac ttctaacaga tcagcctgaa gaagtacttg tgaatgtggt tggggccttg 2340
ggagaatgct gccaagaacg tgaaaaccga gtcattgtcc ggaaatgtgg tggcattcaa 2400
ccacttgtga acctccttgt tggaataaac caagctcttc ttgtgaatgt tacaaaagca 2460
gttggtgctt gtgcagtaga acctgaaagt atgatgataa ttgatcgctt agatggagtt 2520
cgtttgttgt ggtccctgct gaaaaatcct cacccagacg tgaaggccag cgcagcatgg 2580
gcactctgtc catgcatcaa aaatgcaaag gatgctgggg aaatggttcg ttcctttgtt 2640
ggtggtttgg aacttattgt caatttactg aaatcagata acaaagaagt tctggcaagt 2700
gtatgtgctg ccattaccaa catagcaaaa gatcaagaaa atttagctgt tatcacagat 2760
catggagttg ttcctttatt gtccaaactg gcaaatacaa ataacaataa attgagacat 2820
catctagcag aagctatttc acgttgctgt atgtggggca ggaatagagt ggccttcggt 2880
gagcacaaag cagtggctcc actagtgcgt tatctgaaat caaatgacac caacgtgcat 2940
cgggcgacag ctcaggcctt gtaccaactc tcagaagacg ccgataactg catcaccatg 3000
catgagaatg gtgcagtaaa gcttctactg gatatggttg ggtcccctga ccaggatctc 3060
caggaagctg cagctggttg tatatccaat atccgcaggc tggctcttgc tacagagaag 3120
gcaagataca cttga 3135

SEQ ID NO: 6 moltype = DNA length = 2178
FEATURE Location/Qualifiers
source 1..2178
mol_type = other DNA
organism = unidentified
SEQUENCE: 6
atgcaccctg agccctcgga gcctgcgaca ggtggtgcag cagagctgga ttgcgcgcag 60
gagcccggcg tggaggagtc tgcgggtgac cacgggagcg caggccgagg gggctgcaag 120
gaagaaatta atgatcctaa ggaaatatgt gtgggttctt ctgacacatc ctaccacagc 180
cagcagaaac agagtggtga taatgggtca ggtggtcact tcgcacaccc aagagaagac 240
agggaagatc ggggccccag aatgactaaa agttccctgc aaaaactctg caagcagcac 300
aagctttata ttaccccagc attgaatgat acgctgtatt tacactttaa aggttttgat 360
cgcattgaga acctggaaga gtacacaggg ctgcgctgtc tctggctgca gagcaatgga 420
atacagaaaa tcgaaaacct ggaggcccaa actgagttgc gttgcctctt cttgcaaatg 480
aacttgctcc gtaaaattga gaacctggaa cctctgcaga aactggatgc tcttaacctc 540
agcaacaatt acatcaagac cattgaaaac ctctcctgcc tcccagtcct gaacacattg 600
cagatggccc acaatcacct ggagaccgtg gaggacattc agcatctaca agagtgtttg 660
aggctttgtg tccttgacct ttcgcacaac aagctgagtg acccggagat cctgagcatt 720

-continued

```
ctggaaagca tgcccgattt gcgtgtactg aatttgatgg gaaacccggt tatcagacag  780
attcctaatt acagaaggac agtcactgta cgactaaagc acttaacata cctggatgat  840
agaccagtgt ttccaaagga cagagcttgt gcggaggcct gggctagggg agggtacgca  900
gctgaaaagg aggagagaca gcagtgggag agcagggagc ggaagaagat cacagacagc  960
attgaagcct tggccatgat caagcagcgg gcagaggaga ggaaaagaca gagagagagt  1020
caagagagag gggagatgac atcttcagat gatggtgaga atgtgcccgc cagtgcggaa  1080
ggcaaggagg agcctcccgg ggacagagaa acaaggcaga agatggagct atttgttaag  1140
gaaagctttg aggccaagga cgagctctgc ccggaaaagc caagtggaga ggagccgcct  1200
gtggaggcta aaagagagga tggaggtcca gagccagagg ggaccctccc agctgagacc  1260
ctgctactgt cgtcacctgt ggaggttaaa ggagaggacg gagatggaga gccagagggg  1320
accctcccag ctgaggcccc accacccccg ccacctgtgg aggttaaagg agaggatgga  1380
gatcaagagc cagaggggac cctcccagct gagaccctgc tactgtcacc gcctgtgaag  1440
gttaaaggag aggatggaga tcgagagcca gaggggaccc tcccagctga ggccccacca  1500
ccaccgcccc tgggagctgc cagggaagaa ccgactcccc aggctgtggc cactgagggt  1560
gtattcgtta cagaacttga tggaacgaga acggaagatt tagaaaccat tagactggag  1620
acaaaggaga cattctgcat tgatgaccta cctgacttgg aagatgatga tgaaacaggc  1680
aaatctctgg aagaccagaa tatgtgcttt ccgaagattg aggtcatctc gagcttgagt  1740
gatgacagtg accctgaact ggactacacg tcactccctg tgctggaaaa cctccccaca  1800
gacactctgt caaatatatt tgcagtctct aaagacacct caaaggcggc tcgggtgccc  1860
ttcacagaca tctttaaaaa agaagctaag agggacttgg aaatccgaaa acaagacacc  1920
aagtccccaa gacccctgat ccaggagctc agcgacgagg acccctctgg ccagctactg  1980
atgcccccca cctgccaaag agatgctgca ccactcactt ccagtggaga cagggacagc  2040
gacttccttg cagcctcttc tccggtgccg actgagagcg ccgccacacc cccagagacg  2100
tgtgtcggag ttgcccagcc cagccaagct ctgcccacgt gggacctcac tgcattccca  2160
gcaccgaaag catcatag                                                2178
```

```
SEQ ID NO: 7            moltype = DNA  length = 2514
FEATURE                 Location/Qualifiers
source                  1..2514
                        mol_type = other DNA
                        organism = unidentified
SEQUENCE: 7
atggccaaag cggcggcctc ctcgtcgctg gaggacttgg acctgagcgg agaggaggtc  60
cagcggctca cctccgcctt ccaggacccg gagttccggc gaatgttctc ccagtacgcc  120
gaggagctca ccgacccgga gaaccggcgg cgctacgagg cggagatcac cgcgctagag  180
cgtgagcgcg gggtggaagt gcggttcgtg cacccggagc ccggccatgt gctgcgcacc  240
agcctggacg gggcgcggcg ctgctttgtg aatgtctgca gcaacgcgtt ggtgggcgcg  300
cccagcagcc ggcccggctc cggtggcgac cggggcgcag ctcctggcag ccactggtcc  360
ctgccctaca gcctggcgcc cggccgcgag tacgcggggc gcagcagcag ccgctacatg  420
gtctacgacg tggtcttcca tccagacgcg cttgcgctgg cccggcggca cgagggcttc  480
cgccagatgc tggacgccac ggccctggag gccgtcgaga agcagttcgg cgtgaagctg  540
gaccgcagga atgccaagac cctgaaggcc aagtataagg ggaccccaga ggctgcggtg  600
ctgcgcacgc ccctgcccgg ggtcatcccc gcaaggcctg acggggagcc gaagggtcct  660
ctcccggact tcccctaccc ttaccagtac ccggcagccc ccgggccccg ggcgccctcc  720
cctccggaag cggccttgca gcccgccccc accgagcctc gctacagcgt ggtgcagcgc  780
caccacgtgg acctccagga ttaccgctgc tccagggact cagccccgag ccccgtgccc  840
catgagctgg tgatcaccat cgaactgccg ctgttgcgct cggccgagca ggcggcgctg  900
gaggtaacga gaaagctgct gtgcctcgac tcgaggaaac ctgactaccg gctgcggctc  960
tcgctcccgt acccagtgga cgatggccgc ggcaaggcac aattcaacaa ggcccggcgg  1020
cagctggtgg ttacgctgcc agtggtgctg ccggccgcgc gccgggagcc cgctgtcgcc  1080
gtcgccgccg ccgcgccgga agagtccgcg gaccggtccg gaactgacgg ccaggcctgc  1140
gcttccgctc gcgagggggga ggcgggaccc gcgaggagtc gcgcggagga cggaggccac  1200
gatacctgcg tggctggggc tgcgggctcc ggggtcacca ccctgggcga cccggaggtg  1260
gcgcctccgc cggccgcagc tggagaggag cgtgtcccca agccggggga gcaggacttg  1320
agcaggcacg cggggtcacc gccgggcagc gtggaggagc catctcctgg aggagaaaac  1380
tcacctggtg gcggaggctc cccttgtttg tcctcccgga gcctggcgtg gggttcttct  1440
gcgggaagag agagtgcgcg cggagatagc agtgtggaaa cacgcgagga gtcggagggc  1500
acgggcggcc agcgctcagc ctgcgccatg ggtggtcccg ggaccaagag cggggagcct  1560
ttgtgtcctc cgttactgtg taatcaggac aaagaaacct tgactctgct cattcaggtg  1620
cctcggatcc agccgcaaag tcttcaagga gatttgaatc ccctctggta caaattacgc  1680
ttctccgcac aagacttagt ttattccttc tttttgcaat ttgctccaga gaataaattg  1740
agtaccacag aacctgtgat tagcatttct tcaaacaatg cagtgataga actggcaaaa  1800
tctccagaga gccatggaca ttggagagag tggtattatg gtgtaaacaa cgattctttg  1860
gaggaaaggt tatttgtcaa tgaagaaaat gttaatgagt ttcttgaaga ggtcctgagc  1920
tctccattca aacagtctat gtccttgacc ccaccattaa ttgaagttct tcaagttact  1980
gataataaga ttcaaattaa tgcaaagttg caagaatgta gtaactctga tcagctacaa  2040
ggaaaggagg aaagagtaaa tgaagaaagt catctaactg aaaaggaata tatagaacat  2100
tgtaacaccc ctacaactga ttctgattca tctatagcag ttaaagcact acaaatagat  2160
agctttggtt tagttacatg ctttcaacaa gagtctcttg atgtttctca aatgatactt  2220
ggaaaatctc agcaacctga gtcaaaaatg caatctgaat ttataaaaga aaaaagtgct  2280
acttgttcaa atgaggaaaa agataactta aacgagtcag taataactga agagaaagaa  2340
acagatggag atcacctatc ttcattactg aacaaaacta cggttcacaa tatacctgga  2400
ttcgacagca taaaagaaac caatatgcag gatggtagtg tgcaggtcat taaagatcat  2460
gtgaccaatt gtgcattcag ttttcagaat tctttgctat atgatttgga ttaa        2514

SEQ ID NO: 8            moltype = DNA  length = 1263
FEATURE                 Location/Qualifiers
source                  1..1263
                        mol_type = other DNA
```

-continued

```
                        organism = unidentified
SEQUENCE: 8
atgcctcttc aggttagcga ttacagctgg cagcagacga agactgcggt ctttctgtct  60
ctgcccctca aaggcgtgtg cgtcagagac acggacgtgt tctgcacgga aaactatctg  120
aaggtcaact ttcctccatt tttatttgag gcatttcttt atgctcccat agacgatgag  180
agcagcaaag caaagattgg gaatgacacc attgtcttca ccttgtataa aaaagaagcg  240
gccatgtggg agaccctttc tgtgacgggt gttgacaaag agatgatgca aagaattaga  300
gaaaaatcta ttttacaagc acaagagaga gcaaaagaag ctacagaagc aaaagctgca  360
gcaaagcggg aagatcaaaa atacgcacta agtgtcatga tgaagattga agaagaagag  420
aggaaaaaaa tagaagatat gaaagaaaat gaacggataa aagccactaa agcattggaa  480
gcctggaaag aatatcaaag aaaagctgag gagcaaaaaa aaattcagag agaagagaaa  540
ttatgtcaaa aagaaaagca aattaaagaa gaaagaaaaa aaataaaata taagagtctt  600
actagaaatt tggcatctag aaatcttgct ccaaaaggga gaaattcaga aaatatattt  660
actgagaagt taaaggaaga cagtattcct gctcctcgct ctgttggcag tattaaaatc  720
aactttaccc ctcgagtatt cccaacagct cttcgtgaat cacaagtagc agaagaggag  780
gagtggctac acaaacaagc tgaggcacga agagcaatga atactgacat agctgaactt  840
tgcgatttaa aagaagaaga aaagaaccca gaatggttga aggataaagg aaacaaattg  900
tttgcaacgg aaaactattt ggcagctatc aatgcatata atttagccat aagactaaat  960
aataagatgc cactattgta tttgaaccgg gctgcttgcc acctaaaact aaaaaactta  1020
cacaaggcta ttgaagattc ttctaaggca ctggaattat tgatgccacc tgttacagac  1080
aatgctaatg caagaatgaa ggcacatgta cgacgtggaa cagcattctg tcaactagaa  1140
ttgtatgtag aaggcctaca ggattatgaa gcggcactta agattgatcc atccaacaaa  1200
attgtacaaa ttgatgctga gaagattcgg aatgtaattc aaggaacaga actaaaatct  1260
taa                                                                1263

SEQ ID NO: 9            moltype = DNA  length = 1323
FEATURE                 Location/Qualifiers
source                  1..1323
                        mol_type = other DNA
                        organism = unidentified
SEQUENCE: 9
atgggagacc tggaactgct gctgcccggg gaagctgaag tgctggtgcg gggtctgcgc  60
agcttcccgc tacgcgagat gggctccgaa gggtggaacc agcagcatga gaacctggag  120
aagctgaaca tgcaagccat cctcgatgcc acagtcagcc agggcgagcc cattcaggag  180
ctgctggtca cccatgggaa ggtcccaaca ctggtggagg agctgatcgc agtggagatg  240
tggaagcaga aggtgttccc tgtgttctgc agggtggagg acttcaagcc ccagaacacc  300
ttccccatct acatggtggt gcaccacgag gcctccatca tcaacctctt ggagacagtg  360
ttcttccaca aggaggtgtg tgagtcagca gaagacactg tcttggactt ggtagactat  420
tgccaccgca aactgaccct gctggtggcc cagagtggct gtggtggccc ccctgagggg  480
gagggatccc aggacagcaa ccccatgcag gagctgcaga agcaggcaga gctgatggaa  540
tttgagattg cactgaaggc cctctcagta ctacgctaca tcacagactg tgtggacagc  600
ctctctctca gcaccttgag ccgtatgctt agcacacaca acctgccctg cctcctggtg  660
gaactgctgg agcatagtcc ctggagccgg cgggaaggag gcaagctgca gcagttcgag  720
ggcagccgtt ggcatactgt ggccccctca gagcagcaaa agctgagcaa gttggacggg  780
caagtgtgga tcgccctgta caacctgctg ctaagccctg aggctcaggc gcgctactgc  840
ctcacaagtt ttgccaaggg acggctactc aagcttcggg ccttcctcac agacacactg  900
ctggaccagc tgcccaacct ggcccacttg cagagtttcc tggcccatct gaccctaact  960
gaaacccagc ctcctaagaa ggacctggtg ttggaacaga tcccagaaat ctgggagcgg  1020
ctggagcgag aaaacagagg caagtggcag gcaattgcca agcaccagct ccagcatgtg  1080
ttcagcccct cagagcagga cctgcggctg caggcgcgaa ggtgggctga gacctacagg  1140
ctggatgtgc tagaggcagt ggctccagag cggcccccgct gtgcttactg cagtgcagag  1200
gcttctaagc gctgctcacg atgccagaat gagtggtatt gctgcaggga gtgccaagtc  1260
aagcactggg aaaagcatgg aaagacttgt gtcctggcag cccagggtga cagagccaaa  1320
tga                                                                1323

SEQ ID NO: 10           moltype = DNA  length = 2826
FEATURE                 Location/Qualifiers
source                  1..2826
                        mol_type = other DNA
                        organism = unidentified
SEQUENCE: 10
atgagtagcg aattcctggc tgagctgcac tgggaggatg ggttcgccat cccggtggcg  60
aacgaggaga acaagctact ggaagatcag ttgtcaaagc tgaaggatga aagagcaagc  120
ttgcaagatg agttacgtga gtatgaagag cgaattaatt ctatgacttc tcacttcaaa  180
aatgttaagc aagagctctc aattacacag tctctttgca aagcaaggga gcgtgagact  240
gaaagtgaag aacattttaa ggccattgct caaagagaat tgggacgagt gaaagatgaa  300
attcaacggc tggaaaatga gatggcttca atactggaaa agaaaagtga taaagaaaat  360
ggcatattta aagccactca aaaattggat ggtttgaaat gtcaaatgaa ctgggaccag  420
caagcattgg aggcctggtt agaagaatca gctcataaag atagtgatgc tctcactctc  480
cagaagtatg cacaacaaga tgataataaa atcagggcac tgactctgca attagaaaga  540
ctaactttgg aatgtaatca gaaaagaaag atacttgaca acgaacttac agagactata  600
agcgcacagt tagaattgga taaagcagca caagattttc gtaagattca taatgaaaga  660
caagaactca ttaaacaatg ggagaacaca atagaacaga tgcagaagag ggatggagac  720
atagataact gtgctttgga attagcaagg ataaagcagg aaacgagaga aaaagaaaat  780
ttggttaaag aaaagatcaa gtttttggaa agtgagattg ggaataacac agagtttgag  840
aaaagaattt ctgtggctga tcgtaaactt ttaaaatgta gaacggcata tcaggaccat  900
gaaactagta gaattcagct gaagggtgag ctggattctt taaaagccac tgtgaataga  960
acttccagtg atttagaagc tctgaggaaa aatatttcca agataaagaa ggacattcat  1020
gaagaaacag caaggttaca aaaaactaaa aatcataatg agataataca aacaaaatta  1080
```

```
aaggagataa ctgagaaaac catgtctgta gaagagaaag ctactaattt ggaagatatg  1140
ctaaaggagg aggaaaaaga tgtgaaggaa gtagatgttc aactgaacct cataaaaggt  1200
gtgctgttta agaaagctca ggagttacag actgagacaa tgaaagaaaa agctgtttta  1260
tcagaaattg aaggaactcg ttcctctctg aaacatctca accatcagtt acaaaaactg  1320
gattttgaaa ccttgaagca gcaagaaatt atgtacagcc aggattttca cattcaacaa  1380
gtggaacgga gaatgtcacg gttaaaggga gaaattaatt cagaagaaaa acaagcgctt  1440
gaagcaaaaa ttgttgaact taggaagtct ttggaagaga aaaaatctac atgtggcctt  1500
ttggaaacac agatcaagaa gcttcataat gatctttatt ttatcaagaa ggcacatagt  1560
aaaaacagtg atgaaaaaca gtcccttatg accaaaataa atgaactaaa ccttttcatc  1620
gacagatcag agaaagaact tgataaagcc aaaggtttta agcaggattt gatgatagag  1680
gacaatcttt taaaacttga agttaagcgt actcgagaaa tgcttcacag taaggcagaa  1740
gaagttcttt ccctagaaaa aagaaaacag caattataca cagcaatgga agagcgaact  1800
gaagaaatca aggttcataa aacaatgctt gcgtcacaaa taagatatgt tgatcaagaa  1860
cgggaaaaca taagcactga gtttcgcgag cggctaagta aaattgagaa gctgaagaat  1920
agatatgaaa ttctgactgt tgttatgctg cctcctgaag gagaagagga gaaaacacag  1980
gcctattatg taataaaggc tgctcaagaa aaagaagaac ttcaaaggga aggtgactgt  2040
ttggatgcca agatcaacaa agctgaaaaa gaaatctacg ctctagaaaa taccccttcaa  2100
gtgctgaaca gctgtaacaa caattataag caatctttta aaaaagtgac tccatctagt  2160
gatgagtatg agctaaaaat tcaactagaa gaacaaaaaa gagctgttga tgaaaaatac  2220
agatacaaac aaagacaaat cagagaactt caagaagaca tccagagcat ggaaaataca  2280
ttagatgtta tagaacattt ggcaaataat gttaaagaaa agttatcaga gaagcaggct  2340
tattcatttc aactaagtaa agaaacggag gagcagaagc caaaattaga aagagtgacc  2400
aaacagtgtg caaaactcac aaaggaaatc cgtcttttga aagacacaaa agatgaaaca  2460
atggaagaac aagacatcaa acttcgtgaa atgaaacagt ttcacaaagt tattgatgaa  2520
atgttagttg atatcataga agaaaatact gagatccgta ttatccttca aacatacttt  2580
caacagagtg ggttagaact acctacagct agcacaaaag gcagtcgtca gagctctaga  2640
tctccttcac atacttcact atcagcaagg tcatctagga gtacaagtac atctacttct  2700
cagtcttcaa ttaaagtact ggagcttaaa ttcccggcct cctcttcact agtaggcagc  2760
ccttctaggc catctagtgc tagtagtagc tctagtaatg ttaagagcaa aaagagcagc  2820
aaataa                                                             2826
```

```
SEQ ID NO: 11          moltype = DNA  length = 3428
FEATURE                Location/Qualifiers
source                 1..3428
                       mol_type = other DNA
                       organism = unidentified
SEQUENCE: 11
atggcggaac cgggcggcgc ggcgggccgg tcccatccgg aagatggatc ggcttctgag  60
ggagagaagg aagggaataa tgaaagccac atggtgtcac caccagagaa ggatgatgcc  120
agaaaggtga agaagctgtc ggtagcacag agcatcctga ggaagtcaca acccaagcgg  180
aagctgcaat tgaagagggg gaggtggaga cagaagggga agcagcagtg gaaggggaag  240
aggaggctgt gtcctatgga gatgctgaaa gcgaagagga atattactat acagaaactt  300
catccccgga agggcaaatc agtgctgcag atacgactta cccgtatttc agtcctcctc  360
aggaactgcc tggagaggag gcatacgata gtgttagcgg ggaggctggt ctccaaggct  420
tccagcaaga ggccaccggt ccaccagaat ccagagaaag gagggtcacc tccccagagc  480
catcccacgg agtcttaggc ccgtcggagc aaatgggcca ggtcacctct gggccagcag  540
tgggcagatt gacaggatcc acagaggagc cccaggggca ggtgctccca atgggcgtcc  600
agcaccgctt ccggctgagc cacgggagcg acatcgagtc ctcagacctg gaggagttcg  660
tctcgcagga gccagtgatc cccccagggg tgcccgatgc ccaccccagg gaaggagacc  720
tgccagtgtt ccaggaccag atccagcagc ccagcaccga ggagggggcc atggcagaga  780
gagtggagtc cgaggggagt gacgaggaag cagaagacga agggtcccag ctggtggttt  840
tggacccaga ccaccccctg atggtaagat tccaggctgc cctgaagaac tacctgaacc  900
gacagatcga aaagttgaag ctggacctcc aagagctggt tgtggctacc aagcagagcc  960
gagcccagcg gcaggagctg ggggtgaatc tctatgaggt gcagcagcac ctggtacacc  1020
tgcagaagct gctggagaag agtcacgacc gccacgcaat ggcctcgagc gagcgcaggc  1080
agaaggagga ggagctgcag gccgcccgcg ctctctacac caagacctgc gcagccgcca  1140
acgaggagcg caaaaagttg gcggctctgc agactgagat ggagaacttg gccctgcatc  1200
tcttctacat gcagaacatc gaccaggaca tgcgtgacga catccgcgtg atgacacaag  1260
tggtaaagaa ggccgagacg gagaggatcc gggcagaaat cgagaagaaa aagcaggacc  1320
tgtatgtgga ccagctcacc actcgagccc agcaactgga agaagacatt gccctgtttg  1380
aggctcagta cttggcccaa gctgaggaca cccggatttt aaggaaagca gtgagtgagg  1440
cctgcaccga gatcgacgcc atcagcgtgg agaagaggcg catcatgcag caatgggcca  1500
gcagcctggt gggcatgaag caccgcgacg aggcgcacag ggcggtgctg gaggcgctca  1560
gaggatgcca gcatcaagcc aaatccaccg acggcgagat tgaggcctat aagaaatcca  1620
tcatgaagga ggaagaaaag aacgagaagc tggcgagcat cctgaaccgg acagagacgg  1680
aagccacact gctgcagaag ctcaccaccc agtgcctgac caagcaggtg gccctgcaga  1740
gccagttcaa tacctacagg ctcaccctgc aggacacaga ggatgccctc agccaggacc  1800
agctggaaca aatgatactc acggaggagt tgcaggccat ccgccaagcc atccagggcg  1860
agctggagct caggaggaag acggatgctg ccatccggga gaagctgcag gagcacatga  1920
cctccaacaa gaccaccaaa tacttcaacc agctcatcct gaggctgcag aaggagaaga  1980
ccaacatgat gacacatctt tccaaaatca acggtgacat tgcccagacc accctggaca  2040
tcacacacac cagcagcagg ctggacgcac accagaagac cctggtggag ctggaccagg  2100
acgtgaagaa agtcaacgag ctcatcacca acagccagag cgagatctcc cggcgcacga  2160
tcctgatcga gaggaagcaa gggctcatca acttcctcaa caagcagctg gagcggatgg  2220
tctccgagct ggggggggaa gaagtggggc ccctggagct tgaaatcaaa aggctgagca  2280
agctgatcga cgagcacgat ggcaaggcgg tccaggccca ggtgacctgg ctgcgcctgc  2340
agcaggagat ggtcaaggtg acacaggagc aggaggagca gctggcctcc ctggacgcat  2400
ccaagaagga gctccacatc atggagcaga agaaactacg agtagaaagc aagattgagc  2460
aggagaagaa ggagcagaag gagatcgagc accacatgaa ggacctggac aacgacctga  2520
```

-continued

```
agaagctcaa catgttgatg aataaaaacc ggtgcagctc ggaggagctg gagcagaaca  2580
accgggtgac agagaatgag ttcgtgcgct cgctgaaggc ctctgagagg gagaccatca  2640
agatgcagga caagctgaac cagctcagcg aggagaaggc gaccctcctg aatcaactgg  2700
tggaagcaga acaccagatt atgctttggg agaaaaaaat ccaactggca aaagagatgc  2760
gttcctcagt ggattccgag atcggccaga cggagatccg ggccatgaag ggcgagatcc  2820
acaggatgaa ggtcaggctc gggcagctgc tgaagcagca ggagaagatg atccgtgcca  2880
tggagttggc ggttgcccgc agagagaccg tcaccaccca ggccgagggg cagcgcaaga  2940
tggacaggaa ggcgctcacc cgcaccgact tccaccacaa gcagcttgag ctgcgccgga  3000
aaatcaggga cgttcgcaag gccaccgatg agtgcaccaa aaccgtcctg gaactggaag  3060
aaacacaaag aaatgtgagc agctccctcc tagagaagca ggaaaagctg tcggtgattc  3120
aggcagactt cgacacactc gaggccgacc tcacccggct tggggccctc aaacgacaga  3180
acctttcaga gatcgtggcc ctgcagacac gccttaagca cctgcaggct gtgaaggagg  3240
ggcgctacgt gttcctgttc cgctccaagc agtccctagt gctggagcgc cagcgcctgg  3300
acaagcgact ggctctcatc gccaccatcc tggaccgcgt gcgggacgag tacccccagt  3360
tccaggaggc cctgcacaag gtcagccaga tgatcgccaa caagctcgag tcaccagggc  3420
cctcctag                                                           3428

SEQ ID NO: 12          moltype = RNA  length = 38
FEATURE                Location/Qualifiers
source                 1..38
                       mol_type = other RNA
                       organism = synthetic construct
SEQUENCE: 12
aaacgcctga tgaggccgtg aggccgaaag ccagcttg                          38

SEQ ID NO: 13          moltype = RNA  length = 17
FEATURE                Location/Qualifiers
source                 1..17
                       mol_type = other RNA
                       organism = synthetic construct
SEQUENCE: 13
caagctggct agcgttt                                                 17

SEQ ID NO: 14          moltype = RNA  length = 19
FEATURE                Location/Qualifiers
source                 1..19
                       mol_type = other RNA
                       organism = synthetic construct
SEQUENCE: 14
gggagaccca agctggcta                                               19

SEQ ID NO: 15          moltype = RNA  length = 20
FEATURE                Location/Qualifiers
source                 1..20
                       mol_type = other RNA
                       organism = synthetic construct
SEQUENCE: 15
gggagaccca agctggctag                                              20
```